US010131955B2

(12) United States Patent
Darling et al.

(10) Patent No.: US 10,131,955 B2
(45) Date of Patent: Nov. 20, 2018

(54) METHODS FOR DETECTING GENETIC AND PHENOTYPIC BIOMARKERS OF UROTHELIAL CARCINOMA AND TREATMENT THEREOF

(71) Applicant: Pacific Edge Limited, Dunedin (NZ)

(72) Inventors: David Darling, Dunedin (NZ); James Miller Suttie, Dunedin (NZ); Mark Dalphin, Dunedin (NZ); Laimonis Kavalieris, Dunedin (NZ); Paul O'Sullivan, Dunedin (NZ); Satish Kumar, Havelock North (NZ)

(73) Assignee: PACIFIC EDGE LIMITED, Dunedin (NZ)

( * ) Notice: Subject to any disclaimer, the term of this patent is extended or adjusted under 35 U.S.C. 154(b) by 0 days.

(21) Appl. No.: 15/159,359

(22) Filed: May 19, 2016

(65) Prior Publication Data

US 2017/0275697 A1    Sep. 28, 2017

Related U.S. Application Data

(63) Continuation of application No. PCT/US2014/066678, filed on Nov. 20, 2014.

(51) Int. Cl.
| | |
|---|---|
| G01N 33/48 | (2006.01) |
| C12Q 1/6886 | (2018.01) |
| G01N 33/574 | (2006.01) |
| G01N 33/50 | (2006.01) |

(52) U.S. Cl.
CPC ........... *C12Q 1/6886* (2013.01); *G01N 33/50* (2013.01); *G01N 33/57407* (2013.01); *G01N 33/57484* (2013.01); *C12Q 2600/118* (2013.01); *C12Q 2600/158* (2013.01); *C12Q 2600/16* (2013.01); *G01N 2800/60* (2013.01)

(58) Field of Classification Search
None
See application file for complete search history.

(56) References Cited

PUBLICATIONS

Loo et al, "Stratifying risk of urinary tract malignant tumors in patients with asymptomatic microscopic hennaturia," (Mayo Clin. Proc. 2013).*

(Continued)

*Primary Examiner* — Larry D Riggs, II
(74) *Attorney, Agent, or Firm* — D. Benjamin Borson; Borson Law Group PC

(57) ABSTRACT

New methods for identifying patents with hematuria who are at low risk of having urothelial cancer (UC) include combining selected phenotypic variables with levels of genotypic expression into a new metric, the "G+P INDEX." The G+P INDEX combines age, sex, smoking history, presence of hematuria, and frequency of hematuria with genotypic expression of the genetic markers, MDK, CDC2, HOXA13, IGFBP5, and optionally IL8Rb, then determining of the G+P INDEX value obtained for a patient is within one of three groups, either: (1) at High Risk of UC, (2) at Risk of UC, or (3) at Low Risk of UC. For groups 1 and 2, further clinical and laboratory work up is indicated, and patients in group 3 are monitored periodically to determine the need for further clinical workup. Using the G+P INDEX can save substantial time, effort, and funds by avoiding unnecessary medical diagnostic procedures for patients at Low Risk of UC.

3 Claims, 109 Drawing Sheets

Specification includes a Sequence Listing.

(56) References Cited

PUBLICATIONS

International Preliminary Report on Patentability, PCT/US2014/066678, dated Jun. 2, 2016.
International Search Report, PCT/US2014/066678, dated Mar. 25, 2016.

* cited by examiner

```
LOCUS       NM_001557    2680 bp    mRNA
DEFINITION  Homo sapiens chemokine (C-X-C motif) receptor 2 (CXCR2), transcript variant
            1, mRNA.
ACCESSION   NM_001557
VERSION     NM_001557.3  GI:269972857

Protein sequence: "MEDFNMESDSFEDFWKGEDLSNYSYSSTLPPFLLDAAPCEPESL
EINKYFVVIIYALVFLLSLLGNSLVMLVILYSRVGRSVTDVYLLNLALADLLFALTLP
IWAASKVNGWIFGTFLCKVVSLLKEVNFYSGILLLACISVDRYLAIVHATRTLTQKRY
LVKFICLSIWGLSLLLALPVLLFRRTVYSSNVSPACYEDMGNNTANWRMLLRILPQSF
GFIVPLLIMLFCYGFTLRTLFKAHMGQKHRAMRVIFAVVLIFLLCWLPYNLVLLADTL
MRTQVIQETCERRNNIGRALDATEILGFLHSCLNPLIYAFIGQKFRHGLLKILAIHGL
ISKDSLPKDSRPSFVGSSSGHTSTTL"

ORIGIN
        1 aggttcaaaa cattcagaga cagaagtgg atagacaaat ctccacttc agactggtag
       61 gctcctcaag aagcatcag atagcaagat gtgaaaatcc ccagcactca tcccagaatc
      121 actaagtgga acctgtcctg ggcaaaagtc caggacaga cctcattgct cctctgtggg
      181 aatacctccc cagaagggca tactggattc ccccttgca accaggtca gaagtttcat
      241 cgtcaaggtt gttcatctt tttttcctg tctaacaget ctgactacaa cccaacctg
      301 aggcacagtg aagacatcgg tgctcaatac aatasccagca gtcacaget gctcctctgg
      361 aggtgtccta caggtgaaaa gccagcgac ccagtcagga tttaagttta accaaaaat
      421 ggaagatttt aacatggaga gtgacagctt tgaagattc tgcaagttg aagatcttag
      481 taattaaagt tacagctcta cctgccccca tttctacta gatgcagcgc catgtgaacc
      541 agaatcctg gaaatcaaca agtattcatg gtcattatc tatgccctgg tattcctgct
```

Figure 1A

```
 601 gagcctgctg ggaaactccc tcgtgatgct ggtcatctta tacagcaggg tcggccgctc
 661 cgtcactgat gtctacctgc tgaacctagc cttggccgac ctactcttg ccctgccttt
 721 gcccatctgg gccgcctcca aggtgaatgg ctggatttct ggcacattcc tgtgcaaggt
 781 ygtctcacto ctgaaggagc tcaacttcta tagtggcatc ctgctactgg cctgcatcag
 841 tgtggaccgt tacctggcca ttgtccatgc cacacgcaca ctgaccagg agcgctactt
 901 ggtcaaattc atatgtctcc gcatctgggg tctgtccttg ctcctggccc tgcctgtctt
 961 acttttccga aggaccgtct actcatccaa tgttagccca gcctgctatg aggacatggg
1021 caacaataca gcaaactggc ggatgctgtt acggatcctg cccagtcct ttggcttcat
1081 cgtgccactg ctgatcatgc tgttctgcta aggattccgc ctgcgtaccgc tgtttaaggc
1141 ccacatgggg cagaagcacc gggccatgcg ggtcatcttt gctgtcgtcc tcatcttcct
1201 gctctgctgg ctgccctaca acctggtcct gctggcagac accctcatga ggacccaggt
1261 gatccaggag acctgtgagc gccgcaatca catgccccgg gctctggatg ccactgagat
1321 tctgggcatc cttcacagct gcctcaaccc cctcatctac gctttcattg gccagaagtt
1381 tcgccatgga ctcctcaaga ttctagctat acatggcttg atcagcaagg actccctgcc
1441 caaagcagc aggccttcct ttgttggctc ttctcaaggg cccacttcca ctactctcta
1501 agacctcctg cctaagtgcc gccccgtggg gttcctccct tctcttcaca gtcacattcc
1561 aagcctcatg tccactgtt cctcttggtc tcagtgtcaa tgcagccacc attgtggtca
1621 caggaagtag aggaggcac gttcttacta gttcccttg catgttaag aaagcttgcc
1681 ctggtgcctc accccttgcc ataattacta tgtcatttgc tgagacttg cccatcctgc
1741 ccctgagccc atggcactct atgttctaag aagtgaaat ctacactcca gtgagacagc
1801 tctgcatact cattaggatg gctagtatca aagcaagaa aatcaggctg gccaacgggg
1861 tgaaccctg tctctactaa aaatacaaaa aaaaaaaaa attagccggg cgtggtggtg
1921 agtgcctgta atcacagcta cttggagggc tgagatggga gaatcacttg aacccgggag
1981 gcaguggttg cagtgagccg agattgtgcc cctgcactcc agcctgagcg acagtgagac
2041 tctgtctcag tccatgaaga tgtagagag aaactggaac tctcgacgt tgctgggggg
2101 gattgtaaaa tggtgtgacc actgcagaag acagtatggc agctttcctc aaaacttcag
2161 acatagaatt aacacatgat cctgcaattc cacttatagg aattgaccca caagaaatga
2221 aagcagggac ttgaacccat attgtacac caatattcat agcagcttat tcacaagacc
2281 caaaaggcag aagcaaccca aatgttcatc aatgaatgaa tgaatggcta agcaaaatgt
2341 gatatgtacc taacgaagta tcttcagcc tgaagagga atgaagtact catacatgtt
```

Figure 1B

```
2401 acaacacgga cgaaccttga aasctttatg ctaagtgaaa taagccagac atcaacagat
2461 aaatagttta tgattccacc tacatgaggt actgagagtg aacaaattta cagagacaga
2521 aagcagaaca gtgattacca gggactgagg ggagggagc atgggaagtg acggtttaat
2581 gggcacaggg tttatgttta ggatgttgaa aaagttctgc agataaacag tagtgatagt
2641 tgtaccgcaa tgtgacttaa tgccactaaa ttgacactta aaaatggttt aaatggtcaa
2701 ttttgttatg tatattttat atcaatttaa aaaaaaacct gagccccaaa aggtatttta
2761 atcaccaagg ctgattaaac caaggctaga accacctgcc tatatttttt gttaaatgat
2821 ttcattcaat atcttttttt taataaacca tttttacttg ggtgtttata aaaaaaaaaa
```

Figure 1C

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ras homolog gene family, member B (RHOB), mRNA | NP_004031.1 | NM_004040.2 | mwghuman3 OK#A.06114 | -2.684592 | 2.13794E-10 | 2.08759E-09 | -16.53678 | 38 | 8785.5 | 4175 | 25 |
| hypothetical protein FLJ21511 (FLJ21511), mRNA | NP_079363.1 | NM_025087.1 | mwghuman0 OK#A.00410 | -2.069503 | 2.5466E-11 | 3.22908E-09 | -6.928773 | 60 | 14455 | 9272.5 | 0 |
| paired box gene 8 (PAX8), transcript variant PAX8A, mRNA | NP_003457.1 | NM_003466.3 | mwghuman0 OK#F.3548 | -1.961598 | 4.71574E-11 | 4.07014E-09 | -6.606261 | 82 | 19419 | 12999.5 | 0 |
| UPF3 regulator of nonsense transcripts homolog A (yeast) (UPF3A), transcript variant 1, mRNA | NP_975387.1 | NM_023011.2 | mwghuman3 OK#A.06295 | -3.84067 | 1.09703E-13 | 3.24327E-09 | -7.811853 | 86.5 | 6863.5 | 1825 | 0 |
| leukotriene B4 12-hydroxydehydrogenase (LTB4DH), mRNA | NP_036344.1 | NM_012212.2 | mwghuman0 OK#B.3695 | -5.034813 | 3.06973E-10 | 1.41833E-07 | -6.436167 | 122.5 | 11940.5 | 3138 | 0 |

Figure 6A

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| RAB11 family interacting protein 2 (class I) (RAB11FIP2), mRNA | NP_055713.1 | NM_014904.1 | mwghuman3 0K8A:10479 | -1.893528 | 4.57928E-09 | 8.83951E-08 | -7.711094 | 156 | 10636.5 | 12351 | 0 |
| TSC22 domain family, member 1 (TSC22D1) transcript variant 2, mRNA | NP_006013.1 | NM_006022.2 | mwghuman3 0K8A:00577 | -2.130055 | 1.12033E-07 | 1.80-4-8E-07 | -7.898668 | 153.5 | 8415 | 6133 | 1 |
| sulfite oxidase (SUOX), nuclear gene encoding mitochondrial protein, transcript variant 1, mRNA | NP_000447.2 | NM_000456.2 | mwghuman3 0K8A:05812 | -1.822805 | 4.52404E-10 | 5.29156E-09 | -6.728882 | 223 | 11912.5 | 8763.5 | 0 |
| tetratricopeptide repeat domain 21A (TTC21A), mRNA | NP_659498.1 | NM_145755.1 | mwghuman3 0K8A:08975 | -2.678639 | 2.11314E-07 | 4.28868E-07 | -6.268432 | 223 | 8375.5 | 3670.5 | 1 |

Figure 6B

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| RAS p21 protein activator (GTPase activating protein) 1 (RASA1), transcript variant 2, mRNA | NP_072179.1 | NM_002890.1 | mwghuman3 0K9A;06292 | -1.847454 | 3.7459E-09 | 2.6904E-05 | -5.59238 | 235 | 6896.5 | 5277.5 | 7 |
| ensembl genscan prediction | | AC024084.6.1 979/5.119435.1 | mwghuman3 0K9C;6641 | -8.471522 | 4.970E-09 | 1.5458E-06 | -6.069076 | 255.5 | 3327.5 | 1537 | |
| ensembl genscan prediction | | AL031669.28.1.94524.1 | mwghuman3 0K9C;0933 | -1.774125 | 8.7781E-09 | 1.1827E-06 | -6.56115 | 256.5 | 4987 | 5215 | |
| geminin, DNA replication inhibitor (GMNN), mRNA | NP_056979.1 | NM_015895.3 | mwghuman3 0K9A;03635 | -2.046733 | 1.9464E-07 | 4.0288E-06 | -5.99038 | 311 | 11844 | 6413.75 | 2 |
| fatty acid binding protein 1, liver (FABP1), mRNA | NP_001434.1 | NM_001443.1 | mwghuman3 0K9A;09506 | -1.895847 | 2.2014E-06 | 6.6345E-07 | -5.750766 | 512.5 | 2698.5 | 15500.75 | 0 |
| v-jun sarcoma virus 17 oncogene homolog (avian) (JUN), mRNA | NP_002219.1 | NM_002228.3 | mwghuman3 0K9A;04848 | -3.022311 | 6.2171E-07 | 4.5907E-06 | -6.383849 | 318.5 | 12139 | 5321.5 | 11 |

Figure 6C

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| transmembrane and coiled-coil domains 4 (TMCO4), mRNA | NP_852070.2 | NM_181719.2 | mwghuman3 0K#8:3264 | -1.798143 | 8.41413E-09 | 3.21178E-06 | -5.702577 | 322.5 | 4584.5 | 3195 | 5 |
| ensembl genscan prediction | | APC02036.2.3 7398.74567.1 | mwghuman5 0K#C:4055 | -1.960121 | 5.76259E-08 | 1.01121E-07 | -7.000328 | 332.5 | 4072.5 | 2643 | |
| synaptotagmin-like 2 (SYTL2), transcript variant b, mRNA | NP_115755.2 | NM_032378.3 | mwghuman3 0K#8:3411 | -2.343367 | 4.07506E-10 | 9.67464E-08 | -7.063821 | 342 | 19620 | 12053.5 | 0 |
| cyclin G1 (CCNG1), transcript variant 1, mRNA | NP_004051.1 | NM_004060.3 | mwghuman3 0K#5:5254 | -1.83737 | 2.7920E-08 | 4.69388E-07 | -5.214776 | 355 | 9269.5 | 4450 | 7 |
| F-box protein 34 (FBXO34), mRNA | NP_060413.2 | NM_017943.2 | mwghuman3 0K#8:4885 | -1.891846 | 1.15594E-08 | 3.13872E-06 | -7.193500 | 366.5 | 17897.5 | 13192.75 | 5 |
| hypothetical protein xp_037916 loc152562 | | XM_087916 | mwghuman3 0K#8:5338 | -2.291304 | 2.60775E-08 | 3.04082E-06 | -5.299963 | 373 | 3951 | 1276 | |
| RNA pseudouridylate synthase domain containing 4 (RPUSD4), mRNA | NP_116184.1 | NM_032795.1 | mwghuman3 0K#8:6868 | -1.586458 | 2.0145E-10 | 1.14227E-08 | -6.494404 | 407 | 15747.5 | 11247 | 5 |

Figure 6D

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| WD repeat domain 33 (WDR33), transcript variant 2, mRNA | NP_001006623.1 | NM_001006622.1 | mwghuman3 OKRA:08115 | -1.765322 | 1.47292E-07 | 1.4590TE-06 | -6.190567 | 413 | 14876 | 10737.5 | 6 |
| FLJ20859 gene (FLJ20859), transcript variant 1, mRNA | NP_001025162.1 | NM_001029951.1 | mwghuman3 OKRA:10470 | -1.700385 | 8.133E-08 | 1.13272E-06 | -6.182855 | 420.5 | 3781 | 2063.75 | |
| activating transcription factor 3 (ATF3), transcript variant 2, mRNA | NP_004015.3 | NM_004024.3 | mwghuman3 OKRA:00869 | -3.124251 | 8.404378E-08 | 1.51986E-07 | -7.446028 | 421 | 13092.5 | 5361.25 | 2 |
| cytochrome P450, family 3, subfamily A, polypeptide 5 (CYP3A5), mRNA | NP_000768.1 | NM_000777.2 | mwghuman3 OKRA:04580 | -2.482162 | 7.0225E-08 | 1.9772E-06 | -4.813435 | 451.5 | 20850.5 | 12100.5 | 0 |
| ensembl genscan prediction | | AL161725.13.1.181179.3 | mwghuman3 OKRC:3443 | -1.955485 | 1.19555E-09 | 8.24936E-05 | -5.681512 | 465 | 2738.5 | 1799 | |
| KIT ligand (KITLG), transcript variant 3, mRNA | NP_000890.1 | NM_003994.3 | mwghuman3 OKRA:07355 | -4.28251 | 3.8867E-05 | 7.23184E-07 | -6.894125 | 475 | 19437 | 16599.75 | 2 |

Figure 6E

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| decay accelerating factor for complement (CD55, Cromer blood group system) (DAF), mRNA | NP_000565.1 | NM_000574.2 | mwghuman3 OK#A:06705 | -2.148033 | 1.44112E-08 | 6.58262E-06 | -5.038184 | 471.5 | 9606.5 | 4753.25 | 10 |
| solute carrier family 25 (mitochondrial carrier; phosphate carrier), member 23 (SLC25A23), mRNA | NP_077008.2 | NM_024103.2 | mwghuman3 OK#A:05030 | -1.486915 | 7.78425E-09 | 9.80903E-07 | -5.241772 | 437 | 18206.5 | 1241.5.75 | 4 |
| wingless-type MMTV integration site family, member 2B (WNT2B), transcript variant WNT-2B1, mRNA | NP_004176.2 | NM_004185.2 | mwghuman3 OK#A:05986 | -10.740275 | 2.83382E-12 | 3.19726E-07 | -6.175471 | 501 | 10718 | 2816.25 | 0 |
| protocadherin gamma subfamily A, 12 (PCDHGA12), transcript variant 1, mRNA | NP_003735.1 | NM_003735.2 | mwghuman3 OK#A:06604 | -2.070447 | 2.89557E-07 | 6.93435E-06 | -4.362742 | 511 | 6037 | 1691.5 | 0 |

Figure 6F

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC010826.3, 125575.1581 93.2 | mwghuman3 OKBC-4737 | -1.875465 | 2.34946E-07 | 5.18322E-07 | -5.361893 | 511 | 26962 | 25267.75 | |
| olfactory receptor, family 1, subfamily O, member 5 (OR1O5), mRNA | NP_055061.1 | NM_014566.1 | mwghuman3 OK8A:00765 | 1.840751 | 5.89984E-68 | 4.2286E-06 | -5.196756 | 535.5 | 1644 | 1134 | 0 |
| G protein-coupled receptor 128 (GPR128), transcript variant b1, mRNA | NP_940971.1 | NM_138589.1 | mwghuman3 OK8B:3968 | -2.161736 | 3.9002E-07 | 1.0681E-05 | -5.947301 | 548 | 15995.5 | 8040.75 | 0 |
| similar to bc40se5.4 novel protein simple-like cdc42-binding kinase beta cdc42bpb LOC144850 | | XM_096650 | mwghuman3 OK8B:9156 | -4.380057 | 2.8669E-08 | 6.28305E-07 | -6.298929 | 573 | 1764 | 832 | |
| ubiquitin specific peptidase 9, Y-linked (fat facts-like, Drosophila) (USP9Y), mRNA | NP_004645.2 | NM_004654.3 | mwghuman3 OK8A:16865 | -2.584085 | 3.40815E-07 | 6.23595E-06 | -5.287284 | 587 | 10095.5 | 7956.25 | 1 |

Figure 6G

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AC022954.2.1 1723.14597.1 | nwghuman9 OK#C:7523 | -2.600527 | 1.74508E-07 | 8.41199E-07 | -5.832591 | 587 | 3838 | 1298 | |
| solute carrier family 35 (CMP-sialic acid transporter), member A1 (SLC35A1), mRNA | NP_006407.1 | NM_006416.3 | nwghuman9 OK#B:6263 | -1.879113 | 1.20877E-06 | 5.48118E-06 | -5.237894 | 606 | 20539 | 15406.75 | |
| cell line sc20.1 receptor alpha chain v-j positioned region of V 29.1 j11 coding sequence reported apart from nucleotide position | | U14089 | nwghuman9 OK#B:9790 | -2.442854 | 6.94216E-08 | 1.14277E-08 | -7.385079 | 617 | 6973 | 2651.5 | |
| chromosome 2 open reading frame 33 (C2orf33), mRNA | NP_064679.3 | NM_020194.4 | nwghuman9 OK#A:0688 | -1.815311 | 9.24962E-07 | 9.24230E-08 | -5.893032 | 624 | 11336.5 | 8868.25 | 4 |
| ensembl genscan prediction | | AC079398.7.1 14033.192530 | nwghuman9 OK#C:4901 | -2.1076+2 | 1.493E-05 | 1.96894E-06 | 6.345875 | 650.5 | 3963.5 | 5876.75 | |

Figure 6H

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| UDP-N-acetyl-alpha-D-galactosamine:polypeptide N-acetylgalactosaminyltransferase 7 (GalNAc-T7) (GALNT7), mRNA | NP_059119.1 | NM_017423.1 | mwghuman3 0KRA01420 | -1.401045 | 7.50042E-08 | 1.13872E-08 | -5.143961 | 656.5 | 10873 | 8597.75 | 2 |
| chromosome 11 open reading frame 1 (C11orf1), mRNA | NP_079598.1 | NM_022751.1 | mwghuman3 0KRA01834 | -1.81238 | 1.36332E-06 | 1.22937E-05 | -5.104229 | 673.5 | 12025.5 | 9585.25 | 0 |
| heterogeneous nuclear ribonucleoprotein H2 (H') (HNRPH2), transcript variant 1, mRNA | NP_062543.1 | NM_019597.3 | mwghuman3 0KRA08547 | -2.05901 | 2.40365E-06 | 6.18248E-05 | -5.469662 | 684 | 777 | 472 | 9 |
| Werner syndrome (WRN), mRNA | NP_000544.1 | NM_000553.3 | mwghuman3 0KRA20193 | -1.605462 | 7.48708E-06 | 8.18248E-05 | -4.881771 | 688 | 4685 | 4251.25 | 3 |
| ensembl genscan prediction | | AC046180.3.6 1245.136921.5 | mwghuman3 0KAC72317 | -4.953847 | 7.54477E-12 | 1.43866E-08 | -6.802986 | 708.5 | 4523.5 | 744.5 | |

Figure 61

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blop of |
|---|---|---|---|---|---|---|---|---|---|---|---|
| adducin 3 (gamma) (ADD3), transcript variant 1, mRNA | NP_056432.1 | NM_016824.3 | mwghuman9 0K6A;5211 | -2.092475 | 1.3433TE-05 | 1.18155E-05 | -5.883253 | 716 | 7058.5 | 4808.75 | 5 |
| hydroxysteroid dehydrogenase like 2 (HSDL2), mRNA | NP_115879.2 | NM_032303.2 | mwghuman9 0K6G;3686 | -2.1517 | 8.98696E-07 | 5.81298E-08 | -5.68367 | 732.5 | 7276.5 | 5055 | 2 |
| DNA-damage-inducible transcript 4 (DDIT4), mRNA | NP_061931.1 | NM_019058.2 | mwghuman9 0K6G;2115 | -2.686775 | 6.68834E-05 | 6.3921E5E-05 | -5.886252 | 733 | 10860.5 | 5062.75 | 12 |
| RNA binding protein, autoantigenic (hnRNP-associated with lethal yellow homolog (mouse)) (RALY), transcript variant 1, mRNA | NP_057951.1 | NM_016732.1 | mwghuman9 0K6A;9537B | -1.901876 | 1.7075E-07 | 4.32856E-08 | -4.392163 | 750.5 | 977 | 386.5 | 26 |

Figure 6J

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| acyl-CoA synthetase medium-chain family member 3 (ACSM3), transcript variant 1, mRNA | NP_005613.2 | NM_005622.3 | mwghuman3 OKWB.9575 | -1.567123 | 1.7751E-05 | 7.33536E-06 | -5.050721 | 785.5 | 18906.5 | 12052.25 | 3 |
| BCL2-associated athanogene (BAG1), mRNA | NP_004314.3 | NM_004323.3 | mwghuman3 OKWA.06551 | -2.325417 | 2.13163E-08 | 5.290062E-07 | -5.394904 | 775 | 9631 | 4603.5 | 1 |
| neural precursor cell expressed, developmentally down-regulated 4 (NEDD4), transcript variant 1, mRNA | NP_006145.1 | NM_006154.1 | mwghuman3 OKWB.7892 | -1.900918 | 3.7763E-08 | 8.23034E-06 | -5.249282 | 781 | 15497 | 12975 | 2 |
| chromosome 7 open reading frame 19 (C7orf19), mRNA | NP_116220.1 | NM_053831.1 | mwghuman3 OKWB.2325 | -1.760795 | 4.58755E-09 | 0.000016624 | -5.43532 | 783 | 11598.5 | 9704.75 | 19 |
| calpain 13 (CAPN13), mRNA | NP_653173.2 | NM_144575.2 | mwghuman3 OKWB.6754 | -1.542421 | 4.91704E-06 | 5.61228E-06 | -4.943248 | 808.5 | 22318 | 15353.5 | 0 |
| homeo box B2 (HOXB2), mRNA | NP_002106.1 | NM_002145.2 | mwghuman3 OKWA.01633 | -2.702649 | 2.81498E-11 | 5.06294E-06 | -6.774876 | 814.5 | 11537.5 | 6408 | 3 |

Figure 6K

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| coiled-coil domain containing 28A (CCDC28A), mRNA | NP_056254.1 | NM_015439.2 | mwghuman3 0K#B:3159 | -1.900606 | 1.97346E-06 | 5.48118E-05 | -6.330597 | 826 | 19023 | 14223.75 | 4 |
| myofibrillogenesis regulator 1 (MR-1), transcript variant 1, mRNA | NP_056353.2 | NM_015426.3 | mwghuman3 0K#B:3170 | -1.625798 | 1.25984E-05 | 9.82435E-05 | -5.874470 | 832 | 19007 | 18702.75 | 6 |
| guanine nucleotide binding protein (G protein), beta polypeptide 2-like 1 (GNB2L1), mRNA | NP_006089.1 | NM_006098.4 | mwghuman3 0K#C:0541 | -1.789065 | 2.16996E-06 | 4.35416E-05 | -4.900058 | 844.5 | 1710 | 1179 | 108 |
| spectrin repeat containing, nuclear envelope 1 (SYNE1), transcript variant beta, mRNA | NP_056108.1 | NM_015293.1 | mwghuman3 0K#B:9104 | -1.414534 | 7.52735E-07 | 1.02433E-05 | -5.963197 | 851 | 20159.5 | 17230.75 | 64 |
| ensembl genscan prediction | | AL021185.1 / 107803.5 | mwghuman3 0K#C:7304 | -1.766400 | 2.12121E-06 | 2.01356E-05 | -4.493676 | 853 | 129.4 | 847.5 | |

Figure 6L

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| bone morphogenetic protein receptor, type IA (BMPR1A), mRNA | NP_004320.2 | NM_004329.2 | mwghuman3 OKKA:32464 | -1.558808 | 2.223078E-07 | 1.028078E-05 | -4.518211 | 874.5 | 6115 | 5037.5 | 4 |
| IQ motif containing B1 (IQCB1), transcript variant 1, mRNA | NP_001023 64.1 | NM_0010236 70.1 | mwghuman3 OK#B:4C25 | -1.646869 | 2.70486E-05 | 1.02809E-05 | -5.160856 | 832.5 | 10622 | 9773.5 | 2 |
| ensembl genscan prediction | | AC068502.9.1 .183801 | mwghuman3 OK8C:3853 | -1.486573 | 8.04397E-07 | 2.896879E-05 | -4.951829 | 901 | 21678 | 18335 | |
| similar to death associated protein (LOC62196), mRNA | NP_0010179 25.1 | NM_0010179 25.1 | mwghuman3 OK#B:3716 | -2.559467 | 5.7894tE-07 | 7.7815E-07 | -5.221107 | 807 | 32355 | 15868 | 0 |
| ensembl genscan prediction | | AC012203.4.1 05191.12357:1 | mwghuman3 OK#C:4578 | -1.439719 | 1.219 86E-05 | 4.858 6E-07 | -6.969899 | 897 | 27671.5 | 25367.5 | |
| ensembl genscan production mwg oligo matches these RefSeq numbers NM_000385 | | AL158153.9.4 6106.110162.3 | mwghuman3 OK#C:2170 | -6.089228 | 4.805868E-07 | 4.328058E-06 | -5.399407 | 839.5 | 1290 | 1010.25 | |

Figure 6M

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| growth arrest and DNA-damage-inducible, alpha (GADD45A), mRNA | NP_001915.1 | NM_001924.2 | mwghuman3 0X6A04346 | -1.80216 | 7.53906E-06 | 2.6791E-05 | -4.924921 | 915.5 | 11534.5 | 8596.75 | 3 |
| stress 70 protein chaperone, microsome-associated, 60kDa (STCH), mRNA | NP_006979.3 | NM_006948.4 | mwghuman3 0X6A35084 | -1.761234 | 4.59183E-05 | 1.7326E-05 | -5.794774 | 918.5 | 10794 | 6231.25 | 5 |
| ensembl genscan prediction | | Z84474.1.1.1 07526.2 | mwghuman3 0X9C0911 | -1.884439 | 1.62444E-06 | 2.2341E-05 | -5.434325 | 919.5 | 1974 | 1465.5 | |
| family with sequence similarity 44, member B (FAM44B), mRNA | NP_612378.1 | NM_138369.1 | mwghuman3 0X7B4192 | -1.357114 | 7.81833E-07 | 1.8443E-05 | -6.047948 | 949.5 | 15308.5 | 13094.75 | 1 |
| ensembl genscan prediction | | AC078789.15.1.85074.2 | mwghuman3 0X9C6283 | -1.788454 | 1.80936E-05 | 3.7083E-05 | -4.861731 | 949 | 26953.5 | 22890.75 | |
| citrate lyase beta like (CLYBL), transcript variant 1, mRNA | NP_612134.3 | NM_138280.3 | mwghuman3 0X8D9055 | -1.444822 | 1.17936E-05 | 5.1691E-05 | -5.775319 | 953 | 21231 | 18530.25 | 1 |

Figure 6N

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ensembl genscan prediction | | AP001015.3.6 6084.115855. 1 | mwghuman3 OK8C:3536 | -1.708242 | 1.45259E-07 | 7.36585E-05 | -4.904002 | 872.5 | 3374.5 | 2739.5 | |
| ensembl genscan prediction | | AL158169.24. 1.86155.2 | mwghuman3 OK8C:4495 | -1.474035 | 8.96454E-07 | 3.25687E-05 | -5.020854 | 988.5 | 28575 | 28030 | |
| chromosome 6 open reading frame 130 (C6orf130), mRNA | NP_659500.1 | NM_145063.2 | mwghuman3 OK8D:4552 | -1.574298 | 1.77778E-06 | 3.32044E-05 | -4.848271 | 1511.5 | 14804 | 10754.75 | 3 |
| methyltransferase like 7 (METTL7), transcript variant 1, mRNA | NP_055062.1 | NM_005371.5 | mwghuman3 OK8A:0065/ | -1.464425 | 1.73108E-07 | 5.48118E-06 | -5.447813 | 1920 | 943 | 646.5 | 2 |
| nucleosome assembly protein 1-like 4 (NAP1L4), mRNA | NP_005963.1 | NM_005969.2 | mwghuman3 OK8A:0706 | -1.902267 | 1.4461E-06 | 5.95321E-05 | -4.982307 | 1042.5 | 10336.5 | 8976.5 | 12 |
| tumor protein D52 (TPD52), transcript variant 3, mRNA | NP_005970.1 | NM_005079.2 | mwghuman3 OK8A:0633 | -1.55805 | 1.79344E-06 | 3.154C9E-05 | -4.599069 | 1970 | 19553 | 14646.75 | 4 |
| EH-domain containing 4 (EHD4), mRNA | NP_644670.1 | NM_139265.2 | mwghuman3 OK8B:5911 | -1.54335 | 1.97186E-06 | 9.70321E-05 | -4.903805 | 1077 | 12134 | 9137.5 | 4 |

Figure 6O

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| fibroblast growth factor receptor 4 (FGFR4), transcript variant 2, mRNA | NP_075252.2 | NM_022963.2 | mwghuman3 0K#5:0174 | -2.638428 | 2.034028E-05 | 3.21175E-06 | -5.251766 | 1087.5 | 17305 | 9762.5 | 0 |
| KIAA0674 (KIAA0674), mRNA | XP_376303.2 | XM_376363.2 | mwghuman3 0K#5:0240 | -1.362676 | 3.687392E-05 | 3.620656E-06 | -5.432041 | 1092.5 | 18744 | 9097.25 | 4 |
| chromosome 16 bac clone cit987sk-a-362e5 | | U91321 | mwghuman3 0K#2:9375 | -1.568988 | 5.918445E-05 | 6.532558E-06 | -5.349453 | 1114.5 | 10576.5 | 6883.65 | |
| ovarian granulosa production | | AC079510.11, BX491.1024/8 3 | mwghuman3 0K#C:1307 | -1.828100 | 1.886005E-05 | 1.300855E-05 | -5.253574 | 1114.5 | 1484.5 | 737 | |
| androgen receptor (AR), transcript variant 1, mRNA | NP_000035.2 | NM_000044.2 | mwghuman3 0K#A:0100B | -1.575915 | 1.15973E-07 | 1.540355E-06 | -4.231823 | 1120.5 | 16067.5 | 15252.5 | 0 |
| thyroid transcription factor 1 (TITF1), mRNA | NP_003308.1 | NM_003317.3 | mwghuman3 0K#A:0197 | -1.469987 | 8.57965E-07 | 1.545552E-06 | -5.023277 | 1124.5 | 2139 | 1023.25 | 0 |

Figure 6P

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| spectrin repeat containing, nuclear envelope 1 (SYNE1), transcript variant longest, mRNA | NP_892006.1 | NM_182961.1 | mwghuman3 0K9C2040 | -1.449164 | 6.37872E-05 | 2.15085E-05 | -5.806222 | 1124.5 | 26092.5 | 21861.5 | 64 |
| ensembl genscan prediction | | AC019064.7.9 3515.194802.2 | mwghuman3 0K9C5482 | -1.55954 | 1.43692E-05 | 7.77599E-05 | -6.043827 | 1128.5 | 8789.5 | 8789.5 | |
| ensembl genscan prediction | | AC026232.12 3616.157122.4 | mwghuman3 0K9C3868 | -1.663854 | 8.74891E-05 | 0.000123 803 | -4.393563 | 1135.5 | 824 | 489.5 | |
| ensembl genscan prediction | | AP002844.1.9 9823.121676.1 | mwghuman3 0K9C3950 | -1.784079 | 2.96082E-05 | 7.75722E-05 | -4.63759 | 1150 | 18692.5 | 14083.25 | |
| CDC-like kinase 1 (CLK1), transcript variant 1, mRNA | NP_004062.2 | NM_004071.2 | mwghuman3 0K9A07848 | -2.034707 | 6.15081E-05 | 6.93321E-05 | -5.145908 | 1157.5 | 12199 | 7634.75 | 4 |
| lipin 1 (LPIN1), mRNA | NP_663731.1 | NM_145693.1 | mwghuman3 0K9D8172 | -1.851742 | 1.40757E-07 | 2.99759E-05 | -4.301728 | 1159.5 | 3757 | 2602 | 2 |
| lamin A/C (LMNA), transcript variant 2, mRNA | NP_005563.1 | NM_005572.2 | mwghuman3 0K9A09949 | -1.724023 | 9.89727E-06 | 5.87958E-05 | -5.305029 | 1162.5 | 4442 | 3295 | 10 |
| ensembl genscan prediction | | AC079436.15. 119606.15142 0.1 | mwghuman3 0K9C3309 | -1.39562 | 6.38081E-06 | 4.32856E-05 | -6.429508 | 1168.5 | 26766.5 | 26493.5 | |

Figure 6Q

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| similar to clean cdna 1500002E63 clone mgc:12928 image:429841 | | BC007768 | mwghuman3 0K#8:45142 | -1.518082 | 5.312229E-05 | 3.81402E-05 | -4.463202 | 1171 | 21199 | 20375 | |
| ensembl genescan prediction | | AC027365.2,2 3033.31537.1 | mwghuman3 0K#C.5982 | -1.659000 | 1.18112E-11 | 3.57785E-07 | -4.295271 | 1172.5 | 2757 | 2062.78 | |
| hyaluronoglucos aminidase 3 (HYAL3), mRNA | NP_003540.2 | NM_003549.2 | mwghuman3 0K#A.00625 | -2.01977 | 8.70903E-08 | 1.16156E-05 | -4.884969 | 1175 | 4036 | 3464.5 | 4 |
| ensembl genescan prediction | | AC093682.10, 126484.12512 2.1 | mwghuman3 0K#C.9101 | -1.479502 | 8.913119E-06 | 2.83657E-05 | -4.528959 | 1177 | 23091.5 | 20578.5 | |
| VprBP protein (VprBP), mRNA | NP_055518.1 | NM_014703.1 | mwghuman3 0K#8:10333 | -1.760925 | 3.28082E-05 | 2.40122E-05 | -5.345863 | 1178 | 17312.5 | 14031 | 0 |
| nuclear RNA export factor 1 (NXF1), mRNA | NP_006353.2 | NM_006362.3 | mwghuman3 0K#8:1047 | -1.686819 | 7.48559E-05 | 1.62906E-05 | -6.376445 | 1195.5 | 15210 | 14343.75 | 20 |
| empty spiracles homolog 2 (Drosophila) (EMX2), mRNA | NP_004088.1 | NM_004098.2 | mwghuman3 0K#8:9279 | -1.785089 | 5.4636E-08 | 5.84117E-07 | -6.396572 | 1199.5 | 19980 | 16743.25 | 0 |
| homeo box D8 (HOXD8), mRNA | NP_062458.1 | NM_019558.2 | mwghuman3 0K#8:2485 | -1.41565 | 6.70306E-08 | 2.10195E-06 | -6.574131 | 1206 | 9572.5 | 7842.25 | 0 |

Figure 6R

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| protein predicted protein of hq2591 | | AF119858 | mwghuman3 0K#3:1001 | -1.467436 | 7.83971E-05 | 1.30297E-05 | -4.828888 | 1212 | 27543.5 | 28503 | 0 |
| ensembl genscan prediction | | AC018439.3.1 5645.18372.1 | mwghuman3 0K#C:6958 | -9.528975 | 4.36488E-10 | 5.08094E-08 | -6.731611 | 1219.5 | 3962.5 | 1303 | |
| ensembl genscan prediction | | AF286865.1.7 6372.115954.3 | mwghuman3 0K#C:7800 | -1.83051 | 1.14443E-05 | 5.11795E-06 | -4.359169 | 1216 | 21163.5 | 21228.5 | |
| zinc finger protein 25 (KOX 19) (ZNF25), mRNA | NP_659446.1 | NM_145011.2 | mwghuman3 0K#C:1648 | -1.473477 | 8.43814E-08 | 4.35853E-07 | -5.843864 | 1263.5 | 21026.5 | 19177 | 1 |
| zinc finger protein 626 (ZNF626), mRNA | NP_680940.1 | NM_145287.2 | mwghuman3 0K#8:4148 | -1.773185 | 2.01463E-05 | 9.63646E-06 | -4.294351 | 1266 | 14806.5 | 10943 | 1 |
| growth arrest and DNA-damage-inducible, beta (GADD45B), mRNA | NP_056490.1 | NM_015675.1 | mwghuman3 0K#A:20587 | -1.959707 | 0.0002700 32 | 2.63519E-05 | -4.068029 | 1279.5 | 10303 | 8615.5 | 5 |
| nebulette (NEBL), transcript variant 1, mRNA | NP_006384.1 | NM_006393.1 | mwghuman3 0K#A:10498 | -1.513881 | 1.95755E-05 | 3.15409E-06 | -4.789714 | 1276 | 22908 | 20052.5 | 1 |

Figure 6S

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein prc26322 | | NM_018541 | mwghuman3 DKFZ:95371 | -1.457088 | 9.06355E-05 | 6.90321E-05 | -5.164695 | 1289.5 | 16682.5 | 14266.5 | |
| ring finger protein 44 (RNF44), mRNA | NP_955716.1 | NM_014901.4 | mwghuman3 DKFZ:16030 | -1.353365 | 7.76079E-07 | 2.37433E-06 | -5.842885 | 1292 | 6295.5 | 4664.5 | 1 |
| REX1, RNA exonuclease 1 homolog (S. cerevisiae) (REXO1), mRNA | NP_065748.2 | NM_020695.2 | mwghuman3 DKFZ:6218 | -1.38697 | 1.73225E-05 | 2.85069E-05 | -5.111384 | 1305.5 | 4933 | 3309.5 | 5 |
| pyrimidinergic receptor P2Y, G-protein coupled, 4 (P2RY4), mRNA | NP_002355.1 | NM_002565.3 | mwghuman3 DKFZ:GO-C35 | -1.738075 | 5.0199E-06 | 2.88048E-06 | -5.5195M | 1308 | 18327 | 12109.5 | 0 |
| ensembl genscan prediction | | AL023804.2.1 96460.1 | mwghuman3 DKFZ:6405 | -1.533948 | 1.03637E-06 | 2.808E-05 | -4.893772 | 1313 | 28610 | 27960.5 | |
| ensembl genscan prediction | | AL139823.3.4 9422.61911.1 | mwghuman3 DKFZ:8803 | -1.894632 | 4.41409E-05 | 0.000129 14 | -4.950025 | 1325 | 11214.5 | 7546 | |
| similar to hypothetical protein (LOC443904), mRNA | XP_036990.3 | XM_036990.3 | mwghuman3 DKFZ:4832 | -4.042648 | 5.38047E-11 | 1.91898E-07 | -6.379174 | 1332 | 3647 | 998.5 | 0 |

Figure 6T

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome X open reading frame 41 (CXorf41), mRNA | NP_775765.1 | NM_173494.1 | mwghumans3 OK#C:1528 | -1.446391 | 1.77872E-05 | 2.53657E-05 | -5.140193 | 1334 | 27434 | 24062.75 | 0 |
| chromosome 20 open reading frame 152 (C20orf152), mRNA | NP_543024.1 | NM_080823.1 | mwghumans3 OK#6:3251 | -1.948612 | 6.84261E-06 | 1.08135E-05 | -4.957585 | 1349 | 10775 | 8652.5 | 0 |
| ensembl genescan prediction | | AL390766.11, 35656.142362.1 | mwghumans3 OK#C:6548 | -1.516487 | 5.60665E-06 | 4.81914E-05 | -4.642588 | 1352 | 22469.5 | 27079.25 | |
| phosphorylase, glycogen; liver (Hers disease, glycogen storage disease type VI) (PYGL), mRNA | NP_002854.3 | NM_002863.2 | mwghumans3 OK#A:4349 | -2.190201 | 5.14475E-06 | 0.000299 936 | -4.316798 | 1366.5 | 10299.5 | 7222 | 21 |
| ensembl genescan prediction | | AC013754.3.1 17501.157349.1 | mwghumans3 OK#C:3627 | -1.871949 | 6.77866E-06 | 7.35985E-05 | -4.29195 | 1385.5 | 1209 | 826.5 | |
| follistatin-like 4 (FSTL4), mRNA | NP_055897.1 | NM_015082.1 | mwghumans3 OK#B:5510 | -1.344342 | 4.79968E-06 | 4.36419E-05 | -4.607654 | 1405.5 | 17361 | 12319 | 0 |

Figure 6U

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| chromosome 14 open reading frame 169 (C14orf169), mRNA | NP_113646.1 | NM_031427.1 | mwghuman3 0K98-4811 | -1.612002 | 1.55095E-05 | 5.97939E-06 | -4.636177 | 1414 | 15738 | 14760.75 | 1 |
| aldehyde dehydrogenase 7 family, member A1 (ALDH7A1), mRNA | NP_001173.1 | NM_001182.2 | mwghuman3 0K9A-08261 | -1.837545 | 4.80787E-07 | 0.000105 508 | -3.933463 | 1433 | 20183.5 | 14349.5 | 2 |
| ensembl genscan prediction | | AC016904.9.2 85.204257.5 | mwghuman3 0K9C-7420 | -1.40463 | 4.7475SE-05 | 3.07694E-05 | -4.832328 | 1444 | 27423.5 | 25979.25 | |
| kallikrein 8 (neuropsin/ovasin) (KLK8), transcript variant 8, mRNA | NP_853099.1 | NM_144505.1 | mwghuman3 0K88-0129 | -2.081506 | 3.59009E-06 | 2.618556E-06 | -5.051679 | 1449.5 | 8351 | 6488 | 8 |
| leucine zipper, down regulated in cancer 1-like (LDOC1L), mRNA | NP_115863.2 | NM_032287.2 | mwghuman3 0K48-8710 | -1.501821 | 2.6595E-06 | 1.32937E-05 | -4.280727 | 1454.5 | 16509.5 | 14157 | 0 |
| two pore segment channel 1 (TPCN1), mRNA | NP_060371.2 | NM_017901.3 | mwghuman3 0K98-7759 | -1.487443 | 4.82588E-06 | 3.22544E-05 | -4.567011 | 1480.5 | 17545 | 11635.75 | 8 |

Figure 6V

| Gene name/ symbol | protein accession | mRNA ref seq accession | BWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein MGC11242 (MGC11242), mRNA | NP_077296.1 | NM_024320.2 | mwghuman3 0K9A:05139 | -1.527830 | 2.70218E-05 | 1.72268E-05 | -4.004461 | 1493.5 | 17885 | 13134.5 | 0 |
| phosphofurin acidic cluster sorting protein 1 (PACS1), mRNA | NP_060496.2 | NM_018026.2 | mwghuman3 0K9B:7703 | -1.494259 | 5.233618E-05 | 7.36585E-05 | -4.898398 | 1462.5 | 9352 | 7757.75 | 19 |
| hypothetical protein xp_038406 loc91138 | | XM_038406 | mwghuman3 0K9B:8090 | -1.553764 | 1.021618E-05 | 4.58223E-05 | -5.893936 | 1496.5 | 18372.5 | 14682 | |
| KIAA1274 (KIAA1274), mRNA | NP_055346.1 | NM_014431.1 | mwghuman3 0K9B:8047 | -1.41842 | 7.87044E-05 | 5.27279E-05 | -5.659345 | 1498.5 | 3039 | 5066 | 0 |
| ensembl genscan prediction | | AC060861.1.B 901.36861.2 | mwghuman3 0K9C:0027 | -1.525691 | 2.39913E-05 | 7.36585E-05 | -4.820954 | 1493.5 | 21992 | 20253 | |
| hypothetical protein FLJ13111 (FLJ13111), mRNA | NP_079369.1 | NM_025092.1 | mwghuman3 0K9A:2290 | -1.498999 | 3.86096E-05 | 7.08197E-05 | -4.495468 | 1494 | 4851 | 7570.25 | 10 |
| glycophorin C (Gerbich blood group) (GYPC), transcript variant 1, mRNA | NP_056992.1 | NM_002101.3 | mwghuman3 0K9A:9129 | -1.525829 | 9.49623E-05 | 0.000135784 | -4.110107 | 1502 | 3048 | 8771 | 2 |

Figure 6W

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein MGC11242 (MGC11242), mRNA | NP_077295.1 | NM_024320.2 | mwghuman3 OKWA:05190 | -1.527839 | 2.70219E-05 | 1.72268E-05 | -4.004461 | 1463.5 | 17585 | 13134.5 | 0 |
| phosphofurin acidic cluster sorting protein 1 (PACS1), mRNA | NP_060488.2 | NM_018026.2 | mwghuman3 OKWA:7703 | -1.494259 | 5.23361E-05 | 7.36585E-05 | -4.899268 | 1462.5 | 9352 | 7757.75 | 19 |
| hypothetical protein XP_036408 loc91138 | | XM_036408 | mwghuman3 OKWA:8080 | -1.583764 | 1.02151E-05 | 4.59223E-05 | -4.93538 | 1466.5 | 15972.5 | 14552 | |
| KIAA1274 (KIAA1274), mRNA | NP_055248.1 | NM_014431.1 | mwghuman3 OKWA:8047 | -1.41942 | 7.97044E-05 | 2.27270E-05 | -5.855345 | 1488.5 | 9099 | 8065 | 0 |
| ensembl genscan prediction | | AC090661.1.8 901.36861.2 | mwghuman3 OKWC:6027 | -1.525691 | 2.39919E-05 | 7.98585E-05 | -4.020854 | 1488.5 | 21092 | 20263 | |
| hypothetical protein FLJ13111 (FLJ13111) mRNA | NP_079959.1 | NM_025082.1 | mwghuman3 OKWA:02690 | -1.456998 | 3.68968E-05 | 7.08197E-05 | -4.409480 | 1493 | 4851 | 7579.25 | 10 |
| glycophorin C (Gerbich blood group) (GYPC), transcript variant 1, mRNA | NP_002092.1 | NM_002101.3 | mwghuman3 OKWA:01279 | -1.628528 | 9.49623E-05 | 0.000135784 | -4.110107 | 1502 | 8042 | 8771 | 2 |

Figure 6X

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein MGC11242 (MGC11242), mRNA | NP_077296.1 | NM_024920.2 | mwghuman3 OK#A:05130 | -1.527833 | 2.70218E-05 | 1.72263E-05 | -4.004461 | 1463.5 | 17585 | 13134.5 | 0 |
| phosphofurin acidic cluster sorting protein 1 (PACS1), mRNA | NP_060496.2 | NM_018026.2 | mwghuman3 OK#B:7703 | -1.494259 | 5.23351E-05 | 7.36585E-06 | -4.598266 | 1492.5 | 9352 | 7757.75 | 18 |
| hypothetical protein xp_036408 loc91138 | | XM_036408 | mwghuman3 OK#B:8080 | -1.531704 | 1.02161E-05 | 4.50223E-05 | -4.93538 | 1485.5 | 15372.5 | 14652 | |
| KIAA1274 (KIAA1274), mRNA | NP_055248.1 | NM_014431.1 | mwghuman3 OK#B:8047 | -1.41242 | 7.87044E-05 | 2.27275E-05 | -5.659345 | 1488.5 | 8059 | 8065 | 0 |
| ensembl genscan prediction | | AC090861.1.0 901.36861.2 | mwghuman8 OK#C:0027 | -1.525691 | 2.36913E-06 | 7.36585E-05 | -4.620984 | 1489.5 | 21092 | 20253 | |
| hypothetical protein FLJ10111 (FLJ10111), mRNA | NP_079359.1 | NM_025082.1 | mwghuman3 OK#A:02690 | -1.498058 | 3.89096E-05 | 7.08197E-05 | -4.489468 | 1494 | 4851 | 7579.25 | 13 |
| glycophorin C (Gerbich blood group) (GYPC), transcript variant 1, mRNA | NP_002092.1 | NM_002101.3 | mwghuman3 OK#A:01278 | -1.828625 | 5.49023E-06 | 0.000135 784 | -4.110107 | 1502 | 8042 | 6771 | 2 |

Figure 6Y

| Gene name/ symbol | protein accession | mRNA ref seq accession | MWG Probe name | median fold change | t-test | Wilcoxon test | SAM | rank score | tumor tissue median intensity rank | non-malignant tissue median intensity rank | blood |
|---|---|---|---|---|---|---|---|---|---|---|---|
| chromosome 14 open reading frame 154 (C14orf154), transcript variant 1, mRNA | NP_115808.2 | NM_032232.2 | mwghuman3 OK#B.2685 | -1.704669 | 6.00805E-05 | 0.008168 230 | -4.427372 | 1561.5 | 16829 | 15068.75 | 5 |
| hypothetical protein xp_098865 loc198865 | | XM_098865 | mwghuman3 OK#B.6008 | -1.672814 | 4.27782E-05 | 0.008142 749 | -4.312941 | 1568.5 | 8793 | 6547.25 | |
| clone rp2/117 pxp0117 | | AF390895 | mwghuman3 OK#B.0814 | -1.888405 | 3.18377E-05 | 9.6385E-05 | -4.735768 | 1570.5 | 20158 | 14935.5 | 4 |
| prostate and breast cancer overexpressed 1 (P50V1), mRNA | NP_067048.1 | NM_021635.1 | mwghuman3 OK#A.9511# | -1.810346 | 5.40978E-06 | 6.1652E-05 | -4.437567 | 1571.5 | 22494.5 | 19846.75 | 0 |
| esterase D/formylgluath ione hydrolase (ESD), mRNA | NP_001975.1 | NM_001984.1 | mwghuman3 OK#C.2641 | -1.585088 | 6.75303E-05 | 4.84250E-05 | -4.277065 | 1574 | 8049 | 4836.75 | 6 |
| ATG4 autophagy related 4 homolog B (S. cerevisiae) (ATG4B), transcript variant 1, mRNA | NP_037457.2 | NM_013325.4 | mwghuman3 OK#D.2745 | -1.348365 | 6.59727E-05 | 1.0224E-05 | -4.71932 | 1575 | 15168 | 16712.25 | 13 |

Figure 6Z

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| NADPH oxidase 1 (NOX1), transcript variant NOH-1Lv, mRNA | NP_035249.1 | NM_013955.1 | mwghuman3 OK#B-1370 | -1.803806 | 5.04367E-38 | 2.62186E-45 | -3.799677 | 1585.5 | 18937.5 | 17371.5 | 0 |
| in-silico genscan prediction | | AL445675.9.1 .171985.3 | mwghuman3 OK#C-3741 | -1.774798 | 2.80351E-05 | 0.000152 918 | -4.333137 | 1598 | 22483.5 | 18071.5 | |
| putative nuclear protein ORF1-FL49 (ORF1-FL49), mRNA | NP_115788.1 | NM_052912.3 | mwghuman3 OK#D-7958 | -1.489859 | 6.19749E-05 | 3.325448-05 | -4.457268 | 1619.5 | 8698 | 4695 | 0 |
| THUMP domain containing 1 (THUMPD1), mRNA | NP_060200.2 | NM_017736.3 | mwghuman3 OK#B-2668 | -1.313257 | 4.11582E-07 | 6.59382E-06 | -5.326519 | 1651.5 | 14677 | 15313.5 | 0 |
| glutaminyl-peptide cyclotransferase (glutaminyl cyclase) (QPCT), mRNA | NP_002545.1 | NM_012413.3 | mwghuman3 OK#A-09422 | -1.766571 | 4.62609E-07 | 9.000132 803 | -3.882651 | 1651.5 | 11860 | 6037.75 | 2 |
| PHD finger protein 23 (PHF23), mRNA | NP_077273.1 | NM_024297.1 | mwghuman3 OK#A-02672 | -1.396461 | 1.43561E-05 | 0.000100 894 | -4.365774 | 1657.5 | 10696.5 | 9365.75 | 0 |

Figure 6AA

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| nasopharyngeal carcinoma associated gene protein-6 (NAG6), mRNA | NP_053928.1 | NM_014411.2 | mwghuman3 0K#C1482 | -1.388055 | 2.36325E-05 | 5.10584E-05 | -4.601858 | 1660 | 15731.5 | 12181 | 0 |
| ensembl genscan prediction | | AC013487.6.1 C2379.117540.1 | mwghuman3 0K#C3348 | -1.488992 | 9.9001448 57 | 2.37435E-05 | -5.235259 | 1662 | 14711 | 9423 | |
| ensembl genscan prediction | | AC079757.5.5 4097.63672.1 | mwghuman3 0K#C3844 | -1.488502 | 2.9582SE-05 | 4.12786E-05 | -4.795329 | 1664.5 | 25878.5 | 23575.5 | |
| hypothetical protein FLJ22513 (FLJ22513), mRNA | NP_071786.2 | NM_022373.3 | mwghuman3 0K#E3974 | -1.47428 | 9.0501047 25 | 5.87556E-05 | -4.784258 | 1668.5 | 8360.5 | 9165.25 | 2 |
| holocytochrom e c synthase (cytochrome c heme-lyase) (HCCS), mRNA | NP_005324.2 | NM_005333.2 | mwghuman3 0K#A04510 | -2.084412 | 9.0005329 92 | 0.000311 868 | -5.979849 | 1682.5 | 10130.5 | 5483.25 | 4 |
| dual specificity phosphatase 5 (DUSP5), mRNA | NP_004410.3 | NM_004419.3 | mwghuman3 0K#A04026 | -1.866767 | 5.5251SE-05 | 2.27276E-05 | -5.708882 | 1684.5 | 18243.5 | 8925 | 2 |
| hypothetical protein FLJ20245 (FLJ20245), mRNA | NP_060193.1 | NM_017723.1 | mwghuman3 0K#62983 | -1.525801 | 6.09069E-05 | 0.000116 76 | -4.335617 | 1687 | 18122 | 18193 | 3 |

Figure 6BB

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| protein kinase, AMP activated, gamma 2 non-catalytic subunit (PRKAG2), mRNA | NP_057287.2 | NM_016203.2 | mwghuman3 0K#A00771 | -1.405092 | 1.41298E-05 | 6.59966E-05 | -4.495083 | 1697.2 | 16315.5 | 13437.25 | 5 |
| clone rp11-314a4 on chromosome 20, contains part of the eya2 eyes absent drosophila homolog 2 eats an es and gss6_itemis l | | AL355434 | mwghuman3 0K#B5838 | -1.591958 | 1.57257E-05 | 6.56065E-05 | -4.703762 | 1702 | 23046.5 | 23640.75 | |
| hypothetical protein prot598 prot598 | | NM_018603 | mwghuman3 0K#B:0063 | -1.448899 | 3.88533E-06 | 1.30096E-05 | -5.335446 | 1716.5 | 24115.5 | 22818.75 | |
| NIMA (never in mitosis gene a)-related kinase 9 (NEK9), mRNA | NP_148107.3 | NM_033116.3 | mwghuman3 0K#C:0538 | -1.359293 | 3.9285-06 | 4.35419E-05 | -4.72725 | 1722.5 | 19134.5 | 7455.5 | 6 |
| glycine receptor, alpha 3 (GLRA3), mRNA | NP_006520.1 | NM_006529.1 | mwghuman3 0K#A:03690 | -1.412224 | 0.0001037 83 | 6.16805E-05 | 4.59741 | 1726 | 9472.5 | 8083.35 | 2 |

Figure 6CC

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| exon of genscan prediction | | AC004402.1.1 113252.2 | mwghuman3 0K#C-3512 | -1.54076 | 2.53537E-05 | 1.54035E-05 | -3.813774 | 1727 | 2977 | 2622.75 | |
| exon of genscan prediction | | AP001655.2.1 48977.153525 | mwghuman3 0K#C-7868 | -1.285857 | 2.54478E-05 | 1.66029E-05 | -4.861591 | 1745 | 28568 | 26245.5 | |
| HERV-H LTR-associating 3 (HHLA3), transcript variant 3, mRNA | NP_001031722.1 | NM_001036645.1 | mwghuman3 0K#B-1045 | -2.042346 | 8.87677E-05 | 9.53087E-05 | -3.941792 | 1758 | 16925.5 | 11798 | 0 |
| exon of genscan prediction | | AL596467.14.1 2153397.9 | mwghuman3 0K#C-7911 | -3.035765 | 1.10768E-06 | 3.62755E-07 | -6.915780 | 1760 | 5572.5 | 3481.25 | |
| fibronectin leucine rich transmembrane protein 3 (FLRT3), transcript variant 1, mRNA | NP_037415.1 | NM_013281.2 | mwghuman3 0K#A-05022 | -4.204568 | 1.4541E-08 | 8.99201E-07 | -6.942440 | 1770 | 16156 | 9251.25 | 0 |
| cyp3a5 allele cyp3a5*3 alternatively spliced | | AF255802 | mwghuman3 0K#B-1530 | -1.371578 | 7.33233E-06 | 1.91497E-05 | -4.382295 | 1784 | 26168.5 | 24516.25 | |

Figure 6DD

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| microfibrillar-associated protein 3-like (MFAP3L), transcript variant 1, mRNA | NP_067679.5 | NM_021647.5 | meghuman3 OK9BA317 | -1.967417 | 0.0001373 75 | 1.98715E-05 | -4.959479 | 1785 | 22262 | 18475.25 | 9 |
| cell division cycle associated 7 (CDCA7), transcript variant 1, mRNA | NP_114148.2 | NM_031942.3 | meghuman3 OK9B:4819 | -1.952698 | 8.26637E-05 | 0.000150 05 | -4.246099 | 1786 | 14820 | 12577.25 | 1 |
| WD repeat domain 61 (WDR61), mRNA | NP_079510.1 | NM_025234.1 | meghuman3 OK9B:1524 | -1.931766 | 0.0001544 91 | 0.000105 508 | -4.36785 | 1801. 5 | 9756.5 | 8041.75 | 3 |
| protein kinase, AMP-activated, beta 1 non-catalytic subunit (PRKAB1), mRNA | NP_006244.2 | NM_006253.4 | meghuman3 OK9A:04896 | -1.514877 | 9.25449E-05 | 0.000105 508 | -4.4366 | 1805. 5 | 16011.5 | 13954 | 3 |
| zinc finger, A20 domain containing 2 (ZA20D2), mRNA | NP_003698.1 | NM_005077.1 | meghuman3 OK9A:10213 | -1.857323 | 2.78168E-05 | 2.87313E-05 | -4.731221 | 1806. 5 | 6856.5 | 4863.25 | 13 |
| similar to pp21862 loc93374 | | XM_050978 | meghuman3 OK9B:7206 | -1.239995 | 8.46914E-05 | 6.30077E-05 | -5.206744 | 1817 | 19180 | 16498 | |

Figure 6EE

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| catalase (CAT), mRNA | NP_001743.1 | NM_001752.2 | mwghuman3 0K#C:3530 | -2.225675 | 6.1538E-07 | 6.82436E-06 | -4.777325 | 1820 | 7219.5 | 4203.75 | 31 |
| peptidylprolyl isomerase (cyclophilin)-like 2 (PPIL2), transcript variant 2, mRNA | NP_660480.1 | NM_148175.1 | mwghuman3 0K#B:6252 | -1.284363 | 4.77437E-07 | 4.59276E-05 | -5.295075 | 1834.5 | 2806 | 3514 | 5 |
| peroxin (PEX), transcript variant 2, mRNA | NP_079996.1 | NM_181832.1 | mwghuman3 0K#A:0:791 | -1.380199 | 1.0336E-05 | 6.8946E-05 | -4.542994 | 1838 | 19842.5 | 17122.5 | 0 |
| breast carcinoma amplified sequence 3 (BCAS3), mRNA | NP_050149.2 | NM_017679.2 | mwghuman3 0K#A:0:157R | -1.41274 | 6.6423E-07 | 2.84015E-06 | -4.89611 | 1839 | 15754.5 | 17560.25 | 2 |
| HtrA serine peptidase 2 HTRA2 | AAF66596.1 | AF141387.1 | mwghuman3 0K#E:1170 | -1.284282 | 2.27894E-05 | 1.96362E-05 | -4.371262 | 1850 | 22795.5 | 20044.75 | |
| ensembl genscan prediction | | AC012065.13. 12548.17418. 1 | mwghuman3 0K#C:7312 | -1.517688 | 0.000104314 | 0.000172495 | -4.407330 | 1854 | 25139.5 | 25010.5 | |
| forkhead binding protein 4 (FNBP4), mRNA | NP_056123.1 | NM_015236.1 | mwghuman3 0K#E:6897 | -1.380042 | 0.000119422 | 2.15065E-05 | -5.502665 | 1855 | 17142 | 14814.25 | 11 |

Figure 6FF

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| aldehyde dehydrogenase 1 family, member L1 (ALDH1L1), mRNA | NP_036322.2 | NM_012190.2 | mwghuman3 0K#A:07479 | -2.306651 | 2.32803E-05 | 0.000157 701 | -3.740635 | 1885.5 | 13469 | 8189.5 | 3 |
| ensembl genscan prediction | | AFQ01467.3.8 5265.114407.1 | mwghuman3 0K#C:8733 | -1.603991 | 4.06918E-06 | 5.37933E-05 | -4.363485 | 1870 | 3883 | 3994.75 | |
| ensembl genscan prediction | | AC015651.18.1.191563.4 | mwghuman3 0K#C:2191 | -1.392136 | 5.55423E-07 | 1.72358E-05 | -4.582358 | 1875.5 | 2460 | 1928.25 | |
| OTU domain containing 5 (OTUD5), mRNA | NP_060379.1 | NM_017602.2 | mwghuman3 0K#B:7959 | -1.721316 | 3.42743E-06 | 1.37851E-05 | -5.368623 | 1884.5 | 1453 | 1611 | 14 |
| ensembl genscan prediction | | AC005682.5.5 4585.337203.1 | mwghuman3 0K#C:5348 | -1.806723 | 2.7492AE-06 | 2.40123E-05 | -5.209388 | 1898 | 1801 | 1675.5 | |
| chromosome 20 open reading frame 121 (C20orf121), mRNA | NP_077307.1 | NM_024331.2 | mwghuman3 0K#A:03001 | -1.580517 | 5.93303E-06 | 1.82138E-05 | -4.183769 | 1908 | 8788 | 5594 | 2 |
| pyruvate dehydrogenase kinase, isozyme 4 (PDK4), mRNA | NP_002603.1 | NM_002612.2 | mwghuman3 0K#A:07594 | 1.735687 | 1.72394E-05 | 1.22907E-05 | -6.445188 | 1911.5 | 15087 | 13987.25 | 1 |

Figure 6GG

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| KIAA1049 protein (KIAA1049), mRNA | NP_055787.1 | NM_014972.1 | mwghuman3 0K9B:2555 | -1.400381 | 1.00483E-05 | 7.36065E-05 | -4.358733 | 1913.5 | 10979 | 8688.5 | 12 |
| DnaJ (Hsp40) homolog, subfamily B, member 6 (DNAJB6), transcript variant 1, mRNA | NP_490647.1 | NM_058246.3 | mwghuman3 0K9A:04864 | -1.455502 | 9.60314E-05 | 0.000150 | -4.886034 | 1917 | 3809 | 2695.5 | 14 |
| lectin, galactoside-binding, soluble, 3 (galectin 3) (LGALS3), mRNA | NP_002297.1 | NM_002306.1 | mwghuman3 0K9A:16308 | -1.52733 | 6.89527E-05 | 2.65121E-05 | -4.890215 | 1923 | 3753 | 1893.5 | 6 |
| PTPRF interacting protein, binding protein 2 (liprin beta 2) (PPFIBP2), mRNA | NP_003612.1 | NM_003621.1 | mwghuman3 0K9B:0552 | -1.861545 | 1.26489E-05 | 2.98752E-05 | -4.14902 | 1937.5 | 6372.5 | 4594.5 | 2 |
| polymerase (DNA directed), lambda (POLL), mRNA | NP_037406.1 | NM_013274.2 | mwghuman3 0K9B:1279 | -1.399987 | 9.5888E-05 | 2.96750E-05 | -4.733654 | 1938 | 15108.5 | 11461.25 | 8 |

Figure 6HH

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| growth differentiation factor 15 (GDF15), mRNA | NP_004855.1 | NM_004864.1 | mwghuman9 0K9A:37217 | -2.483648 | 0.0063241 34 | 0.000257 25 | -4.296268 | 1944 | 6377 | 3127.5 | 2 |
| hypothetical protein xp_086808 loc156765 | | XM_086808 | mwghuman3 0K9B:847A | -1.231397 | 9.30157E-07 | 2.40122E-05 | -4.093057 | 1949 | 11626.5 | 11522.5 | |
| leucine rich repeat and sterile alpha motif containing 1 (LRSAM1), transcript variant 1, mRNA | NP_612370.3 | NM_138361.3 | mwghuman3 0K9B:4416 | -2.034574 | 0.0061840 31 | 0.000232 837 | -4.13512 | 1959.5 | 7871.0 | 4421.75 | 1 |
| trafficking protein particle complex 6A (TRAPPC6A), mRNA | NP_077012.1 | NM_024108.3 | mwghuman3 0K9A:18117 | -1.462954 | 2.44741E-06 | 2.63657E-05 | -3.509655 | 1985 | 1279 | 1294 | 3 |
| ensembl genscan prediction | | AL357148.10. 1.83484.1 | mwghuman3 0K9C:2606 | -1.287782 | 1.49736E-05 | 9.05474E-05 | -4.926559 | 1989 | 38444.5 | 26083.25 | |
| hypothetical protein MGC14327 (MGC14327), mRNA | NP_A4427R.1 | NM_059045.1 | mwghuman3 0K9B:4427 | -1.534495 | 0.0061602 56 | 0.000174 117 | -4.521635 | 1992 | 15905 | 15440.5 | 4 |

Figure 6H

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| similar to kinesin family member 5b clone mgc:5285 image:4207735 | | BC009353 | mwghuman2 0K9B_4436 | -1.51682 | 0.0031882 14 | 0.000198 131 | -4.531675 | 1992 | 23071.5 | 9:859.75 | |
| potassium channel tetramerisation domain containing 3 (KCTD3), mRNA | NP_057356.2 | NM_016121.3 | mwghuman3 0K9A_04396 | -1.35800 | 1.34583E-05 | 5.38262E-05 | -4.810624 | 1994.5 | 17479.5 | 13263.75 | 3 |
| ensembl genscan prediction | | AC018425.3.1 59134,186978.1 | mwghuman3 0K9C_3925 | -1.49653 | 0.0031489 25 | 0.000192 191 | -4.315206 | 1997 | 25396 | 25414.75 | |
| guanine nucleotide binding protein (G protein), alpha inhibiting activity polypeptide 1 (GNAI1), mRNA | NP_002060.4 | NM_002069.4 | mwghuman3 0K8A_10201 | -1.631361 | 5.34565E-05 | 0.000453 577 | -3.880346 | 2003 | 16903.5 | 14362 | 1 |
| microtubule-associated protein 4 (MAP4), transcript variant 1, mRNA | NP_002365.2 | NM_002375.3 | mwghuman3 0K9B_4355 | -1.498752 | 0.0001551 87 | 0.000257 25 | -4.423897 | 2004 | 16052 | 5980 | 11 |

Figure 6JJ

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| nucleolar protein family 6 (RNA-associated) (NOL6), transcript variant alpha, mRNA | NP_075068.2 | NM_022917.4 | mwghuman3 0K#A:07182 | -1.32357 | 1.12604E-06 | 3.70831E-05 | -4.767639 | 2008 | 19513 | 5821 | 7 |
| cerebral endothelial cell adhesion molecule 1 (CEECAM1), mRNA | NP_057258.2 | NM_016174.3 | mwghuman3 0K#A:19231 | -1.516413 | 4.80848E-05 | 6.09010E-198 | -3.667981 | 2014 | 18662.5 | 13757.75 | 0 |
| ubiquinol-cytochrome c reductase, complex III subunit VII, 9.5kDa (UQCRQ), nuclear gene encoding mitochondrial protein, mRNA | NP_055217.2 | NM_014402.3 | mwghuman3 0K#6:6060 | -1.71227 | 4.79681E-05 | 4.25419E-05 | -5.048156 | 2014 | 4189.5 | 2885.25 | 14 |
| hypothetical protein xp_092745 loc194337 | | XM_092745 | mwghuman3 0K#8:5305 | -1.386871 | 3.28973E-05 | 6.00016E-718 | -4.513374 | 2041 | 19510 | 15741.25 | |

Figure 6KK

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein FLJ22065 (FLJ22965), mRNA | NP_071394.1 | NM_022101.2 | mwghuman9 DK#A5977C | -1.805469 | 7.18955E-06 | 0.600475 | -4.076844 | 2041.5 | 2586 | 2337 | 0 |
| chromosome 9 open reading frame 102 (C9orf102), transcript variant 1, mRNA | NP_064592.1 | NM_020207.2 | mwghuman9 DK#B5956 | -1.369819 | 9.45523E-06 | 0.600105 | -4.976844 | 2049 | 16457.5 | 13970 | 0 |
| sphingosine-1-phosphate phosphatase 1 (SGPP1), mRNA | NP_115185.1 | NM_030791.2 | mwghuman9 DK#B1809 | -1.477332 | 4.60035E-06 | 0.600142 | -4.328187 | 2052.5 | 20994 | 17541.5 | 1 |
| pleckstrin and Sec7 domain containing 3 (PSD3), transcript variant 1, mRNA | NP_056125.2 | NM_015310.2 | mwghuman9 DK#B2519 | -1.305361 | 2.79551E-05 | 0.600142 | -3.953529 | 2072 | 14823 | 13323.25 | 1 |
| hypothetical protein LOC283874 (LOC283874), mRNA | NP_001012749.1 | NM_001012731.1 | mwghuman9 DK#B2101 | 1.275343 | 1.46793E-05 | 2.6791E-05 | -5.079509 | 2095.5 | 23611.5 | 25030 | 1 |

Figure 6LL

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| zinc finger, FYVE domain containing 21 (ZFYVE21), mRNA | NP_078976.1 | NM_054971.2 | mwghuman3 0K6A:05642 | -1.579552 | 0.0001142 53 | 0.000342 645 | -4.239027 | 2094 | 3094.5 | 2740.25 | 0 |
| forkhead box E1 (thyroid transcription factor 2) (FOXE1), mRNA | NP_004464.2 | NM_004473.3 | mwghuman3 0K6A:07699 | -1.875652 | 1.5104E-05 | 0.000192 131 | -3.807954 | 2107 | 7289 | 5298.75 | 0 |
| eukaryotic genome proteolog? | | AL156168.17, 82311,114103 | mwghuman3 0K6C:5882 | -1.54058 | 5.723458-05 | 8.98591E-05 | -4.136599 | 2114 | 38578 | 27753.75 | |
| similar to per-hexamer repeat protein 6 (loc149155) | | XM_085208 | mwghuman3 0K6B:5884 | -1.363207 | 0.0001055 84 | 3.77872E-05 | -3.8371 | 2131 | 27002.5 | 27249.5 | |
| zinc finger, matrin type 1 (ZMAT1), transcript variant 3, mRNA | NP_115817.1 | NM_032441.1 | mwghuman3 0K6C:9106 | -1.462696 | 8.00015E2 57 | 0.000211 865 | -4.530065 | 2134.5 | 20939.5 | 17150.25 | 2 |
| endoplasmic reticulum to nucleus signalling 2 (ERN2), mRNA | NP_150296.2 | NM_033266.2 | mwghuman3 0K6B:5414 | -1.705197 | 1.96155E-05 | 2.70954E-05 | -4.905593 | 2135 | 34789 | 18803 | 0 |

Figure 6MM

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| ring finger protein 38 (RNF38), transcript variant 1, mRNA | NP_073618.3 | NM_022781.3 | mwghuman3 0K#B5968 | -1.232965 | 2.50383E-05 | 7.15035E-05 | -4.985001 | 2138 | 24546.5 | 22148.75 | 1 |
| Myc-induced mitochondria protein (mimitin), mRNA | NP_777546.1 | NM_174869.2 | mwghuman3 0K#B3718 | -1.474873 | 8.4085E-05 | 0.000269 234 | -5.237401 | 2151.5 | 9215 | 7030.25 | 1 |
| TGF beta-inducible nuclear protein 1 (TINP1), mRNA | NP_056701.1 | NM_014866.2 | mwghuman3 0K#A09520 | -1.626993 | 0.00031879 | 0.000571 787 | -4.796546 | 2153 | 7530 | 5545.5 | 6 |
| similar to developmental pluripotency associated 5; embryonal stem cell specific gene 1 (LOC341912), mRNA | XP_292301.2 | XM_292301.2 | mwghuman3 0K#B3134 | -1.638760 | 7.84751E-07 | 4.22855E-06 | -5.437822 | 2155 | 16581.5 | 12815.25 | 1 |
| dehydrogenase/reductase (SDR family) member 3 (DHRS3), mRNA | NP_004744.2 | NM_004753.4 | mwghuman3 0K#B-0738 | -1.408265 | 4.39582E-05 | 0.000222 464 | -5.074187 | 2156.5 | 4626 | 3570 | 3 |

Figure 6NN

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| flavin containing monooxygenase 4 (FMO4), mRNA | NP_002013.1 | NM_002022.1 | mwghuman3 0K#B.2927 | -1.804252 | 0.0051964 57 | 0.500272 664 | -4.150771 | 2173.5 | 21425 | 18041 | 1 |
| ensembl genscan prediction | | AC022528.4.9 087.13827.1 | mwghuman3 0K#C5061 | -1.5*8225 | 0.0901264 28 | 0.500174 117 | -4.437230 | 2174 | 25712.5 | 23316 | |
| serologically defined colon cancer antigen 8 (SDCCAG8), mRNA | NP_006633.1 | NM_006642.1 | mwghuman3 0K#B:4992 | -1.352218 | 3.61032E-06 | 1.22957E-05 | -4.628131 | 2177.5 | 18548 | 16556 | 4 |
| CDC14 cell division cycle 14 homolog B (S. cerevisiae) (CDC14B), transcript variant 2, mRNA | NP_201588.1 | NM_033331.1 | mwghuman3 0K#B:0753 | -1.438488 | 0.0061590 76 | 0.300545 124 | -4.702655 | 2178.5 | 23922 | 22971 | 2 |
| myeloid/lymph oid or mixed-lineage leukemia (trithorax homolog, Drosophila); translocated to 3 (MLLT3), mRNA | NP_004520.1 | NM_004529.1 | mwghuman3 0K#A.00726 | -1.503791 | 3.87447E-06 | 0.300311 503 | -4.282874 | 2188 | 20164.5 | 17482 | 4 |

Figure 6OO

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| cytochrome P450, family 27, subfamily A, polypeptide 1 (CYP27A1), nuclear gene encoding mitochondrial protein, mRNA | NP_000775.1 | NM_000784.2 | mwghuman3 0K&A:07422 | -1.399838 | 4.05019E-05 | 9.51276E-05 | -4.065693 | 2197 | 20714 | 19781.5 | 10 |
| pro-Iink cell associated protein 119 3' end | | L17326 | mwghuman3 0K&B:9026 | -1.343875 | 5.92964E-06 | 9.64322E-05 | -5.065977 | 2201 | 6449.5 | 4787.5 | |
| hepcidin antimicrobial peptide (HAMP), mRNA | NP_066998.1 | NM_021175.2 | mwghuman3 0K&A:06937 | -1.2787x6 | 2.53831E-05 | 1.79258E-05 | -4.883297 | 2205.5 | 3732.5 | 3385.25 | 0 |
| ensembl genscan prediction | | AC079613.13, 1.41262.1 | mwghuman3 0K#C:7792 | -1.549803 | 2.34706E-06 | 7.88194E-05 | -4.262195 | 2213 | 21981.5 | 17900.75 | |
| hypothetical protein DC008862 (LOC90113), mRNA | XP_291077.3 | XM_291077.3 | mwghuman3 0K&B:9956 | -1.768276 | 0.0003405 69 | 0.090454 027 | -4.412577 | 2221.5 | 6951.5 | 6176 | 0 |
| elongation factor, RNA polymerase II, 2 (ELL2), mRNA | NP_036213.1 | NM_012081.3 | mwghuman3 0K&A:00032 | -1.498648 | 5.49285E-05 | 0.000157 701 | -4.384408 | 2223.5 | 14138 | 11702.5 | 4 |

Figure 6PP

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| FGFR1 oncogene partner (FGFR1OP), transcript variant 1, mRNA | NP_008878.1 | NM_007045.2 | mwghuman3 OKaC4678 | -1.515357 | 9.11499E-05 | 0.000233 537 | -4.055106 | 2223.5 | 10894 | 19145.25 | 9 |
| ensembl genscan prediction | | AC025953.2.1 10948.127472 .1 | mwghuman3 OKaC6547 | -2.043212 | 0.0001531 48 | 0.000253 287 | -3.955032 | 2231 | 21041 | 17426.5 | |
| PH domain binding protein 1 (PHBP1), mRNA | NP_056067.1 | NM_015252.2 | mwghuman3 OKaC0355 | -1.36883 | 2.50342E-06 | 6.99321E-05 | -4.828579 | 2249.5 | 15151.5 | 12131 | 9 |
| propionyl Coenzyme A carboxylase, alpha polypeptide (PCCA), mRNA | NP_000273.2 | NM_000282.2 | mwghuman3 OKaC3551 | -1.535038 | 6.411E-05 | 0.000110 993 | -4.042034 | 2251 | 18323 | 13436 | 6 |
| ensembl genscan prediction | | AL136499.4.1 .185713.1 | mwghuman3 OKaC4197 | -1.668604 | 1.85577E-05 | 3.599398E-05 | -3.700791 | 2252.5 | 6728 | 6642.5 | |
| ensembl genscan prediction | | AC025937.3.2 8497.184165.1 | mwghuman3 OKaC9420 | -5.621331 | 1.23565E-11 | 3.14666E-07 | -6.568116 | 2255.5 | 3384 | 1095.5 | |

Figure 6QQ

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| myocilin, trabecular meshwork inducible glucocorticoid response (MYOC), mRNA | NP_000252.1 | NM_000261.1 | mwghuman9 GK#A:03642 | -1.364785 | 4.51814E-06 | 2.5104E-05 | -4.028227 | 2293 | 20815.5 | 22357.25 | 0 |
| bspc074 | | AF161337 | mwghuman3 GK#B:1281 | -1.81808 | 1.54965E-06 | 1.5403E-05 | -4.420700 | 2284.5 | 1792 | 1727 | 3 |
| epoxide hydrolase 2, cytoplasmic (EPHX2), mRNA | NP_001970.2 | NM_001979.4 | mwghuman5 GK#A:09530 | -1.419398 | 5.8546E-06 | 5.9123E-06 | -4.685716 | 2267.5 | 19752.5 | 16357 | 3 |
| centrosome protein C 1 (CENPC1), mRNA | NP_001803.2 | NM_001812.2 | mwghuman05 GK#A:10535 | -1.578112 | 0.00018235 | 0.000192131 | -4.258306 | 2275 | 19346.5 | 14167.25 | 4 |
| poly(A) polymerase beta (testis specific) (PAPOLB), mRNA | NP_064528.4 | NM_020144.4 | mwghuman3 GK#A:03834 | -1.633342 | 0.00017934 | 0.000311503 | -4.111646 | 2294 | 24777 | 23772.75 | 1 |
| oligonucleotide/oligosaccharide-binding fold containing 1 (OBFC1), mRNA | NP_078904.1 | NM_024928.3 | mwghuman8 GK#A:07398 | -1.567232 | 0.00001519 | 0.000150 | -4.338596 | 2292 | 15940.5 | 11600 | 4 |

Figure 6RR

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| tripartite motif-containing 13 (TRIM13), transcript variant 1, mRNA | NP_005795.1 | NM_005273.2 | mwghuman3 0K9A:10515 | -1.780912 | 5.5220E-05 | 5.003139 784 | -4.621742 | 2286.5 | 4080.5 | 1565.5 | 0 |
| Rap2-binding protein 9 (RPIB9), mRNA | NP_612147.1 | NM_138280.1 | mwghuman3 0K9B:7856 | -1.461227 | 1.03873E-06 | 1.37951E-05 | -5.058475 | 2297 | 24136.5 | 22036.5 | 1 |
| hsg17 | | NM_032031 | mwghuman3 0K9B:1666 | -1.576144 | 6.0951419 84 | 5.300828 527 | -4.037961 | 2300.5 | 2058 | 1701.75 | 1 |
| G protein-coupled receptor 83 (GPR83), mRNA | NP_057624.2 | NM_016540.2 | mwghuman3 0K9A:05058 | -1.472486 | 8.54909E-06 | 5.00182 918 | -3.811779 | 2322.5 | 14671.5 | 15879.25 | 0 |
| ensembl genescan prediction | | AC079067.6.1 35718.144151.2 | mwghuman3 0K9C:4632 | -1.500874 | 2.5001E-05 | 1.72268E-05 | -4.515105 | 2322.5 | 25916.6 | 21332.5 | |
| LIM homeobox 9 (LHX9), transcript variant 1, mRNA | NP_064598.2 | NM_020204.2 | mwghuman3 0K9B:2824 | -1.374871 | 4.6621E-06 | 5.24336E-05 | -6.212489 | 2333.5 | 16153 | 13672.25 | 0 |
| pelino homolog 1 (Drosophila) (PELI1), mRNA | NP_055706.2 | NM_020651.2 | mwghuman3 0K9A:10770 | -1.492094 | 8.8086E-06 | 8.23556E-05 | -5.23828 | 2335 | 22421.5 | 17594.5 | Y |

Figure 6SS

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical LOC401500 (LOC401500), mRNA | XP_379829.1 | XM_379829.1 | mwghuman3 0K6B10223 | -1.325358 | 3.27785E-05 | 4.12786E-05 | -4.402696 | 2336.5 | 25315 | 25320.25 | 0 |
| TSC22 domain family, member 3 (TSC22D3), transcript variant 2, mRNA | NP_004080.2 | NM_004089.3 | mwghuman3 0K6B0462 | -1.491298 | 5.41971E-06 | 1.72283E-05 | -3.010311 | 2350.5 | 18893.5 | 13200.5 | 43 |
| G protein-coupled receptor 51 (GPR51), mRNA | NP_005449.5 | NM_005458.5 | mwghuman3 0K6A04815 | -1.269185 | 0.00010107 08 | 2.98783E-05 | -4.345166 | 2361 | 3420 | 2468.25 | 0 |
| chromosome 19 open reading frame 61 (C19orf61), transcript variant 2, mRNA | NP_056446.1 | NM_015631.2 | mwghuman3 0K6B0105 | -1.556093 | 6.00017E-06 95 | 0.000297 098 | -4.519054 | 2366.5 | 10184 | 8091.5 | 3 |
| jumonji domain containing 2C (JMJD2C), mRNA | NP_055876.1 | NM_015061.1 | mwghuman3 0K6B3432 | -1.251474 | 6.41124E-05 | 0.000142 749 | -4.870495 | 2366.5 | 24816.5 | 22272.75 | 11 |
| zinc finger protein 547 (ZNF547), mRNA | NP_775902.2 | NM_173631.2 | mwghuman3 0K6B3716 | -1.62258 | 0.000251174 | 0.000257 35 | -3.964452 | 2370 | 19464 | 19537 | 2 |

Figure 6TT

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| hypothetical protein FLJ20032 (FLJ20032), mRNA | NP_060098.2 | XM_617828.2 | mwghuman3 OKf8:2068 | -1.76414 | 6.51052E-06 | 0.000105 506 | -4.196213 | 2374 | 18233.5 | 9707.75 | 19 |
| ensembl genscan prediction | | AC064677.3.1 21131.169550 | mwghuman3 OKf8C:7456 | -1.319264 | 4.299535E-05 | 2.035186E-05 | -4.562131 | 2374 | 27348 | 25740.25 | |
| ensembl genscan prediction | | AC087755.2.5 1287.9f5395.1 | mwghuman3 OKf8C:3411 | -1.439071 | 0.0001253 01 | 6.095391 474 | -4.145869 | 2378.5 | 14386.5 | 10761.5 | |
| KIAA0660 (KIAA0660), mRNA | NP_055954.1 | NM_015178.2 | mwghuman3 OKf8:7202 | -1.643414 | 0.0001733 38 | 6.000433 377 | -4.08872 | 2380 | 14468 | 11844.25 | 10 |
| SH3 domain binding glutamic acid-rich protein like 2 (SH3BGRL2), mRNA | NP_113657.1 | NM_031469.1 | mwghuman3 OKf8:1794 | -1.989457 | 0.0002795 76 | 6.000375 566 | -4.032794 | 2381 | 9893.5 | 8895.75 | 8 |
| orwz iib21358 fis clone ca20506 unnamed protein product | | AK026047 | mwghuman3 OKf8:2580 | -2.259109 | 0.0004473 76 | 6.000356 234 | -4.071961 | 2387.5 | 17286 | 11825.75 | 9 |
| hypothetical protein xp_038231 loc91568 | | XM_038231 | mwghuman3 OKf8:6491 | -1.337892 | 2.708365E-06 | 0.000174 137 | -4.141157 | 2388 | 24099.5 | 20385 | |

Figure 6UU

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| GPI anchored molecule like protein (GML), mRNA | NP_002057.1 | NM_002066.1 | mwghuman3 0K9A:02108 | -1.438045 | 0.0909724 93 | 6.00012E 14 | -5.18295B | 2405 | 16818 | 14265.75 | 0 |
| small nuclear RNA activating complex, polypeptide 5, 19KDa (SNAPC5), mRNA | NP_036043.1 | NM_006049.1 | mwghuman3 0K9B:0946 | -1.320754 | 1.74702E-05 | 6.000164 727 | -4.006318 | 2444 | 17656.5 | 17969.25 | 0 |
| ensembl genscan prediction | | AC027692.10, 1.180573.5 | mwghuman3 0K9C:9758 | -1.544263 | 0.0908550 69 | 2.95753E -05 | -3.674603 | 2451 | 18628.5 | 19694.25 | |
| mitochondrial tumor suppressor 1 (MTUS1), nuclear gene encoding mitochondrial protein, transcript variant 1, mRNA | NP_0010019 24.1 | NM_001001 24.1 | mwghuman3 0K6B:7725 | -1.715161 | 0.0909030E 93 | 6.000369 305 | -4.490397 | 2461. 5 | 17496 | 15873 | 0 |
| ensembl genscan prediction | | AL049529.4.1 .165932.3 | mwghuman3 0K9C:4548 | -1.402814 | 1.70061E-06 | 2.499276 -05 | -5.01844 | 2471 | 23131 | 26784 | |
| ensembl genscan prediction | | AC084642.1,7 903.106328.1 | mwghuman3 0K9C:7633 | -1.430793 | 0.0908120 94 | 7.96385E -05 | -5.197764 | 2475. 5 | 14235.5 | 11081.25 | |

Figure 6VV

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| SAFB-like, transcription modulator (SLTM), transcript variant 1, mRNA | NP_078881.2 | NM_024755.2 | mwghuman3 OKN9.2154 | -1.303535 | 2.00445E-05 | 8.000122 853 | -4.680433 | 2477.5 | 13490 | 13268 | 12 |
| guanine nucleotide binding protein (G protein), alpha activating activity polypeptide, olfactory type (GNAL), transcript variant 2, mRNA | NP_002062.1 | NM_002071.1 | mwghuman3 OKN9.0628B | -1.836112 | 0.000000 6 | 0.000498 109 | -5.10697 | 2478 | 15358 | 16590.75 | 0 |
| similar to cg14162 product loc148175 | | XM_086352 | mwghuman3 OKN9.7365 | -1.796060 | 0.0001945 23 | 0.000493 377 | -2.812615 | 2487 | 14781.5 | 9814.5 | |
| PH domain and leucine rich repeat protein phosphatase (PHLPP), mRNA | NP_919431.1 | NM_194449.1 | mwghuman3 OKN9.3242 | -2.043619 | 0.0002075 45 | 0.000498 109 | -4.008924 | 2500 | 15126 | 10309.75 | 7 |

Figure 6WW

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| autism susceptibility candidate 2 (AUTS2), mRNA | NP_056385.1 | NM_015570.1 | mwghuman3 OK60:0118 | -1.807633 | 0.000385299 | 0.000385E-14 | -4.213775 | 2503 | 18404 | 14412.75 | 8 |
| hypothetical protein xp_697338 loc147339 | | XM_697338 | mwghuman3 OK68:3852 | -1.428673 | 1.32234E-06 | 2.67918E-05 | -4.387947 | 2513 | 4368 | 2991.75 | |
| leucine-rich repeat-containing G protein-coupled receptor 4 (LGR4), mRNA | NP_060960.1 | NM_018490.1 | mwghuman3 OK6A:08196 | -1.519305 | 7.814185E-06 | 0.000122895 | -3.616559 | 2514.6 | 21417.5 | 18984 | 2 |
| ensembl prediction | | ENSG0000013407 | mwghuman3 OK6C:2890 | -1.740895 | 1.93345E-06 | 3.52911E-05 | -4.385894 | 2525 | 8797.5 | 8259.5 | |
| programmed cell death 1 (PDCD1), mRNA | NP_005009.1 | NM_005018.1 | mwghuman3 OK68:9147 | -1.519488 | 1.50412E-06 | 3.41099E-05 | -5.712069 | 2537 | 8575 | 7138.5 | 0 |
| cadherin 20, type 2 (CDH20), mRNA | NP_114072.2 | NM_031891.2 | mwghuman3 OK6A:7584 | -1.399019 | 1.91804E-06 | 2.79320E-05 | -4.382445 | 2538 | 15668 | 13275.75 | 0 |

Figure 6XX

| Gene name/ symbol | protein accession | mRNA ref seq accession | MWG Probe name | median fold change | t-test | Wilcoxon test | SAM | rank score | tumour tissue median intensity rank | non-malignant tissue median intensity rank | blood |
|---|---|---|---|---|---|---|---|---|---|---|---|
| glycine dehydrogenase (decarboxylating); glycine decarboxylase, glycine cleavage system protein P) (GLDC), mRNA | NP_000161.1 | NM_000170.1 | mwghuman3 OKHS:8959 | -1.405064 | 9.33312E-05 | 0.000118 76 | -4.398337 | 2542.5 | 6092 | 4959.5 | 1 |
| protease, serine, 35 (PRSS35), mRNA | NP_699193.1 | NM_153362.1 | mwghuman3 OKHS:3364 | -1.451818 | 0.0002370 59 | 0.000257 25 | -4.313933 | 2545 | 16909 | 14108 | 0 |
| ensembl genscan prediction | | AC068134.9.1 .175132.1 | mwghuman3 OKHS:3943 | -1.601839 | 0.0003788 4 | 0.000288 833 | -4.042534 | 2545 | 27071.5 | 25825 | |
| ATP-binding cassette, sub-family A (ABC1), member 12 (ABCA12), transcript variant 1, mRNA | NP_775099.2 | NM_173076.2 | mwghuman3 OKHS:3505 | -1.853773 | 0.0002371 78 | 0.000475 552 | -3.927921 | 2551.5 | 19931 | 18593.5 | 0 |
| suppressor of hairy wing homolog 3 (Drosophila) (SUHW3), mRNA | NP_056135.1 | NM_015866.2 | mwghuman3 OKHS:2954 | -1.878198 | 0.0001883 59 | 0.000546 156 | -3.864729 | 2568 | 17597 | 15964.5 | 1 |

Figure 6YY

| Gene name/symbol | protein accession | mRNA ref seq accession | median fold change | rank score | tumour tissue median intensity rank | non-malignant tissue median intensity rank | blood num! |
|---|---|---|---|---|---|---|---|
| hypothetical protein FLJ21511 (FLJ21511), mRNA | NP_079353.1 | NM_025687.1 | -2.080408 | 68 | 14455 | 9872.5 | 0 |
| paired box gene 8 (PAX8), transcript variant PAX8A, mRNA | NP_003457.1 | NM_003466.3 | -1.961846 | 82 | 19419 | 12993.5 | 0 |
| UPF3 regulator of nonsense transcripts homolog A (yeast) (UPF3A), transcript variant 1, mRNA | NP_075387.1 | NM_023011.2 | -2.84007 | 96.5 | 5663.5 | 1825 | 0 |
| leukotriene B4 12-hydroxydehydrogenase (LTB4DH), mRNA | NP_036344.1 | NM_012212.2 | -2.038613 | 122.5 | 11340.5 | 3136 | 0 |
| RAB11 family interacting protein 2 (class I) (RAB11FIP2), mRNA | NP_055719.1 | NM_014904.1 | -1.993629 | 169 | 19836.5 | 12351 | 0 |
| TSC22 domain family, member 1 (TSC22D1), transcript variant 2, mRNA | NP_006013.1 | NM_006022.2 | -2.133095 | 155.5 | 8415 | 6130 | 1 |
| sulfite oxidase (SUOX), nuclear gene encoding mitochondrial protein, transcript variant 1, mRNA | NP_000447.2 | NM_000456.2 | -1.622803 | 223 | 11312.5 | 8788.5 | 0 |
| tetratricopeptide repeat domain 21A (TTC21A), mRNA | NP_689688.1 | NM_145755.1 | -3.978809 | 225 | 5075.5 | 3679.5 | 1 |
| synaptotagmin-like 2 (SYTL2), transcript variant b, mRNA | NP_115755.2 | NM_032379.3 | -2.345857 | 342 | 19920 | 12533.5 | 0 |
| Wingless-type MMTV integration site family, member 2B (WNT2B), transcript variant WNT-2B1, mRNA | NP_004176.2 | NM_004185.2 | -10.745275 | 501 | 15716 | 2016.25 | 0 |
| protocadherin gamma subfamily A, 12 (PCDHGA12), transcript variant 1, mRNA | NP_003725.1 | NM_003735.2 | 2.070447 | 511 | 2537 | 1831.5 | 0 |
| olfactory receptor, family 1, subfamily D, member 5 (OR1D5), mRNA | NP_056361.1 | NM_014568.1 | -1.640751 | 639.5 | 1544 | 1134 | 0 |
| G protein-coupled receptor 126 (GPR126), transcript variant b1, mRNA | NP_940971.1 | NM_198569.1 | -2.161735 | 649 | 15065.5 | 6040.75 | 0 |
| ubiquitin specific peptidase 9, Y-linked (fat facets-like, Drosophila) (USP9Y), mRNA | NP_004645.2 | NM_004654.3 | -1.564865 | 667 | 16035.5 | 7868.25 | |

Figure 7A

| Gene name/symbol | protein accession | mRNA ref seq accession | median fold change | rank score | tumour tissue median intensity rank | non-malignant tissue median intensity rank | blood intensity rank |
|---|---|---|---|---|---|---|---|
| chromosome 11 open reading frame 1 (C11orf1), mRNA | NP_073598.1 | NM_022761.1 | -1.81738 | 873.5 | 12025.5 | 9569.25 | 0 |
| BCL2-associated athanogene (BAG1), mRNA | NP_004314.3 | NM_004323.3 | -2.526417 | 776 | 8091 | 4503.5 | 1 |
| family with sequence similarity 44, member B (FAM44B), mRNA | NP_612378.1 | NM_138369.1 | -1.357114 | 942.5 | 15008.5 | 13004.75 | 1 |
| fibroblast growth factor receptor 4 (FGFR4), transcript variant 2, mRNA | NP_075252.2 | NM_022963.2 | -2.635436 | 1007.5 | 17080 | 9782.5 | 0 |
| thyroid transcription factor 1 (TITF1), mRNA | NP_003308.1 | NM_003317.3 | -1.465987 | 1154.5 | 2139 | 1025.25 | 0 |
| VprBP protein (VprBP), mRNA | NP_055516.1 | NM_014703.1 | -1.723326 | 1178 | 17312.5 | 14031 | 0 |
| empty spiracles homolog 2 (Drosophila) (EMX2), mRNA | NP_004089.1 | NM_004098.2 | -1.745066 | 1199.5 | 19360 | 19749.25 | 0 |
| homeo box D8 (HOXD8), mRNA | NP_062468.1 | NM_019558.2 | -1.41585 | 1206 | 9672.5 | 7512.25 | 0 |
| zinc finger protein 626 (ZNF626), mRNA | NP_660340.1 | NM_145297.3 | -1.773183 | 1255 | 14806.5 | 10245 | 1 |
| ring finger protein 44 (RNF44), mRNA | NP_055716.3 | NM_014901.4 | -1.353266 | 1292 | 6288.5 | 4564.5 | 1 |
| pyrimidinergic receptor P2Y, G-protein coupled, 4 (P2RY4), mRNA | NP_002555.1 | NM_002565.3 | -1.722075 | 1306 | 18307 | 12139.5 | 0 |
| similar to hypothetical protein (LOC440804), mRNA | XP_499936.3 | XM_499936.3 | -4.049648 | 1332 | 3647 | 906.5 | 0 |
| chromosome 20 open reading frame 182 (C20orf182), mRNA | NP_543034.1 | NM_080634.1 | -1.948612 | 1349 | 10775 | 8552.5 | 0 |
| follistatin-like 4 (FSTL4), mRNA | NP_056897.1 | NM_015582.1 | -1.544042 | 1403.5 | 17051 | 12319 | 0 |
| chromosome 14 open reading frame 166 (C14orf166), mRNA | NP_113615.1 | NM_031427.1 | -1.512003 | 1414 | 19738 | 14725.75 | 1 |
| kallikrein 8 (neuropsin/ovasin) (KLK8), transcript variant 5, mRNA | NP_653036.1 | NM_144505.1 | -2.091896 | 1449.5 | 8391 | 8468 | 0 |
| leucine zipper, down-regulated in cancer 1-like (LDOC1L), mRNA | NP_115943.2 | NM_032287.2 | -1.501621 | 1454.5 | 16565.5 | 14157 | 0 |
| hypothetical protein MGC11242 (MGC11242), mRNA | NP_077296.1 | NM_024365.3 | -1.527839 | 1463.5 | 17586 | 13134.5 | 0 |
| KIAA1274 (KIAA1274), mRNA | NP_056246.1 | NM_014431.1 | -1.81942 | 1465.5 | 8059 | 5065 | 0 |
| hypothetical LOC401510 (LOC401510), mRNA | XP_376649.2 | XM_376649.2 | -1.483982 | 1504 | 13863.5 | 11253.25 | 0 |

Figure 7B

| Gene name/symbol | protein accession | mRNA ref seq accession | median fold change | rank score | tumour tissue median intensity rank | non-malignant tissue median intensity rank | blood nurs! |
|---|---|---|---|---|---|---|---|
| plastin 1 (I isoform) (PLS1), mRNA | NP_002651.1 | NM_002670.1 | -1.626256 | 1508.5 | 23940 | 14043.5 | 1 |
| zinc finger, DHHC-type containing 2 (ZDHHC2), mRNA | NP_057437.1 | NM_016353.2 | -1.589633 | 1536 | 13884.5 | 10087.5 | 0 |
| caudal type homeobox (CDX), mRNA | NP_000545.1 | NM_000554.2 | -3.032208 | 1549 | 16588.5 | 7900.5 | 0 |
| PHD finger protein 23 (PHF23), mRNA | NP_077273.1 | NM_024297.1 | -1.398491 | 1557.5 | 10658.5 | 8366.75 | 0 |
| nasopharyngeal carcinoma associated gene protein-6 (NAG6), mRNA | NP_055220.1 | NM_014111.2 | -1.388088 | 1650 | 15701.5 | 12181 | 0 |
| HERV-H LTR-associating 3 (HHLA3), transcript variant 3, mRNA | NP_001031722.1 | NM_001036645.1 | -2.043348 | 1768 | 13625.5 | 11795 | 0 |
| fibronectin leucine rich transmembrane protein 3 (FLRT3), transcript variant 1, mRNA | NP_037413.1 | NM_013281.2 | -4.234609 | 1770 | 18158 | 9381.25 | 0 |
| cell division cycle associated 7 (CDCA7), transcript variant 1, mRNA | NP_114149.2 | NM_031942.3 | -1.559506 | 1728 | 14828 | 12577.25 | 1 |
| pyruvate dehydrogenase kinase, isozyme 4 (PDK4), mRNA | NP_002603.1 | NM_002612.2 | -1.735687 | 1911.5 | 18067 | 13967.25 | 1 |
| leucine rich repeat and sterile alpha motif containing 1 (LRSAM1), transcript variant 1, mRNA | NP_612370.3 | NM_138361.3 | -2.034574 | 1959.5 | 7671.5 | 4421.75 | 1 |
| guanine nucleotide binding protein (G protein), alpha inhibiting activity polypeptide 1 (GNAI1), mRNA | NP_002060.4 | NM_002069.4 | -1.831351 | 2003 | 16803.5 | 14082 | 1 |
| cerebral endothelial cell adhesion molecule 1 (CEECAM1), mRNA | NP_057258.2 | NM_016174.3 | -1.518413 | 2014 | 18862.5 | 15767.75 | 0 |
| hypothetical protein FLJ22365 (FLJ22365), mRNA | NP_071384.1 | NM_022101.2 | -1.903459 | 2041.5 | 2596 | 2307 | 0 |
| chromosome 9 open reading frame 102 (C9orf102), transcript variant 1, mRNA | NP_065592.1 | NM_020207.2 | -1.360619 | 2049 | 18457.5 | 18970 | 0 |
| pleckstrin and Sec7 domain containing 3 (PSD3), transcript variant 1, mRNA | NP_056125.2 | NM_015919.2 | -1.395381 | 2072 | 14933 | 13223.25 | 1 |
| zinc finger, FYVE domain containing 21 (ZFYVE21), mRNA | NP_078876.1 | NM_024671.3 | -1.578692 | 2084 | 2934.5 | 2740.25 | 0 |
| forkhead box E1 (thyroid transcription factor 2) (FOXE1), mRNA | NP_004464.2 | NM_004473.3 | -1.678652 | 2107 | 7269 | 5292.75 | 0 |

Figure 7C

| Gene name/symbol | protein accession | mRNA ref seq accession | median fold change | rank score | tumour tissue median intensity rank | non-malignant tissue median intensity rank | blood num |
|---|---|---|---|---|---|---|---|
| Myc-induced mitochondrial protein (mimitin), mRNA | NP_777549.1 | NM_174889.2 | -1.474873 | 2151.5 | 9215 | 7033.25 | 1 |
| similar to developmental pluripotency associated 5; embryonal stem cell specific gene 1 (LOC341912), mRNA | XP_292301.3 | XM_292301.3 | -1.839785 | 2153 | 13581.5 | 12813.25 | 1 |
| hepcidin antimicrobial peptide (HAMP), mRNA | NP_066998.1 | NM_021175.2 | -1.273742 | 2205.5 | 3723.5 | 3385.25 | 0 |
| hypothetical protein BC008983 (LOC90113), mRNA | XP_291077.3 | XM_291077.3 | -1.768275 | 2221.5 | 9261.5 | 5478 | 3 |
| tripartite motif-containing 10 (TRIM10), transcript variant 1, mRNA | NP_006769.1 | NM_006778.2 | -1.750812 | 2296.5 | 4089.5 | 1595.5 | 0 |
| flag17 flag17 | | NM_207031 | -1.575164 | 2320.5 | 2058 | 1701.75 | 1 |
| LIM homeobox 9 (LHX9), transcript variant 1, mRNA | NP_064589.2 | NM_020204.2 | -1.374871 | 2333.5 | 16152 | 13872.25 | 0 |
| G protein-coupled receptor 51 (GPR51), mRNA | NP_005449.5 | NM_005458.5 | -1.368185 | 2361 | 3420 | 2450.25 | 0 |
| cons. 5\21354 ha clone col02636 unnamed protein product | | AK025047 | -2.258109 | 2387.5 | 17266 | 11928.75 | 0 |
| GPI anchored molecule like protein (GML), mRNA | NP_002057.1 | NM_002066.1 | -1.438045 | 2405 | 16816 | 14295.75 | 3 |
| programmed cell death 1 (PDCD1), mRNA | NP_005009.1 | NM_005018.1 | -1.519488 | 2537 | 8575 | 7118.5 | 0 |
| cadherin 23, type 2 (CDH23), mRNA | NP_114097.2 | NM_031801.2 | -1.363019 | 2538 | 16988 | 12275.75 | 3 |
| glycine dehydrogenase (decarboxylating): glycine decarboxylase, glycine cleavage system protein P) (GLDC), mRNA | NP_000161.1 | NM_000170.1 | 1.405054 | 2542.5 | 6029 | 4550.5 | 1 |
| protease, serine, 35 (PRSS35), mRNA | NP_699193.1 | NM_153362.1 | -1.451819 | 2545 | 16909 | 14108 | 0 |

Figure 7D

| | No specific diagnosis (N=164) | Non-malignant disease (N=255) | TCC (N=66) | Overall (N=485) |
|---|---|---|---|---|
| Country, n (%) | | | | |
| New Zealand | 147 (89.6) | 239 (93.7) | 64 (97.0) | 450 (92.8) |
| Australia | 17 (10.4) | 16 (6.27) | 2 (3.0) | 35 (7.2) |
| Age, median (IQ range) | 64 (55, 75) | 71 (62, 78) | 71 (63, 80) | 69 (59, 77) |
| Sex, n (%) | | | | |
| Male | 112 (68.3) | 216 (84.7) | 61 (92.4) | 389 (80.2) |
| Female | 52 (31.7) | 39 (15.3) | 5 (7.5) | 96 (19.8) |
| Ethnicity, n (%) | | | | |
| European | 133 (81.1) | 228 (89.4) | 62 (93.9) | 423 (87.2) |
| Maori | 15 (9.1) | 17 (6.7) | 1 (1.5) | 33 (6.8) |
| Other | 16 (9.8) | 10 (3.9) | 3 (4.5) | 29 (6.0) |
| Haematuria, n (%) | | | | |
| Years since onset | | | | |
| <6 mths | 131 (79.9) | 198 (77.6) | 57 (86.4) | 386 (79.6) |
| 6 mths-1 yr | 11 (6.7) | 25 (9.8) | 6 (9.1) | 42 (8.7) |
| 1-2 yrs | 11 (6.7) | 18 (7.1) | 3 (4.5) | 32 (6.6) |
| 3-5 yrs | 5 (3.0) | 5 (2.0) | 0 (0.0) | 10 (2.1) |
| > 5 yrs | 6 (3.7) | 9 (3.5) | 0 (0.0) | 15 (3.1) |
| End of last episode | | | | |
| 1-7 days | 9 (5.5) | 26 (10.2) | 20 (30.3) | 55 (11.3) |
| 8-28 days | 14 (8.5) | 27 (10.6) | 13 (19.7) | 54 (11.1) |
| 1-2 Months | 60 (36.6) | 86 (33.7) | 14 (21.2) | 160 (33.0) |
| 3-6 Months | 70 (42.7) | 100 (39.2) | 19 (28.8) | 189 (39.0) |
| > 6 months | 11 (6.7) | 15 (5.9) | 0 (0.0) | 26 (5.4) |
| Unknown | 0 (0.0) | 1 (0.4) | 0 (0.0) | 1 (0.2) |
| Frequency | | | | |
| <=1 per day | 104 (63.4) | 160 (62.7) | 30 (45.5) | 294 (60.6) |
| >1 per day | 59 (36.0) | 95 (37.3) | 36 (54.5) | 190 (39.2) |
| Unknown | 1 (0.6) | 0 (0.0) | 0 (0.0) | 1 (0.2) |
| Smoking status, n (%) | | | | |
| Current smoker | 34 (20.7) | 28 (11.0) | 14 (21.2) | 76 (15.7) |
| Ex-smoker | 66 (40.2) | 114 (44.7) | 35 (53.0) | 215 (44.3) |
| Never smoker | 64 (39.0) | 113 (44.3) | 17 (25.8) | 194 (40.0) |

Figure 9

| Test | Overall Sensitivity | Overall Specificity |
|---|---|---|
| uRNA-D | 62.1% (49.3 73.8) | 85.2% (fixed) |
| NMP22 Elisa | 50.0% (37.4, 62.6) | 88.0% (84.6, 91.0) |
| NMP22 BladderChek | 37.9% (26.2, 50.7) | 96.4% (94.2, 98.0) |
| Cytology* | 56.1% (43.3, 68,3) | 94.5 (91.9, 96.5) |
| Five Genes (including IL8BRb)† | 81.8% | 85.1% (fixed) |
| Five Genes (including IL8BRb)† (90% specificity) | 72.7% | 89.9% (fixed) |

* Included in determination of TCC for some patients
† Determined on study data so confidence intervals are not presented

Figure 10

Area under ROC curve = 0.8745

|  | Cytology | NMP22 Elisa | BladderChek | uRNA-D | Five Markers |
|---|---|---|---|---|---|
| Stage (n=66) | n, % (95% CI) | n, % (95% CI) | n, % (95% CI) | n, % (95% CI) | n, % |
| Tis (n=2) | 2, 100% (16, 100) | 0, 0% (0, 84) | 0, 0% (0, 84) | 1, 50% (1, 99) | 2, 100% |
| Ta (n=37) | 13, 35% (20, 53) | 13, 35% (20, 53) | 14, 38% (22, 55) | 15, 41% (25, 58) | 25, 68% |
| T1 (n=16) | 11, 69% (41, 89) | 12, 75% (48, 93) | 8, 50% (25, 75) | 15, 94 (70, 100) | 16, 100% |
| T2 (n=9) | 9, 100% (66, 100) | 6, 67% (30, 93) | 2, 22% (3, 60) | 9, 100 (66, 100) | 9, 100% |
| ≥T3 (n=2) | 2, 100% (16, 100) | 2, 100% (16, 100) | 1, 50% (11, 99) | 1, 50% (1.3, 99) | 2, 100% |
| Grade WHO 73 (n=65) |  |  |  |  | $p^*=0.019$ |
| 1 (n=3) | 1, 33% (1, 91) | 1, 33% (1, 91) | 1, 33% (1, 91)) | 1, 33% (1, 91)) | 1, 33% |
| 2 (n=38) | 17, 44% (29, 62) | 15, 39% (24, 57) | 13, 34% (20, 51) | 21, 55% (38, 71) | 29, 76% |
| 3 (n=24) | 19, 79% (58, 93) | 17, 71% (49, 87) | 11, 46% (26, 67) | 19, 79% (58, 93) | 23, 96% |
| Grade WHO ISUP 1998 (n=65) |  |  |  |  | $p^*=0.016$ |
| Low (n=32) | 9, 28% (14, 47) | 10, 31% (16, 50) | 13, 41% (24, 59) | 13, 41% (24, 59) | 22, 69% |
| Mixed (n=4) | 4, 100% (40, 100) | 3, 75% (19, 99) | 1, 25% (1, 81) | 4, 100 (40,100) | 4, 100% |
| High (n=29) | 24, 83% (64, 94) | 20, 69% (49, 85) | 11, 38% (21, 58) | 24, 83% (64, 94) | 28, 97% |
| Tumour location (n=66) |  |  |  |  | $p^*=0.012$ |
| Bladder (n=62) | 35, 56% (43, 69) | 30, 48% (35, 61) | 25, 40% (28, 54) | 39, 63% (50, 75) | 50, 81% |
| Up. tract (n=4) | 2, 50% (7, 93) | 3, 75% (19, 99) | 0, 0% (0, 60) | 2, 50% (7, 93) | 4, 100% |
| Multiplicity (n=66) |  |  |  |  | $p^*=0.33$ |
| Single (n=52) | 27, 52% (38, 66) | 23, 44% (30, 59) | 17, 33% (20, 47) | 30, 58% (43, 71) | 41, 79% |
| Multifocal (n=13) | 10, 77% (46, 95) | 10, 77% (46, 95) | 8, 62% (32, 86) | 11, 85% (55, 98) | 12, 92% |
| Microhaematuria (n=65) |  |  |  |  | $p^*=0.43$ |
| Yes (n=43) | 27, 63% (47, 77) | 27, 63% (47, 77) | 20, 47% (31, 62) | 31, 72% (56, 85) | 41, 95% |
| No (n=22) | 9, 41% (21, 64)) | 5, 23% (8, 45) | 4, 18% (5, 40) | 9, 41% (21, 64) | 12, 55% |
| Creatinine (n=55) |  |  |  |  | $p^*<0.0005$ |
| 0-4.3 (n=11) | 5, 45 (17, 77) | 3, 27% (6,61) | 4, 36% (11, 69) | 4, 36% (11, 69) | 7, 64% |
| 4.3-7.1 (n=14) | 9, 64% (35, 87) | 6, 43% (18,71) | 4, 29% (8, 58) | 8, 57% (29, 82) | 12, 86% |
| 7.1-11.2 (n=22) | 11, 50% (28, 72) | 14, 64% (41, 83) | 11, 50% (28, 72) | 16, 73% (50, 89) | 18, 82% |
| ≥11.2 (n=8) | 6, 75% (35, 97) | 3, 38% (9, 76) | 2, 25% (3, 65) | 6, 75% (35, 97) | 8, 100% |
| Sex (n=66) |  |  |  |  | $p^*=0.29$ |
| Male (n=61) | 35, 57% (44, 70) | 29, 48% (35, 61) | 23, 38% (26, 51) | 37, 61% (47, 73) | 49, 80% |
| Female (n=5) | 2, 40% (5, 85) | 4, 80% (28, 99) | 2, 40% (5, 85) | 4, 80% (28, 99) | 5, 100% |
|  |  |  |  |  | $p^*=0.58$ |

*p-values from Fisher's exact test of association between each TCC characteristic and Cxbladder test result

Figure 12

| | Cytology | NMP22 Elisa | NMP22 BladderChek | uRNA-D* | Five Markers* |
|---|---|---|---|---|---|
| | n, % 95% CI) | n, % 95% CI) | n, % 95% CI) | n, % | n, % |
| Diagnosis | | | | | |
| No diagnosis (n=164) | | | | | |
| | 154, 94% (89, 97) | 144, 88% (82, 92) | 160, 98% (94, 99) | 144, 88% | 144, 88% |
| Non-malignant diagnosis | | | | | |
| Benign prostatic hypertrophy/prostatitis (n=130) | | | | | |
| | 123, 95% (89, 98) | 117, 90.% (84, 95) | 127, 98% (93, 100) | 113, 87% | 109/128=85% |
| Cystitis/infection or inflammation of the urinary tract (n=39) | | | | | |
| | 36, 92% (79, 98) | 34, 87% (73, 96) | 34, 87% (73, 96) | 28, 72% | 32, 82% |
| Calculi (n=28) | | | | | |
| | 25, 89% (72, 98) | 23, 82% (63, 94) | 27, 96% (82, 100) | 20, 71% | 19, 68% |
| Haematuria secondary to warfarin (n=10) | | | | | |
| | 10, 100% (69, 100) | 9, 90% (55, 100) | 10, 100% (69, 100) | 8, 80% | 8, 80% |
| Other urological cancer (n=5) | | | | | |
| | 5, 100% (48, 100) | 4, 80% (28, 99) | 5, 100% (48, 100) | 5, 100% | 4, 80% |
| Microhaematuria (n=417) | | | | | | p†=0.12 |
| Yes n=99 | 87, 88% (80, 94) | 81, 82% (73, 89) | 91, 92% (85, 96) | 74, 75% | 73/97=75% |
| No n=318 | 307, 97% (94, 98) | 287, 90% (86, 93) | 311, 98% (96, 99) | 281, 88% | 279/317=88% |
| Creatinine (n=386) | | | | | p†=0.602 |
| 0 - 4.3, n=97 | 95, 98% (93, 100) | 90, 93% (86, 97) | 95, 98% (93, 100) | 87, 90% | 83/96=86% |
| 4.3 - 7.1, n=94 | 92, 98% (93, 100) | 81, 86% (78, 92) | 90, 96% (89, 99) | 81, 86% | 84/93=90% |
| 7.1 - 11.2, n=92 | 79, 86% (77, 92) | 83, 90% (82, 95) | 90, 98% (92, 100) | 76, 83% | 76/92=83% |
| ≥11.2, n=103 | 101 98% (93, 100) | 91, 88% (81, 94) | 101, 98% (93, 100) | 88, 85% | 82/102=80% |
| Sex (n=419) | | | | | p†=0.32 |
| Male n=328 | 311, 95% (92, 97) | 290, 88% (84, 92) | 316, 96% (94, 98) | 291, 89% | 280/325=86% |
| Female, n=91 | 85, 93% (86, 98) | 79, 87% (78, 93) | 88 97% (91, 99) | 65, 71% | 74/91=81% |
| | | | | | p†=0.25 |

*overall specificity fixed at 85%

†p-value from Chi square test of association between each characteristic (diagnosis, microhaematuria, creatinine sex) and Cxbladder test result

Figure 13

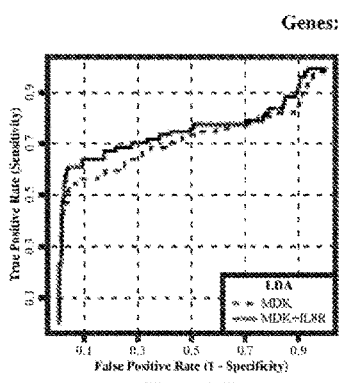
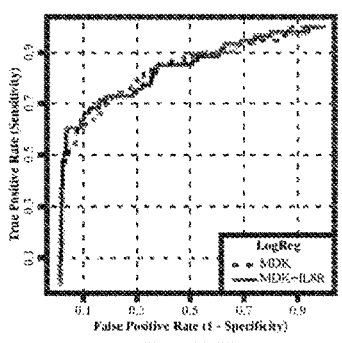
Fig. 14A(I)  Fig. 14A(II)
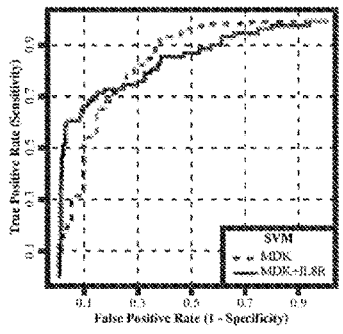
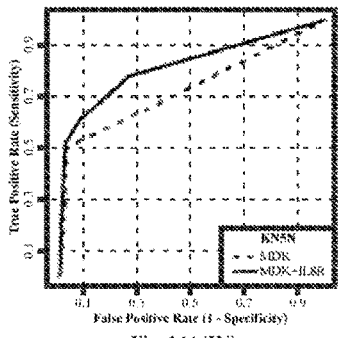
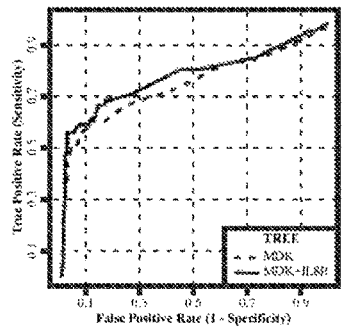
Fig. 14A(III)  Fig. 14A(IV)  Fig. 14A(V)

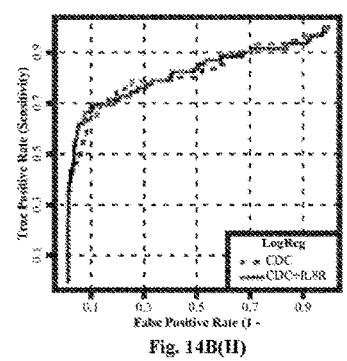
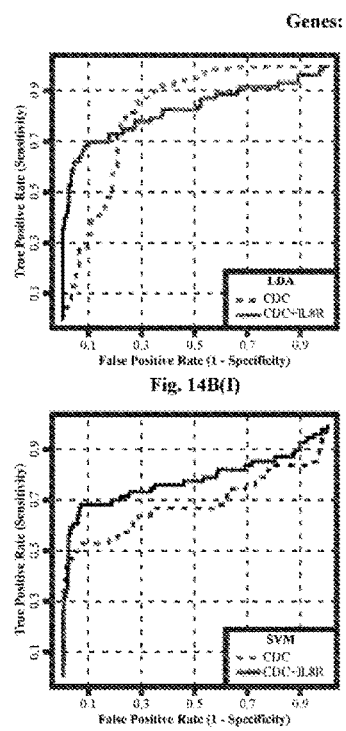
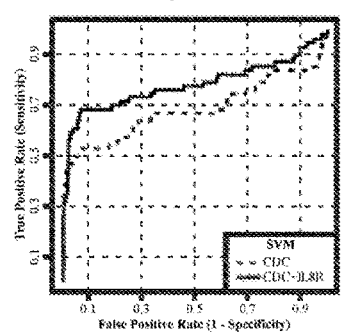
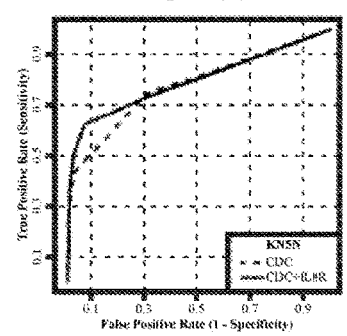
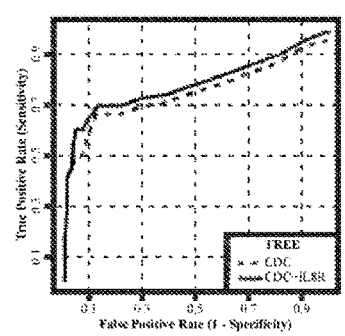
Fig. 14B(I)  Fig. 14B(II)  Fig. 14B(III)  Fig. 14B(IV)  Fig. 14B(V)

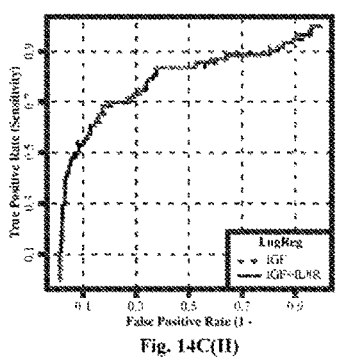
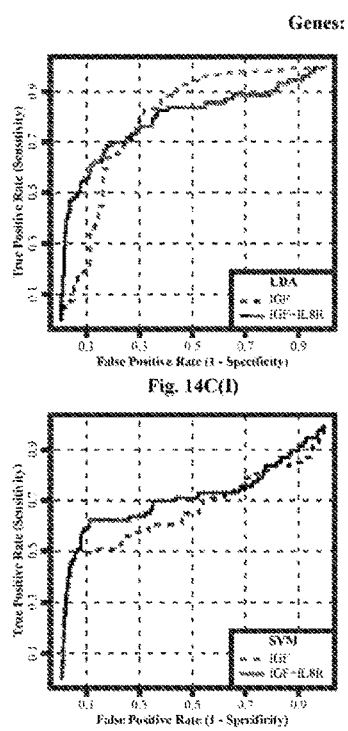
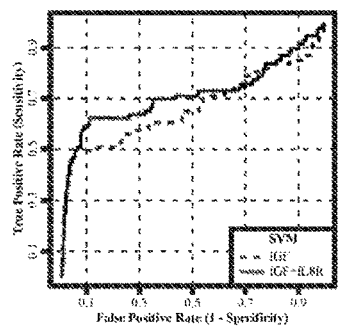
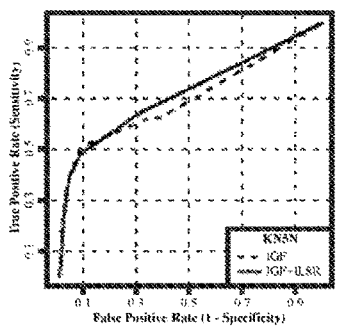
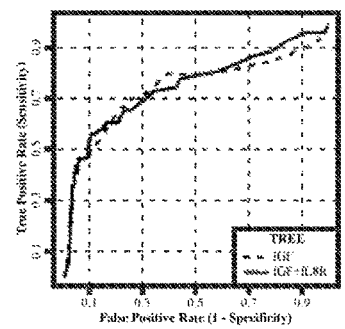
Fig. 14C(I)
Fig. 14C(II)
Fig. 14C(III)
Fig. 14C(IV)
Fig. 14C(V)

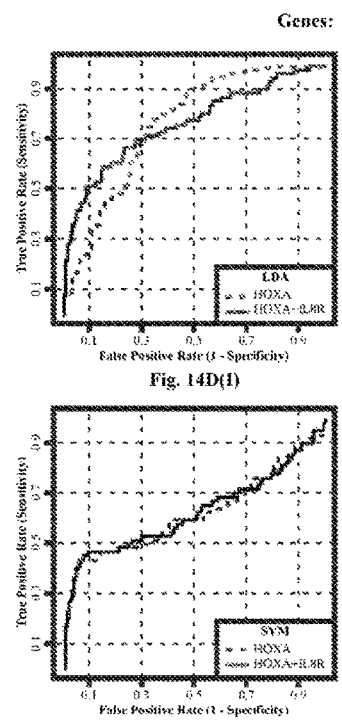
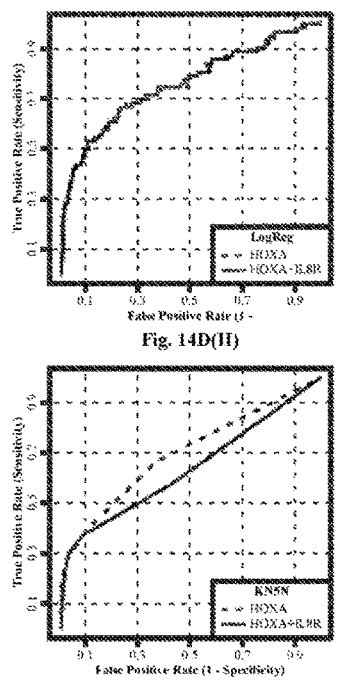
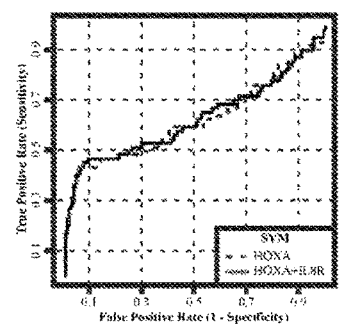
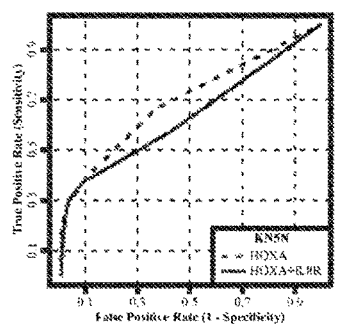
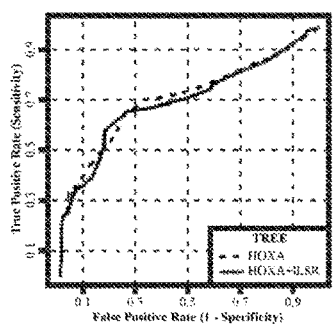
Fig. 14D(I) Fig. 14D(II) Fig. 14D(III) Fig. 14D(IV) Fig. 14D(V)

Genes: MDK + CDC (± IK8R)
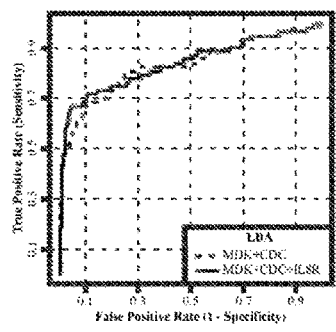
Fig. 14E(I)
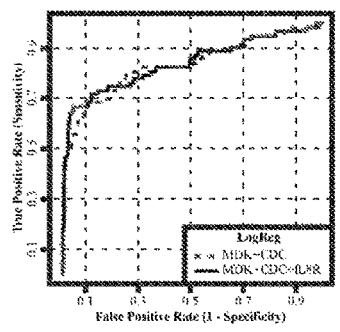
Fig. 14E(II)
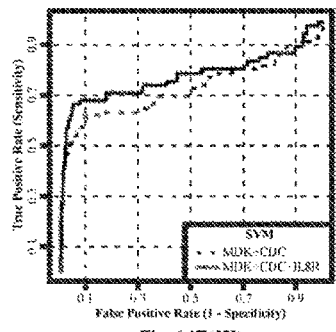
Fig. 14E(III)
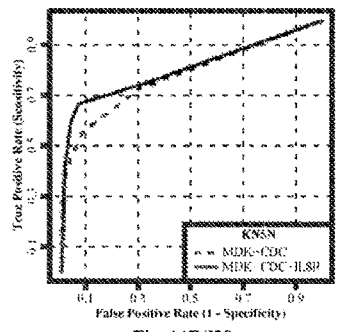
Fig. 14E(IV)
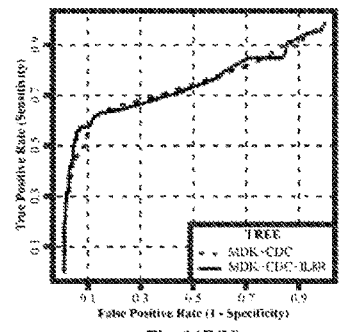
Fig. 14E(V)

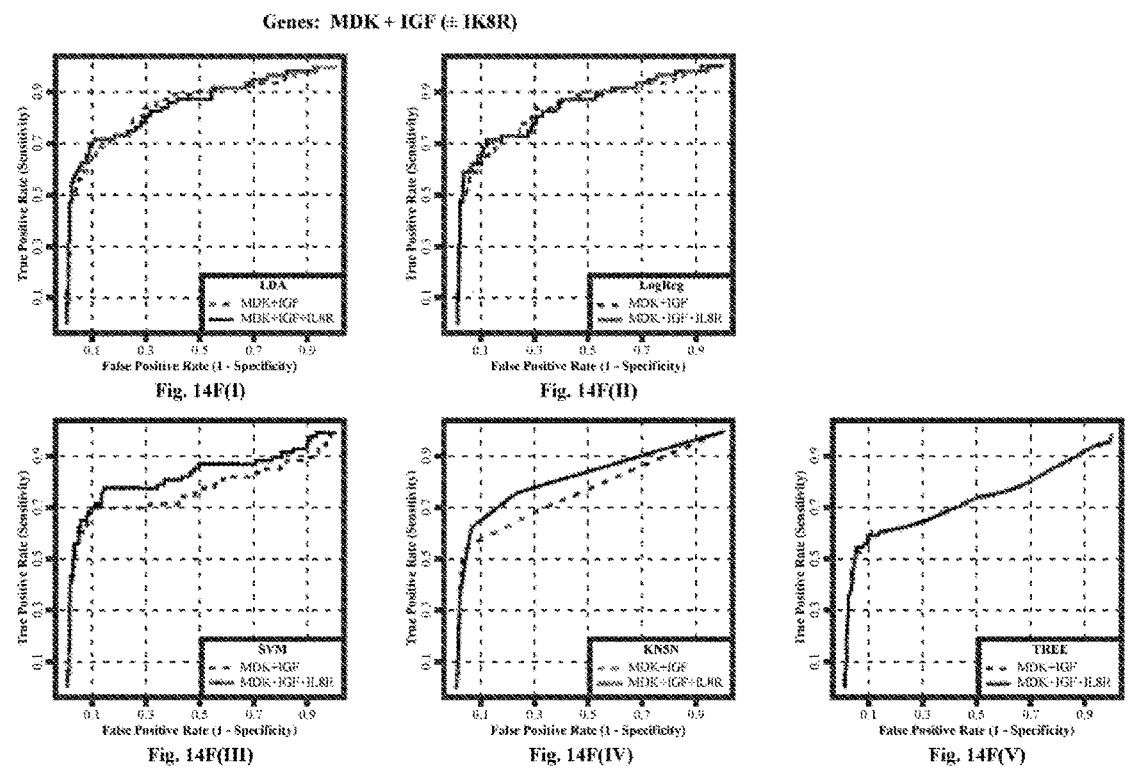
Fig. 14F(I)  Fig. 14F(II)  Fig. 14F(III)  Fig. 14F(IV)  Fig. 14F(V)

Genes: MDK + HOXA (± IK8R)
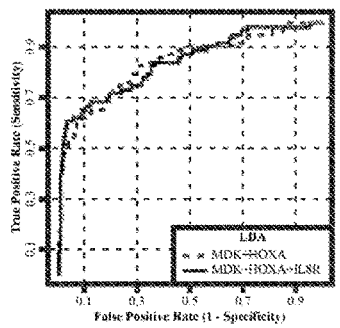
Fig. 14G(I)
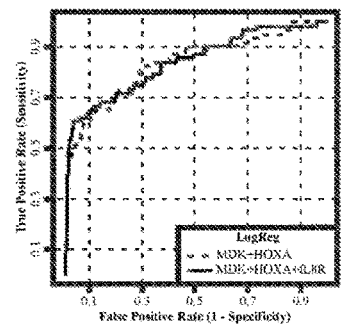
Fig. 14G(II)
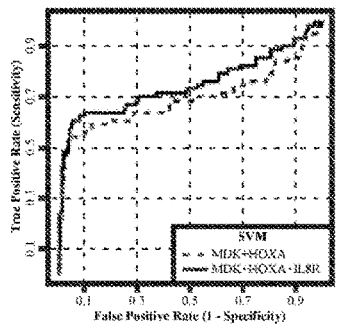
Fig. 14G(III)
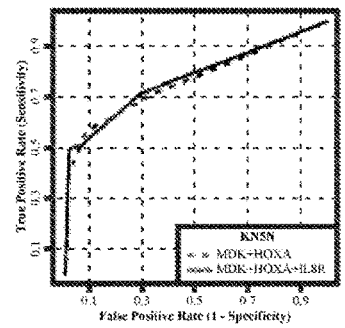
Fig. 14G(IV)
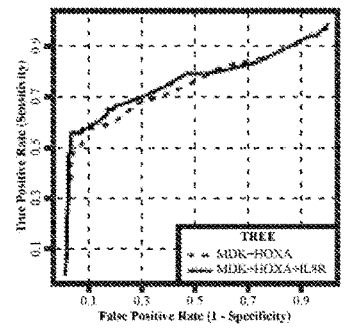
Fig. 14G(V)

Genes: CDC + IGF (± IK8R)
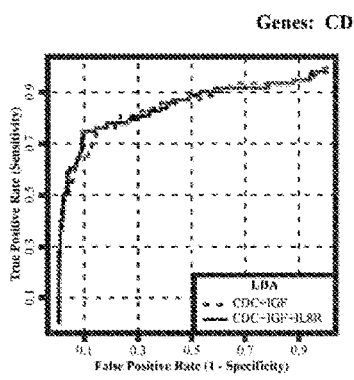
Fig. 14H(I)
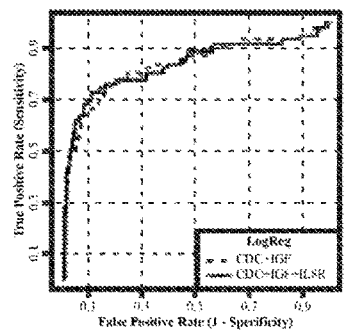
Fig. 14H(II)
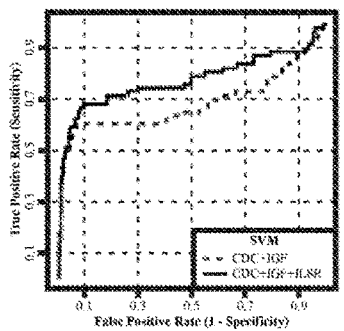
Fig. 14H(III)
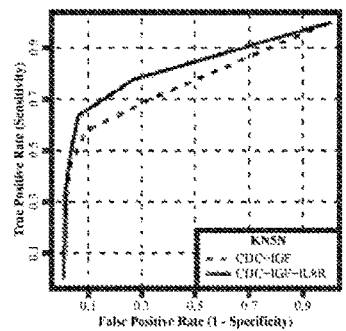
Fig. 14H(IV)
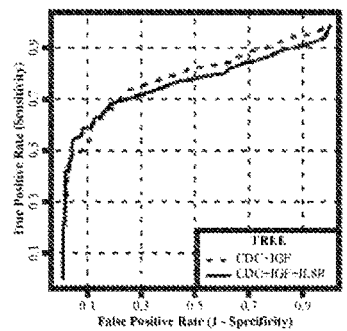
Fig. 14H(V)

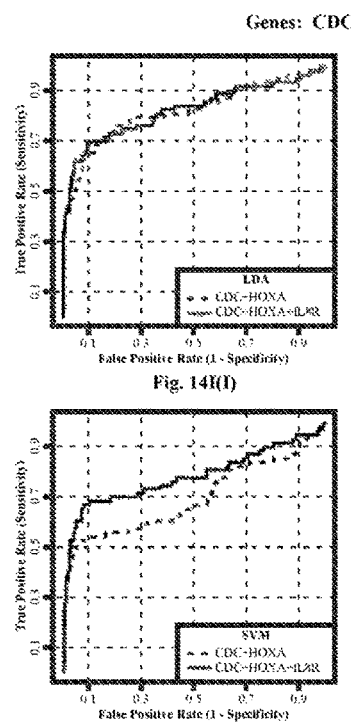
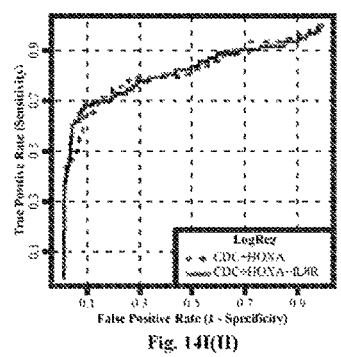
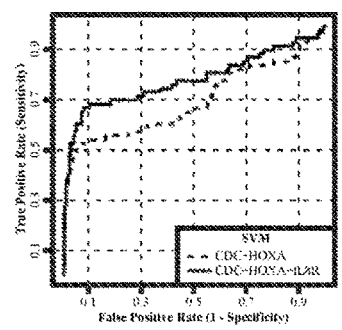
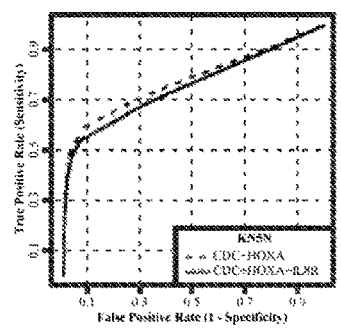
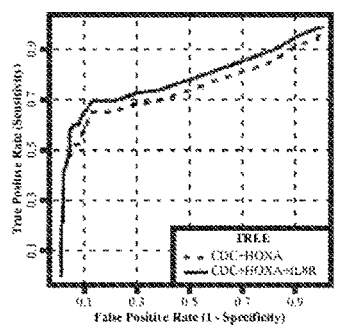
Fig. 14I(I)   Fig. 14I(II)
Fig. 14I(III)   Fig. 14I(IV)   Fig. 14I(V)

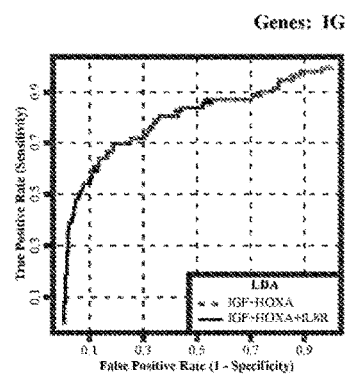
Fig. 14J(I)
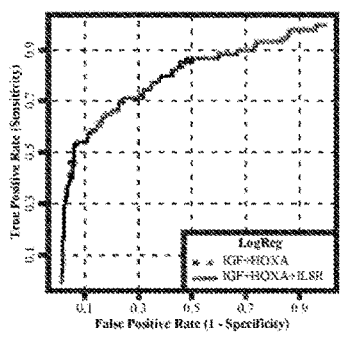
Fig. 14J(II)
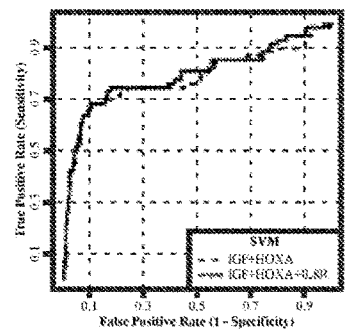
Fig. 14J(III)
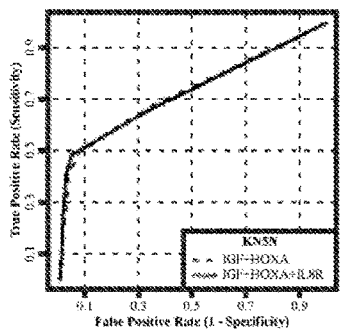
Fig. 14J(IV)
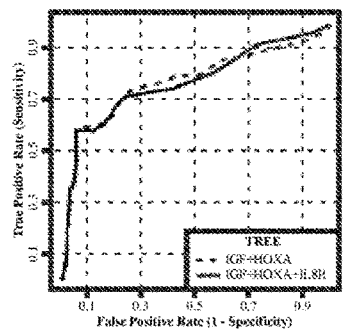
Fig. 14J(V)

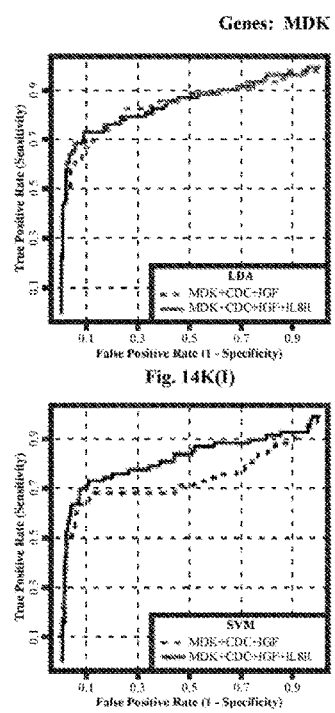
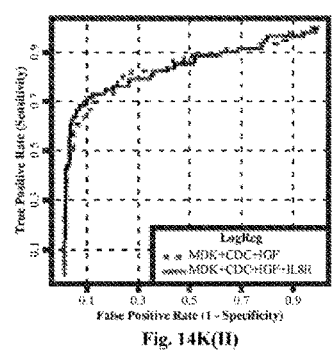
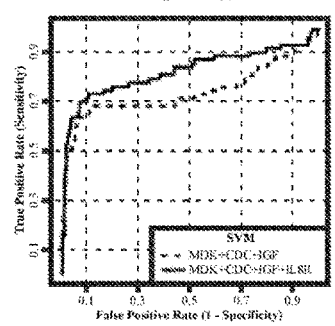
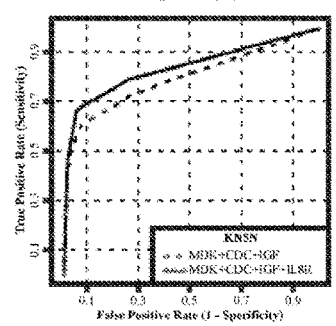
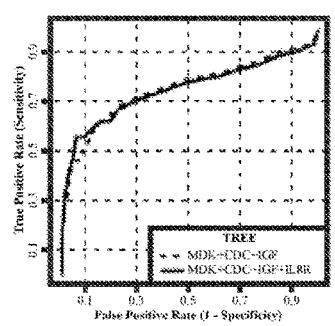
Fig. 14K(I)  Fig. 14K(II)  Fig. 14K(III)  Fig. 14K(IV)  Fig. 14K(V)

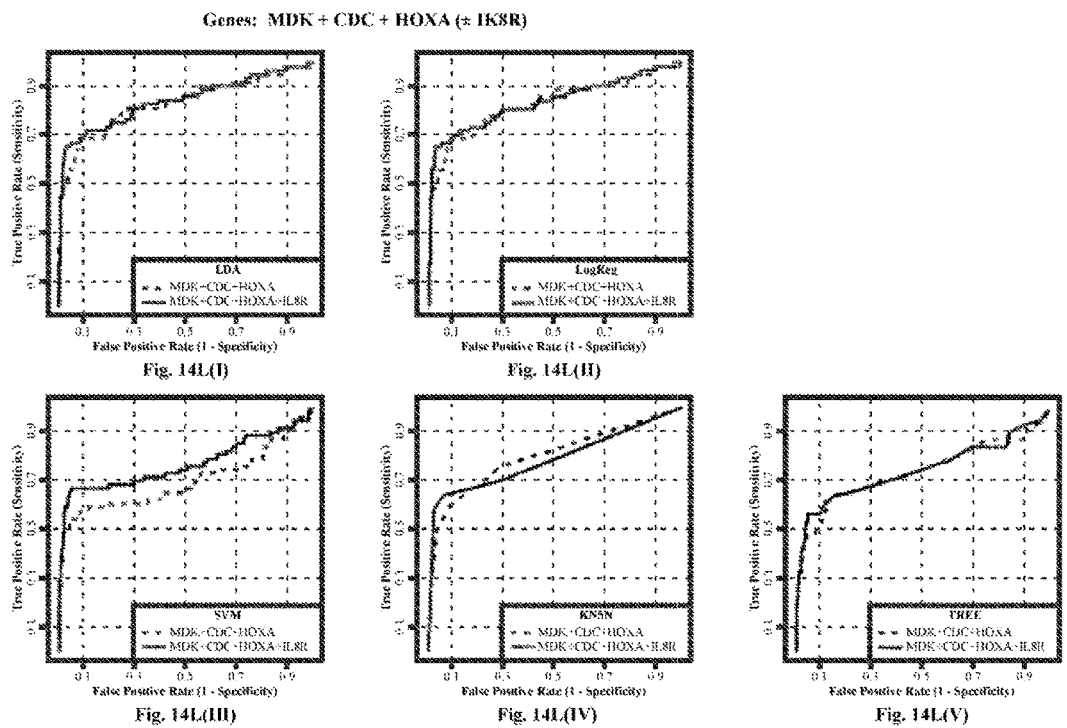

Genes: MDK + IGF + HOXA (± IK8R)
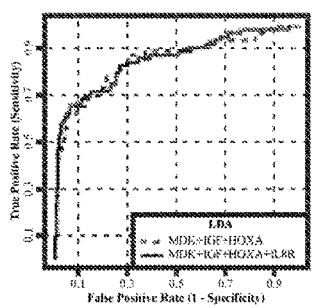
Fig. 14M(I)
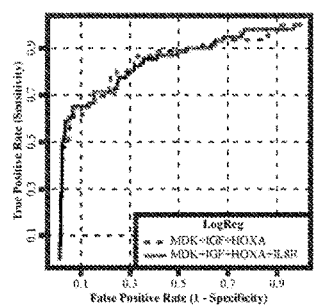
Fig. 14M(II)
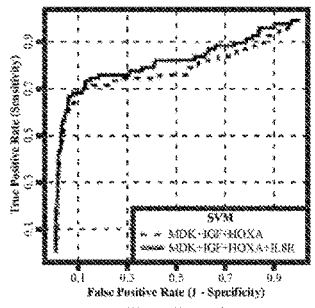
Fig. 14M(III)
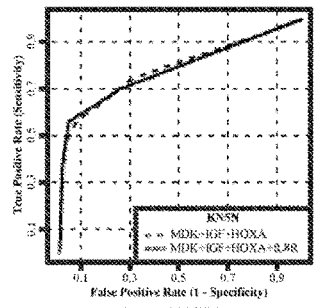
Fig. 14M(IV)
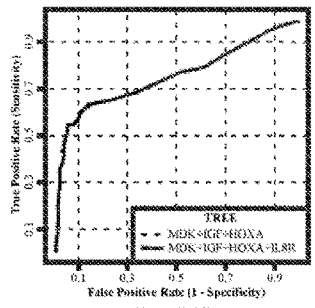
Fig. 14M(V)

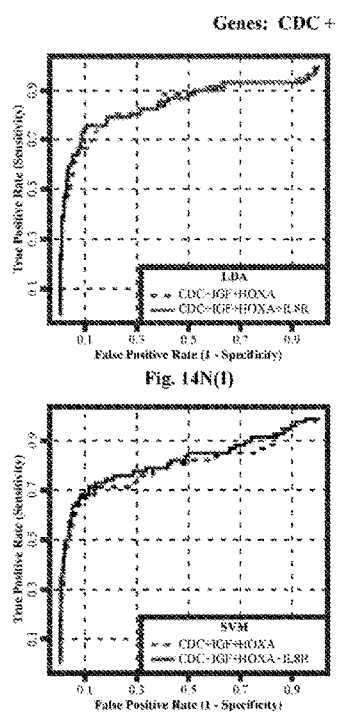
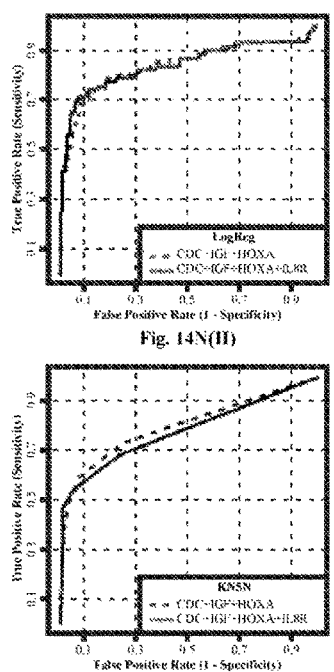
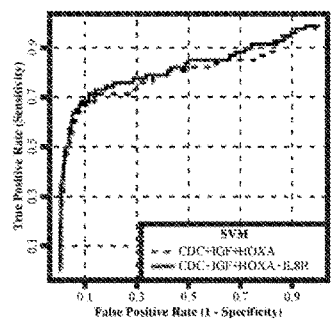
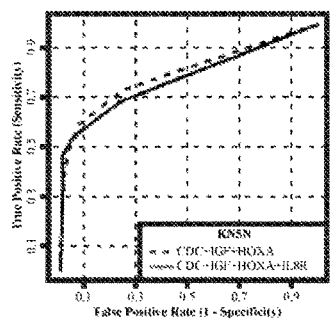
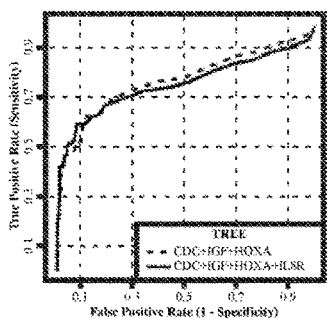
Fig. 14N(I)  Fig. 14N(II)  Fig. 14N(III)  Fig. 14N(IV)  Fig. 14N(V)

Genes: MDK + CDC + IGF + HOXA (± IK8R)
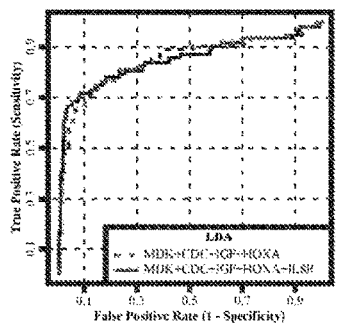
Fig. 14O(I)
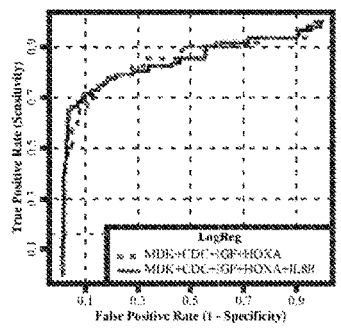
Fig. 14O(II)
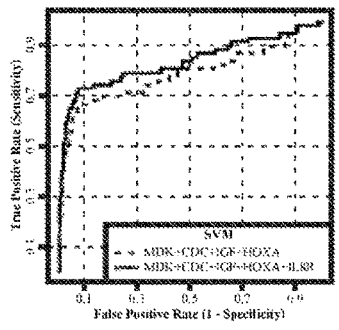
Fig. 14O(III)
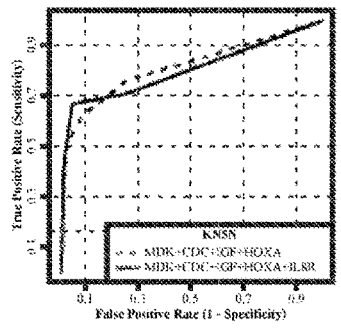
Fig. 14O(IV)
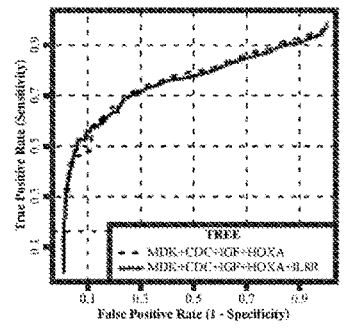
Fig. 14O(V)

| Model | LDA | | LogReg | | SVM | | KN5N | | TREE | |
|---|---|---|---|---|---|---|---|---|---|---|
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.087 | 0.127 | 0.119 | 0.127 | 0.107 | 0.121 | 0.100 | 0.120 | 0.107 | 0.117 |
| CDC2 | 0.062 | 0.129 | 0.124 | 0.129 | 0.102 | 0.127 | 0.102 | 0.121 | 0.114 | 0.124 |
| IGFBP5 | 0.060 | 0.108 | 0.109 | 0.108 | 0.094 | 0.107 | 0.093 | 0.090 | 0.093 | 0.096 |
| HOXA13 | 0.058 | 0.094 | 0.094 | 0.094 | 0.082 | 0.084 | 0.075 | 0.071 | 0.078 | 0.075 |
| MDK + CDC2 | 0.124 | 0.134 | 0.124 | 0.133 | 0.115 | 0.131 | 0.109 | 0.128 | 0.107 | 0.111 |
| MDK + IGFBP5 | 0.122 | 0.129 | 0.121 | 0.129 | 0.125 | 0.133 | 0.111 | 0.122 | 0.107 | 0.107 |
| MDK + HOXA13 | 0.119 | 0.126 | 0.118 | 0.125 | 0.108 | 0.118 | 0.107 | 0.107 | 0.107 | 0.114 |
| CDC2 + IGFBP5 | 0.128 | 0.134 | 0.127 | 0.133 | 0.114 | 0.125 | 0.109 | 0.125 | 0.109 | 0.115 |
| CDC + HOXA13 | 0.122 | 0.128 | 0.123 | 0.129 | 0.103 | 0.125 | 0.116 | 0.108 | 0.113 | 0.123 |
| IGF + HOXA13 | 0.109 | 0.109 | 0.108 | 0.107 | 0.119 | 0.121 | 0.096 | 0.098 | 0.102 | 0.101 |
| MDK + CDC2 + IGFBP5 | 0.127 | 0.135 | 0.127 | 0.135 | 0.123 | 0.134 | 0.119 | 0.132 | 0.103 | 0.108 |
| MDK + CDC2 + HOXA13 | 0.125 | 0.133 | 0.125 | 0.134 | 0.109 | 0.127 | 0.113 | 0.122 | 0.104 | 0.111 |
| MDK + IGFBP5 + HOXA13 | 0.122 | 0.128 | 0.121 | 0.127 | 0.126 | 0.132 | 0.111 | 0.115 | 0.110 | 0.109 |
| CDC2 + IGFBP5 + HOXA13 | 0.129 | 0.136 | 0.131 | 0.136 | 0.126 | 0.131 | 0.117 | 0.114 | 0.108 | 0.111 |
| MDK+CDC2+IGFBP5+HOXA13 | 0.130 | 0.137 | 0.130 | 0.138 | 0.124 | 0.137 | 0.122 | 0.129 | 0.103 | 0.106 |

Area Under the ROC Curve (AUC) for False Positive Rate from 0.00 to 0.20

Figure 15a

| Model | LDA | LogReg | SVM | KN5N | TREE |
|---|---|---|---|---|---|
| MDK | 0.040 | 0.008 | 0.014 | 0.019 | 0.010 |
| CDC2 | 0.067 | 0.005 | 0.025 | 0.018 | 0.009 |
| IGFBP5 | 0.048 | -0.001 | 0.013 | -0.003 | 0.002 |
| HOXA13 | 0.036 | 0.000 | 0.001 | -0.004 | -0.003 |
| MDK + CDC2 | 0.009 | 0.009 | 0.015 | 0.019 | 0.005 |
| MDK + IGFBP5 | 0.007 | 0.007 | 0.008 | 0.011 | -0.000 |
| MDK + HOXA13 | 0.007 | 0.007 | 0.010 | 0.000 | 0.007 |
| CDC2 + IGFBP5 | 0.007 | 0.006 | 0.012 | 0.016 | 0.006 |
| CDC + HOXA13 | 0.006 | 0.006 | 0.022 | -0.007 | 0.010 |
| IGF + HOXA13 | 0.000 | -0.001 | 0.002 | 0.002 | -0.000 |
| MDK + CDC2 + IGFBP5 | 0.009 | 0.008 | 0.012 | 0.013 | 0.004 |
| MDK + CDC2 + HOXA13 | 0.008 | 0.008 | 0.018 | 0.009 | 0.006 |
| MDK + IGFBP5 + HOXA13 | 0.006 | 0.006 | 0.006 | 0.004 | -0.001 |
| CDC2 + IGFBP5 + HOXA13 | 0.006 | 0.006 | 0.005 | -0.003 | 0.004 |
| MDK+CDC2+IGFBP5+HOXA13 | 0.007 | 0.007 | 0.013 | 0.007 | 0.002 |

Gain in AUC (over FPR from 0.0 to 0.2)

Figure 15b

| Model | LDA | | LogReg | | SVM | | KN5N | | TREE | |
|---|---|---|---|---|---|---|---|---|---|---|
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.721 | 0.734 | 0.734 | 0.734 | 0.594 | 0.672 | 0.531 | 0.781 | 0.625 | 0.688 |
| CDC2 | 0.753 | 0.734 | 0.750 | 0.734 | 0.562 | 0.703 | 0.750 | 0.734 | 0.672 | 0.703 |
| IGFBP5 | 0.657 | 0.703 | 0.688 | 0.703 | 0.516 | 0.625 | 0.516 | 0.656 | 0.656 | 0.609 |
| HOXA13 | 0.486 | 0.609 | 0.625 | 0.609 | 0.484 | 0.469 | 0.406 | 0.375 | 0.547 | 0.578 |
| MDK + CDC2 | 0.734 | 0.750 | 0.734 | 0.750 | 0.641 | 0.719 | 0.734 | 0.750 | 0.672 | 0.641 |
| MDK + IGFBP5 | 0.734 | 0.734 | 0.734 | 0.734 | 0.703 | 0.781 | 0.688 | 0.766 | 0.625 | 0.625 |
| MDK + HOXA13 | 0.719 | 0.719 | 0.734 | 0.719 | 0.609 | 0.641 | 0.703 | 0.719 | 0.609 | 0.672 |
| CDC2 + IGFBP5 | 0.766 | 0.781 | 0.766 | 0.781 | 0.609 | 0.719 | 0.688 | 0.781 | 0.672 | 0.688 |
| CDC + HOXA13 | 0.750 | 0.734 | 0.750 | 0.734 | 0.562 | 0.703 | 0.703 | 0.688 | 0.656 | 0.703 |
| IGF + HOXA13 | 0.703 | 0.703 | 0.672 | 0.672 | 0.719 | 0.750 | 0.500 | 0.641 | 0.688 | 0.672 |
| MDK + CDC2 + IGFBP5 | 0.766 | 0.766 | 0.766 | 0.766 | 0.688 | 0.766 | 0.734 | 0.797 | 0.656 | 0.625 |
| MDK + CDC2 + HOXA13 | 0.734 | 0.734 | 0.734 | 0.734 | 0.609 | 0.688 | 0.766 | 0.703 | 0.656 | 0.656 |
| MDK + IGFBP5 + HOXA13 | 0.734 | 0.719 | 0.734 | 0.719 | 0.719 | 0.766 | 0.750 | 0.703 | 0.656 | 0.656 |
| CDC2 + IGFBP5 + HOXA13 | 0.797 | 0.797 | 0.812 | 0.781 | 0.719 | 0.750 | 0.734 | 0.688 | 0.672 | 0.672 |
| MDK+CDC2+IGFBP5+HOXA13 | 0.766 | 0.781 | 0.781 | 0.797 | 0.703 | 0.766 | 0.766 | 0.719 | 0.656 | 0.641 |

Sensitivity at Specificity: Sp.80

Figure 16a

| b | Model | LDA | | LogReg | | SVM | | KN5N | | TREE | |
|---|---|---|---|---|---|---|---|---|---|---|---|
| | | -IL8Rb | +IL8Rb | -IL8Rb | +IL8Rb | -IL8Rb | +IL8Rb | -IL8Rb | +IL8Rb | -IL8Rb | +IL8Rb |
| | MDK | 0.657 | 0.719 | 0.672 | 0.719 | 0.578 | 0.641 | 0.531 | 0.609 | 0.609 | 0.672 |
| | CDC2 | 0.481 | 0.703 | 0.719 | 0.703 | 0.531 | 0.688 | 0.500 | 0.625 | 0.672 | 0.703 |
| | IGFBP5 | 0.595 | 0.641 | 0.625 | 0.656 | 0.516 | 0.625 | 0.516 | 0.484 | 0.562 | 0.578 |
| | HOXA13 | 0.462 | 0.594 | 0.562 | 0.562 | 0.469 | 0.469 | 0.406 | 0.375 | 0.500 | 0.406 |
| | MDK + CDC2 | 0.688 | 0.734 | 0.688 | 0.734 | 0.641 | 0.688 | 0.562 | 0.672 | 0.641 | 0.641 |
| | MDK + IGFBP5 | 0.703 | 0.719 | 0.703 | 0.719 | 0.703 | 0.781 | 0.562 | 0.766 | 0.609 | 0.609 |
| | MDK + HOXA13 | 0.656 | 0.688 | 0.656 | 0.688 | 0.594 | 0.641 | 0.562 | 0.516 | 0.594 | 0.625 |
| | CDC2 + IGFBP5 | 0.750 | 0.766 | 0.750 | 0.766 | 0.609 | 0.688 | 0.578 | 0.641 | 0.625 | 0.641 |
| | CDC + HOXA13 | 0.719 | 0.703 | 0.719 | 0.703 | 0.547 | 0.688 | 0.594 | 0.547 | 0.656 | 0.703 |
| | IGF + HOXA13 | 0.641 | 0.641 | 0.641 | 0.641 | 0.688 | 0.719 | 0.500 | 0.484 | 0.609 | 0.609 |
| | MDK + CDC2 + IGFBP5 | 0.734 | 0.734 | 0.734 | 0.734 | 0.688 | 0.734 | 0.609 | 0.797 | 0.609 | 0.625 |
| | MDK + CDC2 + HOXA13 | 0.688 | 0.719 | 0.688 | 0.719 | 0.594 | 0.672 | 0.609 | 0.641 | 0.641 | 0.641 |
| | MDK + IGFBP5 + HOXA13 | 0.703 | 0.719 | 0.703 | 0.719 | 0.719 | 0.750 | 0.562 | 0.703 | 0.641 | 0.641 |
| | CDC2 + IGFBP5 + HOXA13 | 0.750 | 0.766 | 0.750 | 0.766 | 0.719 | 0.734 | 0.594 | 0.688 | 0.625 | 0.625 |
| | MDK+CDC2+IGFBP5+HOXA13 | 0.766 | 0.750 | 0.750 | 0.750 | 0.688 | 0.750 | 0.625 | 0.719 | 0.609 | 0.594 |

Sensitivity at Specificity: Sp.85

Figure 16b

| c | Model | LDA | | LogReg | | SVM | | KN5N | | TREE | |
|---|---|---|---|---|---|---|---|---|---|---|---|
| | | -IL8Rb | +IL8Rb | -IL8Rb | +IL8Rb | -IL8Rb | +IL8Rb | -IL8Rb | +IL8Rb | -IL8Rb | +IL8Rb |
| | MDK | 0.511 | 0.672 | 0.625 | 0.672 | 0.562 | 0.641 | 0.531 | 0.609 | 0.609 | 0.594 |
| | CDC2 | 0.338 | 0.703 | 0.656 | 0.703 | 0.531 | 0.688 | 0.500 | 0.625 | 0.625 | 0.672 |
| | IGFBP5 | 0.212 | 0.562 | 0.562 | 0.562 | 0.500 | 0.594 | 0.516 | 0.484 | 0.500 | 0.562 |
| | HOXA13 | 0.257 | 0.516 | 0.500 | 0.531 | 0.438 | 0.469 | 0.406 | 0.375 | 0.391 | 0.359 |
| | MDK + CDC2 | 0.688 | 0.703 | 0.688 | 0.688 | 0.625 | 0.688 | 0.562 | 0.672 | 0.562 | 0.578 |
| | MDK + IGFBP5 | 0.641 | 0.719 | 0.641 | 0.688 | 0.703 | 0.719 | 0.562 | 0.625 | 0.578 | 0.594 |
| | MDK + HOXA13 | 0.641 | 0.672 | 0.625 | 0.656 | 0.562 | 0.641 | 0.562 | 0.516 | 0.594 | 0.578 |
| | CDC2 + IGFBP5 | 0.656 | 0.750 | 0.672 | 0.734 | 0.609 | 0.688 | 0.578 | 0.641 | 0.547 | 0.594 |
| | CDC + HOXA13 | 0.641 | 0.703 | 0.656 | 0.688 | 0.547 | 0.688 | 0.594 | 0.547 | 0.594 | 0.672 |
| | IGF + HOXA13 | 0.594 | 0.594 | 0.578 | 0.578 | 0.672 | 0.688 | 0.500 | 0.484 | 0.594 | 0.578 |
| | MDK + CDC2 + IGFBP5 | 0.672 | 0.734 | 0.672 | 0.719 | 0.656 | 0.688 | 0.609 | 0.672 | 0.531 | 0.578 |
| | MDK + CDC2 + HOXA13 | 0.688 | 0.688 | 0.688 | 0.703 | 0.578 | 0.672 | 0.609 | 0.641 | 0.531 | 0.562 |
| | MDK + IGFBP5 + HOXA13 | 0.641 | 0.672 | 0.625 | 0.656 | 0.688 | 0.688 | 0.562 | 0.562 | 0.609 | 0.594 |
| | CDC2 + IGFBP5 + HOXA13 | 0.672 | 0.766 | 0.703 | 0.734 | 0.672 | 0.688 | 0.594 | 0.547 | 0.578 | 0.594 |
| | MDK+CDC2+IGFBP5+HOXA13 | 0.688 | 0.719 | 0.703 | 0.719 | 0.672 | 0.734 | 0.625 | 0.672 | 0.500 | 0.562 |

Sensitivity at Specificity: Sp.90

Figure 16c

| Model | LDA | | LogReg | | SVM | | KN5N | | TREE | |
|---|---|---|---|---|---|---|---|---|---|---|
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.304 | 0.609 | 0.547 | 0.609 | 0.531 | 0.609 | 0.500 | 0.609 | 0.500 | 0.562 |
| CDC2 | 0.180 | 0.625 | 0.516 | 0.625 | 0.500 | 0.609 | 0.438 | 0.625 | 0.500 | 0.609 |
| IGFBP5 | 0.148 | 0.484 | 0.484 | 0.484 | 0.500 | 0.500 | 0.359 | 0.391 | 0.469 | 0.438 |
| HOXA13 | 0.173 | 0.422 | 0.438 | 0.422 | 0.422 | 0.406 | 0.297 | 0.297 | 0.344 | 0.297 |
| MDK + CDC2 | 0.562 | 0.672 | 0.562 | 0.672 | 0.547 | 0.672 | 0.453 | 0.672 | 0.453 | 0.562 |
| MDK + IGFBP5 | 0.562 | 0.609 | 0.578 | 0.609 | 0.609 | 0.656 | 0.562 | 0.625 | 0.531 | 0.547 |
| MDK + HOXA13 | 0.531 | 0.609 | 0.531 | 0.609 | 0.531 | 0.609 | 0.562 | 0.516 | 0.500 | 0.562 |
| CDC2 + IGFBP5 | 0.562 | 0.609 | 0.562 | 0.625 | 0.562 | 0.594 | 0.453 | 0.641 | 0.500 | 0.547 |
| CDC + HOXA13 | 0.516 | 0.625 | 0.500 | 0.625 | 0.516 | 0.609 | 0.594 | 0.547 | 0.516 | 0.609 |
| IGF + HOXA13 | 0.484 | 0.484 | 0.531 | 0.531 | 0.547 | 0.531 | 0.500 | 0.484 | 0.406 | 0.406 |
| MDK + CDC2 + IGFBP5 | 0.594 | 0.656 | 0.609 | 0.672 | 0.578 | 0.641 | 0.609 | 0.672 | 0.469 | 0.500 |
| MDK + CDC2 + HOXA13 | 0.562 | 0.672 | 0.562 | 0.672 | 0.547 | 0.672 | 0.516 | 0.641 | 0.484 | 0.562 |
| MDK + IGFBP5 + HOXA13 | 0.609 | 0.625 | 0.609 | 0.609 | 0.609 | 0.656 | 0.562 | 0.562 | 0.531 | 0.547 |
| CDC2 + IGFBP5 + HOXA13 | 0.609 | 0.641 | 0.578 | 0.656 | 0.594 | 0.641 | 0.594 | 0.547 | 0.484 | 0.516 |
| MDK+CDC2+IGFBP5+HOXA13 | 0.609 | 0.688 | 0.594 | 0.672 | 0.625 | 0.672 | 0.625 | 0.672 | 0.469 | 0.484 |

Sensitivity at Specificity Sp.95

Figure 16d

| e | | | | | | | | | | |
|---|---|---|---|---|---|---|---|---|---|---|
| Model | LDA | | LogReg | | SVM | | KN5N | | TREE | |
| | -IL8Rb | +IL8Rb | -IL8Rb | +IL8Rb | -IL8Rb | +IL8Rb | -IL8Rb | +IL8Rb | -IL8Rb | +IL8Rb |
| MDK | 0.163 | 0.516 | 0.484 | 0.516 | 0.469 | 0.547 | 0.312 | 0.516 | 0.359 | 0.562 |
| CDC2 | 0.047 | 0.453 | 0.469 | 0.469 | 0.453 | 0.562 | 0.438 | 0.500 | 0.469 | 0.422 |
| IGFBP5 | 0.054 | 0.391 | 0.391 | 0.391 | 0.359 | 0.375 | 0.234 | 0.266 | 0.219 | 0.266 |
| HOXA13 | 0.089 | 0.281 | 0.312 | 0.281 | 0.297 | 0.281 | 0.203 | 0.297 | 0.234 | 0.234 |
| MDK + CDC2 | 0.484 | 0.578 | 0.500 | 0.578 | 0.469 | 0.578 | 0.375 | 0.422 | 0.359 | 0.391 |
| MDK + IGFBP5 | 0.484 | 0.547 | 0.484 | 0.547 | 0.469 | 0.500 | 0.531 | 0.344 | 0.359 | 0.359 |
| MDK + HOXA13 | 0.484 | 0.547 | 0.469 | 0.547 | 0.469 | 0.484 | 0.422 | 0.500 | 0.359 | 0.562 |
| CDC2 + IGFBP5 | 0.484 | 0.500 | 0.484 | 0.500 | 0.422 | 0.484 | 0.453 | 0.484 | 0.438 | 0.422 |
| CDC + HOXA13 | 0.469 | 0.422 | 0.453 | 0.469 | 0.375 | 0.422 | 0.484 | 0.406 | 0.453 | 0.453 |
| IGF + HOXA13 | 0.391 | 0.391 | 0.375 | 0.375 | 0.500 | 0.562 | 0.234 | 0.406 | 0.219 | 0.250 |
| MDK + CDC2 + IGFBP5 | 0.484 | 0.578 | 0.484 | 0.562 | 0.484 | 0.578 | 0.500 | 0.484 | 0.312 | 0.391 |
| MDK + CDC2 + HOXA13 | 0.484 | 0.609 | 0.484 | 0.609 | 0.484 | 0.578 | 0.344 | 0.578 | 0.359 | 0.391 |
| MDK + IGFBP5 + HOXA13 | 0.469 | 0.531 | 0.500 | 0.547 | 0.469 | 0.516 | 0.469 | 0.406 | 0.359 | 0.359 |
| CDC2 + IGFBP5 + HOXA13 | 0.469 | 0.484 | 0.469 | 0.484 | 0.469 | 0.500 | 0.469 | 0.469 | 0.453 | 0.422 |
| MDK+CDC2+IGFBP5+HOXA13 | 0.484 | 0.609 | 0.484 | 0.609 | 0.469 | 0.531 | 0.516 | 0.484 | 0.344 | 0.391 |

Sensitivity at Specificity: Sp.98

Figure 16e

| Model | LDA | LogReg | SVM | KN5N | TREE |
|---|---|---|---|---|---|
| MDK | 0.013 | 0.000 | 0.078 | 0.250 | 0.062 |
| CDC2 | -0.019 | -0.016 | 0.141 | -0.016 | 0.031 |
| IGFBP5 | 0.046 | 0.016 | 0.109 | 0.141 | -0.047 |
| HOXA13 | 0.123 | -0.016 | -0.016 | -0.031 | 0.031 |
| MDK + CDC2 | 0.016 | 0.016 | 0.078 | 0.016 | -0.031 |
| MDK + IGFBP5 | 0.000 | 0.000 | 0.078 | 0.078 | 0.000 |
| MDK + HOXA13 | 0.000 | -0.016 | 0.031 | 0.016 | 0.062 |
| CDC2 + IGFBP5 | 0.016 | -0.016 | 0.109 | 0.094 | 0.016 |
| CDC + HOXA13 | -0.016 | -0.016 | 0.141 | -0.016 | 0.047 |
| IGF + HOXA13 | 0.000 | 0.000 | 0.031 | 0.141 | -0.016 |
| MDK + CDC2 + IGFBP5 | 0.000 | 0.000 | 0.078 | 0.062 | -0.031 |
| MDK + CDC2 + HOXA13 | 0.000 | 0.000 | 0.078 | -0.062 | 0.000 |
| MDK + IGFBP5 + HOXA13 | -0.016 | -0.016 | 0.047 | -0.047 | 0.000 |
| CDC2 + IGFBP5 + HOXA13 | 0.000 | -0.031 | 0.031 | -0.047 | 0.000 |
| MDK+CDC2+IGFBP5+HOXA13 | 0.016 | 0.016 | 0.062 | -0.047 | -0.016 |

Gain in sensitivity, starting at specificity=0.80

Figure 17a

| Model | LDA | LogReg | SVM | KN5N | TREE |
|---|---|---|---|---|---|
| MDK | 0.062 | 0.047 | 0.047 | 0.078 | 0.062 |
| CDC2 | 0.222 | -0.016 | -0.016 | 0.125 | 0.031 |
| IGFBP5 | 0.046 | 0.031 | 0.031 | -0.031 | 0.016 |
| HOXA13 | 0.132 | 0.000 | 0.031 | -0.031 | -0.094 |
| MDK + CDC2 | 0.047 | 0.047 | 0.016 | 0.109 | 0.000 |
| MDK + IGFBP5 | 0.016 | 0.016 | 0.016 | 0.203 | 0.000 |
| MDK + HOXA13 | 0.031 | 0.031 | 0.016 | -0.047 | 0.031 |
| CDC2 + IGFBP5 | 0.016 | 0.016 | 0.016 | 0.062 | 0.016 |
| CDC + HOXA13 | -0.016 | -0.016 | -0.016 | -0.047 | 0.047 |
| IGF + HOXA13 | 0.000 | 0.000 | 0.062 | -0.016 | 0.000 |
| MDK + CDC2 + IGFBP5 | 0.000 | 0.000 | 0.016 | 0.188 | 0.016 |
| MDK + CDC2 + HOXA13 | 0.031 | 0.031 | 0.000 | 0.031 | 0.000 |
| MDK + IGFBP5 + HOXA13 | 0.016 | 0.016 | 0.047 | 0.141 | 0.000 |
| CDC2 + IGFBP5 + HOXA13 | 0.016 | 0.016 | 0.031 | 0.094 | 0.000 |
| MDK+CDC2+IGFBP5+HOXA13 | -0.016 | 0.000 | -0.016 | 0.094 | -0.016 |
| Gain in sensitivity, starting at specificity=0.85 | | | | | |

Figure 17b

| Model | LDA | LogReg | SVM | KN5N | TREE |
|---|---|---|---|---|---|
| MDK | 0.161 | 0.047 | 0.078 | 0.078 | -0.016 |
| CDC2 | 0.365 | 0.047 | 0.156 | 0.125 | 0.047 |
| IGFBP5 | 0.350 | 0.000 | 0.094 | -0.031 | 0.062 |
| HOXA13 | 0.259 | 0.031 | 0.031 | -0.031 | -0.031 |
| MDK + CDC2 | 0.016 | 0.000 | 0.062 | 0.109 | 0.016 |
| MDK + IGFBP5 | 0.078 | 0.047 | 0.016 | 0.062 | 0.016 |
| MDK + HOXA13 | 0.091 | 0.031 | 0.078 | -0.047 | -0.016 |
| CDC2 + IGFBP5 | 0.094 | 0.062 | 0.078 | 0.062 | 0.047 |
| CDC + HOXA13 | 0.062 | 0.031 | 0.141 | -0.047 | 0.078 |
| IGF + HOXA13 | 0.000 | 0.000 | 0.016 | -0.016 | -0.016 |
| MDK + CDC2 + IGFBP5 | 0.062 | 0.047 | 0.078 | 0.062 | 0.047 |
| MDK + CDC2 + HOXA13 | 0.000 | 0.016 | 0.094 | 0.031 | 0.031 |
| MDK + IGFBP5 + HOXA13 | 0.031 | 0.031 | 0.000 | 0.000 | -0.016 |
| CDC2 + IGFBP5 + HOXA13 | 0.094 | 0.031 | 0.016 | -0.047 | 0.016 |
| MDK+CDC2+IGFBP5+HOXA13 | 0.031 | 0.016 | 0.062 | 0.047 | 0.062 |

Gain in sensitivity, starting at specificity=0.90

Figure 17c

| Model | LDA | LogReg | SVM | KN5N | TREE |
|---|---|---|---|---|---|
| MDK | 0.306 | 0.062 | 0.078 | 0.109 | 0.062 |
| CDC2 | 0.445 | 0.109 | 0.109 | 0.188 | 0.109 |
| IGFBP5 | 0.336 | 0.000 | 0.000 | 0.031 | -0.031 |
| HOXA13 | 0.249 | -0.016 | -0.016 | 0.000 | -0.047 |
| MDK + CDC2 | 0.109 | 0.109 | 0.125 | 0.219 | 0.109 |
| MDK + IGFBP5 | 0.047 | 0.031 | 0.047 | 0.062 | 0.016 |
| MDK + HOXA13 | 0.078 | 0.078 | 0.078 | -0.047 | 0.062 |
| CDC2 + IGFBP5 | 0.047 | 0.062 | 0.031 | 0.188 | 0.047 |
| CDC + HOXA13 | 0.109 | 0.125 | 0.094 | -0.047 | 0.094 |
| IGF + HOXA13 | 0.000 | 0.000 | -0.016 | -0.016 | 0.000 |
| MDK + CDC2 + IGFBP5 | 0.062 | 0.062 | 0.062 | 0.062 | 0.031 |
| MDK + CDC2 + HOXA13 | 0.109 | 0.109 | 0.125 | 0.125 | 0.078 |
| MDK + IGFBP5 + HOXA13 | 0.016 | 0.000 | 0.047 | 0.000 | 0.016 |
| CDC2 + IGFBP5 + HOXA13 | 0.031 | 0.078 | 0.047 | -0.047 | 0.031 |
| MDK+CDC2+IGFBP5+HOXA13 | 0.078 | 0.078 | 0.047 | 0.047 | 0.016 |

Gain in sensitivity, starting at specificity=0.95

Figure 17d

| Model | LDA | LogReg | SVM | KN5N | TREE |
|---|---|---|---|---|---|
| MDK | 0.353 | 0.031 | 0.078 | 0.203 | 0.203 |
| CDC2 | 0.406 | 0.000 | 0.109 | 0.062 | -0.047 |
| IGFBP5 | 0.336 | 0.000 | 0.016 | 0.031 | 0.047 |
| HOXA13 | 0.192 | -0.031 | -0.016 | 0.094 | 0.000 |
| MDK + CDC2 | 0.094 | 0.078 | 0.109 | 0.047 | 0.031 |
| MDK + IGFBP5 | 0.062 | 0.062 | 0.031 | -0.188 | 0.000 |
| MDK + HOXA13 | 0.062 | 0.078 | 0.016 | 0.078 | 0.203 |
| CDC2 + IGFBP5 | 0.016 | 0.016 | 0.016 | 0.031 | -0.016 |
| CDC + HOXA13 | -0.047 | 0.016 | 0.062 | -0.078 | 0.000 |
| IGF + HOXA13 | 0.000 | 0.000 | 0.047 | 0.172 | 0.031 |
| MDK + CDC2 + IGFBP5 | 0.094 | 0.078 | 0.062 | -0.016 | 0.078 |
| MDK + CDC2 + HOXA13 | 0.125 | 0.125 | 0.094 | 0.234 | 0.031 |
| MDK + IGFBP5 + HOXA13 | 0.062 | 0.047 | 0.047 | -0.062 | 0.000 |
| CDC2 + IGFBP5 + HOXA13 | 0.016 | 0.016 | 0.031 | 0.000 | -0.031 |
| MDK+CDC2+IGFBP5+HOXA13 | 0.125 | 0.125 | 0.062 | -0.031 | 0.047 |

Gain in sensitivity, starting at specificity=0.98

Figure 17e

| Model | LDA | LogReg | SVM | KN5N | TREE |
|---|---|---|---|---|---|
| MDK | 0.030 | 0.000 | 0.168 | 0.180 | 0.069 |
| CDC2 | -0.025 | -0.040 | 0.178 | -0.104 | 0.094 |
| IGFBP5 | 0.037 | 0.022 | 0.131 | 0.119 | -0.025 |
| HOXA13 | 0.114 | -0.007 | -0.002 | 0.116 | 0.027 |
| MDK + CDC2 | 0.012 | 0.030 | 0.158 | -0.101 | -0.049 |
| MDK + IGFBP5 | 0.000 | 0.000 | 0.101 | 0.146 | -0.022 |
| MDK + HOXA13 | 0.000 | -0.054 | 0.126 | -0.089 | 0.072 |
| CDC2 + IGFBP5 | 0.022 | 0.012 | 0.143 | 0.146 | 0.035 |
| CDC2 + HOXA13 | -0.025 | -0.040 | 0.158 | -0.109 | 0.106 |
| IGF + HOXA13 | 0.000 | 0.000 | 0.042 | 0.158 | 0.005 |
| MDK + CDC2 + IGFBP5 | 0.000 | 0.000 | 0.133 | 0.151 | -0.012 |
| MDK + CDC2 + HOXA13 | 0.000 | 0.000 | 0.165 | -0.091 | -0.035 |
| MDK + IGFBP5 + HOXA13 | -0.022 | -0.022 | 0.081 | -0.042 | -0.032 |
| CDC2 + IGFBP5 + HOXA13 | 0.000 | -0.094 | 0.064 | -0.032 | 0.015 |
| MDK+CDC2+IGFBP5+HOXA13 | 0.027 | 0.000 | 0.138 | -0.057 | -0.010 |

Gain in specificity, starting at specificity=0.80

Figure 17f

| Model | LDA | LogReg | SVM | KN5N | TREE |
|---|---|---|---|---|---|
| MDK | 0.059 | 0.041 | 0.123 | 0.130 | 0.039 |
| CDC2 | 0.125 | -0.023 | 0.130 | 0.130 | 0.044 |
| IGFBP5 | 0.041 | 0.009 | 0.081 | 0.069 | 0.036 |
| HOXA13 | 0.064 | -0.001 | -0.001 | 0.066 | -0.015 |
| MDK + CDC2 | 0.054 | 0.046 | 0.108 | 0.118 | -0.001 |
| MDK + IGFBP5 | 0.051 | 0.041 | 0.051 | 0.096 | 0.019 |
| MDK + HOXA13 | 0.051 | 0.044 | 0.103 | 0.086 | 0.041 |
| CDC2 + IGFBP5 | 0.017 | 0.002 | 0.093 | 0.096 | 0.031 |
| CDC + HOXA13 | -0.018 | -0.028 | 0.113 | 0.086 | 0.056 |
| IGF + HOXA13 | -0.001 | -0.001 | 0.002 | 0.108 | -0.008 |
| MDK + CDC2 + IGFBP5 | -0.001 | -0.001 | 0.083 | 0.101 | 0.014 |
| MDK + CDC2 + HOXA13 | 0.049 | 0.054 | 0.118 | 0.130 | -0.001 |
| MDK + IGFBP5 + HOXA13 | 0.007 | 0.014 | 0.031 | 0.113 | 0.009 |
| CDC2 + IGFBP5 + HOXA13 | 0.051 | 0.007 | 0.014 | 0.101 | -0.003 |
| MDK+CDC2+IGFBP5+HOXA13 | -0.015 | -0.001 | 0.088 | 0.110 | 0.004 |

Gain in specificity, starting at specificity=0.85

Figure 17g

| Model | LDA | LogReg | SVM | KN5N | TREE |
|---|---|---|---|---|---|
| MDK | 0.078 | 0.021 | 0.075 | 0.080 | -0.011 |
| CDC2 | 0.098 | 0.038 | 0.080 | 0.080 | 0.028 |
| IGFBP5 | 0.090 | 0.001 | 0.043 | 0.019 | 0.011 |
| HOXA13 | 0.088 | 0.004 | 0.028 | 0.016 | -0.026 |
| MDK + CDC2 | 0.004 | 0.001 | 0.058 | 0.068 | 0.043 |
| MDK + IGFBP5 | 0.028 | 0.026 | 0.001 | 0.046 | 0.009 |
| MDK + HOXA13 | 0.011 | 0.016 | 0.063 | 0.036 | -0.009 |
| CDC2 + IGFBP5 | 0.021 | 0.028 | 0.043 | 0.046 | 0.058 |
| CDC2 + HOXA13 | 0.019 | 0.033 | 0.063 | 0.036 | 0.053 |
| IGF + HOXA13 | 0.001 | 0.001 | 0.004 | 0.058 | -0.031 |
| MDK + CDC2 + IGFBP5 | 0.048 | 0.043 | 0.036 | 0.051 | 0.048 |
| MDK + CDC2 + HOXA13 | 0.001 | 0.004 | 0.075 | 0.080 | 0.053 |
| MDK + IGFBP5 + HOXA13 | 0.041 | 0.046 | 0.001 | 0.063 | 0.004 |
| CDC2 + IGFBP5 + HOXA13 | 0.021 | 0.033 | 0.021 | 0.051 | -0.001 |
| MDK+CDC2+IGFBP5+HOXA13 | 0.031 | 0.021 | 0.048 | 0.060 | 0.046 |

Gain in specificity, starting at specificity=0.90

Figure 17h

| Model | LDA | LogReg | SVM | KN5N | TREE |
|---|---|---|---|---|---|
| MDK | 0.043 | 0.025 | 0.030 | 0.030 | 0.028 |
| CDC2 | 0.050 | 0.025 | 0.030 | 0.030 | 0.023 |
| IGFBP5 | 0.043 | 0.001 | 0.001 | 0.015 | -0.007 |
| HOXA13 | 0.045 | -0.002 | -0.004 | 0.020 | -0.012 |
| MDK + CDC2 | 0.030 | 0.030 | 0.033 | 0.038 | 0.013 |
| MDK + IGFBP5 | 0.023 | 0.025 | 0.010 | -0.004 | 0.006 |
| MDK + HOXA13 | 0.030 | 0.030 | 0.013 | -0.014 | 0.028 |
| CDC2 + IGFBP5 | 0.020 | 0.018 | 0.015 | 0.025 | 0.015 |
| CDC2 + HOXA13 | 0.023 | 0.025 | 0.025 | -0.014 | 0.015 |
| IGF + HOXA13 | 0.001 | 0.001 | -0.007 | 0.008 | 0.003 |
| MDK + CDC2 + IGFBP5 | 0.025 | 0.023 | 0.023 | 0.001 | 0.010 |
| MDK + CDC2 + HOXA13 | 0.035 | 0.033 | 0.033 | 0.030 | 0.013 |
| MDK + IGFBP5 + HOXA13 | 0.006 | 0.001 | 0.003 | 0.013 | 0.006 |
| CDC2 + IGFBP5 + HOXA13 | 0.003 | 0.015 | 0.008 | 0.001 | 0.008 |
| MDK+CDC2+IGFBP5+HOXA13 | 0.028 | 0.030 | 0.015 | 0.010 | 0.010 |

Gain in specificity, starting at specificity=0.95

Figure 17i

| Model | LDA | LogReg | SVM | KN5N | TREE |
|---|---|---|---|---|---|
| MDK | 0.015 | 0.005 | 0.008 | 0.005 | 0.008 |
| CDC2 | 0.020 | 0.000 | 0.000 | 0.000 | -0.007 |
| IGFBP5 | 0.018 | 0.000 | 0.000 | 0.000 | 0.003 |
| HOXA13 | 0.015 | -0.007 | -0.007 | 0.010 | 0.000 |
| MDK + CDC2 | 0.003 | 0.003 | 0.005 | 0.008 | 0.003 |
| MDK + IGFBP5 | 0.000 | 0.000 | 0.000 | -0.010 | 0.000 |
| MDK + HOXA13 | 0.008 | 0.008 | 0.008 | 0.010 | 0.008 |
| CDC2 + IGFBP5 | 0.005 | 0.000 | 0.003 | -0.005 | 0.000 |
| CDC + HOXA13 | -0.002 | 0.000 | 0.000 | -0.010 | -0.002 |
| IGF + HOXA13 | 0.000 | 0.000 | 0.003 | 0.008 | 0.003 |
| MDK + CDC2 + IGFBP5 | 0.003 | 0.003 | 0.005 | 0.005 | 0.010 |
| MDK + CDC2 + HOXA13 | 0.008 | 0.008 | 0.003 | 0.005 | 0.003 |
| MDK + IGFBP5 + HOXA13 | 0.008 | 0.005 | 0.000 | 0.005 | 0.000 |
| CDC2 + IGFBP5 + HOXA13 | 0.000 | 0.000 | 0.008 | 0.013 | -0.007 |
| MDK+CDC2+IGFBP5+HOXA13 | 0.005 | 0.005 | 0.005 | 0.005 | 0.010 |

Gain in specificity, starting at specificity=0.98

Figure 17j

```
                          SEQUENCE LISTING

<160> NUMBER OF SEQ ID NOS: 17

<210> SEQ ID NO 1
<211> LENGTH: 360
<212> TYPE: PRT
<213> ORGANISM: Homo sapiens

<400> SEQUENCE: 1

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
```

```
            340             345             350
Ser Gly His Thr Ser Thr Thr Leu
        355             360

<210> SEQ ID NO 2
<211> LENGTH: 2880
<212> TYPE: DNA
<213> ORGANISM: Homo sapiens

<400> SEQUENCE: 2
aggttcaaaa cattcagaga cagaaggtgg atagacaaat ctccaccttc agactggtag      60
gctcctccag aagccatcag acaggaagat gtgaaaatcc ccagcactca tcccagaatc     120
actaagtggc acctgtcctg ggccaaagtc ccaggacaga cctcattgtt cctctgtggg     180
aatacctccc caggagggca tcctggattt ccccttgca acccaggtca gaagtttcat      240
cgtcaaggtt gtttcatctt ttttttcctg tctaacagct ctgactacca cccaaccttg     300
aggcacagtg aagacatcgg tggccactcc aataacagca ggtcacagct gctcttctgg     360
aggtgtccta caggtgaaaa gcccagcgac ccagtcagga tttaagttta cctcaaaaat     420
ggaagatttt aacatggaga gtgacagctt tgaagatttc tggaaaggtg aagatcttag     480
taattacagt tacagctcta ccctgccccc ttttctacta gatgccgccc catgtgaacc     540
agaatccctg gaaatcaaca agtattttgt ggtcattatc tatgccctgg tattcctgct     600
gagcctgctg ggaaactccc tcgtgatgct ggtcatctta tacagcaggg tcggccgctc     660
cgtcactgat gtctacctgc tgaacctagc cttggccgac ctactctttg ccctgacctt     720
gcccatctgg gccgcctcca ggtgaatgg ctggattttt ggcacattcc tgtgcaaggt      780
ggtctcactc ctgaaggaag tcaacttcta tagtggcatc ctgctactgg cctgcatcag     840
tgtggaccgt tacctggcca ttgtccatgc cacacgcaca ctgacccaga gcgctactt      900 ggtcaaattc atatgtctca gcatctgggg tctgtccttg ctcctggccc tgcctgtctt     960
acttttccga aggaccgtct actcatccaa tgttagccca gcctgctatg aggacatggg    1020
caacaataca gcaaactggc ggatgctgtt acgatcctg ccccagtcct ttggcttcat     1080
cgtgccactg ctgatcatgc tgttctgcta cggattcacc ctgcgtacgc tgtttaaggc    1140
ccacatgggg cagaagcacc gggccatgcg ggtcatcttt gctgtcgtcc tcatcttcct    1200
gctctgctgg ctgccctaca acctggtcct gctggcagac accctcatga ggacccaggt    1260
gatccaggag acctgtgagc gccgcaatca catcgaccgg gctctggatg ccaccgagat    1320
tctgggcatc cttcacagct gcctcaaccc cctcatctac gccttcattg ccagaagtt    1380 tcgccatgga ctcctcaaga ttctagctat acatggcttg atcagcaagg actccctgcc    1440
caaagacagc aggccttcct tgttggctc ttcttcaggg cacacttcca ctactctcta    1500
agacctcctg cctaagtgca gcccgtggg gttcctccct tctcttcaca gtcacattcc    1560
aagcctcatg tccactggtt cttcttggtc tcagtgtcaa tgcagccccc attgtggtca    1620
caggaagtag aggaggccac gttcttacta gtttcccttg catggtttag aaagcttgcc    1680
ctggtgcctc acccccttgcc ataattacta tgtcatttgc tggagctctg cccatcctgc    1740
ccctgagccc atggcactct atgttctaag aagtgaaaat ctacactcca gtgagacagc    1800
tctgcatact cattaggatg gctagtatca aagaaagaa atcaggctg gccaacgggg     1860 tgaaaccctg tctctactaa aaatacaaaa aaaaaaaaaa attagccggg cgtggtggtg    1920
agtgcctgta atcacagcta cttgggaggc tgagatggga gaatcacttg aacccgggag    1980
```

```
gcagaggttg cagtgagccg agattgtgcc cctgcactcc agcctgagcg acagtgagac    2040
tctgtctcag tccatgaaga tgtagaggag aaactggaac tctcgagcgt tgctgggggg    2100
gattgtaaaa tggtgtgacc actgcagaag acagtatggc agctttcctc aaaacttcag    2160
acatagaatt aacacatgat cctgcaattc cacttatagg aattgaccca caagaaatga    2220
aagcagggac ttgaacccat atttgtacac caatattcat agcagcttat tcacaagacc    2280
caaaaggcag aagcaaccca aatgttcatc aatgaatgaa tgaatggcta agcaaaatgt    2340
gatatgtacc taacgaagta tccttcagcc tgaaagagga atgaagtact catacatgtt    2400
acaacacgga cgaaccttga aactttatg ctaagtgaaa taagccagac atcaacagat     2460
aaatagttta tgattccacc tacatgaggt actgagagtg aacaaattta cagagacaga    2520
aagcagaaca gtgattacca gggactgagg ggagggagc atgggaagtg acggtttaat     2580
gggcacaggg tttatgttta ggatgttgaa aaagttctgc agataaacag tagtgatagt    2640
tgtaccgcaa tgtgacttaa tgccactaaa ttgacactta aaaatggttt aaatggtcaa    2700
ttttgttatg tatattttat atcaatttaa aaaaaaacct gagccccaaa aggtatttta    2760
atcaccaagg ctgattaaac caaggctaga accacctgcc tatattttt gttaaatgat      2820 ttcattcaat atcttttttt taataaacca tttttacttg ggtgtttata aaaaaaaaa      2880
```

<210> SEQ ID NO 3
<211> LENGTH: 18
<212> TYPE: DNA
<213> ORGANISM: Artificial sequence
<220> FEATURE:
<223> OTHER INFORMATION: Synthetic

<400> SEQUENCE: 3
tgcaccccca agaccaaa                                                    18

<210> SEQ ID NO 4
<211> LENGTH: 26
<212> TYPE: DNA
<213> ORGANISM: Artificial sequence
<220> FEATURE:
<223> OTHER INFORMATION: Synthetic

<400> SEQUENCE: 4
tgattaaagc taacgagcag acagaa                                           26

<210> SEQ ID NO 5
<211> LENGTH: 26
<212> TYPE: DNA
<213> ORGANISM: Artificial sequence
<220> FEATURE:
<223> OTHER INFORMATION: Synthetic

<400> SEQUENCE: 5
ccttcccttt cttggctttg gccttt                                           26

<210> SEQ ID NO 6
<211> LENGTH: 22
<212> TYPE: DNA
<213> ORGANISM: Artificial sequence
<220> FEATURE:
<223> OTHER INFORMATION: Synthetic

<400> SEQUENCE: 6
cgttgtacct gcccaattgt ga                                               22

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
gggacgcatc actcaacgtt                                               20

<210> SEQ ID NO 8
<211> LENGTH: 27
<212> TYPE: DNA
<213> ORGANISM: Artificial sequence
<220> FEATURE:
<223> OTHER INFORMATION: Synthetic

<400> SEQUENCE: 8
aagagaaagc agtgcaaacc ttcccgt                                       27

<210> SEQ ID NO 9
<211> LENGTH: 16
<212> TYPE: DNA
<213> ORGANISM: Artificial sequence
<220> FEATURE:
<223> OTHER INFORMATION: Synthetic

<400> SEQUENCE: 9
gccgccgcgg aataat                                                   16

<210> SEQ ID NO 10
<211> LENGTH: 28
<212> TYPE: DNA
<213> ORGANISM: Artificial sequence
<220> FEATURE:
<223> OTHER INFORMATION: Synthetic

<400> SEQUENCE: 10
tgtctaccct tatacacaac tccatagg                                      28

<210> SEQ ID NO 11
<211> LENGTH: 31
<212> TYPE: DNA
<213> ORGANISM: Artificial sequence
<220> FEATURE:
<223> OTHER INFORMATION: Synthetic

<400> SEQUENCE: 11
agccgggatc taccataccc attgactaac t                                  31

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
tggaacggcc aaatgtactg                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic

```
<400> SEQUENCE: 13
tggcgtattc ccgttcaagt                                          20

<210> SEQ ID NO 14
<211> LENGTH: 23
<212> TYPE: DNA
<213> ORGANISM: Artificial sequence
<220> FEATURE:
<223> OTHER INFORMATION: Synthetic

<400> SEQUENCE: 14
actctgcccg acgtggtctc cca                                      23

<210> SEQ ID NO 15
<211> LENGTH: 23
<212> TYPE: DNA
<213> ORGANISM: Artificial sequence
<220> FEATURE:
<223> OTHER INFORMATION: Synthetic

<400> SEQUENCE: 15
ccttgaggca cagtgaagac atc                                      23

<210> SEQ ID NO 16
<211> LENGTH: 23
<212> TYPE: DNA
<213> ORGANISM: Artificial sequence
<220> FEATURE:
<223> OTHER INFORMATION: Synthetic

<400> SEQUENCE: 16
cctgtaggac acctccagaa gag                                      23

<210> SEQ ID NO 17
<211> LENGTH: 27
<212> TYPE: DNA
<213> ORGANISM: Artificial sequence
<220> FEATURE:
<223> OTHER INFORMATION: Synthetic

<400> SEQUENCE: 17
tggccactcc aataacagca ggtcaca                                  27
```

METHODS FOR DETECTING GENETIC AND PHENOTYPIC BIOMARKERS OF UROTHELIAL CARCINOMA AND TREATMENT THEREOF

CLAIM OF PRIORITY

This application is a Continuation under 35 U.S.C. 111(a) of International Patent Application No. PCT/US2014066678 filed 20 Nov. 2014, which claims priority to U.S. Provisional Patent Application No. 61/907,013 filed 21 Nov. 2013; Inventors David Darling, Satish Kumar, Mark Dalphin, and Paul O'Sullivan. These Applications are herein incorporated fully by reference.

FIELD OF THE INVENTION

This invention relates to the detection of patients not having disease. Specifically, this invention relates to the use of genetic markers and phenotypic markers for triaging patients that present with hematuria without cancer. Particularly, this invention relates to analysis of genetic markers and phenotypic markers in triaging patients with either macroscopic or microscopic hematuria. More particularly, this invention relates to use of genetic and phenotypic markers in combination to triage patients with asymptomatic macroscopic or microscopic hematuria and to predict whether a patient's condition warrants further clinical procedures.

BACKGROUND

Survival of cancer patients is greatly enhanced when the cancer is treated early. In the case of bladder cancer, patients diagnosed with disease that is confined to the primary site have a 5 year survival rate of 73%, compared to 6% for patients with metastatic disease (Altekruse et al). Therefore, developments that lead to early and accurate diagnosis of bladder cancer can lead to an improved prognosis for the patients. To aid in early detection of cancer a number of cancer specific markers have been identified. However the use of these markers can result in false positive results in patients having inflammatory bladder diseases, and not bladder cancer.

Asymptomatic hematuria ("AH") is one of the most frequent urological findings, with incidence rates of between 2% and 30% depending on the population (Schwartz G: Proper evaluation of asymptomatic microscopic hematuria in the era of evidence-based medicine-progress is being made. Mayo Clin Proc. 2013, 88(2); 123-125, McDonald M, Swagerty D, Wetzel L: Assessment of Microscopic hematuria in adults. AFP 2006 73:10, Grossfield G, Wolf J, Litwan M, Hricak H, Shuler C, Agerter D, et al. Asymptomatic microscopic hematuria in adults: summary of AUA best practice policy recommendations. AFP 2001:63:1145-54).

AH is, however, indicative of broad range of pathologies with urinary tract malignancy incidences in the AH population ranging from 1.9-7%. Full diagnostic work up on all confirmed AH patients puts a considerable burden on many healthcare systems. Use of phenotypic indicators to segregate high and low risk patients has been explored in a recent study by Loo et al. (Loo R, Lieberman S, Slezak J, Landa H, Mariani A, Nicolaisen G, Aspera A and Jaconsen S: Stratifying risk of urinary tract malignant tumors in patients with asymptomatic microscopic hematuria. Mayo Clin Proc. 2013, 88(2); 129-138).

The above-mentioned study of 4414 patients presenting with confirmed AH showed that 73% of patients had no cause identified, while 26% of patients warranted some form of urological work up to identify the cause. Approximately 2.5% of patients presenting with AH were diagnosed with urothelial malignancy, with other conditions such as urinary tract infection (UTI) (2.3%), kidney stones (16.2%), prostatic bleeding (4%), and contamination (0.4%) making up the alternative diagnoses (Loo et al., Id.).

SUMMARY

We have identified a new problem in the field, namely how to identify patients presenting with hematuria who do not have or are at low risk for having bladder cancer. This solves the problem that many patients with hematuria and without bladder cancer may undergo expensive and invasive further workup when such workups are not needed. Thus, this invention is useful to exclude individuals from the hazards and costs associated with full work-up for bladder cancer when a combination of genetic information and phenotypic information provides identification of patients that do not have, or are at low risk of having bladder cancer, and to effectively triage patients having no cancer, from those having cancerous conditions, including urothelial carcinomas, transitional cell carcinoma (TCC) and non-cancerous conditions, including inflammatory disease. This invention represents a new approach to a new problem, in that it is unexpectedly useful, not to diagnose cancer, but rather to diagnose non-cancers. The use of combinations of genetic and phenotypic criteria provide unexpectedly better discrimination than either genetic or phenotypic variables alone. Data were obtained from 541 observations from validated under CLIA standards and CURT+North Shore product trial using bootstrap procedures for internal validation. Phenotypic variables included presence of: (1) smoking history, (2) hematuria, (3) gender, and (4) age. Genetic variables included analysis of expression of IGF, HOXA13, MDK, CDC, and IL8R. The genetic+phenotypic model ("G+P") performed unexpectedly better than either genetic or phenotypic variables alone.

Macrohematuria, or finding of visually identified blood in the urine is a common finding in patients with bladder cancer. For those patients, it is often standard practice to perform additional diagnostic procedures to diagnose bladder cancer. However, readily identifying patients with microhematuria and understanding the implications of microhematuria in urothelial carcinomas, remained a problem.

We herein provide improved methods for determining whether a patient presenting with either macrohematuria or microhematuria could avoid invasive and expensive further clinical procedures to detect urothelial carcinomas (UC) including bladder cancer, if such patient is at a sufficiently low probability of having bladder cancer to warrant not carrying out additional procedures.

Factors attributable to high probability of urothelial carcinoma (UC) are described. Demographic factors such as gender, race and age in addition to environmental factors such as smoking history and occupational exposure to aromatic amines contribute significantly to the risk of developing UC. Characterization of patients in healthcare assessment based on these factors is used routinely on an ad-hoc basis. For example, it is well accepted that a 60 year old male with smoking history presenting with hematuria has a higher probability of being positive for UC than a 35 year old non-smoking female presenting with the same symptoms, however these differences have not been quantitated to contribute to the overall probability of the patient having UC. Attribution of specific weights to various genotypic and phenotypic factors and combining these with a diagnostic test output can add significantly to the accuracy of the diagnostic power of non-invasive tests and provide clinicians with greater certainty in segregating patients on the basis of their probability of having UC as defined by the clinical and biomarker test results.

Although there are methods available to detect the presence of bladder cancer, there are no reliable and accurate methods to determine whether a patient does not have, or is at low risk of having bladder cancer. To address this need, we have developed new analytical methods for distinguishing between cancerous conditions from non-cancerous ones in patients presenting with hematuria, either macrohematuria or microhematuria. In some aspects of this invention, we combine quantified phenotypic variables and quantified expression of genetic markers to form a combined segregation index (the "G+P INDEX") in order to effectively triage out AH patients with a low probability of having UC from those AH patients that have high probability of UC. This segregation defines those that don't need a complete urological workup from those that do require a complete workup and thereby avoids unnecessary work-ups on patients of low probability of UC.

Phenotypic Assays

Phenotypic variables evaluated in the G+P INDEX include frequency of hematuria (HFREQ), age, gender, smoking history, and red blood count (RBC). These terms are defined herein below. Phenotypic variables are defined herein to include clinical findings and observations.

Genotypic Assays

In general, preferred genotypic assays developed by Pacific Edge Ltd. include quantification of expression of the genetic markers CDC2, HOXA13, MDK and IGFBP5 (a "4-marker assay"). In another preferred assay, the above 4 markers and a fifth marker, IL8R, is quantified (a "5-marker" or Cxbladder® assay; a trademark of Pacific Edge Ltd., Dunedin, New Zealand) (Holyoake A, O'Sullivan P, Pollock R et al: Development of a multiplex RNA urine test for the detection and stratification of transitional cell carcinoma of the bladder. Clin Cancer Res 2008; 14: 742, and O'Sullivan P, Sharples K, Dalphin M et al: A Multigene Urine Test for the Detection and Stratification of Bladder Cancer in Patients Presenting with Hematuria. J Urol 2012, Vol. 188 No 3; 746), and International Patent Application No. PCT/NZ2011/000238, entitled "Novel Markers for Detection of Bladder Cancer." Each of these publications and patent application are herein incorporated fully by reference as if separately so incorporated.

In preferred embodiments, a 4-marker assay can be performed on unfractionated urine using PCR amplification to quantify four mRNA markers (for CDC2, HOXA13, MDK and IGFBP5), which are overexpressed in urothelial carcinoma. IL8R is highly overexpressed in neutrophils and is consequently elevated in non-malignant inflammatory conditions. Inclusion of this 5th mRNA marker significantly reduced the risk of false positive detection of transitional cell carcinoma (TCC). From the patient's perspective, the test is non-invasive and very simple. A single sample of urine often mid-stream urine but not exclusively, is taken, and this can often be done at home without coming into the clinic.

The Cxbladder® assay has been shown to be considerably more sensitive than cytology in patients presenting with macroscopic hematuria. Most notably, the Cxbladder® assay achieved a sensitivity of 100% (at a pre-specified specificity of 85%) for all urothelial carcinomas with a stage greater than Ta, and 97% for all high-grade tumors. The Cxbladder® assay attributes a single value score that combines the quantitative gene expression of five genes represented in the patients urine. The score segregates patients into three classes based on the probability that the patient has a urothelial carcinoma.

For patients presenting with hematuria, (either macrohematuria or microhematuria), this invention has been shown to enhance these genotypic tools (either the 4-marker assay or Cxbladder® assay) with the addition of phenotypic variables collected from the patient over the same time period, and to combine these into a new tool, an index that can be used to segregate patients into three defined risk classes relative to the patient's probability of having urothelial carcinoma ("UC").

Aspects

Aspects of this invention are illustrated below. It can be understood that these are not the only aspects or embodiments of this invention. Persons of ordinary skill can combine one or more aspects together to produce additional aspects or embodiments.

One aspect includes a method for determining, in a patient presenting with hematuria, or the level of risk for having urothelial cancer, comprising:

providing a sample of urine from said patient;

quantifying a value, MI, comprising quantifying the levels of expression of human MDK, CDC2, HOXA13, and IGFBP5 in said sample;

assessing the phenotypic variables HFREQ, AgeGT, sex, SMK, and RBC of said patient;

calculating G+P INDEX according to either:

$$G+P \text{ INDEX}=(1*\text{HFREQ}+3*\text{Gender}+4*\text{SMK})+ (5*M1+2*\text{IL-8}), \text{ or} \quad \text{formula (i)},$$

$$G+P \text{ INDEX}=(w1*\text{HFREQ}+w2*\text{AgeGT50}+ w3*\text{Gender}+w4*\text{SMK}+w5*\text{RBC})+(w6*M1+ w7*\text{IL-8}), \text{ or}$$

$$G+P \text{ INDEX}=-8.46+0.79 \text{ IGF}-1.60 \text{ HOXA}+2.10 \text{ MDK}+0.95 \text{ CDC}-0.38 \text{ IL8R}+0.98 \text{ SNS}+0.56 \text{ Hfreq}+1.11 \text{ Gender}+0.64 \text{ Age; and} \quad \text{formula (ii)},$$

determining whether the G+P INDEX is greater than a threshold indicating the level of risk that the patient has urothelial cancer.

Additional aspects include the method of the other aspect, where said threshold is selected from the group of G+P INDEX values of from 0 to 5, from 6 to 10, or from 11-15, where said value of from 0 to 5 indicates Low Risk, 6 to 10 indicates Moderate Risk, and 11-15 indicates High Risk.

Further aspects include the method of any other aspect, where if said threshold is a G+P INDEX value of from 6-10, said patient undergoes additional clinical or laboratory tests.

Yet further aspects include the method of any prior aspect, where if said threshold is a G+P INDEX value of from 11-15, said patient undergoes additional clinical or laboratory tests.

Still further aspects include the method of any other aspect, where if said threshold is a G+P INDEX value of from 0-5, the patient is placed on a watch list for further clinical or laboratory tests.

Additional aspects include the method of any other aspect, where the threshold is established using a statistical method.

Still further aspects include the method of any other aspect, wherein the statistical method is any one of Linear Discriminant Analysis (LDA), Logistic Regression (LogReg), Support Vector Machine (SVM), K-nearest neighbors (KN5N), and Partition Tree Classifier (TREE).

Additional aspects include the method of any other aspect, further comprising quantifying expression of one additional genotypic marker selected from FIG. 6 or FIG. 7.

Other aspects include the method of any previous aspect, where said step of quantifying genetic expression is carried out by detecting the levels of mRNA.

Further aspects include the method of any other aspect, wherein said step of quantifying genetic expression is carried out by detecting the levels of cDNA.

Yet further aspects include the method of any of any other aspect, where said step of quantifying genetic expression is carried out using an oligonucleotide complementary to at least a portion of said cDNA.

Additional aspects include the method of any other aspect, where said step of quantifying genetic expression is carried out using qRT-PCR method using a forward primer and a reverse primer.

Yet additional aspects include the method of any other aspect, where said step of quantifying genetic expression is carried out by detecting the levels of a protein.

Still other aspects include the method of any other aspect, where said step of quantifying genetic expression is carried out by detecting the levels of a peptide.

Additional aspects include the method of any of any other aspect, where said step of quantifying genetic expression is carried out using an antibody directed against said marker.

Yet further additional aspects include the method of any of claim 1 to 8 or 13-15, where said step of quantifying genetic expression is carried out using a sandwich-type immunoassay method, or using an antibody chip.

Still further aspects include the method of any other aspect, where said quantifying genetic expression is carried out using a monoclonal antibody.

Other aspects include the method any of any other aspect, where said quantifying genetic expression is carried out using a polyclonal antiserum.

G+P Index

Phenotypic and genotypic variables described above are combined into a G+P INDEX according to the following relationship:

$$G+P \text{ INDEX}=(w1*\text{HFREQ}+w2*\text{AgeGT50}+w3*\text{Gender}+w4*\text{SMK}+w5*\text{RBC})+(w6*M1+w7*\text{IL-8}),$$

where HFREQ means the frequency of finding 3 or more red blood cells per high power field in a 6-month period; if frequency is low then HFREQ=0, and if higher than 3 red blood cells per high power field, then 1. AgeGT50 refers to subject's age, if greater than 50 years then AgeGT50=1, and if less than 50 years, then 0. Gender is assigned a value of 1 for male, and 0 for female. SMK means whether the subject is a current or ex-smoker; if non-smoker then SMK=0 and if a smoker, then 1. RBC means red blood cell count; if 25 or more then RBC is set to 1, and if less than 25, then 0. MI is a combination of expression of the genetic markers MDK, CDC, IGFBP5, and HOXA13; if M1>4.5 then set it to 1, if less than 4.5, 0. IL-8 refers to expression level of RNA for IL-8; if IL-8>2.5 then IL-8 is set to 1, if ness than 2.5, 0. The symbols "*" means the multiplication operator, and weighting factors, w1-w7 are respectively the weights assigned to each of the variables listed above in the G+P INDEX.

In other preferred embodiments, (AgeGT50 and RBC) may be dropped from the model as shown below:

$$G+P \text{ INDEX}=(1*\text{HFREQ}+3*\text{Gender}+4*\text{SMK})+(5*M1+2*\text{IL-8})$$

The G+P INDEX produces a value between 0 and 15. A patient with G+P INDEX value of 11 to 15 is considered to be at "High Risk" for bladder cancer, and indicates the need for additional work up for bladder cancer. A patient with a G+P INDEX value of 6 to 10 is considered to be at "Moderate Risk" for developing bladder cancer, and additional work up is indicated. A patient with a G+P INDEX of 0 to 5 is considered to be at "Low Risk" for developing bladder cancer. Patients in the "Low Risk" group are placed on a watchful waiting list, and if additional symptoms appear, or if recurrent episodes of microhematuria occur, they are reevaluated for possible further work up.

As described more fully in Example 3 (FIGS. 18 and 19), we found that the ROC curve for the quantified phenotypic variables alone produced a modest level of diagnostic power. The ROC curve for the quantified genotypic markers alone produced a significant level of diagnostic power. We found an unexpectedly better diagnostic power when both genotypic and phenotypic variables were combined into a G+P INDEX.

Quantification of Genetic Expression

Proteins or nucleic acids that are secreted by or cleaved from the cell, or lost by apoptotic mechanisms, either alone or in combination with each other, have utility as serum or body fluid markers for the diagnosis of disease, including inflammatory disease in bladder and/or bladder cancer or as markers for monitoring the progression of established disease. Detection of protein and cell markers can be carried out using methods known in the art, and include the use of RT-PCT, qRT-PCR, monoclonal antibodies, polyclonal antisera and the like.

Specifically the present invention provides methods for triaging patients presenting with hematuria, (either macrohematuria or microhematuria), comprising: (i) providing a biological sample; (ii) detecting one or more bladder tumor markers (BTMs) in said sample. Bladder tumor markers of particular interest include MDK, CDC2, HOXA13, and IGFBP5 (a "4-marker assay"). Optionally, one can also detect the levels of human neutrophil marker interleukin 8 receptor B (IL8Rb) in the sample (Cxbladder® assay). The presence of cancer can be established by comparing the levels of the one or more BTMs with the levels in normal patients, patients having early stage bladder cancer, and/or patients having an inflammatory disease. For example, the presence of cancer can be established by comparing the expression of BTMs against a threshold of expression. The threshold may be in the order of expression that is at least 1.1, 1.2, 1.3, 1.4, 1.5, 1.6, 1.7, 1.8, 1.9, 2, 3, 4, 5, 6, 7, 8, 9, or 10, 100, 1000, or up to 10,000 times the level of expression in a group of patients not having cancer. In other aspects, a high expression of IL8Rb without altered expression of a bladder tumor marker can be indicative of an inflammatory disease rather than cancer.

The methods of the present invention can be used in conjunction with any suitable marker for detecting bladder cancer. Examples of suitable markers for use in the invention are outlined in FIG. 6 or 7. The present invention includes the use of any one or more of the markers outlined in FIG. 6 or 7.

Optionally, in other preferred embodiments, the present invention can include any combination of IL8Rb with one or more of the markers MDK, CDC2, HOXA13, and IGFBP5, which can also be in combination with one or more other marker suitable for detecting bladder cancer, for example, any one of more of the markers outlined in FIG. 6 or 7. More specifically, the present invention includes quantification of expression of any one or more combination of markers: IL8Rb/MDK, IL8Rb/CDC2, IL8Rb/HOXA13, IL8Rb/IGFBP5, IL8Rb/MDK/CDC2, IL8Rb/MDK/HOXA13, IL8Rb/MDK/IGFBP5, IL8Rb/CDC2/HOXA13, IL8Rb/CDC2/IGFBP5, IL8Rb/HOXA13/IGFBP5, IL8Rb/MDK/CDC2/HOXA13, IL8Rb/MDK/CDC2/IGFBP5, IL8Rb/CDC2/HOXA13/IGFBP5, and IL8Rb/MDK/CDC2/HOXA13/IGFBP5. These combinations can optionally include one or more further markers suitable for detecting bladder cancer, for example any one of more of the markers outlined in FIG. 6 or 7.

The present invention also provides for a method for detecting inflammatory conditions of the bladder, comprising: (i) providing a biological sample from a patient; and (ii) detecting the levels of human neutrophil marker interleukin 8 receptor B (IL8Rb) in said sample. The presence of inflammatory conditions of the bladder is established by comparing the levels of IL8Rb with the levels in normal patients, patients having hematuria, and patients having an inflammatory condition of the bladder. For example, the presence of an inflammatory condition of the bladder can be established by comparing the expression of the marker IL8Rb against a threshold, The threshold may be in the order of expression that is at least 1.1, 1.2, 1.3, 1.4, 1.5, 1.6, 1.7, 1.8, 1.9, 2, 3, 4, 5, 6, 7, 8, 9, 10, 100, 1000, or up to 10,000 times the level of expression in another group of patients.

Preferred genotypic methods of the present invention can be carried out by detecting any suitable marker of gene expression, for example determining the levels of mRNA, cDNA, a protein or peptide utilizing any suitable method.

The establishment of a diagnosis can be established through the use classifier system, for example Linear Discriminant Analysis (LDA), Logistic Regression (LogReg), Support Vector Machine (SVM), K-nearest 5 neighbors (KN5N), and Partition Tree Classifier (TREE).

BRIEF DESCRIPTION OF THE FIGURES

This invention is described with reference to specific embodiments thereof and with reference to the figures (the same as FIG., Fig., and Figure), in which:

FIGS. 1A, 1B, and 1C depict protein and mRNA sequences of IL8Rb (also known as CXCR2).

FIG. 2A. MDK/IGFBP5;
FIG. 2B. MDK/HOXA13;
FIG. 2C. MDK/IL8Rb;
FIG. 2D. CDC2/IGFBP5;
FIG. 2E. CDC2/HOXA13;
FIG. 2F. CDC2/IL8Rb.

FIG. 3A. LD1 (solid) and LD2 (dashed).

FIG. 3B. LR1 (solid) and LR2 (dashed). IL8Rb is included in LD2 and LR2.

FIG. 4a. LD1 (solid) and LD2 (dashed).

FIG. 4b. LR1 (dashed) and LR2 (solid). IL8Rb is included in LD2 and LR2.

FIGS. 6A-6YY depict markers known to be over expressed in bladder cancer, and are suitable for use in the present invention.

FIGS. 7A-7D depict markers known to be under expressed in bladder cancer, and are suitable for use in the present invention.

FIG. 9 depicts baseline clinical and demographic characteristics of the patients by disease status at 3 months.

FIG. 10 depicts overall sensitivity and specificity of the urine tests.

FIG. 11A depicts ROC curves for NMP22 ELISA and uRNA-D (test comprising the four markers MDK+CDC2+IGFBP5+HOXA13); and FIG. 11B depicts ROC curve for the five markers MDK, CDC2, HOXA13, IGFBP5 and IL8Rb.

FIG. 12 depicts the sensitivity of urine tests by stage, grade, location of tumour, multiplicity of tumor, hematuria status, creatinine of urine sample and sex. Tables show numbers and percent with a positive urine test among those with TCC.

FIG. 13 depicts specificity of urine tests by diagnosis, macrohematuria or, creatinine and sex. Tables show number and % with a negative urine test result among those without TCC.

FIGS. 14A(I)-14O(V): depict ROC curves for the combinations of markers:
FIGS. 14A(I)(-14A(V): MDK,
FIGS. 14B(I)-14B(V): CDC,
FIGS. 14C(I)-14C(V): IGFBP5,
FIGS. 14D(I)-14D(V): HOXA13,
FIGS. 14E(i)-14E(v): MDK+CDC2,
FIGS. 14F(i)-14F(v): MDK+IGFBP5,
FIGS. 14G(i)-14G(v): MDK+HOXA13,
FIGS. 14H(I)-14H(V): CDC2+IGFBP5,
FIGS. 14I(I)-14I(V): CDC+HOXA13,
FIGS. 14J(I)-16J)V): IGF+HOXA13,
FIGS. 14K(I)-14K(V): MDK+CDC2+IGFBP5,
FIGS. 14L(I)-14L(V): MDK+CDC2+HOXA13,
FIGS. 14M(I)-14M(V): MDK+IGFBP5+HOXA13,
FIGS. 14N(I)-14N(V): CDC2+IGFBP5+HOXA13,
FIGS. 14O(I)-14O(V): MDK+CDC2+IGFBP5+HOXA13, plus or minus IL8Rb, using five different classifier models (i) Linear Discriminant Analysis (LDA), (ii) Logistic Regression (LogReg), (iii) Support Vector Machine (SVM), (iv) K-nearest 5 neighbors (KN5N), and (v) Partition Tree Classifier (TREE).

FIGS. 15A-15B depict results of sensitivity selectivity studies.

FIG. 15A depicts "Area Under the Curve" (AUC) for up to 20% false positive rate (at 80% specificity) of the ROC curves from FIG. 14 and FIG. 15B shows the difference the AUC resulting from the inclusion of IL8Rb.

FIGS. 16a-16e depict graphs of the sensitivity of the combinations of the four markers MDK, CDC2, IGFBP5, and HOXA13, plus or minus IL8Rb, using five different classifier models (i) Linear Discriminant Analysis (LDA), (ii) Logistic Regression (LogReg), (iii) Support Vector Machine (SVM), (iv) K-nearest 5 neighbors (KN5N), and (v) Partition Tree Classifier (TREE), at different set specificities; (a) 80%, (b) 85%, (c) 90%, (d) 95%, (e) 98%.

FIGS. 17a-17j depict the gains in sensitivity from adding IL8Rb at different set specificities FIG. 17a 80%, FIG. 17b 85%, FIG. 17c 90%, FIG. 17d 95%, FIG. 17e 98%, and the resulting gains in specificity from adding IL8Rb at different set specificities FIG. 17f 80%, FIG. 17g 85%, FIG. 17h 90%, FIG. 17i 95%, FIG. 17j 98%.

FIG. 20A depicts a flow chart for patients with macrohaematuria across all three cohorts in this study.

FIG. 20B depicts flow chart for reporting diagnostic accuracy in patients with microhematuria included in this study.

DETAILED DESCRIPTION

Definitions

Figure 2A:
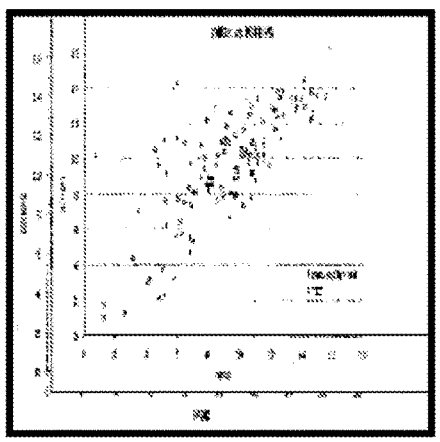
FIGS. 2A-2F depict graphs of scatter plots showing the effect of IL8Rb on the separation of TCC from non-malignant disease (prostate disease, cystitis, urinary tract infection and urolithiasis). IL8Rb has been substituted for different bladder cancer RNA markers in FIGS. 2C and 2F.
Figure 2B:
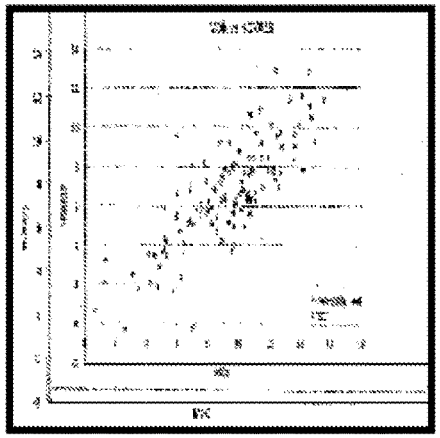
Figure 2C:
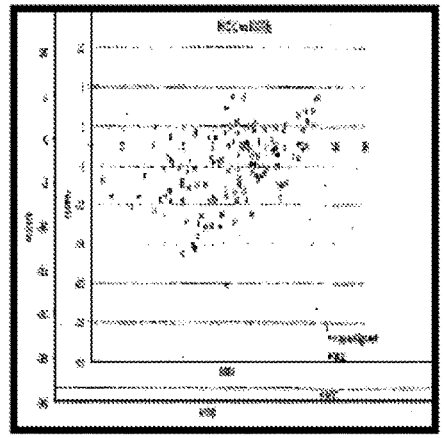

Before describing the embodiments of the invention in detail, it will be useful to provide some definitions of terms as used herein.

The term "marker" refers to a molecule that is associated quantitatively or qualitatively with the presence of a biological phenomenon. Examples of "markers" include a polynucleotide, such as a gene or gene fragment, whether coding or non-coding, DNA or DNA fragment RNA or RNA fragment, whether coding or non-coding; or a gene product, including a polypeptide such as a peptide, oligopeptide, protein, or protein fragment; or any related metabolites, by products, or any other identifying molecules, such as antibodies or antibody fragments, whether related directly or indirectly to a mechanism underlying the phenomenon. The markers of the invention include the nucleotide sequences (e.g., GenBank sequences) as disclosed herein, in particular, the full-length sequences, any coding sequences, any fragments, any possible probes (e.g., created across an exon-exon boundary), including those with capture motifs, hairpins or fluorophores, or any complements thereof, and any measurable marker thereof as defined above.

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence. Further included are camelid antibodies, shark antibodies or nanobodies.

The terms "cancer" and "cancerous" refer to or describe the physiological condition in mammals that is typically characterized by abnormal or unregulated cell growth. Cancer and cancer pathology can be associated, for example, with metastasis, interference with the normal functioning of neighboring cells, release of cytokines or other secretory products at abnormal levels, suppression or aggravation of inflammatory or immunological response, neoplasia, pre-malignancy, malignancy, invasion of surrounding or distant tissues or organs, such as lymph nodes, etc.

The term "tumor" refers to all neoplastic cell growth and proliferation, whether malignant or benign, and all pre-cancerous and cancerous cells and tissues.

The term "bladder cancer" refers to a tumor originating in the bladder. These tumors are able to metastasize to any organ.

The term "BTM" or "bladder tumor marker" or "BTM family member" means a Tumor Marker™ that is associated with urothelial cancers, bladder cancer, transitional cell carcinoma of the bladder (TCC), squamous cell carcinomas, and adenocarcinomas of the bladder. The term BTM also includes combinations of individual markers, whose combination improves the sensitivity and specificity of detecting bladder cancer. It is to be understood that the term BTM does not require that the marker be specific only for bladder tumors. Rather, expression of BTM can be altered in other types of cells, diseased cells, tumors, including malignant tumors.

The term "under expressing BTM" means a marker that shows lower expression in bladder tumors than in non-malignant bladder tissue.

The term "over expressing BTM" means a marker that shows higher expression in bladder tumors than in non-malignant tissue.

The terms "differentially expressed," "differential expression," and like phrases, refer to a gene marker whose expression is activated to a higher or lower level in a subject (e.g., test sample) having a condition, specifically cancer, such as melanoma, relative to its expression in a control subject (e.g., reference sample). The terms also include markers whose expression is activated to a higher or lower level at different stages of the same condition; in diseases with a good or poor prognosis; or in cells with higher or lower levels of proliferation. A differentially expressed marker may be either activated or inhibited at the polynucleotide level or polypeptide level, or may be subject to alternative splicing to result in a different polypeptide product. Such differences may be evidenced by a change in mRNA levels, surface expression, secretion or other partitioning of a polypeptide, for example.

Differential expression may include a comparison of expression between two or more markers (e.g., genes or their gene products); or a comparison of the ratios of the expression between two or more markers (e.g., genes or their gene products); or a comparison of two differently processed products (e.g., transcripts or polypeptides) of the same marker, which differ between normal subjects and diseased subjects; or between various stages of the same disease; or between diseases having a good or poor prognosis; or between cells with higher and lower levels of proliferation; or between normal tissue and diseased tissue, specifically cancer, or melanoma. Differential expression includes both quantitative, as well as qualitative, differences in the temporal or cellular expression pattern in a gene or its expression products among, for example, normal and diseased cells, or among cells which have undergone different disease events or disease stages, or cells with different levels of proliferation.

The term "expression" includes production of polynucleotides and polypeptides, in particular, the production of RNA (e.g., mRNA) from a gene or portion of a gene, and includes the production of a polypeptide encoded by an RNA or gene or portion of a gene, and the appearance of a detectable material associated with expression. For example, the formation of a complex, for example, from a polypeptide-polypeptide interaction, polypeptide-nucleotide interaction, or the like, is included within the scope of the term "expression". Another example is the binding of a binding ligand, such as a hybridization probe or antibody, to a gene or other polynucleotide or oligonucleotide, a polypeptide or a protein fragment, and the visualization of the binding ligand. Thus, the intensity of a spot on a microarray, on a hybridization blot such as a Northern blot, or on an immunoblot such as a Western blot, or on a bead array, or by PCR analysis, is included within the term "expression" of the underlying biological molecule.

The terms "gene expression threshold," and "defined expression threshold" are used interchangeably and refer to the level of a marker in question, outside which the expression level of the polynucleotide or polypeptide serves as a predictive marker for a condition in the patient. For example, the expression of IL8Rb above a certain threshold is diagnostic that the patient has an inflammatory condition. A threshold can also be used when testing a patient for suspected bladder cancer, using bladder cancer makers. Expression levels above a threshold indicates that the patient has an inflammatory bladder condition, likely to cause a false positive test for cancer, whereas an expression level of IL8Rb below a threshold is predictive that the patient does not have an inflammatory bladder condition. By including the measurement of IL8Rb any result from the expression of the bladder tumor markers can be relied upon if the levels of IL8Rb is below the threshold (i.e. a positive result is likely to be positive for the patient having cancer rather than increased levels of the bladder tumor markers actually resulting from exfoliation of non-malignant cells from the mucosa from inflammation).

The term "diagnostic threshold" refers to a threshold in which a patient can be said to have been diagnosed either with or without a given condition, for example bladder cancer. A diagnostic threshold is generally set to achieve a desired sensitivity and specificity, depending on factors such as population, prevalence, and likely clinical outcome. In general the diagnostic threshold can be calculated and/or established using algorithms, and/or computerized data analysis.

The exact threshold will be dependent on the population and also any model being used to predict disease (predictive model). A threshold is established experimentally from clinical studies such as those described in the Examples below. Depending on the prediction model used, the expression threshold may be set to achieve maximum sensitivity, or for maximum specificity, or for minimum error (maximum classification rate). For example a higher threshold may be set to achieve minimum errors, but this may result in a lower sensitivity. Therefore, for any given predictive model, clinical studies will be used to set an expression threshold that generally achieves the highest sensitivity while having a minimal error rate.

The term "sensitivity" means the proportion of individuals with the disease who test (by the model) positive. Thus, increased sensitivity means fewer false negative test results.

The term "specificity" means the proportion of individuals without the disease who test (by the model) negative. Thus, increased specificity means fewer false positive test results.

The term "Receiver Operating Characteristic" ("ROC curve") means a plot of the true positive rate (sensitivity) against the false positive rate (specificity) for different cut off points for a particular marker or test. Each point on the ROC curve represents a specific sensitivity/specificity point that will correspond to a given threshold. ROC curves can be important to establish a threshold to give a desired outcome. The area under a ROC curve represents (expressed as an Area Under the Curve (AUC) analysis, can be a measure of how well a given marker or test consisting of a number of markers, can distinguish between two or more diagnostic outcomes. ROC curves can also be used to compare the accuracy of two different tests.

The term "oligonucleotide" refers to a polynucleotide, typically a probe or primer, including, without limitation, single-stranded deoxyribonucleotides, single- or double-stranded ribonucleotides, RNA: DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "overexpression" or "overexpressed" refers to an expression level of a gene or marker in a patient that is above that seen in normal tissue. Expression may be considered to be overexpressed if it is 1.1, 1.2, 1.3, 1.4, 1.5, 1.6, 1.7, 1.8, 1.9, 2, 10, 100, 1000, or up to 10,000 times the expression in normal tissue or in tissues from another group of patients.

The term "polynucleotide," when used in the singular or plural, generally refers to any polyribonucleotide or polydeoxribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences. It will be understood that each reference to a "polynucleotide" or like term, herein, will include the full-length sequences as well as any fragments, derivatives, or variants thereof.

The term "phenotypic," means a trait that is observable in a clinical setting, or in a clinical interview, or in a patient's history. When used in a formula for calculating G+P index, "phenotypic" or "P" means the patient's age, sex, incidence of hematuria, and smoking history.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

The term "qPCR" or "QPCR" refers to quantitative polymerase chain reaction as described, for example, in PCR Technique: Quantitative PCR, J. W. Larrick, ed., Eaton Publishing, 1997, and A-Z of Quantitative PCR, S. Bustin, ed., IUL Press, 2004.

The term "Reverse Transcription" means a process in which an oligoribonucleotide, including a messenger RNA ("mRNA") is used as a template for biochemical synthesis of a complementary oligodeoxyribonucleotide ("cDNA") using an enzyme ("Reverse Transcriptase"), which binds to the template RNA, and catalyzes a series of addition reactions that sequentially attaches deoxyribonucleotide bases to form an oligodeoxyribonucleotide strand that is complementary to the RNA template.

The term "Hematuria" is defined as the presence of blood in the urine. It may present as macroscopic hematura (visible traces of blood cells) or microscopic hematuria (microscopic traces of blood) within the urine. A confirmed indication of microhematuria is defined as 3 or more red blood cells present per microscopic high-powered field (HPF) on a minimum of 3 properly collected urine samples. Microhematuria may also be detected by urine dipstick (colorimetric comparison estimate) at clinic. Hematuria (either microscopic or macroscopic) may be asymptomatic (no additional symptoms associated with hematuria) or symptomatic. Additional symptoms include dysuria (painful urination), a feeling of incomplete emptying of the bladder or increased frequency or urination.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. Additional details and explanation of stringency of hybridization reactions, are found e.g., in Ausubel et al., Current Protocols in Molecular Biology, Wiley Interscience Publishers, (1995).

"Stringent conditions" or "high stringency conditions", as defined herein, typically: (1) employ low ionic strength and high temperature for washing. For example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Fico11/0.1% polyvinylpyrrolidone/50 mM sodium phosphate, buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×, Denhardt's solution, sonicated salmon sperm DNA (50 ug/ml), 0.1% SDS, and 10% dextran sulfate at 42° C., with washes at 42° C. in 0.2×SSC (sodium chloride/sodium citrate) and 50% formamide at 55° C., followed by a high-stringency wash comprising 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e. g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "IL8Rb" means neutrophil marker interleukin 8 receptor B (also known as chemokine (C-X-C motif) receptor 2 [CXCR2]) (FIG. 1; SEQ ID NOs. 1 and 2), and includes the marker IL8Rb. The term includes a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments.

The term "reliability" includes the low incidence of false positives and/or false negatives. Thus, with higher reliability of a marker, fewer false positives and/or false negatives are associated with diagnoses made using that marker.

"Accuracy" is the proportion of true results (true positives plus true negatives) divided by the number of total cases in the population, according to the formula:

$$\frac{\text{True Positives} + \text{True Negatives}}{\text{Total Number of Measurements}}$$

The term "triage" means to differentiate patients with hematuria that have a low probability of having bladder cancer from those patients with hematuria that have a reasonable probability of having bladder cancer and requiring further clinical work up, including cystoscopy or other clinical procedure.

Embodiments

Therefore, in certain preferred embodiments, a combination of genetic markers and phenotypic markers are provided that permit differentiating patients having a low probability of having bladder cancer from those patients with a sufficient risk of having bladder to warrant further clinical work up, possibly including cystoscopy or other procedures. In other embodiments, markers are provided that have reliability greater than about 70%; in other embodiments, greater than about 73%, in still other embodiments, greater than about 80%, in yet further embodiments, greater than about 90%, in still others, greater than about 95%, in yet further embodiments greater than about 98%, and in certain embodiments, about 100% reliability.

For genetic analysis, the practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, 2nd edition, Sambrook et al., 1989; Oligonucleotide Synthesis, M J Gait, ed., 1984; Animal Cell Culture, R. I. Freshney, ed., 1987; Methods in Enzymology, Academic Press, Inc.; Handbook of Experimental Immunology, 4th edition, D. M. Weir & CC. Blackwell, eds., Blackwell Science Inc., 1987; Gene Transfer Vectors for Mammalian Cells, J. M. Miller & M. P. Calos, eds., 1987; Current Protocols in Molecular Biology, F. M. Ausubel et al., eds., 1987; and PCR: The Polymerase Chain Reaction, Mullis et al., eds., 1994.

It is to be understood that the above terms may refer to protein, DNA sequence and/or RNA sequence. It is also to be understood that the above terms also refer to non-human proteins, DNA and/or RNA having homologous sequences as depicted herein.

Embodiments of this Invention

Often patients referred to a urologist with hematuria are booked to be seen in a dedicated hematuria clinic. Patients with macroscopic hematuria are often prioritized over those with micro hematuria. The information provided at the time of referral from the primary care provider can be highly variable, making accurate stratification of patients by probability of having a urothelial cancer difficult. Often urine cytology is routinely requested before the patient is seen and, if positive, is used to increase the patients priority of receiving a full clinical work-up, however urine cytology, whilst highly specific, has a very low sensitivity and hence is of little practical value with its high rate of false-negatives [6].

Phenotypic and Genotypic Analysis of Patients with Hematuria not Having Bladder Cancer G+P Index Phenotypic and genotypic variables described above are combined into a G+P INDEX according to the following relationship:

$$G+P\ INDEX = (w1*HFREQ + w2*AgeGT50 + w3*Gender + w4*SMK + w5*RBC) + (w6*M1 + w7*IL-8),$$

where HFREQ means the frequency of finding 3 or more red blood cells per high power field in a 6-month period; if frequency is low then HFREQ=0, and if higher than 3 red blood cells per high power field, then 1. AgeGT50 refers to subject's age, if greater than 50 years then AgeGT50=1, and if less than 50 years, then 0. Gender is assigned a value of 1 for male, and 0 for female. SMK means whether the subject is a current or ex-smoker; if non-smoker then SMK=0 and if a smoker, then 1. RBC means red blood cell count; if 25 or more then RBC is set to 1, and if less than 25, then 0. M1 is a combination of expression of the genetic markers MDK, CDC, IGFBP5, and HOXA13; if M1>4.5 then set it to 1, if less than 4.5, 0. IL-8 refers to expression level of RNA for IL-8; if IL-8>2.5 then IL-8 is set to 1, if ness than 2.5, 0. The symbols "*" means the multiplication operator, and weighting factors, w1-w7 are respectively the weights assigned to each of the variables listed above in the G+P INDEX.

In other preferred embodiments, (AgeGT50 and RBC) may be dropped from the model as shown below:

$$G+P\ INDEX = (1*HFREQ + 3*Gender + 4*SMK) + (5*M1 + 2*IL-8)$$

The G+P INDEX produces a value between 0 and 15. A patient with G+P INDEX value of 11 to 15 is considered to be at "High Risk" for bladder cancer, and indicates the need for additional work up for bladder cancer. A patient with a G+P INDEX value of 6 to 10 is considered to be at "Moderate Risk" for developing bladder cancer, and additional work up is indicated. A patient with a G+P INDEX of 0 to 5 is considered to be at "Low Risk" for developing bladder cancer. Patients in the "Low Risk" group are placed on a watchful waiting list, and if additional symptoms appear, or if recurrent episodes of microhematuria occur, they are reevaluated for possible further work up.

Genotypic variables useful for differentiating patients without and with bladder cancer include expression of RNA markers "M1" being a combination of MDK, CDC, IGFBP5 (IGBP5), and HOXA13. Another genotypic variable is expression of RNA for IL8R. Coefficients for these genotypic variables are shown in Table 7 below. A threshold of 4.5 and 2.5 was used for M1 and IL8R, respectively, and a coefficient of 5 and 2, respectively, were assigned.

The G+P INDEX produces a value between 0 and 15. A G+P INDEX value of 11 to 15 is considered "High Risk" for bladder cancer, and indicates the need for additional work up for bladder cancer. A G+P INDEX value of 6 to 10 is considered "Moderate Risk" for developing bladder cancer, and additional work up is indicated. A G+P INDEX of 0 to 5 is considered "Low Risk" for developing bladder cancer, and these patients are placed on a waiting list, and if additional symptoms appear, or if recurrent episodes of microhematuria occur, are reevaluated for possible fuller work up.

As described more fully in Example 3 (FIGS. 18 and 19), we found that the ROC curve for phenotypic data alone produced a modest level of diagnostic power. The ROC curve for genotypic data alone produced a significant level of diagnostic power. We found an unexpectedly better diagnostic power when both genotypic and phenotypic data was combined into a G+P INDEX.

Genetic Analysis of Patients not Having Bladder Cancer

In some preferred embodiments, this invention combines use of a 4-marker assay or a Cxbladder® assay (genotypic variables) and one or more of five key risk factors (phenotypic variables) to produce a selection index that can be used to triage patients with microscopic or macroscopic hematuria in terms of their potential risk of having urothelial cancer. While not precluding the need for a flexible cystoscopy, patients deemed at high risk of urothelial cancer based on phenotypic variables and genotypic variables may be seen earlier, potentially improving overall patient outcome.

Genotypic markers can be used as tools to detect cancer-free patients or to select patient groups that are at low, medium or high risk of having a disease. The markers can, for example, be differentially expressed between disease tissue and corresponding non-disease tissue. In this situation, the detection of differential expression is associated with the presence of the disease. Alternatively, the marker can be associated directly with changes occurring in the disease tissues, or changes resulting from the disease. Inflammatory diseases are associated with an increase in neutrophils. It has been found that the neutrophil marker interleukin 8 receptor B (IL8Rb; FIG. 1; SEQ ID NOs 1 and 2), can provide a good marker for the presence of neutrophils in a sample, and therefore can be used as a diagnostic marker for the detection of inflammatory disease in a sample, and in particular, in the detection of inflammatory disease of the bladder.

Figure 5:
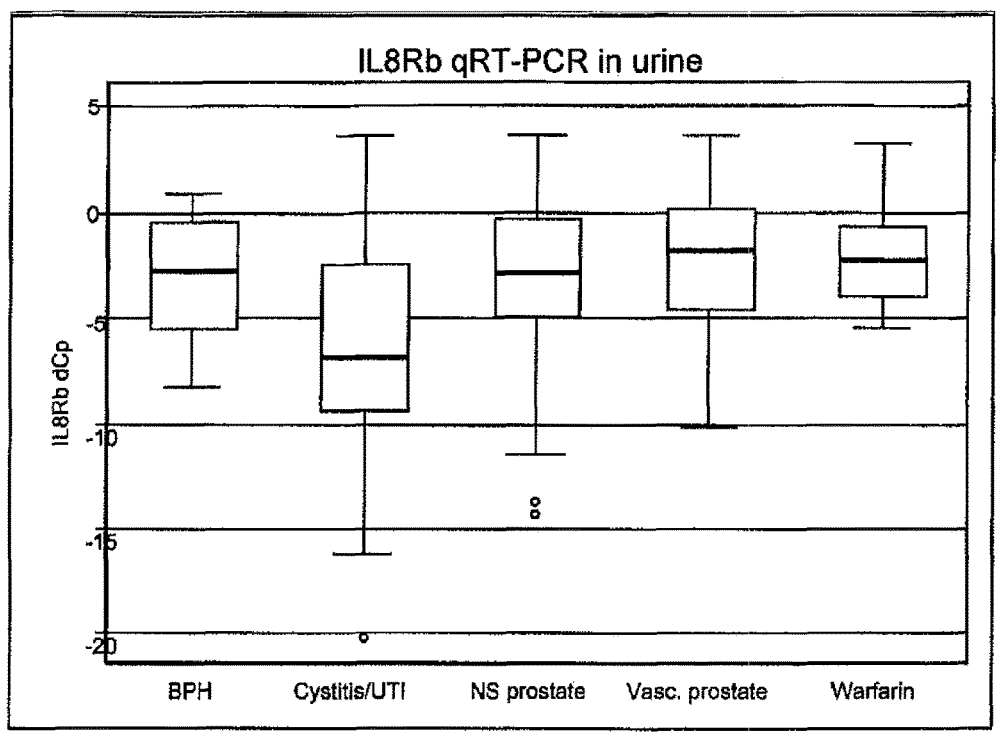
FIG. 5 depicts box plots showing the accumulation of IL8Rb mRNA in the urine of patients with non-malignant urological disease. The RNA has been quantified by qRT-PCR using the delta-Ct method (Holyoake et al, 2008). With this method a lower Ct reflects higher RNA levels. BPH: benign prostatic hyperplasia; UTI: urinary tract infection; NS prostate: non-specific prostate diseases; Vasc. Prostate: vascular prostate; warfarin: hematuria secondary to warfarin use. The observations in patients with cystitis/UTI are significantly different (p=0.001) to the other non-malignant presentations shown.

As shown in FIG. 5, accumulation of IL8Rb in urine is indicative of the presence of inflammatory disease of the bladder. Specifically, FIG. 5 shows the accumulation of IL8Rb in the urine of patients having the conditions; benign prostatic hyperplasia, urinary tract infection, non-specific prostate diseases, vascular prostate and secondary warfarin use. It will be appreciated however, that the use of IL8Rb is not be limited to the detection of these diseases only, but that these examples show that IL8Rb does increase in samples from patients having an inflammatory disease of the bladder. That is, IL8Rb can be used as a marker of inflammation associated with bladder disease and therefore is suitable for use in detecting any condition associated with inflammation. Therefore, the detection of the amount of IL8Rb can be used as a marker for inflammatory disease of the bladder. More particularly, IL8Rb can be used to detect inflammatory disease of the bladder associated with the accumulation of neutrophils.

Urine tests for TCC rely largely on the presence of markers in the urine derived from exfoliated tumor cells. The ability to detect these cells can be masked by the presence of large numbers of contaminating cells, such as, blood and inflammatory cells. Moreover, inflammation of the bladder lining can result in the increased exfoliation of non-malignant cells from the mucosa. As a result, urine tests that use markers derived from bladder transitional cells have a higher likelihood of giving a false positive result from urine samples taken from patients with cystitis, urinary tract infection or other conditions resulting in urinary tract inflammation or transitional cell exfoliation, such as, urolithiasis (Sanchez-Carbayo et al).

One way to try and avoid such false positive results has been to select markers with low relative expression in blood or inflammatory cells. The use of such markers results in fewer false positives in TCC patients presenting with non-malignant, inflammatory conditions. However, low expression of the markers in hematologically-derived cells fails to compensate for the enhanced rate of exfoliation of non-malignant transitional cells.

It has been discovered that the negative impact of exfoliated transitional cells from inflamed tissue has on the accuracy of bladder cancer urine tests can be minimized by improving the identification of patients with inflammatory conditions of the urinary tract. Here it has been surprisingly found that using the marker IL8Rb in combination with one or more bladder tumor markers (BTM's) provides for a more accurate detection of bladder cancer. In particular, a marker based test for bladder cancer that includes the marker IL8Rb is less susceptible to false positive results, which can result in patients suffering from an inflammatory non-cancer condition.

In general, the presence or absence of an inflammatory condition is established by having a threshold of gene expression, above which expression of IL8Rb is indicative of an inflammatory condition. For example, the expression of IL8Rb above a certain threshold is diagnostic that the patient has an inflammatory condition (see thresholds described above)

When IL8Rb is used in conjunction with one or more markers predictive for the presence of bladder cancer, the presence of elevated expression of the bladder tumor marker(s), and expression of IL8Rb, above a certain threshold, is predictive of the patient having an inflammatory condition and not cancer. Furthermore, if the test is preformed on urine from the patient, then this result is predictive of the patient having an inflammatory bladder condition. The high levels of the bladder tumor markers are most likely the result of non-malignant cells coming from the mucosa as a result of the inflammation. That is, the patient, although having high levels of the bladder tumor marker(s) does not actually have bladder cancer—a false positive.

Alternatively, if the patient has abnormally high levels or diagnostic levels of one or more bladder tumor markers, but the level of IL8Rb is below a threshold, then the patient is likely to have cancer, and in particular bladder or urothelial cancer. This is especially so, if the test is preformed on urine from the patient. This result is of significant benefit to the health provider because they can be sure that the patient does have cancer, and can start treatment immediately, and not be concerned that the result is actually caused an inflammatory condition giving a false positive result.

It has been surprisingly shown that the quantification of RNA from the gene encoding the neutrophil marker interleukin 8 receptor B (IL8Rb) improves the overall performance of detecting patients with TCC, using known TCC or BTM markers. The reference sequences for IL8Rb are shown in FIG. 1 and SEQ ID NOs 1 and 2). In addition to its role in TCC detection, it has been explored whether IL8Rb could be used as a urine marker to aid in the diagnosis of inflammatory disease (FIG. 5).

The use of IL8Rb marker can be used in isolation for the detection of inflammatory conditions of the bladder utilizing known methods for detecting gene expression levels. Examples of methods for detecting gene expression are outlined below.

Alternatively, IL8Rb can be combined with one of more BTMs to detect bladder cancer. It has been shown that by utilizing the inflammatory disease marker IL8Rb as part of the test for bladder cancer, the influence of inflamed tissue on creating a false positive result is minimized. The marker IL8Rb can be used in association with any bladder cancer markers, or alternatively can be used with two or more markers, as part of a signature, for detecting bladder cancer.

Reducing the number of false positive results means that fewer patients not having bladder cancer are subjected to potentially unnecessary procedures, including cystoscopy, which carries its own risks. Reducing the number of false negative results means that it is more likely that a patient with bladder cancer is detected, and can therefore be further evaluated for cancer.

The action of IL8Rb to improve the detection of bladder cancer results from the ability to separate non-malignant conditions from patients having bladder cancer. This is achieved because an increase of IL8Rb is indicative of an increase in the presence of neutrophils in a sample. Therefore, the ability of IL8Rb is not dependent on the bladder tumor marker used. As shown in FIGS. 2, and 12 to 15, when combined with a variety of bladder tumor markers and combinations of bladder tumor markers, IL8Rb had the general effect of increasing the specificity of the ability of the marker(s) to detect cancer in the subjects.

One example of a signature according to the present invention is the use of IL8Rb in combination with MDK, CDC2, IGFBP5 and HOXA13, which may also be in combination with one or more other marker suitable for detecting bladder cancer, for example any one of more of the markers outlined in FIG. 6 or 7. As shown in FIGS. 14 and 15, IL8Rb can be used in any combination of the markers, specifically the combinations IL8Rb/MDK, IL8Rb/CDC2, IL8Rb/HOXA13, IL8Rb/IGFBP5, IL8Rb/MDK/CDC2, IL8Rb/MDK/HOXA13, IL8Rb/MDK/IGFBP5, IL8Rb/CDC2/HOXA13, IL8Rb/CDC2/IGFBP5, IL8Rb/HOXA13/IGFBP5, IL8Rb/MDK/CDC2/HOXA13, IL8Rb/MDK/CDC2/IGFBP5, IL8Rb/CDC2/HOXA13/IGFBP5, and IL8Rb/MDK/CDC2/HOXA13/IGFBP5. As shown in FIGS. 14 and 15, the inclusion of IL8Rb increased the ability of the marker, or the combination of markers to accurately diagnose bladder cancer in a subject. The present invention is not to be limited to these specific combinations but can optionally include one or more further markers suitable for detecting bladder cancer, for example any one of more of the markers outlined in FIG. 6 or 7. Table 1 below shows the identifiers for the specific markers MDK, CDC2, IGFBP5 and HOXA13 and IL8Rb.

through 17 also show the effect of IL8Rb in the various combinations of the four markers MDK, CDC2, IGFBP5 and HOXA13.

FIG. 14 shows the ROC curves for all the combinations of the four markers MDK, CDC2, IGFBP5 and HOXA13, with and without IL8Rb, calculated using five different classifier models (i) Linear Discriminant Analysis (LDA), (ii) Logistic Regression (LogReg), (iii) Support Vector Machines (SVM), (iv) K-nearest 5 neighbors (KN5N), and (v) Partition Tree Classifier (TREE). FIG. 15 tabulates the Area Under the Curve (AUC) for all 5 classifiers and all 15 combinations of the 4 biomarkers, with and without IL8Rb. This AUC calculation is restricted to the area from a false positive rate of 0 to a false positive rate of 20%, covering the useful ranges of specificity (80-100%). The AUC quantifies the visible differences on the ROC curves of FIG. 14. FIG. 16 shows the sensitivity of all combinations of the four markers measured with and without IL8Rb at specificities of FIG. 16(a) 80%, FIG. 16(b) 85%, FIG. 16(c) 90%, FIG. 16(d) 95%, and FIG. 16(e) 98%. FIG. 17 tabulates the changes in either sensitivity (vertical direction on the ROC curves; better is "up") or specificity (horizontal direction on the ROC curve; better is to the left) at the fixed specificities of FIGS. 17(a, f) 80%, FIGS. 17(b, g) 85%, FIGS. 17(c, h) 90%, FIGS. 17(d, I) 95%, and FIGS. 17(e, j) 98%, respectively.

These results show that IL8Rb, in general, improves the ability of the biomarkers (MDK, CDC, IGFBP5, and HOXA13), singly or in combination, to classify tumor from normal samples.

TABLE 1

Identifiers for Bladder Tumor Markers

| PE Gene Name | HGNC Gene Name (Official) | NCBI RefSeq | NCBI Entrez Gene ID | HGNC URL |
|---|---|---|---|---|
| MDK | MDK | NM_002391 | 4192 | http://www.genenames.org/data/hgnc_data.php?hgnc_id=6972 |
| CDC | CDK1 | NM_001170406 | 983 | http://www.genenames.org/data/hgnc_data.php?hgnc_id=1722 |
| IGF | IGFBP5 | NM_000599 | 3488 | http://www.genenames.org/data/hgnc_data.php?hgnc_id=5474 |
| HOXA | HOXA13 | NM_000522 | 3209 | http://www.genenames.org/data/hgnc_data.php?hgnc_id=5102 |
| IL8Rb | CXCR2 | NM_001168298 | 3579 | http://www.genenames.org/data/hgnc_data.php?hgnc_id=6027 |

FIGS. 2 to 4 and 12 to 17 show the effect of using IL8Rb in combination with four known, representative, markers of bladder cancer; MDK, CDC2, IGFBP5 and HOXA13. The results show that by incorporating the use if IL8Rb individually with each marker (FIGS. 2, 14 and 15 to 17), but also when used with all possible combinations of the four BTM markers as a signature, there is an improvement in the ability to separate the samples of patients with TCC and those with non-malignant conditions.

As shown in FIGS. 10 to 13, the inclusion of IL8Rb with the four markers MDK, CDC2, IGFBP5 and HOXA13 (uRNA-D) not only increased the overall performance of the test compared to the four markers alone, the test also compared extremely favorably with other known tests, NMP22® "a registered trademark of Matritech, Inc., of Massachusetts, United States" Elisa, NMP22 BladderChek® (a registered trademark of Matritech, Inc., of Massachusetts, United States), and cytology. FIGS. 14

These results generally show that the IL8Rb was able to increase the accuracy at which the test could detect bladder or urothelial cancer. The biggest gains were seen with either markers that did not perform as well without the inclusion of IL8Rb or with classifiers that did not perform as well. Smaller gains were seen for markers and/or classifiers that performed well prior to adding IL8Rb and therefore there was less room for improvement. It is important to note that the results show a population based analysis and the benefit of incorporating IL8Rb could be greater when diagnosis individual patients, especially those whose diagnosis on the expression of the BTM markers maybe unclear.

These results show that not only can IL8Rb be used to detect inflammatory disease of the bladder, but also when used in combination with markers for bladder cancer, results in an improved detection of bladder cancer, arising from a reduction in "false positive" results.

These results also show the utility of IL8Rb in that it affects the overall performance of the various markers combinations, and confirms the ability of IL8Rb to improve the performance of one or more bladder cancer markers to accurately detect cancer in a patient. Further, FIG. 14 and FIG. 15 show that the same results can be achieved using a range of classifier models, and shows that the result is not dependent on a classifier model or algorithm, but rather the combination of markers used. These results confirm that any suitable classifier model or algorithm could be used in the present invention. In particular, FIG. 14 and FIG. 15 show that IL8Rb has a greater effect at the higher specificities, and in particular in the most clinically applicable ranges.

Therefore, using the G+P Index of this invention, we are able to accurately triage patients with hematuria based on phenotypic and genetic variables into groups being at "High Risk" for having urothelial cancer and warrant immediate further work-up, "At Risk" and warrant immediate work-up, and those with "Low Risk" who may be placed on a watch list for later evaluation.

Detection of Genetic Markers in Body Samples

In several preferred embodiments, assays for cancer can be desirably carried out on samples obtained from blood, plasma, serum, peritoneal fluid obtained for example using peritoneal washes, or other body fluids, such as urine, lymph, cerebrospinal fluid, gastric fluid or stool samples. For the detection of inflammatory conditions of the bladder or bladder cancer the test is ideally preformed on a urine sample.

Specifically, present methods for detecting inflammatory bladder disease or bladder cancer can be conducted on any suitable sample from the body that would be indicative of the urine, but ideally the level of IL8Rb, and any further cancer marker is established directly from a urine sample.

A test can either be performed directly on a urine sample, or the sample may be stabilized by the addition of any suitable compounds or buffers known in the art to stabilize and prevent the breakdown of RNA and/or protein in the sample so that it can be analyzed at a later date, or even to ensure that the RNA and/or protein is stabilized during the analysis.

The determination of either the protein and/or RNA level in the subject's urine can be performed directly on the urine, or the urine can be treated to further purify and/or concentrate the RNA and/or protein. Many methods for extracting and/or concentrating proteins and/or RNA are well known in the art and could be used in the present invention.

It can be appreciated that many methods are well known in the art for establishing the expression level of a particular gene, either at the RNA and/or protein level, and any suitable method can be used in the present invention. Some common methods are outlined below, however, the invention is not restricted to these methods and any method for quantifying protein and/or RNA levels is suitable for use in the present invention.

General Approaches to Disease and Cancer Detection Using Genotypic Markers

General methodologies for determining expression levels are outlined below, although it will be appreciated that any method for determining expression levels would be suitable.

Quantitative PCR (qPCR)

Quantitative PCR (qPCR) can be carried out on tumor samples, on serum and plasma using specific primers and probes. In controlled reactions, the amount of product formed in a PCR reaction (Sambrook, J., E Fritsch, E. and T Maniatis, Molecular Cloning: A Laboratory Manual $3^{rd}$. Cold Spring Harbor Laboratory Press: Cold Spring Harbor (2001)) correlates with the amount of starting template. Quantification of the PCR product can be carried out by stopping the PCR reaction when it is in log phase, before reagents become limiting. The PCR products are then electrophoresed in agarose or polyacrylamide gels, stained with ethidium bromide or a comparable DNA stain, and the intensity of staining measured by densitometry. Alternatively, the progression of a PCR reaction can be measured using PCR machines such as the Applied Biosystems' Prism 700™ (a trademark of Applera Corporation, Connecticut, United States) or the Roche LightCycler™ (a trademark of Roche Molecular Systems, Inc., California, United States), which measure product accumulation in real-time. Real-time PCR measures either the fluorescence of DNA intercalating dyes such as Sybr Green into the synthesized PCR product, or the fluorescence released by a reporter molecule when cleaved from a quencher molecule; the reporter and quencher molecules are incorporated into an oligonucleotide probe which hybridizes to the target DNA molecule following DNA strand extension from the primer oligonucleotides. The oligonucleotide probe is displaced and degraded by the enzymatic action of the Taq polymerase in the next PCR cycle, releasing the reporter from the quencher molecule. In one variation, known as Scorpion, the probe is covalently linked to the primer.

Reverse Transcription PCR (RT-PCR)

RT-PCR can be used to compare RNA levels in different sample populations, in normal and tumor tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from human tumors or tumor cell lines, and corresponding normal tissues or cell lines, respectively. RNA can be isolated from a variety of samples, such as tumor samples from breast, lung, colon (e.g., large bowel or small bowel), colorectal, gastric, esophageal, anal, rectal, prostate, brain, liver, kidney, pancreas, spleen, thymus, testis, ovary, uterus, bladder etc., tissues, from primary tumors, or tumor cell lines, and from pooled samples from healthy donors. If the source of RNA is a tumor, RNA can be extracted, for example, from frozen or archived paraffin-embedded and fixed (e.g., formalin-fixed) tissue samples.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp® RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3-5' proofreading endonuclease activity. Thus, Taq-Man® qPCR (a registered trademark of Roche Molecular Systems, Inc., California, United States) typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR (a registered trademark of Roche Molecular Systems, Inc., California, United States) can be performed using commercially available equipment, such as, for example, ABI PRISM 7700™ Sequence Detection System (a trademark of Applera Corporation, Connecticut, United States) (Perkin-Elmer-Applied Biosystems, Foster City, Calif., USA), or Lightcycler™ (a registered trademark of Roche Molecular Systems, Inc., California, United States ((Roche Molecular Biochemicals, Mannheim, Germany). In a preferred embodiment, the 5' nuclease procedure is run on a real-time quantitative PCR device such as the ABI PRISM 7700™ Sequence Detection System. The system consists of a thermocycler, laser, charge-coupled device (CCD), camera, and computer. The system amplifies samples in a 96-well format on a thermocycler. During amplification, laser-induced fluorescent signal is collected in real-time through fiberoptic cables for all 96 wells, and detected at the CCD. The system includes software for running the instrument and for analyzing the data.

5' nuclease assay data are initially expressed as Cp, or the threshold cycle. As discussed above, fluorescence values are recorded during every cycle and represent the amount of product amplified to that point in the amplification reaction. The point when the fluorescent signal is first recorded as statistically significant is the threshold cycle, Cp.

Real-Time Quantitative PCR (qRT-PCR)

A more recent variation of the RT-PCR technique is the real time quantitative PCR, which measures PCR product accumulation through a dual-labeled fluorigenic probe (i.e., TaqMan® probe. Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996).

Expression levels can be determined using fixed, paraffin-embedded tissues as the RNA source. According to one aspect of the present invention, PCR primers are designed to flank intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the VIMNV for general users and for biologist programmers in: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3' end sequence. In general, optimal PCR primers are generally 1730 bases in length, and contain about 20-80%, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by reference.

Microarray Analysis

Differential expression can also be identified, or confirmed using the microarray technique. Thus, the expression profile of disease specific markers can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences (i.e., capture probes) are then hybridized with specific polynucleotides from cells or tissues of interest (i.e., targets). Just as in the RT-PCR method, the source of RNA typically is total RNA isolated from human tumors or tumor cell lines, and corresponding normal tissues or cell lines. Thus RNA can be isolated from a variety of primary tumors or tumor cell lines. If the source of RNA is a primary tumor, RNA can be extracted, for example, from frozen or archived formalin fixed paraffin-embedded (FFPE) tissue samples and fixed (e.g., formalin-fixed) tissue samples, which are routinely prepared and preserved in everyday clinical practice.

In a specific embodiment of the microarray technique, PCR amplified inserts of cDNA clones are applied to a substrate. The substrate can include up to 1, 2, 5, 10, 15, 20, 25, 30, 35, 40, 45, 50, or 75 nucleotide sequences. In other aspects, the substrate can include at least 10,000 nucleotide sequences. The microarrayed sequences, immobilized on the microchip, are suitable for hybridization under stringent conditions. As other embodiments, the targets for the microarrays can be at least 50, 100, 200, 400, 500, 1000, or 2000 bases in length; or 50-100, 100-200, 100-500, 100-1000, 100-2000, or 500-5000 bases in length. As further embodiments, the capture probes for the microarrays can be at least 10, 15, 20, 25, 50, 75, 80, or 100 bases in length; or 10-15, 10-20, 10-25, 10-50, 10-75, 10-80, or 20-80 bases in length.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual colour fluorescence, separately labeled cDNA probes generated from two sources of RNA are hybridized pairwise to the array. The relative abundance of the transcripts from the two sources corresponding to each specified gene is thus determined simultaneously.

The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93 (2): 106-149 (1996)). Microarray analysis can be performed by commercially available equipment, following manufacturer's protocols, such as by using the Affymetrix GenChip® technology, Illumina microarray technology or Incyte's microarray technology. The development of microarray methods for large-scale analysis of gene expression makes it possible to search systematically for molecular markers of cancer classification and outcome prediction in a variety of tumor types.

RNA Isolation, Purification, and Amplification

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56: A67 (1987), and De Sandres et al., BioTechniques 18: 42044 (1995). In particular, RNA isolation can be performed using purification kit, buffer set, and protease from commercial manufacturers, such as Qiagen, according to the manufacturer's instructions. For example, total RNA from cells in culture can be isolated using Qiagen RNeasy® "a registered trademark of Qiagen GmbH, Hilden, Germany" mini-columns. Other commercially available RNA isolation kits include MasterPure™ Complete DNA and RNA Purification Kit (EPICENTRE (D, Madison, Wis.), and Paraffin Block RNA Isolation Kit (Ambion, Inc.). Total RNA from tissue samples can be isolated using RNA Stat-60 (Tel-Test). RNA prepared from tumour can be isolated, for example, by cesium chloride density gradient centrifugation.

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 micron thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined.

Immunohistochemistry and Proteomics

Immunohistochemistry methods are also suitable for detecting the expression levels of the proliferation markers of the present invention. Thus, antibodies or antisera, preferably polyclonal antisera, and most preferably monoclonal antibodies specific for each marker, are used to detect expression. The antibodies can be detected by direct labeling of the antibodies themselves, for example, with radioactive labels, fluorescent labels, hapten labels such as, biotin, or an enzyme such as horseradish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomics can be used to analyze the polypeptides present in a sample (e.g., tissue, organism, or cell culture) at a certain point of time. In particular, proteomic techniques can be used to assess the global changes of polypeptide expression in a sample (also referred to as expression proteomics). Proteomic analysis typically includes: (1) separation of individual polypeptides in a sample by 2-D polyacrylamide gel electrophoresis (2-D PAGE); (2) identification of the individual polypeptides recovered from the gel, e.g., by mass spectrometry or N-terminal sequencing, and (3) analysis of the data using bioinformatics. Proteomics methods are valuable supplements to other methods of gene expression profiling, and can be used, alone or in combination with other methods, to detect the products of the proliferation markers of the present invention.

Hybridization Methods Using Nucleic Acid Probes Selective for a Marker

These methods involve binding the nucleic acid probe to a support, and hybridizing under appropriate conditions with RNA or cDNA derived from the test sample (Sambrook, J., E Fritsch, E. and T Maniatis, Molecular Cloning: A Laboratory Manual $3^{rd}$. Cold Spring Harbor Laboratory Press: Cold Spring Harbor (2001)). These methods can be applied to markers derived from a tumour tissue or fluid sample. The RNA or cDNA preparations are typically labeled with a fluorescent or radioactive molecule to enable detection and quantification. In some applications, the hybridizing DNA can be tagged with a branched, fluorescently labeled structure to enhance signal intensity (Nolte, F. S., Branched DNA signal amplification for direct quantitation of nucleic acid sequences in clinical specimens. Adv. Clin. Chem. 33, 201-35 (1998)). Unhybridized label is removed by extensive washing in low salt solutions such as 0.1×SSC, 0.5% SDS before quantifying the amount of hybridization by fluorescence detection or densitometry of gel images. The supports can be solid, such as nylon or nitrocellulose membranes, or consist of microspheres or beads that are hybridized when in liquid suspension. To allow washing and purification, the beads may be magnetic (Haukanes, B-1 and Kvam, C., Application of magnetic beads in bioassays. Bio/Technology 11, 60-63 (1993)) or fluorescently-labeled to enable flow cytometry (see for example: Spiro, A., Lowe, M. and Brown, D., A Bead-Based Method for Multiplexed Identification and Quantitation of DNA Sequences Using Flow Cytometry. Appl. Env. Micro. 66, 4258-4265 (2000)).

A variation of hybridization technology is the QuantiGene Plex® assay (a registered trademark of Panomics, of California, United States) (Genospectra, Fremont) which combines a fluorescent bead support with branched DNA signal amplification. Still another variation on hybridization technology is the Quantikine® mRNA assay (R&D Systems, Minneapolis). Methodology is as described in the manufacturer's instructions. Briefly the assay uses oligonucleotide hybridization probes conjugated to Digoxigenin. Hybridization is detected using anti-Digoxigenin antibodies coupled to alkaline phosphatase in colorometric assays.

Additional methods are well known in the art and need not be described further herein.

Enzyme-Linked Immunological Assays (ELISA)

Briefly, in sandwich ELISA assays, a polyclonal or monoclonal antibody against the marker is bound to a solid support (Crowther, J. R. The ELISA guidebook. Humana Press: New Jersey (2000); Harlow, E. and Lane, D., Using antibodies: a laboratory manual. Cold Spring Harbor Laboratory Press: Cold Spring Harbor (1999)) or suspension beads. Other methods are known in the art and need not be described herein further. Monoclonal antibodies can be hybridoma-derived or selected from phage antibody libraries (Hust M. and Dubel S., Phage display vectors for the in vitro generation of human antibody fragments. Methods Mol Biol. 295:71-96 (2005)). Nonspecific binding sites are blocked with non-target protein preparations and detergents. The capture antibody is then incubated with a preparation of sample or tissue from the patient containing the antigen. The mixture is washed before the antibody/antigen complex is incubated with a second antibody that detects the target marker. The second antibody is typically conjugated to a fluorescent molecule or other reporter molecule that can either be detected in an enzymatic reaction or with a third antibody conjugated to a reporter (Crowther, Id.). Alternatively, in direct ELISAs, the preparation containing the marker can be bound to the support or bead and the target antigen detected directly with an antibody-reporter conjugate (Crowther, Id.).

Methods for producing monoclonal antibodies and polyclonal antisera are well known in the art and need not be described herein further.

Immunodetection

The methods can also be used for immunodetection of marker family members in sera or plasma from bladder cancer patients taken before and after surgery to remove the tumour, immunodetection of marker family members in patients with other cancers, including but not limited to, colorectal, pancreatic, ovarian, melanoma, liver, oesophageal, stomach, endometrial, and brain and immunodetection of marker family members in urine and stool from bladder cancer patients.

Disease markers can also be detected in tissues or samples using other standard immunodetection techniques such as immunoblotting or immunoprecipitation (Harlow, E. and Lane, D., Using antibodies: a laboratory manual. Cold Spring Harbor Laboratory Press: Cold Spring Harbor (1999)). In immunoblotting, protein preparations from tissue or fluid containing the marker are electrophoresed through polyacrylamide gels under denaturing or non-denaturing conditions. The proteins are then transferred to a membrane support such as nylon. The marker is then reacted directly or indirectly with monoclonal or polyclonal antibodies as described for immunohistochemistry. Alternatively, in some preparations, the proteins can be spotted directly onto membranes without prior electrophoretic separation. Signal can be quantified by densitometry.

In immunoprecipitation, a soluble preparation containing the marker is incubated with a monoclonal or polyclonal antibody against the marker. The reaction is then incubated with inert beads made of agarose or polyacrylamide with covalently attached protein A or protein G. The protein A or G beads specifically interact with the antibodies forming an immobilized complex of antibody-marker-antigen bound to the bead. Following washing the bound marker can be detected and quantified by immunoblotting or ELISA.

Establishing a Diagnosis Based on Genotypic Analysis

Once the level of expression of IL8Rb, and optionally one or more further cancer markers, has been obtained then a diagnosis for that subject can be established. If the expression of IL8Rb is above the expression seen in subjects that do not have an inflammatory bladder disease, and/or is consistent with the level of expression in subjects known to have an inflammatory bladder disease, then the subject will be diagnosed as having an inflammatory bladder disease. Alternatively, if the expression is not above the expression seen in subjects that do not have an inflammatory bladder disease, and/or is below the levels of expression in subjects known to have an inflammatory bladder disease, then the subject will be diagnosed as not an inflammatory bladder disease.

In the situation where IL8Rb is used in conjunction with one or more markers for Bladder cancer, then the expression level of IL8Rb will be compared with the level of expression of subjects without an inflammatory bladder disease, and/or subjects known to have an inflammatory bladder disease. The one or more cancer markers are compared to the expression level in subjects without bladder cancer and/or subjects known to have bladder cancer. If the expression level of the IL8Rb is consistent with a subject that does not have an inflammatory bladder disease (less than a subject having an inflammatory bladder disease) and the expression level of the one or more bladder cancer markers are consistent with a subject having bladder cancer (differential to a subject that does not have bladder cancer), then the subject is diagnosed as having bladder cancer. If the expression level of the IL8Rb is greater than a subject that does not have an inflammatory bladder disease (consistent with a subject having an inflammatory bladder disease) and the expression level of the one or more bladder cancer markers are consistent with a subject having bladder cancer (differential to a subject that does not have bladder cancer), then the subject is diagnosed as having an inflammatory bladder disease. If the expression level of the IL8Rb is consistent with a subject that does not have an inflammatory bladder disease (less than a subject having an inflammatory bladder disease) and the expression level of the one or more bladder cancer markers are consistent with a subject that does not have bladder cancer (differential to a subject that does have bladder cancer), then the subject is diagnosed as having neither bladder cancer or an inflammatory bladder disease.

Because there is often an overlap in expression levels between the normal and disease expression of a diagnostic marker, in order to establish a diagnosis for a subject it is typical to establish a classifying threshold. A classifying threshold is a value or threshold which distinguishes subjects into disease or non disease categories. A threshold is commonly evaluated with the use of a Receiver Operating Characteristic (ROC) curve, which plots the sensitivity against specificity for all possible thresholds.

Determination of Diagnostic Thresholds

For tests using disease markers, diagnostic thresholds can be derived that enable a sample to be called either positive or negative for the disease, e.g., bladder cancer. These diagnostic thresholds are determined by the analysis of cohorts of patients that are investigated for the presence of bladder cancer or inflammatory bladder disease. Diagnostic thresholds may vary for different test applications; for example, diagnostic thresholds for use of the test in population screening are determined using cohorts of patients who are largely free of urological symptoms, and these diagnostic thresholds may be different to those used in tests for patients who are under surveillance for bladder cancer recurrence. A diagnostic threshold can be selected to provide a practical level of test specificity in the required clinical setting; that is, a specificity that allows reasonable sensitivity without excessive numbers of patients receiving false positive results. This specificity may be within the range of 80-100%.

A diagnostic threshold is determined by applying an algorithm that combines the genotypic expression levels of each marker to each sample from a prospective clinical trial.

Samples used are from patients with bladder cancer and a range of non-malignant urological disorders. A diagnostic threshold is selected by determining the score of the algorithm that resulted in the desired specificity. For example, in some applications a specificity of 85% is desired. A diagnostic threshold is then set by selecting an algorithm score that results in 85% of patients without bladder cancer being correctly classed as negative for cancer. In other applications (such as population screening), higher specificity, such as 90%, is favoured. To set a threshold for this application, an algorithm score that results in 90% of patients without bladder cancer being correctly classed as negative for cancer is selected. Examples of the use of an algorithm is outlined in the Examples.

As an alternative to single thresholds, the test may use test intervals which provide different degrees of likelihood of presence of disease and which have different clinical consequences associated with them. For example, a test may have three intervals; one associated with a high (e.g. 90%) risk of the presence of bladder cancer, a second associated with a low risk of bladder cancer and a third regarded as being suspicious of disease. The "suspicious" interval could be associated with a recommendation for a repeat test in a defined period of time.

Data Analysis

Once the method to test for the amount of RNA and/or protein has been completed, the data then has to be analyzed in order to determine the distribution of biomarker values associated with tumor and non-tumor samples. This typically involves normalizing the raw data, i.e., removing background "noise" etc and averaging any duplicates (or more), comparison with standards and establishing cut-offs or thresholds to optimally separate the two classes of samples. Many methods are known to do this, and the exact method will depend on specific method for determining the amount of RNA and/or protein used.

Below is an example of how the data analysis could be performed when using qRT-PCR. However, it will be appreciated the general process could be adapted to be used for other methods of establishing the RNA and/or protein content, or other methods could be established by someone skilled in the art to achieve the same result.

Data

Measurements of fluorescence are taken at wavelengths $\omega_i$, $i=1,2$ at each cycle of the PCR. Thus for each well we observe a pair of fluorescence curves, denoted by $f_t(\omega_i)$, where $t=1, \ldots, k$ denotes cycle number and $i=1,2$ indexes the wavelengths.

Fluorescence curves have a sigmoidal shape beginning with a near horizontal baseline and increasing smoothly to an upper asymptote. The location of a point $C_p$ where the fluorescence curve departs from the linear baseline will be used to characterize the concentration of the target gene. A precise definition of $C_p$ follows later. The following is an example of a scheme to process these data.

Compensate for fluorescence overlap between frequency bands,
Estimate a smooth model for each fluorescence curve in order to estimate $C_p$
Combine data from replicated wells.
Estimate standard curves
Compute a concentration relative to the standard.
Each biological sample yields relative concentrations of 5 genes, which are the inputs to the discriminant function.

Color Compensation

Denote the level of fluorescence of dye $j$ at cycle t and frequency $\omega$ by $W_{tj}(\omega)$. In a multiplexed assay the measured response at any frequency $\omega$ is the sum of contributions from all dyes at that frequency, so for each cycle.

$$f_t(\omega) = W_{t1}(\omega) + W_{t2}(\omega) + \ldots$$

The purpose of color compensation is to extract the individual contributions $W_{tj}(\omega)$, from the observed mixtures $f_t(\omega)$.

In the ideal situation, fluorescence $W_{tj}(\omega_o)$, due to dye j at a frequency $\omega$ is proportional to its fluorescence $W_{tj}(\omega_o)$ at reference frequency $\omega_o$, regardless of the level of $W_{tj}(\omega_o)$. This suggests the linear relationship $$\begin{bmatrix} f_t(\omega_1) \\ f_t(\omega_2) \end{bmatrix} = \begin{bmatrix} W_{t1}(\omega_1) + W_{t2}(\omega_1) \\ W_{t1}(\omega_2) + W_{t2}(\omega_2) \end{bmatrix} = \begin{bmatrix} 1 & A_{12} \\ A_{21} & 1 \end{bmatrix} \begin{bmatrix} W_{t1}(\omega_1) \\ W_{t2}(\omega_2) \end{bmatrix}$$

for some proportionality constants $A_{12}$ and $A_{21}$ that are to be determined.

In reality, there are additional effects, which are effectively modeled by introducing linear terms in this system, so $$\begin{bmatrix} f_t(\omega_1) \\ f_t(\omega_2) \end{bmatrix} = \begin{bmatrix} 1 & A_{12} \\ A_{21} & 1 \end{bmatrix} \begin{bmatrix} W_{t1}(\omega_1) \\ W_{t2}(\omega_2) \end{bmatrix} + \begin{bmatrix} a_1 + b_1 t \\ a_2 + b_2 t \end{bmatrix}$$

After estimating the "color compensation" parameters $A_{12}$ and $A_{21}$ we can recover $W_{t1}(\omega_1)$ and $W_{t2}(\omega_2)$, albeit distorted by a linear baseline, by matrix multiplication:

$$\begin{bmatrix} W_{t1}(\omega_1) \\ W_{t2}(\omega_2) \end{bmatrix} = \begin{bmatrix} 1 & A_{12} \\ A_{21} & 1 \end{bmatrix}^{-1} \begin{bmatrix} f_t(\omega_1) \\ f_t(\omega_2) \end{bmatrix} + \begin{bmatrix} a_1^* + b_1^* t \\ a_2^* + b_2^* t \end{bmatrix}$$

$W_{t1}(\omega_1)$ and $W_{t2}(\omega_2)$ are called "color compensated" data. The linear distortions $a_i + b_i^* t$ in the last term of this expression will be accommodated in the baseline estimate when estimating a model for the colour compensated data below 2. It has no influence on the estimate of $C_p$.

Estimation of the color compensation coefficients requires a separate assay using single (as opposed to duplex) probes. Then $W_{t2}(\omega_2) = 0$ giving:

$$\begin{bmatrix} f_t(\omega_1) \\ f_t(\omega_2) \end{bmatrix} = \begin{bmatrix} 1 & A_{12} \\ A_{21} & 1 \end{bmatrix} \begin{bmatrix} W_{t1}(\omega_1) \\ 0 \end{bmatrix} + \begin{bmatrix} a_1 + b_1 t \\ a_2 + b_2 t \end{bmatrix}$$

Thus, $$f_t(\omega_2) = A_{21} f_t(\omega_1) + a^* + b^* t$$

The coefficient $A_{21}$ can be estimated by ordinary linear regression of $f_t(\omega_2)$ on $f_t(\omega_1)$ and PCR cycle t for $t=1, \ldots, k$.

Model Estimation

In this section, let $y_t, t=1, \ldots, k$ denote a color compensated fluorescence curve.

Amplification

Models are only estimated for fluorescence curves that show non-trivial amplification. We define the term "amplification" as a non-trivial departure from the linear baseline of the color compensated fluorescence curve. Use signal to noise ratio (SNR) to quantify amplification. Here SNR is defined as the ratio of signal variance to noise variance. Noise variance is set as part of calibration of the assay procedure and remains unchanged: for this purpose, use the residual variance from a linear model for the baseline from wells that can have no amplification, i.e., wells without RNA. For each fluorescence curve, estimate the signal variance as the residual variance from the best fitting straight line ("best" is meant in the least squares sense.)

If SNR is less than a specified threshold, the fluorescence curve is close to linear and no amplification is present. Then there is no point of departure from the baseline and the concentration in the sample may be declared as zero.

If the SNR is above the threshold, amplification is present and a concentration can be estimated.

Thresholds for the (dimensionless) SNR are selected to provide clear discrimination between "amplified" and "non amplified" curves. For example, the following ranges for thresholds are effective for the markers.

| Fluor | Gene | Range |
|-------|------|-------|
| JOE | MDK | 40-120 |
| JOE | CDC | 35-70 |
| JOE | IL8R | 30-60 |
| FAM | IGF | 50-80 |
| FAM | HOXA | 50-150 |
| FAM | XENO | 50-80 |

Model

Estimate a sigmoidal model for each fluorescence curve. Any suitable parametric form of model can be used, but it must be able to model the following features:

linear baseline that may have a non-zero slope,
asymmetries about the mid point.
asymptotes at lower and upper levels
smooth increase from baseline to upper asymptote An example of a model that achieves these requirements is $$g_t(\theta) = A + A_s t + \frac{D}{\left(1 + \left(\frac{t}{B}\right)^E\right)^F}$$

We call this the "6PL model". The parameter vector $\theta=[A, A_s, D, B, E, F]$ is subject to the following constraints to ensure that $g_t(\theta)$ is an increasing function of t and has the empirical properties of a fluorescence curve.

$D>0, B>0, E<0, F<0$

The other two parameters determine the base line $A+A_s t$, and these parameters do not need explicit constraints though A is always positive and the slope parameter $A_s$ is always small. The parameter D determines the level of amplification above the baseline. The remaining parameters B.E.F have no intrinsic interpretation in themselves but control the shape of the curve. These parameters are also the only parameters that influence the estimate of $C_p$. When $A_s=0$ this is known as the five-parameter logistic function (5PL) and if, in addition, F=1 this model reduces four-parameter logistic model (4PL), Gottschalk and Dunn (2005), Spiess et al. (2008).

Initialization

Initial values for non-linear estimation are set as $A_s=0, F=1$
$A=\text{mean}(y, \ldots, y_5)$
$D=\text{range}(y_1, \ldots, yk)$
B=cycle corresponding to half height
E is initialized by converting $g_t(\theta)$ into a linear form having set the values of the remaining parameters to their initial values defined above. Linearization obtains $$E\log\left(1 + \frac{t}{B}\right) = \log\left(\frac{D}{y_t - A}\right)$$

Now estimate E by regression of log $$\left(\frac{D}{y_t - A}\right)$$

on log $$\left(1 + \frac{t}{B}\right)$$

for t selected so that $$A + \frac{D}{10} < y_t < A + \frac{9D}{10}$$

An alternative form of this model that leads to an almost identical analysis (with its own initialization) is:

$$A + A_s t + \frac{D}{\left(1 + \exp\left(-\frac{t-B}{E}\right)\right)^F}$$

When $A_s=0$ this is sometimes known as the Richards equation, Richards (1959).

Estimation Criterion

Estimate parameters to minimize a penalized sum of squares criterion:

$$\sum_t (y_t - g_t(\theta))^2 + \lambda(\theta)$$

Here $\lambda(\theta)$ is a non-negative function that penalizes large values of some (or all) of the parameters in $\theta$. This method is known as regularization or ridge regression (Hoerl, 1962) and may be derived from a Bayesian viewpoint by setting a suitable prior distribution for the parameter vector $\theta$. A satisfactory choice for the penalty is:

$$\lambda(\theta)=\lambda(B^2+D^2+E^2+F^2)$$

Large values of $\lambda$ bias the parameter estimates towards zero and reduce the variance of the parameter estimates. Conversely, small (or zero) $\lambda$ leads to unstable parameter estimates and convergence difficulties in minimization algorithms. The choice of λ is a compromise between bias and variance or stability. Empirical evidence shows that a satisfactory compromise between bias and variance may be achieved if λ is chosen in the range:

0.01>λ>0.0001.

This choice also ensures convergence of the optimization algorithm.

Algorithm Choice

For any choice of λ in the above range, the description in the previous paragraph completely defines the parameter estimates. A non-linear least squares procedure based on the classical Gauss-Newton procedure (such as the Levenberg-Marquardt algorithm as implemented in More, 1978) has been successfully used and is a suitable approach. General purpose optimizing algorithms such as Nelder and Mead, 1965, or Broyden-Fletcher algorithm as implemented by Byrd, et al., 1995) have also been successfully trialed in this context.

$C_p$ Estimate $C_p$ is the point at time t that maximizes the second derivative of $g_t(\theta)$. Each fluorescence curve yields a $C_p$ that characterizes the concentration of the target gene. The average of the estimated $C_p$s for each set of technical replicates is computed and used in the subsequent analysis.

Standard Curves

Absolute or relative concentrations are derived from a comparison with standard curves on the same PCR plate. Model a dilution series using the linear model:

$$C_p = R + S \log_{10} \text{Conc}$$

where Conc is an absolute or relative concentration of the standard. The intercept and slope parameters are plate specific. Model the between-plate variability in the intercept and slope parameters by setting population models $$R \sim N(\mu_R, \sigma_R^2)$$

$$S \sim N(\mu_S, \sigma_S^2)$$

where the parameters $\mu_R$, $\sigma_R^2$, $\sigma_S^2$ are set on the basis of prior data as described below. Then for a given plate R and S can be interpreted as observations from these populations.

For replicate i of standard at concentration $\text{Conc}_j$ the following model can be used:

$$C_p(i,j) = R + S \log_{10} \text{Conc}_j + \epsilon_{ij}$$

where $\epsilon_{ij} \sim N(0, \sigma_j^2)$. Note that the variance of the residuals depends on $C_p$. Empirical estimates of $\text{Var}(\epsilon_{ij})$ are given in Table 2. Estimate the parameters R and S using by maximizing the likelihood function. Interpret the slope parameter in terms of the efficiency of the PCR process through the expression:

$$S = -\frac{1}{\log_{10} \text{Efficiency}}$$

This model has a Bayesian interpretation: Give vague (non-informative) prior distributions to the parameters $\mu_R$, $\sigma_R^2$, $\sigma_S^2$. Then the population models for R and S and for $C_p(i,j)$ fully determine a probability model for the prior data. A Markov chain Monte Carlo (MCMC) algorithm (Lunn et al., 2009) allows estimation of $\mu_R$, $\sigma_R^2$, $\mu_S$, $\sigma_S^2$. If the prior distribution is omitted, a traditional frequentist interpretation results. Following this estimation procedure it is possible to obtain the gene-dependent population parameter estimates in Table 3.

TABLE 2

| Variance of Residuals | |
|---|---|
| $C_p$ | $\sigma^2$ |
| 12 | 0.0100 |
| 13 | 0.0108 |
| 14 | 0.0119 |
| 15 | 0.0134 |
| 16 | 0.0155 |
| 17 | 0.0184 |
| 18 | 0.0224 |
| 19 | 0.0279 |
| 20 | 0.0356 |
| 21 | 0.0466 |
| 22 | 0.0625 |
| 23 | 0.0860 |
| 24 | 0.1212 |
| 25 | 0.1750 |
| 26 | 0.2591 |
| 27 | 0.3931 |
| 28 | 0.6112 |
| 29 | 0.9741 |

TABLE 3

| Population Parameters for Slopes and Intercepts of Standard Curves | | | | |
|---|---|---|---|---|
| | $\mu_R$ | $\sigma_R^2$ | $\mu_S$ | $\sigma_S^2$ |
| MDK | 19.49 | 0.5112 | −3.426 | 0.0481 |
| CDC | 18.91 | 0.2343 | −3.414 | 0.0198 |
| IL8R | 31.43 | 0.0919 | −3.192 | 0.0017 |
| IGF | 20.63 | 0.3835 | −3.275 | 0.0247 |
| HOXA | 22.51 | 0.1544 | −3.270 | 0.0037 |

The estimates of intercept and slope of the standard curve are denoted by $\hat{R}$ and $\hat{S}$.

Relative Concentrations $\Delta C_p$

Use the standard curve to compute $C_{p(REF)}$ at the concentration $\text{Conc}_{REF}$ from the expression: $C_{p(REF)} = \hat{R} + \hat{S} \log_{10} \text{Conc}_{REF}$. The relative concentration of a sample is given by the expression:

$$\Delta C_p = \frac{C_p - C_{p(REF)}}{\hat{S}} = \log_{10} \frac{\text{Conc}_{SAMPLE}}{\text{Conc}_{REF}}$$

Alternatively $\hat{S}$ may be approximated at a fixed level corresponding to a PCR efficiency of 2. Then $\hat{S} = -1/\log_{10}(2) = -3.32$. Use the same notation $\Delta C_p$ for either choice. The resulting $\Delta C_p$ estimates, one for each gene, are inputs to the discriminant function in the next step.

Discriminant Function

The $\Delta C_p$ values correspond to a relative biomarker value with plate-to-plate variation removed. Examination of the 5 $\Delta C_p$ values in comparison with each other (for example, see FIG. 2), shows how tumor samples typically have different biomarker values than non-tumor samples. Furthermore, while there is overlap in the areas for tumor and normal, a large number of samples are effectively well separated. Under these circumstances, many different statistical classifiers could be used to separate the normal from the tumor samples. We show here that a sample of several classifiers do work to separate these samples. We used 5 different classification methods: 1) Linear Discriminant Analysis (LDA), 2)

Logistic Regression (LogReg); 3) Support Vector Machines (SVM); 4) K-nearest-neighbor (KNN) based on 5 neighbors (KNSN); and 5) Recursive partitioning trees (TREE) (Cite: Venables & Ripley and Dalgaard).

Creation of a classifier requires a dataset containing the biomarker values for a large number of samples which should represent the ultimate population to be tested by the classifier. For example, if a classifier is to be used for screening an at-risk population (eg age 50 and older, smokers), then the set of data required for creating the classifier (called the "training set") should mirror that population and contain only samples from people older than 50 who smoke. Typically to obtain measurement precision of smaller than 10% error for parameters like sensitivity and specificity, the training set needs to be larger than 300 samples.

Estimation of the effectiveness of a classifier can be made using cross-validation. In cross-validation (Wikipedia: Cross-validation), the dataset is divided into a small number of equally sized partitions (typically 3 to 10). One section is left out and the remaining sections used to build a classifier; then the left out section is tested by the new classifier and its predictions noted. This is done for each section in turn and all the predictions combined and analysed to compute the characteristics of the classifier: Sensitivity, Specificity, etc. If the cross-validation is performed by partitioning the data into 10 parts, it is called 10-fold cross-validation; similarly, 3 parts would be 3-fold cross-validation. If the data are partitioned into as many classes are there are samples, this is called "leave one out cross-validation". By testing on data not used to build the classifier, this method provides an estimate of the classifier performance in the absence of additional samples.

We have built classifiers using all 15 combinations of 4 biomarkers, MDK, IGFBP5, CDC2, and HOXA13, all with and without the IL8Rb biomarker, using the clinical trial dataset described elsewhere in this document (Example 1) and tested those 30 classifiers using 10-fold cross-validation. This was done for each of the 5 classifier types listed above and the ROC curves computed. All work was performed using the R Statistical Programming Environment (CITE). These results (FIG. 14) show that in most cases, the classifier with IL8Rb is more sensitive for values of specificity which are useful diagnostically (False Positive Rate of 0 to 20%; Specificity from 100 to 80%). The Area Under the Curve (AUC) for the region with diagnostic utility of specificities is used to quantify how well classifiers perform with larger values indicating better classifier performance. FIG. 15a tabulates the AUC for each classifier and biomarker combination, while FIG. 15b shows the amount of increase in AUC for each condition when IL8Rb is added. In most cases, the addition of IL8Rb improves the ability to make accurate diagnoses. Specific sensitivity values for diagnostically useful specificity values are tabulated for all the classifiers in FIGS. 16a-16e. In addition, FIGS. 17a-17j tabulate the amount of gain in sensitivity or specificity which the addition of IL8Rb provides.

The utility of the classifier is created when, having created it and tested it, it is used to test a new sample. To simplify the interpretation of results, a cut-off score or threshold is established; samples on one side of the cut-off are considered positive and on the other side, negative for tumors. Additional cut-offs may be established for example to indicate increasing levels of certainty of results. In this case, we have established a cut-off which gives a false positive rate of 15% in our training set. Using our cross-validated ROC curves, we can then estimate our sensitivity. Typically, we also establish a cut-off at a positive predictive value of 75%. To use these cut-offs we establish a "negative" result for scores less than the cut-off established by the 85% specificity. Scores greater than the 75% PPV are called "positive" and score between the two are called "indeterminate"" or "suspicious".

Antibodies to IL8Rb

In additional aspects, this invention includes manufacture of antibodies against IL8Rb. The marker IL8Rb can be produced in sufficient amount to be suitable for eliciting an immunological response. In some cases, a full-length IL8Rb can be used, and in others, a peptide fragment of a IL8Rb may be sufficient as an immunogen. The immunogen can be injected into a suitable host (e.g., mouse, rabbit, etc) and if desired, an adjuvant, such as Freund's complete adjuvant or Freund's incomplete adjuvant can be injected to increase the immune response. It can be appreciated that making antibodies is routine in the immunological arts and need not be described herein further. As a result, one can produce antibodies, including monoclonal or phage-display antibodies, against IL8Rb.

In yet further embodiments, antibodies can be made against the protein or the protein core of the tumor markers identified herein or against an oligonucleotide sequence unique to a IL8Rb. Although certain proteins can be glycosylated, variations in the pattern of glycosylation can, in certain circumstances, lead to mis-detection of forms of IL8Rb that lack usual glycosylation patterns. Thus, in certain aspects of this invention, IL8Rb immunogens can include deglycosylated IL8Rb or deglycosylated IL8Rb fragments. Deglycosylation can be accomplished using one or more glycosidases known in the art. Alternatively, IL8Rb cDNA can be expressed in glycosylation-deficient cell lines, such as prokaryotic cell lines, including $E.\ coli$ and the like.

Expression vectors can be made having IL8Rb-encoding oligonucleotides therein. Many such vectors can be based on standard vectors known in the art. Vectors can be used to transfect a variety of cell lines to produce IL8Rb-producing cell lines, which can be used to produce desired quantities of IL8Rb for development of specific antibodies or other reagents for detection of IL8Rb or for standardizing developed assays for IL8Rb.

Kits

Based on the discoveries of this invention, several types of test kits can be envisioned and produced. First, kits can be made that have a detection device pre-loaded with a detection molecule (or "capture reagent"). In embodiments for detection of IL8Rb mRNA, such devices can comprise a substrate (e.g., glass, silicon, quartz, metal, etc) on which oligonucleotides as capture reagents that hybridize with the mRNA to be detected is bound. In some embodiments, direct detection of mRNA can be accomplished by hybridizing mRNA (labeled with cy3, cy5, radiolabel or other label) to the oligonucleotides on the substrate. In other embodiments, detection of mRNA can be accomplished by first making complementary DNA (cDNA) to the desired mRNA. Then, labeled cDNA can be hybridized to the oligonucleotides on the substrate and detected.

Antibodies can also be used in kits as capture reagents. In some embodiments, a substrate (e.g., a multi-well plate) can have a specific IL8Rb and BTM capture reagents attached thereto. In some embodiments, a kit can have a blocking reagent included. Blocking reagents can be used to reduce non-specific binding. For example, non-specific oligonucleotide binding can be reduced using excess DNA from any convenient source that does not contain IL8Rb and BTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect marker associated molecules can be used and be considered within the scope of this invention.

Antibodies can also be used when bound to a solid support, for example using an antibody chip, which would allow for the detection of multiple markers with a single chip.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Detection of IL8Rb and BTMs in a sample can be performed using any suitable technique, and can include, but are not limited to, oligonucleotide probes, qPCR or antibodies raised against cancer markers.

It will be appreciated that the sample to be tested is not restricted to a sample of the tissue suspected of being an inflammatory disease or tumor. The marker may be secreted into the serum or other body fluid. Therefore, a sample can include any bodily sample, and includes biopsies, blood, serum, peritoneal washes, cerebrospinal fluid, urine and stool samples.

It will also be appreciate that the present invention is not restricted to the detection of cancer in humans, but is suitable for the detection of cancer in any animal, including, but not limited to dogs, cats, horses, cattle, sheep, deer, pigs and any other animal known to get cancer.

General Tests for Inflammatory Disease or Cancer Markers in Body Fluids

In general, methods for assaying for oligonucleotides, proteins and peptides in these fluids are known in the art. Detection of oligonucleotides can be carried out using hybridization methods such as Northern blots, Southern blots or microarray methods, or qPCR. Methods for detecting proteins include such as enzyme linked immunosorbent assays (ELISA), protein chips having antibodies, suspension beads radioimmunoassay (RIA), Western blotting and lectin binding. However, for purposes of illustration, fluid levels of a disease markers can be quantified using a sandwich-type enzyme-linked immunosorbent assay (ELISA). For plasma assays, a 5 uL aliquot of a properly diluted sample or serially diluted standard marker and 75 uL of peroxidase-conjugated anti-human marker antibody are added to wells of a microtiter plate. After a 30 minute incubation period at 30° C., the wells are washed with 0.05% Tween 20 in phosphate-buffered saline (PBS) to remove unbound antibody. Bound complexes of marker and anti-marker antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader.

It can be appreciated that anti-IL8Rb antibodies can be monoclonal antibodies or polyclonal antisera. It can also be appreciated that any other body fluid can be suitably studied.

It is not necessary for a marker to be secreted, in a physiological sense, to be useful. Rather, any mechanism by which a marker protein or gene enters the serum can be effective in producing a detectable, quantifiable level of the marker. Thus, normal secretion of soluble proteins from cells, sloughing of membrane proteins from plasma membranes, secretion of alternatively spliced forms of mRNA or proteins expressed therefrom, cell death (either apoptotic) can produce sufficient levels of the marker to be useful.

There is increasing support for the use of serum markers as tools to diagnose and/or evaluate efficacy of therapy for a variety of cancer types.

EXAMPLES

The examples described herein are for purposes of illustrating embodiments of the invention. Other embodiments, methods and types of analyses are within the scope of persons of ordinary skill in the molecular diagnostic arts and need not be described in detail hereon. Other embodiments within the scope of the art are considered to be part of this invention.

Example 1: Genotypic Analysis of Bladder Cancer

Methods
Patients:

Between April 2008 and September 2009, 485 patients presenting with macroscopic hematuria, but no prior history of urinary tract malignancy, were recruited at eleven urology clinics in New Zealand and Australia. Each patient provided a urine sample immediately prior to undergoing cystoscopy and any additional diagnostic procedures. A diagnosis was made by three months following enrollment in the study. Of these 485 patients, gene expression data on all five study genes was successfully obtained for 442 patients using the methods described below. The characteristics of these patients are shown in Table 4.

TABLE 4

Characteristics of the Study Population I

| Diagnosis | Number |
| --- | --- |
| Benign prostatic hyperplasia | 18 |
| Cystitis | 18 |
| Exercise-induced hematuria | 3 |
| Non-specific kidney disease | 3 |
| Non-specific neoplasia | 3 |
| Non-specific prostate disease | 63 |
| Vascular prostate | 49 |
| Other urological cancer (non-TCC) | 5 |
| Superficial vessels | 3 |
| Urethral stricture | 6 |
| Urinary tract infection | 18 |
| Urolithiasis | 25 |
| Warfarin use | 10 |
| Unknown etiology | 155 |
| Miscellaneous | 7 |
| TCC | 56 |
| Total | 442 |

Table 4 shows the number of patients in each of the main diagnostic categories at three months after the patient's initial presentation with gross hematuria.

Urine Analysis:

Urine samples were analyzed by central review cytology (Southern Community Laboratories, Dunedin, New Zealand). The diagnostic tests NMP22 BladderChek® (Matritech) and NMP22 ELISA (Matritech) were carried out according to the manufacturer's instructions at the clinical site (BladderChek®) or by Southern Community Laboratories (NMP22 ELISA).

RNA Quantification:

2 mls or urine from each patient was mixed with RNA extraction buffer containing 5.64M guanidine thiocyanate, 0.5% sarkosyl and 50 mM NaoAc pH6.5. Total RNA was then extracted by Trizol extraction (Invitrogen) and the RNeasy procedure (Qiagen), as previously described1. RNA was eluted from the columns in 35 ul water and 3 ul was used in each subsequent monoplex or duplex quantitative reverse transcription polymerase chain reaction (qRT-PCR) assay. Each 16 ul qRT-PCR reaction contained 0.3U RNAse-OUT (Invitrogen), 0.225 uM each Taqman probe, 1.25U Superscript III (Invitrogen), 0.275 uM each primer, 1.5U Fast Start Taq polymerase (Roche), 10 mM DTT, 0.375 mM dNTPs, 4.5 mM MgSO4, 1.6 ul 10× Fast Start PCR buffer (Roche) and 2.6 ul GC Rich solution (Roche). Primers and fluorescently dual-labeled probes were obtained from Integrated DNA Technologies (Coralville USA) for each of the five study genes: MDK, CDC2, HOXA13, IGFBP5 and IL8Rb. Primer/probe sequences are shown in Table 2. Reactions were set up in 96 well plates and cycled as follows on a Roche Light Cycler® 480: 50° C., 15 mins; 95° C. 8 mins; 10 cycles of 95° C. 15 sec, 60° C. 2 mins and 30 cycles of 95° C. 15 secs, 60° C. 1 min. Standard curves of 1/16 serial dilutions of a reference RNA (derived from pooled cell line RNAs) were included on each plate to generate range of 0.3 pg/µl to 20 ng/µl. Data was collected at the extension phase of the final 30 thermocycles and exported as a raw text file. Table 5 below depicts primers and probe sequences used for qRT-PCR quantification of the five RNA markers.

TABLE 5

| Marker | Forward Seq | Reverse Seq | Probe |
|---|---|---|---|
| MDK | TGC ACC CCC AAG ACC AAA (SEQ ID NO. 3) | TGA TTA AAG CTA ACG AGC AGA CAG AA (SEQ ID NO. 4) | CCT TCC CTT TCT TGG CTT TGG CCT TT (SEQ ID NO. 5) |
| IGFBP5 | CGT TGT ACC TGC CCA ATT GTG A (SEQ ID NO. 6) | GGG ACG CAT CAC TCA ACG TT (SEQ ID NO. 7) | AAG AGA AAG CAG TGC AAA CCT TCC CGT (SEQ ID NO. 8) |
| CDC2 | GCC GCC GCG GAA TAA T (SEQ ID NO. 9) | TGT CTA CCC TTA TAC ACA ACT CCA TAG G (SEQ ID NO. 10) | AGC CGG GAT CTA CCA TAC CCA TTG ACT AAC T (SEQ ID NO. 11) |
| HOXA13 | TGG AAC GGC CAA ATG TAC TG (SEQ ID NO. 12) | TGG CGT ATT CCC GTT CAA GT (SEQ ID NO. 13) | ACT CTG CCC GAC GTG GTC TCC CA (SEQ ID NO. 14) |
| IL8Rb | CCT TGA GGC ACA GTG AAG ACA TC (SEQ ID NO. 15) | CCT GTA GGA CAC CTC CAG AAG AG (SEQ ID NO. 16) | TGG CCA CTC CAA TAA CAG CAG GTC ACA (SEQ ID NO. 17) | qRT-PCR Data Analysis

Raw fluorescence data was exported from the Roche LightCycler® 480 as a tab-delimited file containing cycle number versus two channels of fluorescence data for all wells on the plate. The data were processed using an R program that applied color compensation (Bernard1999) to the data to correct for bleed over from one fluorescent channel into another. It then fitted a 5-point logistic model to estimate the $C_P$ using the second derivative maximum (Spiess2008).

All samples and controls were applied in duplicate to the PCR plates. The $C_P$ values from the duplicate wells were averaged before use. If the difference between the two $C_P$ values exceeded 3 units, that sample was repeated. To provide standardization across PCR plates, $C_P$'s were expressed as $\Delta C_P$'s relative to a reference RNA (derived from pooled cell line RNAs) at 20 ng/µl: $\Delta C_P = C_P$ (sample) $- C_P$ (reference RNA)

Statistical Analysis qRT-PCR $\Delta C_P$ values from MDK, CDC2, HOXA13, IGFBP5 and IL8Rb were used to generate classifiers to separate samples containing TCCs from samples containing no TCCs, based on Linear Discriminant Analysis or Logistic Regression (Venables2002). In both cases, interactions between genes were permitted in the classifier models. The generation of the LDA followed standard procedures, as described, for example in "Modern Applied Statistics with S, 4th edition" by W. N. Venables and B. D. Ripley (2002), Springer. The dataset from the study was cleaned of any incomplete data then the R Statistical Environment (R Development Core Team (2009) and the function "lda" from the package MASS (Venables and Ripley (2002)) were used to generate and test the linear discriminant on the clinical trial data.

The generation of the Logistic Regression classifier was performed in a similar manner to the generation of the LDA. Again, the study data was cleaned of incomplete data. A logistic regression classifier was created using R; no additional packages were required. Logistic regression was performed as described by Dalgaard (2008). Comparison among classifiers was made using ROC curves, using the R package, ROCR (Sing et al. 2009). Confidence intervals for ROC curves were generated using the methods of Macskassy et al (Macskassy2005). The following algorithms were generated:

Linear Discriminant Classifier

The first classifier, a linear discriminant, (called LDA-3), Is based on five gene values (normalized to a Reference value by subtracting the reference value) allowing for multiway interactions between the genes. The classifier was built in R using the 'lda( )' function from the package called "MASS". (R version 2.9.1; MASS version 7.2-49). The classifier was built using the following equation:

$$lda3 \leftarrow lda(TCC.YN \sim MDK*IGF*CDC*HOXA*IL8R, data=uRNA.Trial)$$

Where lda3 is the created model; TCC.YN is the true value for "presence of TCC in urine"(Yes or No) as determined by cystoscopy; MDK, IGF, CDC, HOXA and IL8R are the normalized gene Cp value; and uRNA Trial is a data file containing the Cp values for the each of the 5 genes and TCC.YN (yes or no) from the clinical trial. Use of the ASTERISK, '*', in the formula signifies multiplication. Evaluation of the classifier score takes as input a new data frame containing the five gene values as well as the classifier, lda3, to output a classifier score:

$$score \leftarrow c(predict(lda3, new.data)\$x),$$

where "score" is the output used from the classifier to predict the presence of TCCs; "lda3" is the classifier created above and "new.data" is a data FILE containing the measured values of the five genes called by the same names as used in classifier creation. The syntax, lx' and "c( . . . )" is present to extract the score specifically from the large amount of information returned by the predict function. Setting the score cut off to 0.112 and above, sets our specificity to 85% for presence of TCCs in the urine sample. The coefficients for LDA-3 are shown in Table 6.

TABLE 6

| | |
|---|---|
| MDK.d.R100 | 5.333639e+00 |
| IGF.d.R100 | 3.905978e+00 |
| CDC.d.R100 | 6.877143e−01 |
| HOXA.d.R100 | 6.073742e+00 |
| IL8R.d.R100 | −1.229466e+00 |
| MDK.d.R100:IGF.d.R100 | −7.420480e−01 |
| MDK.d.R100:CDC.d.R100 | −2.611158e−01 |
| IGF.d.R100:CDC.d.R100 | −1.965410e−01 |
| MDK.d.R100:HOXA.d.R100 | −8.491556e−01 |
| IGF.d.R100:HOXA.d.R100 | −4.037102e−01 |
| CDC.d.R100:HOXA.d.R100 | −3.429627e−01 |
| MDK.d.R100:IL8R.d.R100 | 1.903118e−01 |
| IGF.d.R100:IL8R.d.R100 | 2.684005e−01 |
| CDC.d.R100:IL8R.d.R100 | −1.229809e−01 |
| HOXA.d.R100:IL8R.d.R100 | 2.909062e−01 |
| MDK.d.R100:IGF.d.R100:CDC.d.R100 | 4.108895e−02 |
| MDK.d.R100:IGF.d.R100:HOXA.d.R100 | 7.664999e−02 |
| MDK.d.R100:CDC.d.R100:HOXA.d.R100 | 4.832034e−02 |
| IGF.d.R100:CDC.d.R100:HOXA.d.R100 | 2.116340e−02 |
| MDK.d.R100:IGF.d.R100:IL8R.d.R100 | −3.750854e−02 |
| MDK.d.R100:CDC.d.R100:IL8R.d.R100 | 1.664612e−02 |
| IGF.d.R100:CDC.d.R100:IL8R.d.R100 | 2.089442e−03 |
| MDK.d.R100:HOXA.d.R100:IL8R.d.R100 | −1.539486e−02 |
| IGF.d.R100:HOXA.d.R100:IL8R.d.R100 | −3.894153e−02 |
| CDC.d.R100:HOXA.d.R100:IL8R.d.R100 | 6.295032e−03 |
| MDK.d.R100:IGF.d.R100:CDC.d.R100:HOXA.d.R100 | −4.359738e−03 |
| MDK.d.R100:IGF.d.R100:CDC.d.R100:IL8R.d.R100 | −2.019317e−04 |
| MDK.d.R100:IGF.d.R100:HOXA.d.R100:IL8R.d.R100 | 3.746882e−03 |
| MDK.d.R100:CDC.d.R100:HOXA.d.R100:IL8R.d.R100 | −2.902150e−03 |
| IGF.d.R100:CDC.d.R100:HOXA.d.R100:IL8R.d.R100 | 4.799489e−04 |
| MDK.d.R100:IGF.d.R100:CDC.d.R100:HOXA.d.R100: IL8R.d.R100 | 7.512308e−05 |

Logistic Regression Classifier

A second classifier based on Logistic Regression was derived from the same cleaned dataset as LDA-3. Instead of using the lda( ) function, however, we used the glm( ) function from the package stats (included with a base install of R) as shown below:

lr1←glm(TCC.YN~CDC*IGF*HOXA*IL8R*MDK, family=binomial("logit"),data=uRNA.Trial), where "lr1" is the classifier created and the other parameters are as described for the linear discriminant. Once again, full interaction is specified using the operator. Classification is performed in a manner very similar to that for LDA-3:

score←predict(lr1,new.data,type='response'), where "score" is the value used to classify urine samples based on the measurement of the five genes in "new.data", as above. The cut off for lr1 is set to 0.102 to achieve a specificity of 85%; values about the cut off are considered to be positive to TCCs. The coefficients for the classifier are:
−103.0818143+
3.9043769*CDC.d.R100+
13.1120675*IGF.d.R100+
17.4771819*HOXA.d.R100+
−10.7711519*IL8R.d.R100+
21.1027595*MDK.d.R100+
−0.5938881*CDC.d.R100*IGF.d.R100+
−1.0736184*CDC.d.R100*HOXA.d.R100+
−1.3340189*IGF.d.R100*HOXA.d.R100+
0.3126461*CDC.d.R100*IL8R.d.R100+
1.4597355*IGF.d.R100*IL8R.d.R100+
1.8739459*HOXA.d.R100*IL8R.d.R100+
−1.035054*CDC.d.R100*MDK.d.R100+
−2.5885156*IGF.d.R100*MDK.d.R100+
−2.7013483*HOXA.d.R100*MDK.d.R100+
1.4546134*IL8R.d.R100*MDK.d.R100+
0.0767503*CDC.d.R100*IGF.d.R100*HOXA.d.R100+
−0.0663361*CDC.d.R100*IGF.d.R100*IL8R.d.R100+
−0.1015552*CDC.d.R100*HOXA.d.R100*IL8R.d.R100+
−0.2110656*IGF.d.R100*HOXA.d.R100*IL8R.d.R100+
0.1361215*CDC.d.R100*IGF.d.R100*MDK.d.R100+
0.1601118*CDC.d.R100*HOXA.d.R100*MDK.d.R100+
0.259745*IGF.d.R100*HOXA.d.R100*MDK.d.R100+
−0.0106468*CDC.d.R100*IL8R.d.R100*MDK.d.R100+
−0.1947899*IGF.d.R100*IL8R.d.R100*MDK.d.R100+
−0.185286*HOXA.d.R100*IL8R.d.R100*MDK.d.R100+
0.0136603*CDC.d.R100*IGF.d.R100*HOXA.d.R100*IL8R.d.R100+
−0.0151368*CDC.d.R100*IGF.d.R100*HOXA.d.R100*MDK.d.R100+
0.0056651*CDC.d.R100*IGF.d.R100*IL8R.d.R100*MDK.d.R100+
0.0030538*CDC.d.R100*HOXA.d.R100*IL8R.d.R100*MDK.d.R100+
0.0232556*IGF.d.R100*HOXA.d.R100*IL8R.d.R100*MDK.d.R100+
−0.000867*CDC.d.R100*IGF.d.R100*HOXA.d.R100*IL8R.d.R100*MDK.d.R100

Results qRT-PCR Analysis of Urine Samples

Figure 2D:
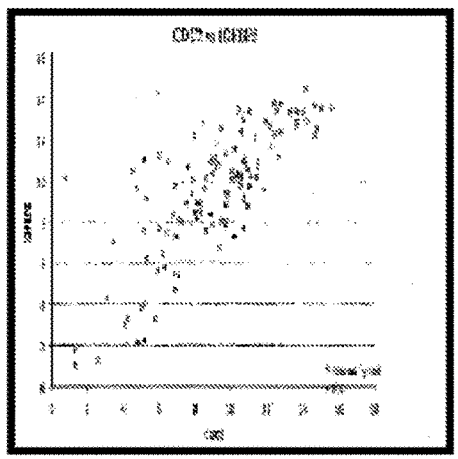
Figure 2E:
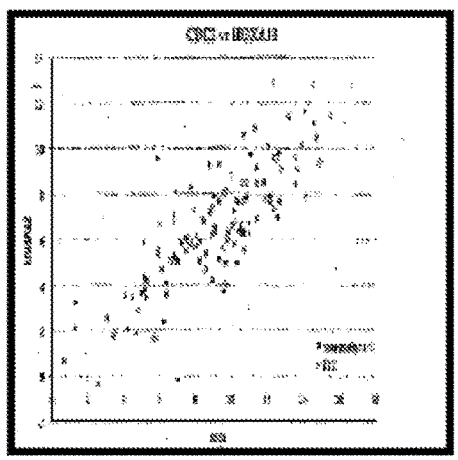
Figure 2F:
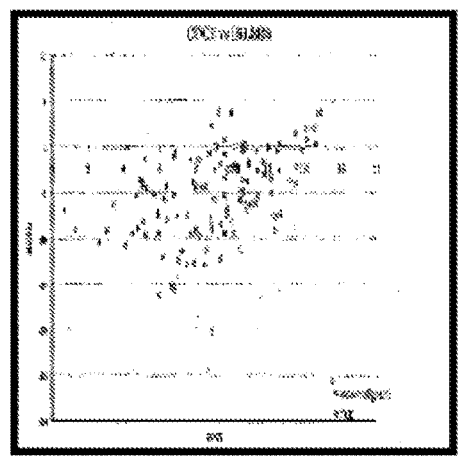

To obtain an overview of the effect of IL8Rb on TCC detection, two dimensional scatter plots were constructed using qRT-PCR data obtained from the urine of patients with either TCC (n=56) or the non-malignant conditions urolithiasis (n=25), urinary tract infection (n=18) or cystitis (n=18). The scatter plots were constructed using pairs of genes from a four gene signature (MDK, CDC2, HOXA13, IGFBP5). IL8Rb was then substituted for one gene of each pair and the data re-plotted. These plots are shown in FIGS. 2a-2f. Substitution of IL8Rb for IGFBP5 and HOXA13 in plots with MDK (FIGS. 2a-2c) showed improved separation between samples from patients with TCC and those with non-malignant conditions. The same trend was observed in plots with CDC2 in which IL8Rb was substituted for IGFBP5 and HOXA13 (FIGS. 2d-2f).

Figure 3A:
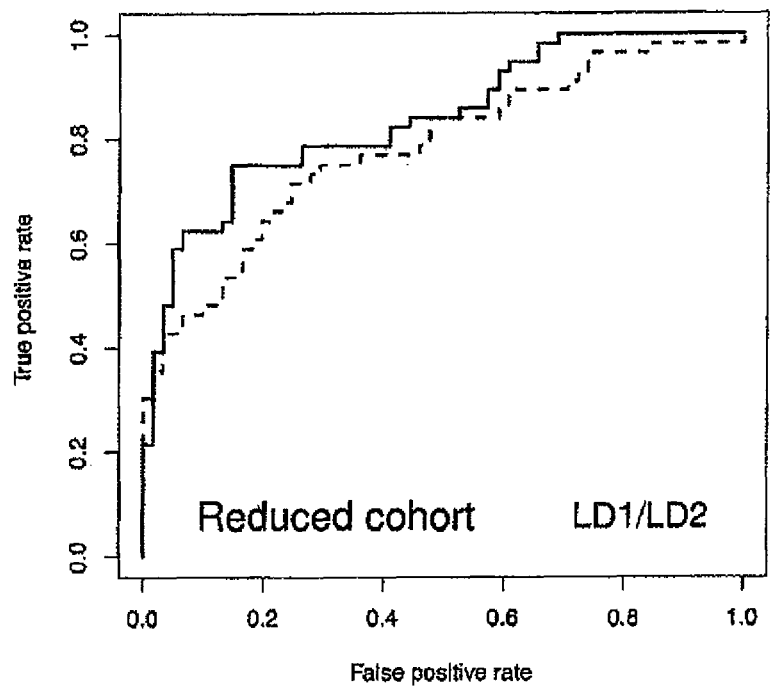
FIGS. 3A-3B depict ROC curve analysis (sensitivity vs specificity) showing the effect of including IL8Rb in diagnostic algorithms derived using linear discriminate analysis (LD) and linear regression (LR). The ROC curves were derived from patients with TCC and upper urinary tract cancers (n=61), and the non-malignant diseases cystitis, urinary tract infection and urolithiasis (n=61).
Figure 3B:
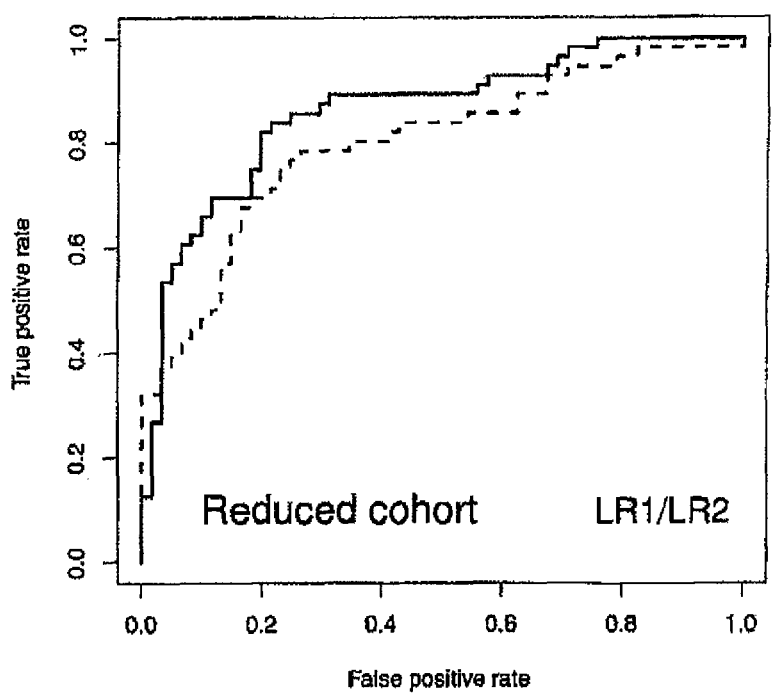

The contribution of IL8Rb to the correct diagnosis of TCC in patients presenting with gross hematuria was then quantified by ROC curve analysis. qRT-PCR data for each gene in the signature (MDK, CDC2, IGFBP5 and HOXA13) and IL8Rb was used to develop linear discriminate algorithms that maximized the discrimination between the patients with TCC and those without. Two linear discriminate algorithms were developed using the entire cohort of 442 samples: LD1, which used the qRT-PCR data from MDK, CDC2, HOXA13 and IGFBP5 and LD2, which used MDK, CDC2, HOXA13, IGFBP5 and IL8Rb. LD1 and LD2 were then used to generate ROC curves showing the sensitivity and specificity of TCC detection in the group of patients with confirmed TCC (n=56) or the non-malignant conditions urolithiasis (n=25), urinary tract infection (n=18) or cystitis (n=18). FIG. 3a shows the ROC curves for LD1 and LD2. The area under the ROC curve for LD1 was 78% compared to 84% for LD2.

As an alternative to linear discriminate analysis, logistic regression was used as an independent method to develop an algorithm for the discrimination between patients with TCC and those with non-malignant disease. As for the linear discriminate analysis, the logistic regression algorithms were developed using the entire cohort of 442 samples. The ROC curves obtained using logistic regression and the 56 TCC and 61 non-malignant samples described above are shown in FIG. 3b. The area under the ROC curve for LR1 (obtained using qRT-PCR data from MDK, CDC2, HOXA13 and IGFBP5) was 80% compared to 86% for LR2 (obtained using qRT-PCR data from MDK, CDC2, HOXA13, IGFBP5 and IL8Rb). This data clearly illustrates that inclusion of IL8Rb in methods for the detection of TCC using urine samples can lead to improved discrimination between patients with TCC and non-malignant diseases such as cystitis, urinary tract infection and urolithiasis.

Figure 4A:
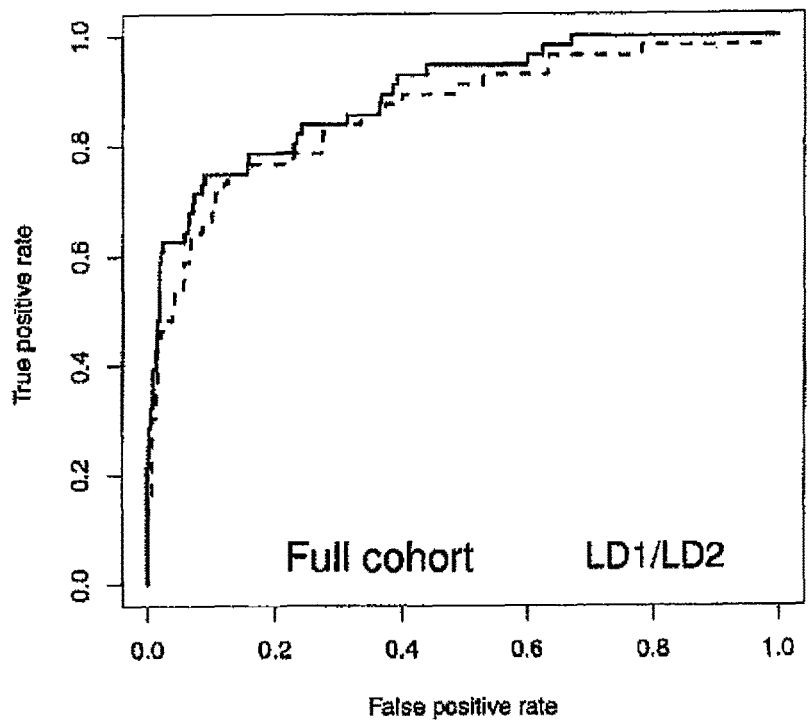
FIGS. 4a and 4b depict extended ROC curve analysis showing the effect of including IL8Rb in diagnostic algorithms derived using linear discriminate analysis (LD) and linear regression (LR). The ROC curves are derived from patients with TCC (n=56) and, unlike FIG. 3, any non-malignant disease in the cohort (n=386).
Figure 4B:
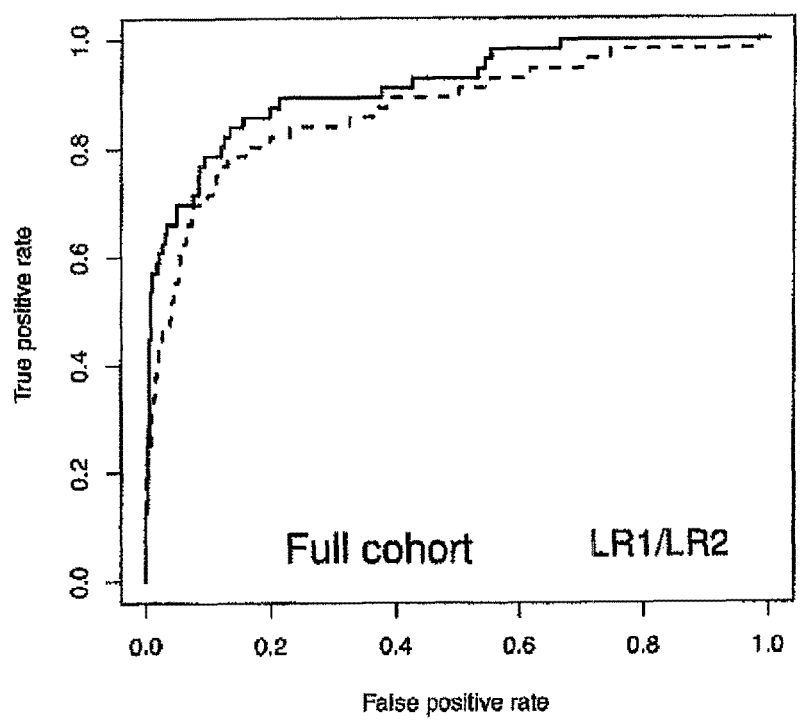

To confirm the improved accuracy afforded by IL8Rb for the discrimination between patients with TCC and urolithiasis, urinary tract infection or cystitis was maintained in an unselected cohort of patients comprising a larger number and diversity of non-malignant patients, the ROC curve analyses were repeated with the entire cohort of 442 samples described in Table 1. In this analysis, the area under the curve for LD1 and LD2 was 86 and 89%, respectively (FIG. 4a). Similarly, the area under the curve for LR1 was 87% and for LR2 91% (FIG. 4b). This result confirms that IL8Rb leads to improved accuracy in the detection of TCC using urine samples.

This improvement in cancer detection due to the inclusion of IL8Rb was further illustrated by applying LD1/LD2 and LR1/LR2 to the 442 patient cohort and then determining the sensitivity of detection of stage Ta TCC alone. Stage Ta tumors are smaller, more differentiated tumors that are typically more difficult to detect than higher stage tumors. LD1 detected 18/31 (58%) of the Ta tumors compared to 19/31 (61%) for LD2 at a specificity of 85%. LR1 detected 21/31 (68%) compared to 24/31 (77%) for LR2 (specificity of 85%). This data shows that the inclusion of IL8Rb into the LD and LR algorithms increased the sensitivity of detection of stage Ta tumors by up to 9%. In comparison to these RNA tests, the three other bladder cancer tests in this study showed markedly lower accuracy for the detection of Ta tumors: urine cytology (39% sensitivity, 94% specificity), NMP22 ELISA (35% sensitivity, 88% specificity) and NMP22 (BladderChek® "a registered trademark of Matritech, Inc. of Massachusetts, United States") (39% sensitivity, 96% specificity).

IL8Rb as an Aid in the Diagnosis of Inflammation of the Urinary Tract

To determine the ability of IL8Rb to be used in the diagnosis of patients with inflammation of the urinary tract due to causes such as cystitis or urinary tract infections, the urine levels of IL8Rb mRNA in hematuria patients diagnosed with benign prostate hyperplasia, non-specific prostate disease, vascular prostate, hematuria secondary to warfarin use, and cystitis/urinary tract infection were determined by qRT-PCR. The mean IL8Rb ΔCt levels for each of these conditions were −3.12, −3.10, −2.84, −1.98 and −5.27, respectively. The difference between the mean of the IL8Rb level in patients with cystitis/urinary tract infection and the other non-malignant states combined was determined to be significant (p=0.001) using the Wilcoxon rank sum test. Box plots portraying this data are shown in FIG. 5. This data shows an elevation of IL8Rb levels in the majority of patients diagnosed with either cystitis or urinary tract infection compared to the other non-malignant conditions examined. Overlap between plots is likely to be explained by a combination of three factors: (i) the inability of standard clinical practice to correctly diagnose each condition, (ii) co-morbidity (e.g., infection and benign prostate hyperplasia), and (iii) the normal association of high urine neutrophil counts in a subset of patients with benign prostate hyperplasia, non-specific prostate disease, vascular prostate or hematuria secondary to warfarin use. Regardless, given the strict association between inflammation and neutrophil numbers, the quantification of IL8Rb in urine provides an accurate method of detecting inflammation of the urinary tract, be it as a consequence of infection or in association with other non-malignant conditions.

Example 2

Methods

Study Population

A consecutive series of patients without a prior history of TCC were recruited prospectively from nine urology clinics in New Zealand and two in Australia between 28$^{th}$ April 2008 and 11$^{th}$ August 2009. The patient set included the patients used in example 1, but included an additional 46 patients, whose data was not available for the first analysis. The further studying also includes further analysis of the results obtained. The samples were collected and RNA collected and tested as described in Example 1.

RNA Test Development uRNA® consists of four mRNA markers, CDC2, HOXA13, MDK and IGFBP5. These markers were selected on the basis of their low expression in blood and inflammatory cells and over-expression in TCC.[2] In this cohort study, we prospectively specified a linear discriminate algorithm (uRNA-D) that combined the four markers into a single score. uRNA-D was independent, being developed on an earlier dataset. It was not however, derived using a strictly characterized patient group representing the intended target population for the test. As a consequence, the study protocol also defined the development of a new algorithm (Classifier-D) for the use of the five markers CDC2, HOXA13, MDK, IGFBP5 and IL8Rb using data obtained from the patients recruited to the current cohort study.

In addition to Classifier-D, a second algorithm (Classifier-S) was derived using the cohort study data to enable identification of tumors that were either of advancing stage (≥stage 1) or high grade (WHO/ISUP 1998 classification). Algorithm-S comprised all five markers, including CDC2 and HOXA13 which had previously been shown to be differentially expressed between Stage Ta tumors and those ≥stage 1.

Classifier Development

Development of two classifiers for the use of the five markers CDC2, HOXA13, MDK, IGFBP5 and IL8Rb (Classifier-D and Classifier-S) were based on data obtained in this study, in accordance with the methods outlined in this specification. Briefly, logistic regression models were made using the statistical programming environment, R (R Development Core Team (2011). R: A language and environment for statistical computing. R Foundation for Statistical Computing, Vienna, Austria. ISBN 3-900051-07-0, URL http://www.R-project.org/). Models made using $\Delta C_P$ values for each of the five markers and their two way interactions (e.g., MDK×CDC2, MDK×IGFBP5, etc) were evaluated for their ability to classify; those with the lowest AIC values were evaluated in a leave-one-out cross validation procedure for their sensitivity when the specificity was set to 85%. Several models demonstrated comparable performance for each of Classifier-D and Classifier-S, with the model with the fewest numbers of parameters being selected.

Statistical Methods

Where a diagnostic test was specified in the protocol, proportions and 95% confidence intervals were calculated for sensitivity and specificity. Receiver operating characteristic (ROC) curves were plotted and compared using the Stata roctab and roccomp commands (Statacorp and Delong). For Classifier-D confidence intervals are not appropriate, but Fishers exact or Chi squared tests (where sample sizes allow) were used to test for an association between TCC or patient characteristics and chances of true positive or false positive results. Logistic regression models were used to explore factors associated with false positive and false negative results. All analyses were carried out in Stata version 11.2.

Results

Figure 8:
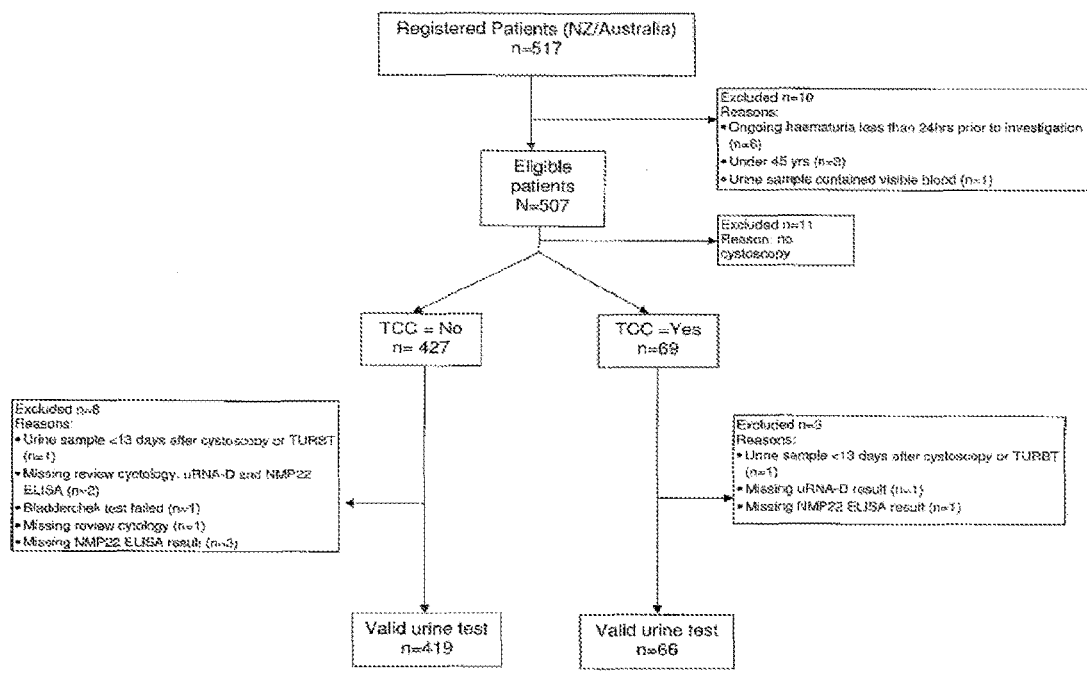
FIG. 8 depicts a flow chart for the patient recruitment procedures and numbers for Example 2.
Figure 11A:
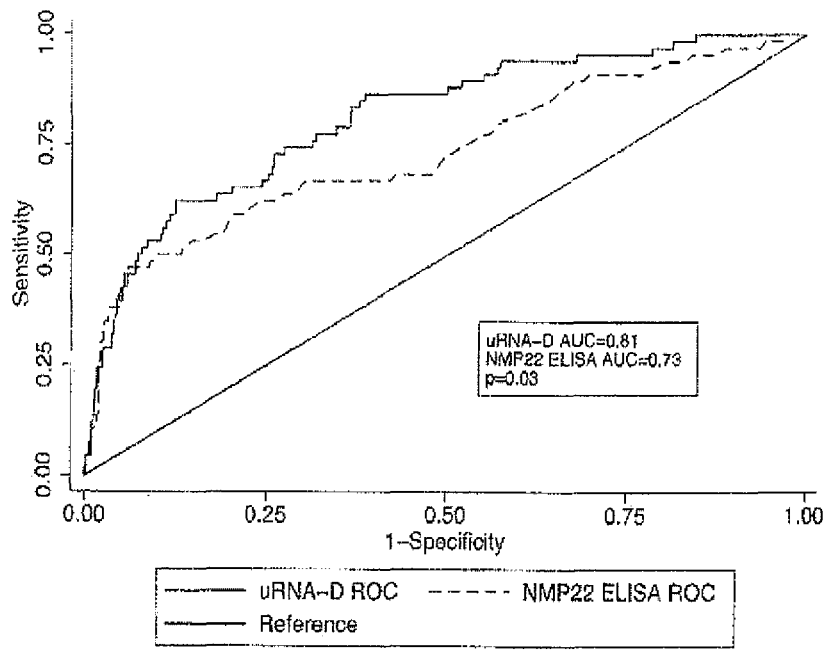
FIGS. 11A-11B depict various ROC curves.
Figure 11B:
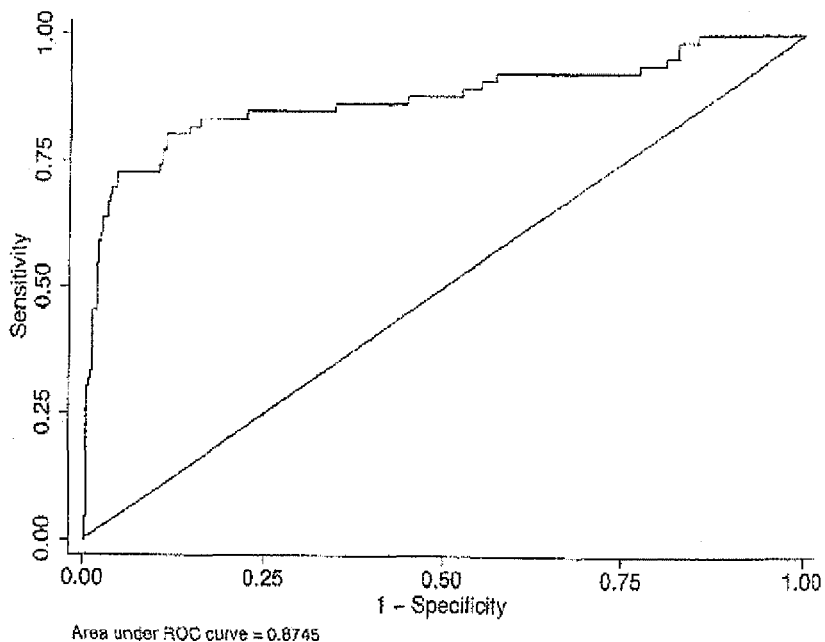

A total of 517 patients were initially recruited to the study; 4% of patients were excluded because they were found to be ineligible (n=10), did not undergo cystoscopy (n=9), TCC status was not stated (n=2) or they did not provide an acceptable urine sample (n=2) (FIG. 8). A further 10 patients were excluded from the analysis because they did not have results for one or more of the urine tests. The baseline demographic and clinical characteristics of the 485 remaining patients are shown in FIG. 9.

The prevalence of TCC in the cohort was 13.6%. Two were missing a review stage (both were Ta by local review) and two were not given a review grade (one was grade 1 by the local pathologist, the other low). Of the 66 tumors, 55 were superficial (stage Ta, T1 or Tis) and 11 were muscle invasive (T2). No patients had detectable metastases or involvement of regional lymph nodes. Using the 1973 grading system, 24 were classified as grade 3, 38 grade 2, three grade 1 and one unknown. With the WHO98 system, 29 were classified as high grade, four mixed, 32 low grade and one unknown. In addition to the TCCs, two patients were diagnosed with a papilloma, and seven with other neoplasms (five of these urological).

Figure 21:
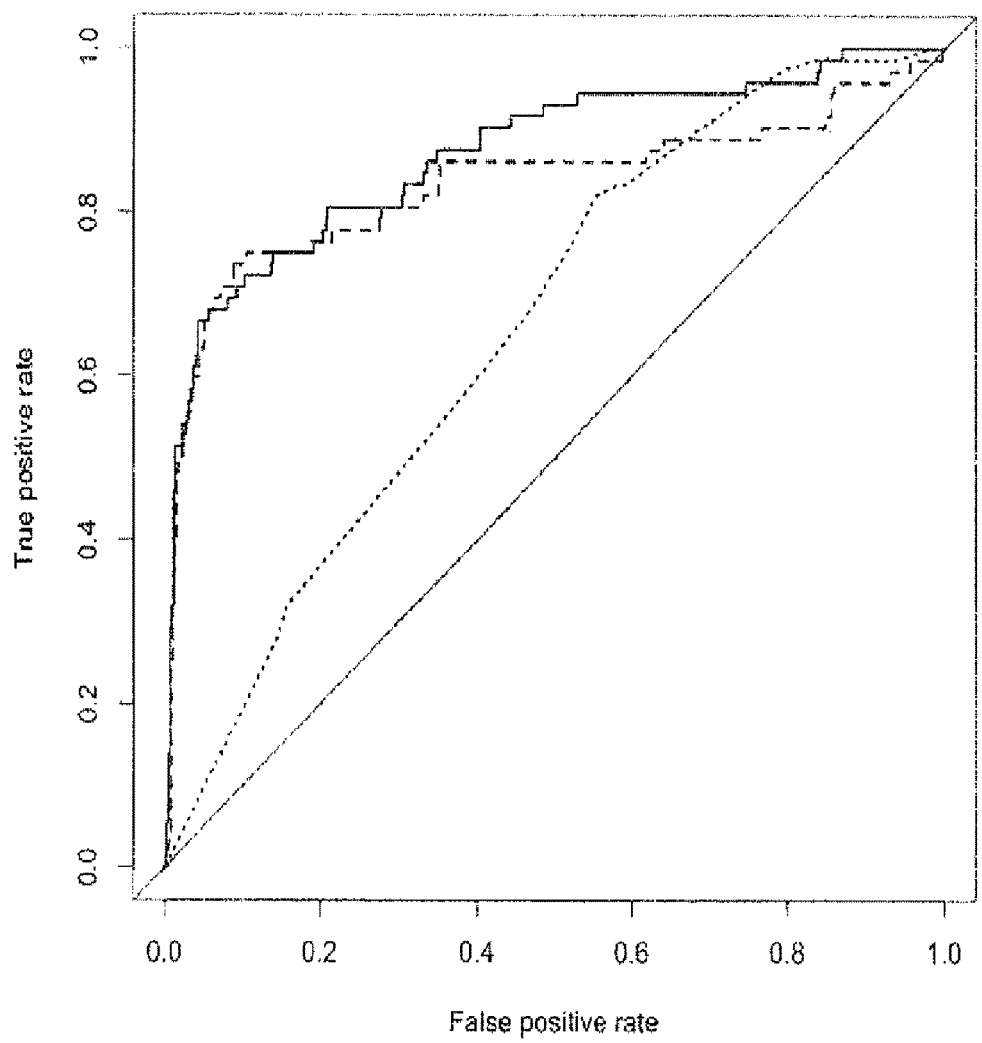
FIG. 21 depicts ROC curves representing the three classification models. P INDEX (dotted line), G INDEX (dashed line) and G+P INDEX (solid line).

The cutoff for the uRNA-D test was determined on the study cohort, with specificity set at 85%. With this cutoff, uRNA-D detected 41 of the 66 TCC cases (sensitivity of 62%), compared with NMP22™ ELISA (50%), Bladderchek® (38%) and cytology (56%). The RNA test developed on the cohort data Classifier-D detected 54 of the TCC cases (82%) at a specificity of 85% and 48 (73%) at a specificity of 90%. uRNA-D and NMP22™ ELISA values can be directly compared as both tests were fully specified prior to the study. FIG. 21 shows the ROC curves; the area under the curves (AUCs) are 0.81 and 0.73 respectively (p=0.03). The ROC curve for Classifier-D was 0.87 (FIG. 21), and the improvement in performance relative to uRNA-D appears to be mostly in the range of clinically relevant specificities (above 80%).

Overall, Classifier-D detected 97% of the high/grade 3 tumors, compared to uRNA-D (83%), cytology (83%), NMP22 ELISA (69%) and Bladderchek® (38%). Classifier-D was also more sensitive for the detection of low-grade tumors (69%), with the other tests ranging from 28-41% (FIG. 12) Classifier-D was positive for all the TCC cases of Stage ≥1 plus both Tis, but the sensitivity was 68% for stage Ta (p=0.016, FIG. 12). This was still substantially higher than the other tests, with uRNA-D being the next highest at 41%. TCC patients with macrohematuria or microhematuria evident in their urine sample were more likely to have their TCC detected by including IL8Rb than those without macrohematuria or microhematuria (p<0.0005), though this is likely to be at least partially a result of the higher proportion of high stage and grade TCCs among those with macrohematuria or microhematuria. Numbers were insufficient to explore this further in regression analyses.

Of the 12 cases missed by Classifier-D, all were stage Ta and all except one were low grade (WHO ISUP 1998). Only two of the twelve (both low grade, stage Ta TCC) were picked up by another test (one by both NMP22™ ELISA and BladderChek® and one by uRNA-D). Of the 12 cases missed by Classifier-D, all were stage Ta and all except one were low grade (WHO ISUP 1998). Only two of the twelve (both low grade, stage Ta TCC) were picked up by another test (one by both NMP22™ ELISA and BladderChek® and one by uRNA-D). Cytology did not pick up any TCCs that Classifier-D missed.

Patient A: High Grade renal pelvic T2 tumour, no concurrent Tis, no size given.

Patient B: High grade Bladder T3a no concurrent Tis, 2×3 cm

Patient C: a high grade tumour measuring 4.8×5.6 cm with extensive stromal and muscularis propria invasion, extending to the perivescical fat with no evidence of metastasis.

The specificity of the urine tests among those with alternative diagnoses and according to urine sample characteristics are shown in FIG. 13. Control patients with macrohematuria or microhematuria were more likely to have false positive tests than those without macrohematuria or microhematuria (p=0.002), and there was a trend that patients with calculi may as well, although the differences in specificity by diagnosis were not statistically significant overall (p=0.12). There were five patients with other urological cancers; only one of these gave a positive Classifier-D test result. Results from fitting logistic regression models were similar. In a logistic regression model with diagnosis and macrohematuria or microhematuria, the association with macrohematuria or microhematuria status remained significant (p=0.006) and, when compared directly to no diagnosis those with calculi had a 2.7 fold increased odds of a false positive test (95% CI (1.1 to 6.4), p=0.03). Age did not affect the specificity of the test.

Macrohematuria or microhematuria detected in the urine sample was the only factor clearly associated with test sensitivity. The predictive value of a positive test in this cohort was 63% for those with macrohematuria or microhematuria and 24% for those without, largely reflecting the greater prevalence of TCC in the patients with macrohematuria or microhematuria (39% vs 6%).

There were 54 patients with TCC in whom the Classifier-D test was positive. These patients were classified into severe and less severe TCC using Classifier-S. Severe TCC was defined as stage ≥1 or grade 3 at any stage. At a specificity of 90%, Classifier-S correctly classified 32/35 (91%) of the severe TCC cases.

Example 3: Combined Genotype and Phenotype Analysis of Patients with Hematuria I This study focuses on patients presenting with confirmed asymptomatic microscopic hematuria (AH) who are undergoing a full clinical work-up for the investigation of possible urothelial cancer (UC). Approximately 500 patients are enrolled to participate in the study.

As used herein, terms are defined below in additional examples.

Objectives

Objectives are to determine the: (1) efficacy of a genotypic and phenotypic algorithm in patients presenting with micro hematuria who are scheduled for a full urological clinical work-up, (2) performance characteristics (sensitivity, specificity, area under the ROC curve, positive and negative predictive values) of the genotypic and phenotypic algorithm G+P INDEX for the detection of primary UC in patients presenting with confirmed microscopic hematuria, and (3) number of patients correctly diagnosed as negative for UC by a genotypic and phenotypic tool, the G+P INDEX and therefore do not require investigative cystoscopy.

Study Population

The study population consists of patients presenting with confirmed micro-hematuria who fulfill study requirements. Patients are recruited from general practices that refer patients to the urological clinics.

Informed Consent

Patients scheduled for investigative cystoscopy are contacted to discuss possible participation. Patients are informed of the nature of the study and consent is obtained. Patients provide demographic, occupational, and smoking history information, and ensure that they fully understand the patient information and consent forms prior to provision of their urine samples. Study coordinators complete a CRF page detailing the relevant inputs to the genotypic and phenotypic index and transfer the data for analysis.

Inclusion Criteria

Patients undergoing cystoscopic investigation for Urothelial Carcinoma following a confirmed clinical finding of microscopic hematuria (Minimum of 3 RBC per high power field (HPF)) on 2 or 3 properly collected urine specimens[(3)].

Patients are willing to comply with study requirements.

Patients are over 18 years of age.

Exclusion Criteria

Prior history of urothelial caarcinoma (UC).

Current presentation of macroscopic hematuria

Prior history (past 12 months of an episode of Macroscopic Hematuria with confirmed diagnosis (malignant or otherwise).

G+P Index

We developed a novel index, the "G+P Index," which comprises of a combination of both genotypic and phenotypic data. The Genotypic ("G") component utilizes RNA biomarker expression information in conjunction with five clinical factors collected from the patient in the same time window (Phenotypic data "P") to determine the risk of UC in AH patients.

All patients receive a standard clinical work-up to determine true clinical outcome and the outputs from this study are simulated outputs based on the clinical data collected and the genotypic data collected from the patients' urine samples. As such, patient care is not altered as a result of the study output. Patients provide urine samples, which are sent for genetic analysis.

Patient Tirage

No change to overall standard of care is made for patients participating in the study. All patients scheduled for a full urological work-up undertake the appropriate investigations according to the current standard of care.

Study Data

Demographic and risk factor information are inputs to the genotypic and phenotypic index. Final disease state (as determined by flexible cystoscopy and follow up) are collated with ($\phi$) results and demographic information and subjected to statistical analysis.

Determination of the G+P Index

Using datasets obtained from samples collected from a large number of sites in New Zealand and Australia from approximately 500 patients, a training model to predict the probability of 'TCC=Yes' was developed.

Data Collected for Variables Used in the Training and Validation Populations

Phenotypic Variables

Clinical findings are: Gender, Age, Smoking history, and HFREQNEW ($\leq$=1 denoted as Low; >1 denoted as High).

Genotypic Variables

Genotypic Variables include expression of RNA markers: M1 (=MDK+CDC+IGBP5−HOXA13) and IL8R. Table 7 below shows estimates of the coefficients of each of the factors in the validation G+P INDEX:

TABLE 7

Analysis of Maximum Likelihood Estimates

| Parameter | | DF | Estimate | Standard Error | Wald Chi-Square | Pr > ChISq | Exp (Est) |
|---|---|---|---|---|---|---|---|
| Intercept | | 1 | −4.8445 | 0.6532 | 55.0092 | <.0001 | 0.008 |
| gender | 2 | 1 | −1.8544 | 0.6750 | 7.5484 | 0.0060 | 0.157 |
| smoke | 2 | 1 | −0.9049 | 0.4537 | 3.9775 | 0.0461 | 0.405 |
| smoke | 3 | 1 | −1.3407 | 0.4936 | 7.3756 | 0.0066 | 0.262 |
| HFREQNEW | Low | 1 | −0.7015 | 0.3478 | 4.0681 | 0.0437 | 0.496 |
| M1 | | 1 | 1.2221 | 0.1553 | 61.9328 | <.0001 | 3.394 |
| IL8R | | 1 | −0.2408 | 0.1789 | 1.8112 | 0.1784 | 0.786 |

Figure 18:
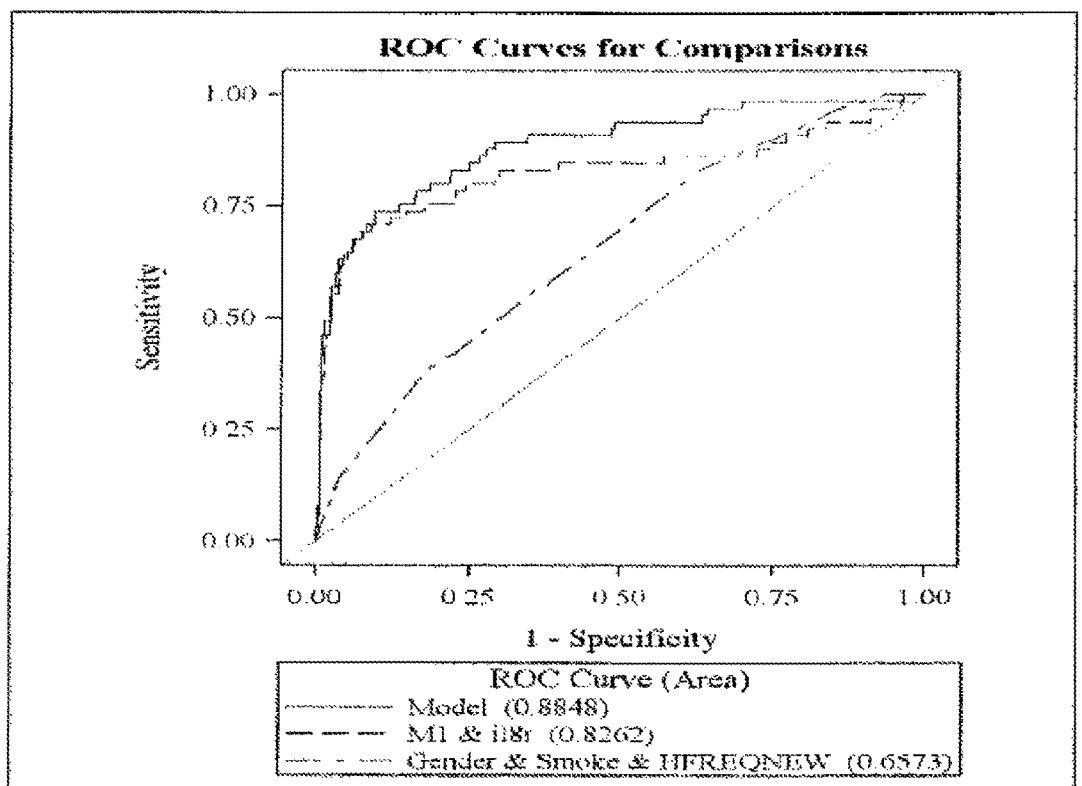
FIG. 18 depicts ROC curves for testing of patients having hematuria studied using either genetic testing alone, phenotype evaluation alone, and/or both genetic testing and phenotypic evaluation.

FIG. 18 depicts ROC curves for the G+P Index. FIG. 18 is a graph of sensitivity (vertical axis) versus 1-specificity (horizontal axis) for results according to an embodiment of this invention. For comparison, a diagonal line depicts the model. The outcomes based solely upon Phenotypic information is shown as the dash-dotted line, the outcome based solely upon Genotypic information is shown as the dashed line, and the outcomes based on the G+P Index are shown as the solid line. These results indicate that the combination of Genotypic and Phenotypic information provides an unexpected, substantial improvement in prediction of outcome.

Exploratory models considered seven phenotypic variables, but AgeGT50 showed insignificant effect while there was insufficient data for RBC, so both of these variables were dropped from the final model. Based on the significance level of the remaining five phenotypic variables and the two RNA markers, an index was constructed. Using relationship between M1, IL8R and TCC (=yes) in the training dataset, a threshold of 4.5 and 2.5 was used for M1 and IL8R respectively. A score of 5, 4, 3, 2 and 1 was assigned to M1, Smokers, Male, IL8R, and HFREQ—which result in an index score ranging from 0 to 15. The integrated algorithm based on co-efficient is given below as the combined G+P index:

$$G+P \text{ INDEX} = (1*HFREQ + 3*Gender + 4*SMK) + (5*M1 + 2*IL\text{-}8)$$

Figure 19:
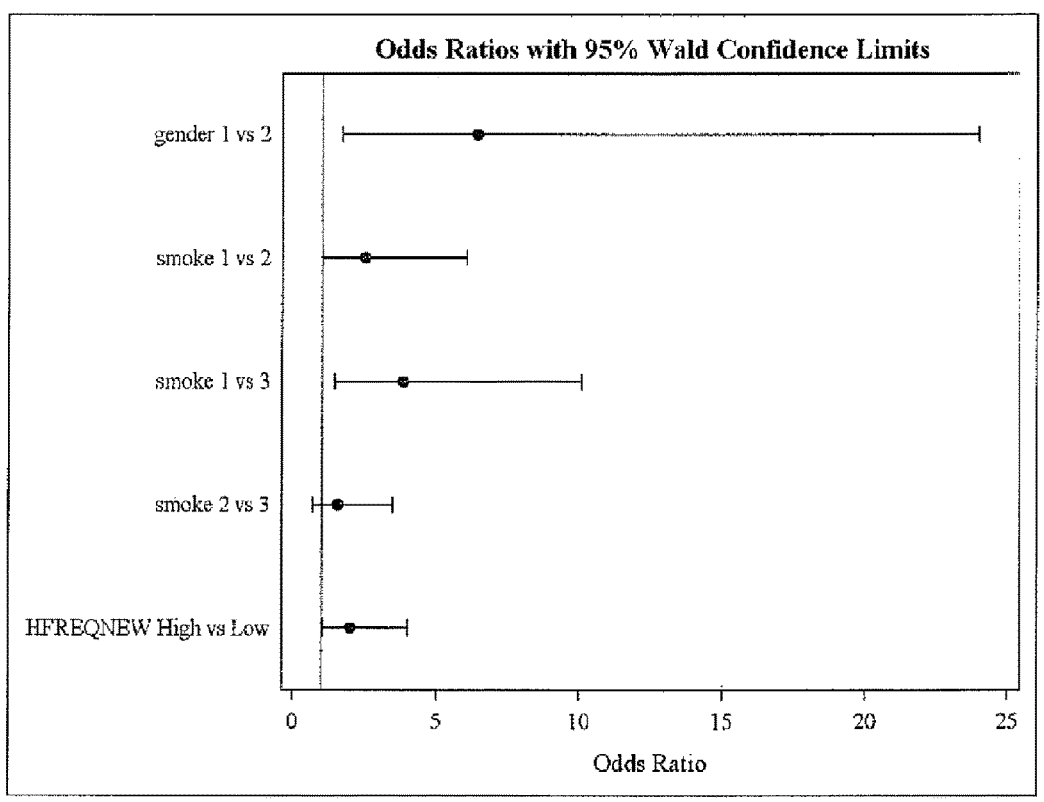
FIG. 19 depicts a graph of odds ratios (horizontal axis) for variables gender, smoking history and HFREQNEW of this invention.

Odds ratios for different clinical factors that were retained in the final model are shown in FIG. 19. An odds ratio can be interpreted as having a harmful or protective effect upon the subject depending on how far it deviates from 1 (i.e., no effect). Odds ratios whose confidence limits exclude 1 are statistically significant. Generally, the factors with higher odd ratio (e.g. SMK, Gender) are assigned larger weights compared to factors with small odds ratio (e.g. HFREQ).

The classification table for the full model is presented below in Table 8.

TABLE 8

Classification Table

| Prob Level | Correct Event | Correct Non-Event | Incorrect Event | Incorrect Non-Event | Correct | Sensitivity | Specificity | False POS | False NEG |
|---|---|---|---|---|---|---|---|---|---|
| 0.000 | 66 | 0 | 415 | 0 | 13.7 | 100.0 | 0.0 | 86.3 | . |
| 0.050 | 61 | 245 | 170 | 5 | 63.6 | 92.4 | 59.0 | 73.6 | 2.0 |
| 0.100 | 54 | 319 | 96 | 12 | 77.5 | 81.8 | 76.9 | 64.0 | 3.6 |
| 0.150 | 47 | 358 | 57 | 19 | 84.2 | 71.2 | 86.3 | 54.8 | 5.0 |
| 0.200 | 45 | 376 | 39 | 21 | 87.5 | 68.2 | 90.6 | 46.4 | 5.3 |
| 0.250 | 40 | 381 | 34 | 26 | 87.5 | 60.6 | 91.8 | 45.9 | 6.4 |
| 0.300 | 37 | 391 | 24 | 29 | 89.0 | 56.1 | 94.2 | 39.3 | 6.9 |
| 0.350 | 36 | 398 | 17 | 30 | 90.2 | 54.5 | 95.9 | 32.1 | 7.0 |
| 0.400 | 35 | 402 | 13 | 31 | 90.9 | 53.0 | 96.9 | 27.1 | 7.2 |
| 0.450 | 35 | 403 | 12 | 31 | 91.1 | 53.0 | 97.1 | 25.5 | 7.1 |
| 0.500 | 31 | 407 | 8 | 35 | 91.1 | 47.0 | 98.1 | 20.5 | 7.9 |
| 0.550 | 29 | 408 | 7 | 37 | 90.9 | 43.9 | 98.3 | 19.4 | 8.3 |
| 0.600 | 29 | 408 | 7 | 37 | 90.9 | 43.9 | 98.3 | 19.4 | 8.3 |
| 0.650 | 28 | 409 | 6 | 38 | 90.9 | 42.4 | 98.6 | 17.6 | 8.5 |
| 0.700 | 24 | 409 | 6 | 42 | 90.0 | 36.4 | 98.6 | 20.0 | 9.3 |
| 0.750 | 20 | 409 | 6 | 46 | 89.2 | 30.3 | 98.6 | 23.1 | 10.1 |
| 0.800 | 12 | 410 | 5 | 54 | 87.7 | 18.2 | 98.8 | 29.4 | 11.6 |
| 0.850 | 11 | 411 | 4 | 55 | 87.7 | 16.7 | 99.0 | 26.7 | 11.8 |
| 0.900 | 6 | 412 | 3 | 60 | 86.9 | 9.1 | 99.3 | 33.3 | 12.7 |
| 0.950 | 1 | 413 | 2 | 65 | 86.1 | 1.5 | 99.5 | 66.7 | 13.6 |
| 1.000 | 0 | 415 | 0 | 66 | 86.3 | 0.0 | 100.0 | . | 13.7 |

Preliminary Validation Study of G+P Index

To further test the use of the G+P Index, we carried out another study. Based on the statistical significance of various clinical and RNA markers, an index was constructed. There were 98 subjects whose TCC status (yes or no) as well as G+P INDEX variables were available.

A score of 5, 4, 3, 2 and 1 was assigned to M1 (genetic tests), Smokers, Male, IL8R, and HFREQ—which results in an index score ranging from 0 to 15. The number of true positives and true negatives were 6 and 84 respectively. Similarly, the number of false positives and false negatives were 5 and 3 respectively. Thus, the overall accuracy of the proposed index was 0.92.

Implications and Follow Up Based on the G+P Index

If the G+P INDEX result indicates a "High Risk" of UC defined as a score of 11-15 or above, the patient is prioritized for a flexible cystoscopy and abdominal ultrasound as clinically indicated.

If the G+P INDEX result indicates an "Moderate Risk" of UC, defined as a score of from 6-10, the patient is reviewed and followed up as per clinical practice. Consideration may be given to the use of cytology, uretoscopy and/or a CT scan.

If the G+P INDEX result indicates a "Low Risk" of UC, defined as a score of from 0-5, the patient will receive the normal standard of care and be placed on the appropriate waiting list.

References

The following references relate to the disclosure above.

Agresti, A. and Coull, B. A. (1998) Approximate is better than "ex-act" for interval estimation of binomial proportions. The American Statistician, 52, 119-126.

Altekruse S F, Kosary C L, Krapcho M, Neyman N, Aminou R, Waldron W, Ruhl J, Howlader N, Tatalovich Z, Cho H, Mariotto A, Eisner M P, Lewis D R, Cronin K, Chen H S, Feuer E J, Stinchcomh D G, Edwards B K (eds). SEER Cancer Statistics Review, 1975-2007, National Cancer Institute. Bethesda, Md., http://seer.cancer.gov/csr/1975_2007/, based on November 2009 SEER data submission, posted to the SEER web site, 2010.

Brown, L. D. Cai, T. T. and DasGupta, A. (2001) Interval estimation for a binomial proportion. Statistical Science, 16, 101-133.

Buckhaults et al., (Cancer Research 61:6996-7001 (2002) describes certain secreted and cell surface genes expressed in colorectal tumours.

Byrd, R. H., Lu, P., Nocedal, J. and Zhu, C. (1995) A limited memory algorithm for bound constrained optimization. *SIAM J. Scientific Computing*, 16, 1190-1208.

Dalgaard (2008). "Introductory Statistics with R, 2nd edition"; Peter Dalgaard, Chapter 13 (2008), Springer, ISBN 978-0-387-79053-4.

DeLong, E. R., D. M. DeLong, and D. L. Clarke-Pearson. 1988. Comparing the areas under two or more correlated receiver operating characteristic curves: A nonparametric approach. Biometrics 44: 837-845.

Gottschalk, P. G. and Dunn, J. R. (2005) The five-parameter logistic: A characterization and comparison with the four-parameter logistic. *Analytic Biochemistry*, 343, 54-65. Doi: 10.1016/j.ab.2005.04.035

Grossfield G, Wolf J, Litwan M, Hricak H, Shuler C, Agerter D, et al. Asymptomatic microscopic hematuria in adults: summary of AUA best practice policy recommendations. AFP 2001:63:1145-54.

Hall et al (Laryngoscope 113(1):77-81 (2003) (PMID: 12679418) (Abstract) described predictive value of serum thyroglobulin in thyroid cancer.

Hoerl, A. E. (1962) Application of ridge analysis to regression problems. *Chemical Engineering Progress*, 58, 54-59.

Holyoake A, O'Sullivan P, Pollock R, Best T, Watanabe J, Kajita Y, et al. Development of a multiplex RNA urine test for the detection and stratification of transitional cell carcinoma of the bladder. Clin Cancer Res. 2008 Feb. 1; 14(3):742-9.

Hotte et al., (A J. American Cancer Society 95(3):507-512 (2002) describes plasma osteopontin as a protein detectable in human body fluids and is associated with certain malignancies.

Kim et al., (JAMA 287(13):1671-1679 (2002) describes osteopontin as a potential diagnostic biomarker for ovarian cancer.

Koopman et al., (Cancer Epidemiol. Biomarkers Pre$^y$ 13(3): 487-491 (2004) (Abstract) describes osteopontin as a biomarker for pancreatic adenocarcinoma.

Kuo et al (Clin. Chim. Acta. 294(1-2):157-168 (2000) (Abstract) describes serum matrix metalloproteinase-2 and -9 in HCF- and HBV-infected patients.

Leman et al., (Urology, 69(4) 714-20 (2007) (Abstract) describes EPCA-2 as a serum marker for prostate cancer.

Loo R, Lieberman S, Slezak J, Landa H, Mariani A, Nicolaisen G, Aspera A and Jaconsen S: Stratifying risk of urinary tract malignant tumors in patients with asymptomatic microscopic hematuria. Mayo Clin Proc. 2013, 88(2); 129-138.

Lunn, D., Spiegelhalter, D., Thomas, A. and Best, N. (2009) The BUGS project: Evolution, critique and future directions (with discussion), *Statistics in Medicine* 28: 3049-3082.

Marchi et al., (Cancer 112, 1313-1324 (2008) (Abstract) describes ProApolipoprotein A1 as a serum marker of brain metastases in lung cancer patients.

Martin et al., (Prostate Cancer Prostatic Dis. Mar. 9, 2004 (PMID: 15007379) (Abstract) described use of human kallikrein 2, prostate-specific antigen (PSA) and free PSA as markers for detection of prostate cancer.

Mazzaferri et al., (J. Clin. Endocrinol. Metab. 88(4):1433-1441 (2003) (Abstract) describes thyroglobulin as a potential monitoring method for patients with thyroid carcinoma.

McDonald M, Swagerty D, Wetzel L: Assessment of Microscopic hematuria in adults. AFP 2006 73:10.

Melle et al., (Clin. Chem. 53(4), 629-635 (2007) (Abstract) describes HSP27 as a serum marker for pancreatic adenocarcinoma.

Moré, J. J. (1978) The Levenberg-Marquardt algorithm: implementation and theory, in *Lecture Notes in Mathematics* 630: Numerical Analysis, G. A. Watson (Ed.), Springer-Verlag: Berlin, pp. 105-116.

Nelder, J. A. and Mead, R. (1965) *A simplex* algorithm for function minimization. Computer Journal 7, 308-31.

O'Sullivan P, Sharples K, Dalphin M et al: A Multigene Urine Test for the Detection and Stratification of Bladder Cancer in Patients Presenting with Hematuria. J Urol 2012, Vol 188 No 3; 746

Pellegrini et al., (Cancer Immunol. Immunother. 49(7):388-394 (2000) (Abstract) describes measurement of soluble carcinoembryonic antigen and TIMP 1 as markers for pre-invasive colorectal cancer.

(R Development Core Team (2009). R: A language and environment for statistical computing. R Foundation for Statistical Computing, Vienna, Austria. ISBN 3-900051-07-0, URL http://www.R-project.org/)

Richards, F. J. (1959) A flexible growth function for empirical use. *Journal of Experimental Botany.* 10, 290-300.

Rudland et al., (Cancer Rese arch 62: 3417-3427 (2002) describes osteopontin as a metastasis associated protein in human breast cancer.

Sing et al (2009). (Tobias Sing, Oliver Sander, Niko Beerenwinkel and Thomas Lengauer (2009). ROCR: Visualizing the performance of scoring classifiers. R package version 1.0-4. http://CRAN.R-project.org/package=ROCR).

Speiss, A.-N., Feig, C. and Ritz, C. (2008) Highly accurate sigmoidal fitting of real-time RCR data by introducing a parameter for asymmetry. BMC Bioinformatics, 9, 221. Doi:10.1186/1471-2105-9-211.

Sprenger H, Lloyd A R, Lautens L L, Bonner T I, Kelvin D J. Structure, genomic organization, and expression of the human interleukin-8 receptor B gene. J Biol Chem. 1994 Apr. 15; 269(15):11065-72.

StataCorp. 2009. *Stata Statistical Software: Release* 11. College Station, Tex.: StataCorp LP.

Schwartz G: Proper evaluation of asymptomatic microscopic hematuria in the era of evidence-based medicine-progress is being made. Mayo Clin Proc. 2013, 88(2); 123-125.

Trivedi C and Messing E M: Commentary: the role of cytologic analysis of voided urine in the work-up of asymptomatic microhematuria. *BMC Urology* 2009, 9:13

Tsigkou et al., (I Clin Endocrinol Metab, 92(7) 2526-31 (2007) (Abstract) describes total inhibin as a potential serum marker for ovarian cancer.

Tsigkou et al., (I Clin Endocrinol Metab, 92(7) 2526-31 (2007) (Abstract) describes total inhibin as a potential serum marker for ovarian cancer.

Venables, W. N. & Ripley, B. D. (2002). Modern Applied Statistics with S. Fourth Edition. Springer, New York. ISBN 0-387-95457-0).

Whitley et al, (Dim Lab. Med. 24(1):29-47 (2004) (Abstract) describes thyroglobulin as a serum marker for thyroid carcinoma.

Yoshikawa et al., (Cancer Letters, 151: 81-86 (2000) describes tissue inhibitor of matrix metalloproteinase-1 in plasma of patients with gastric cancer.

Example 4: Triage of Patients Presenting with Hematuria Using G+P Index II

The G+P INDEX indicates a Positive when it takes values in the range of 11 to 15.

Definitions

As used herein, the following definitions are used in this and the following examples.

"AMH" means asymptomatic microhematuria;
"AUA" means American Urological Association;
"AUC" means area under the curve;
"CI" means confidence interval;
"CT" means computed tomography;
"ELIS A" means enzyme-linked immunosorbent assay;
"FISH" means fluorescence in situ hybridization;
"HPF" means high-powered field;
"logOR" means log odds ratio;
"Hfreq" means average daily frequency of hematuria during the most recent hematuria episode;
"ISUP" means International Society of Urological Pathology;
"MRI" means magnetic resonance imaging;
"NPV" means negative predictive value;
"OR" means odds ratio;
"QC" means quality control;
"QoL" means quality of life;
"Phenotypic' is used to define clinical prognostic characteristics and to distinguish them from gene expression-based biomarkers that have been broadly defined as 'genotypic' variables.
"RBC" means red blood cell;
"ROC" means receiver operating curve;
"RT-qPCR" means quantitative reverse transcription polymerase chain reaction;
"STARD" means Standards for Reporting of Diagnostic Accuracy;
"UC" means urothelial carcinoma;
"WHO" means World Health Organization.

Introduction

Hematuria, which is most often associated with causes such as benign prostatic enlargement, infection or urinary calculi, but is also symptomatic of urothelial carcinoma (UC), is estimated to occur in between 1 and 22% of patients in a general population [1,2]. Macroscopic (macro-) hematuria is characterized by a visible colour change in the urine of patients, while microscopic (micro-) hematuria is defined more precisely as the presence of ≥3 red blood cells per high-powered field (RBCs/HPF) in three concurrently collected urine samples [2]. The overall prevalence of UC in patients with microhematuria has been reported to be approximately 4%, whereas several studies have consistently shown that the prevalence of UC is much higher in patients with macrohematuria, ranging from approximately 12-23% [2-6], yet up to four times as many patients with micro-versus macrohematuria present for urological evaluation [7]. Notably, given that recent changes to the American Urological Association (AUA) guidelines [2] have seen the threshold for asymptomatic microhematuria (AMH) lowered to ≥3 RBCs/HPF in a single sample, and even lower thresholds (≥1 RBC/HPF) have been proposed [8], a consequential increase in the number of patients with hematuria who will undergo a urological work-up to investigate potential UC and a corresponding increase in the overall clinical and financial burden of these patients on healthcare systems is expected.

Such hematuria-related referrals place a significant clinical burden on urologists, as all patients must undergo a full work-up to provide an often inconclusive diagnosis. Furthermore, the existing diagnostic tests—many of which are invasive or have high radiation loadings—can have a detrimental effect on patient quality of life (QoL), especially if the patient receives repeated cystoscopies as mandated in the current guidelines [2]. It has been reported that for cystoscopies performed without prophylactic antibiotics, 22% of patients had asymptomatic bacteriuria and 1.9% of patients developed a febrile urinary tract infection (UTI) within 30 days [9]. Other studies have also reported a high prevalence of macrohematuria, pain on voiding and transient erectile dysfunction in men following cystoscopy [10,11].

Healthcare systems also incur a significant financial burden as a result of patients with hematuria undergoing a full urological work up [12,13] and it has been concluded that urine cytology adds costs without offering any significant diagnostic benefit [14-16]. Consequently, integrating an accurate, non-invasive test into the primary clinical work-up of patients presenting with hematuria allows physicians to effectively triage patients with hematuria, thereby reducing the number of patients undergoing a full urological work-up and investigative cystoscopy for UC, and offers significant benefits to both patients and healthcare systems [15-19].

Several clinical prognostic characteristics, including age, gender, smoking history and degree of hematuria, are well-established as risk factors for UC in patients with hematuria [3,20-22]. Recently, several groups have attempted to develop models based on clinical prognostic characteristics to predict the risk of UC in patients with hematuria [20-22], but critically, these models offer limited accuracy and have largely been focused on detecting patients with UC rather than ruling out patients who do not have disease. These detection-focused models have therefore been insufficient to reliably identify patients with disease during a primary evaluation, even if used in combination with urine cytology [20-22].

Despite the higher incidence of UC in patients presenting with macrohematuria, a number of studies show there is no significant difference in the distribution of UC by grade and stage in patients presenting with micro-compared with those presenting with macrohematuria [5,23-25]. Therefore, the AUA recommends that all patients with macrohematuria or AMH be referred to a urologist for a full urological work-up, as severity of hematuria is not sufficiently predictive for the presence of UC [2]. However, as patients with hematuria may only undergo limited urinalysis in a primary evaluation, consisting of cytology and in some cases imaging studies, such as ultrasound, a full urological work-up is often necessary to conclusively detect or rule out UC. While urine cytology is specified in current guidelines and routinely used in patients with suspected UC, cytology results are often inconclusive with atypical or suspicious findings and also suffer from a low diagnostic yield driven by a relatively high risk of false negative results for patients with UC-related hematuria [2,26,27]. Consequently, it can be difficult to rule out benign causes of hematuria, whether macrohematuria or AMH, during a primary evaluation, especially if UC-related hematuria is intermittent and appears to resolve following treatment for a benign cause [12].

A number of gene-based studies have set out to profile urinary biomarkers in patients with UC, and these biomarkers may be useful in their own right for detecting disease [28,29]. An opportunity also exists to triage out patients on the basis of their clinical characteristics and gene expression profile. Combining NMP22 enzyme-linked immunosorbent assay (ELISA) tests or a panel of gene markers with clinical characteristics has been shown to improve diagnostic accuracy compared with clinical characteristics alone, but these combined models have not yet delivered significant advances in overall diagnostic accuracy, especially when attempting to identify low-risk patients [30,31]. Nevertheless it is considered that incorporating clinical factors and specific gene expression into a combined algorithm is likely to provide the best guidance for diagnosing and managing patients with hematuria or UC [32].

Cxbladder™ Detect (Pacific Edge Ltd., Dunedin, New Zealand), a multigene test performed on unfractionated urine has previously been shown to be more sensitive than urine cytology and NMP22 for detecting UC in patients with macrohematuria [33] and more accurate than urine cytology, NMP22 and fluorescence in situ hybridization (FISH) in a comparative analysis (Kasabov, Darling, Breen, et al., unpublished observations). Cxbladder Detect uses quantitative reverse transcription polymerase chain reaction (RT-qPCR) technology to quantify five mRNA markers, four markers that are overexpressed in UC alongside a fifth marker that is elevated in non-malignant inflammatory conditions, and offers a high level of specificity and sensitivity when used to detect UC in patients presenting with hematuria [33]. It was hypothesized that an integrated model combining high-performance genetic biomarkers with phenotypic variables collected from the same patients will provide superior clinical resolution using high sensitivity (i.e. a low probability of a patient with UC receiving a false negative result), high negative predictive value (i.e. a high proportion of all negative results being true) and a high test-negative rate to enable the accurate triage of patients who have a low probability of UC. These genotypic and phenotypic variables when combined into a novel segregation model enable patients with hematuria who have a low probability of UC to be identified and triaged, as opposed to undergoing a full urological work-up.

Methods

Patient Selection

A prospective sample of 695 patients have been analysed, where true clinical outcome was determined using a conventional clinical evaluation. The study sample consists of an initial cohort of patients with hematuria was consented and sampled as previously described [33], where a consecutive series of 517 patients with a recent history of macrohematuria, aged ≥45 years and without a prior history of UC, were recruited prospectively from nine urology clinics in Australia and New Zealand. These patients were followed for three months for determination of UC status or alternative diagnosis following multigene analysis of urine samples, with a positive UC diagnosis being based on cystoscopical appearance and histopathological examination. The stage of disease was classified according to the TNM staging criteria determined by pathology and diagnostic imaging investigations and tumor grade was classified according to local pathology practice, using the 1998 World Health Organization (WHO)/International Society of Urological Pathology (ISUP) consensus classification [34].

Additional cohorts of 94 and 84 patients undergoing urological investigations following a macrohematuria event were subsequently recruited from two centers in New Zealand between March 2012 and April 2013 and included in the development of models. Centers were selected to participate on the basis of their previous experience participating in the initial study and their willingness to evaluate the Cxbladder Detect product within individual clinical settings.

An additional representative test set of 45 patients presenting with microhematuria were prospectively collected and used for further validation of the G+P INDEX, as set out below.

Eligibility criteria were similar to those of [33], except that patients aged ≥18 years and those who had previously undergone a cystoscopy to investigate UC that proved to be negative were eligible for enrolment. Furthermore, as in [33], patients exhibiting symptoms indicative of a UTI, or bladder or renal calculi, were excluded.

Ethical approval for this study was granted by all participating centers and informed consent obtained from all patients providing samples.

Urine Sample Collection and Assessment

To provide gene expression data, a single mid-stream urine sample was collected from participants using the Urine Sampling System from Pacific Edge. Multigene analysis of samples from all studies was carried out in accordance with the standard operating procedure, as is used for the commercially available Cxbladder Detect multigenic test. All urine samples (4.5 mL) from the initial cohort were collected at a clinic prior to cystoscopy and transferred to a stabilization liquid via vacuum driven aspiration and sent to Pacific Edge within 48 hours. The samples were then stored at −80° C. until required for batch analysis. Samples from the subsequent cohorts were collected in the same manner, but shipped to Pacific Edge at ambient temperature and processed within 7 days of sample collection in accordance with revised quality control (QC) limits and tolerance testing performed at the Pacific Edge diagnostic laboratory.

Statistical Analysis

Univariate logistic regression was used to estimate the unadjusted (raw) log odds ratio (logOR) co-efficients for four binary phenotypic variables associated with UC: age, gender, smoking history and average daily frequency of hematuria during the patient's most recent hematuria episode (Hfreq; see Table 9).

TABLE 9

Definitions of binary phenotypic variables associated with UC and their corresponding scores

| Phenotypic parameter | Score 0 | Score 1 |
|---|---|---|
| Gender | Female | Male |
| Age | <60 years | ≥60 years |
| Smoking history | Never smoked | Current or past smoker |
| Hfreq | ≤1 episode/day | >1 episode/day |

Multivariate logistic regression on all four phenotypic variables was used to generate adjusted logOR co-efficients in the phenotypic model (P INDEX).

G INDEX was developed using logistic regression to determine the association between UC and mRNA concentrations for the five Cxbladder® Detect genes (IGFBP5, HOXA13, MDK, CDK1 and CXCR2) in urine samples. A multivariate genotypic-phenotypic model (G+P INDEX) was generated using a combination of all nine variables from the G INDEX and P INDEX. These linear models determined the logOR from which the probability of a patient having UC was derived.

The relative performance of each of model was illustrated in receiver operating curves (ROCs) plotting the false positive rate versus the true positive rate when testing for UC, as determined by each model. Area under the curve (AUC) was used to compare the relative efficiency of each model with an AUC approaching 1 deemed to be optimal.

To reduce potential bias when model estimation and prediction are performed on the same data set, a bias-corrected AUC was calculated for each of the three logistic regression models using bootstrap resampling [35]. The difference between the nominal AUC from the original sample and the average AUC from the bootstrap samples is an estimate of the sample bias and the nominal AUCs were adjusted accordingly. Bootstrap estimates of bias-corrected confidence intervals (CIs) were also obtained [36].

Furthermore, it was a design criteria for this clinical test that the performance characteristics of each model must exceed a threshold NPV of 0.97, with as high a sensitivity as possible with the further caveat of having a high test-negative rate. The test negative rate is selected to provide a high clinical resolution when triaging out patients presenting with hematuria who have a low probability of having UC. Comparisons were made between the G INDEX, P INDEX and G+P INDEX and the performance of each model was determined in terms of sensitivity and NPV with a sufficiently high test-negative rate to provide an effective tool for triaging out patients with haematuria who have a low probability of UC.

Results

Sample Demographics

Figure 20A:
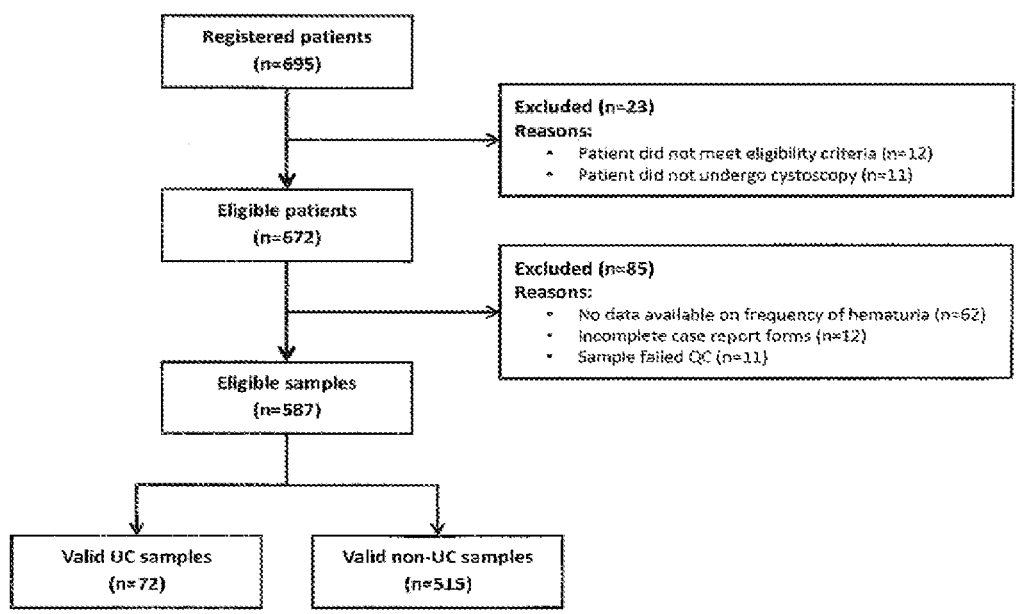
FIGS. 20A and 20B depict flow charts for standards of reporting diagnostic accuracy.

Of the 695 patients with macrohematuria registered across the three cohorts, 23 were deemed to be ineligible and samples from a further 85 patients were excluded after enrolment due to the absence of sufficient data or samples failing to meet QC standards (see FIG. 20A). In total, samples from 587 patients were available for modelling comprising 72 UC-positive and 515 UC-negative samples.

Figure 20B:
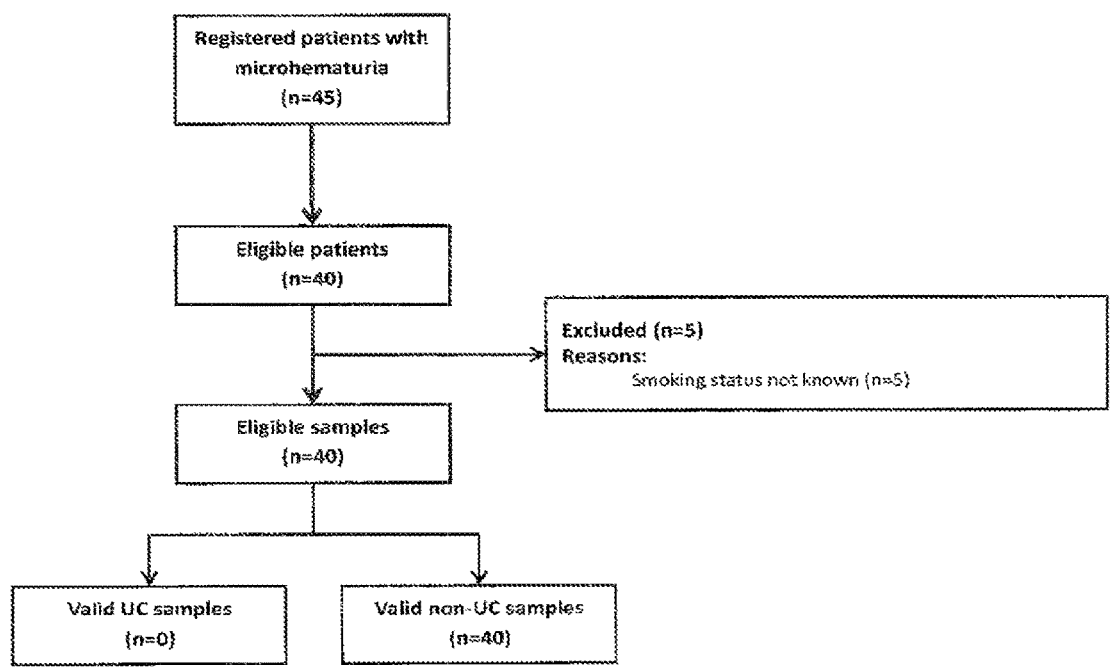

Of the 45 samples from patients with microhematuria provided, 40 were suitable for analysis with 5 patients deemed ineligible and excluded from the analysis (see FIG. 20B). All 45 patients had received a full urological evaluation and clinical truth was confirmed as UC-negative. Full demographic data from both sample populations is presented in Table 10.

TABLE 10

Sample population demographics for patients with macro- and microhematuria with complete data

| Parameter | | Patients with macrohematuria (N = 587), n (%) | Patients with microhematuria (N = 40), n (%) |
|---|---|---|---|
| Age, years | 0-49 | 65 (11.1) | 21 (52.5) |
| | 50-59 | 111 (18.9) | |
| | 60-69 | 145 (24.7) | 19 (47.5) |
| | 70-79 | 175 (29.8) | |
| | 80-100 | 91 (15.5) | |
| Gender | Female | 113 (19.3) | 25 (62.5) |
| | Male | 474 (80.7) | 15 (37.5) |
| Smoking history | Never smoked | 246 (41.9) | 25 (62.5) |
| | Current or past smoker | 341 (58.1) | 15 (37.5) |
| Hfreq (episodes/day) | ≤1 | 332 (56.6) | 40 (100) |
| | >1 | 255 (43.4) | — |
| Tumor stage | Normal | 515 (87.7) | 40 (100) |
| | T1 | 16 (2.7) | — |
| | T2 | 11 (1.9) | — |
| | T3 | 2 (0.3) | — |
| | Ta | 40 (6.8) | — |
| | Tis | 3 (0.5) | — |

Relationship Between Phenotypic Variables and Risk of UC in Patients with Macrohematuria Unadjusted univariate logistic regression analyses of each of the four binary phenotypic variables indicated that age ≥60 years, male gender, a history of smoking and a high frequency of macrohematuria were all associated with an increased risk of UC (Table 11).

TABLE 11

Unadjusted and adjusted ORs for UC by phenotypic and genotypic factors for patients with hematuria

| Phenotypic variables | | Control | UC | Unadjusted OR (95% CI) | Adjusted P variable OR (95% CI) | Adjusted G + P variable OR (95% CI) |
|---|---|---|---|---|---|---|
| Age, years | <60 | 151 | 11 | 2.30 | 2.24 | 1.89 |
| | ≥60 | 364 | 61 | (1.22-4.73) | (1.18-4.65) | (0.85-4.64) |
| Gender | Female | 105 | 8 | 2.05 | 1.58 | 3.03 |
| | Male | 410 | 64 | (1.01-4.75) | (0.76-3.72) | (1.12-9.36) |
| Smoking history | Never smoked | 227 | 19 | 2.20 | 2.19 | 2.67 |
| | Current or past smoker | 288 | 53 | (1.29-3.91) | (1.27-3.92) | (1.34-5.64) |
| Hfreq (average episodes/day) | ≤1 | 300 | 32 | 1.74 | 1.80 | 1.76 |
| | >1 | 215 | 40 | (1.06-2.88) | (1.08-3.00) | (0.93-3.35) |

| Genotypic variables | Unadjusted OR (95% CI) | Adjusted G variable OR (95% CI) | Adjusted G + P variable OR (95% CI) |
|---|---|---|---|
| IGFBP5 | 7.34 | 2.15 | 2.21 |
| | (4.59-12.33) | (1.03-4.58) | (1.03-4.83) |
| HOXA13 | 6.27 | 0.33 | 0.20 |
| | (3.92-10.34) | (0.13-0.83) | (0.07-0.56) |
| MDK | 7.10 | 4.76 | 8.14 |
| | (4.73-11.10) | (1.74-13.62) | (2.64-26.60) |
| CDK1 | 7.80 | 3.47 | 2.59 |
| | (5.11-12.39) | (1.39-9.13) | (0.98-7.18) |
| CXCR2 | 1.69 | 0.65 | 0.69 |
| | (1.36-2.10) | (0.45-0.92) | (0.47-0.98) |

Adjusted P INDEX, G INDEX and G+P INDEX variable ORs are the exponentiated co-efficients in the P INDEX, G INDEX and G+P INDEX, respectively.

Adjusted logOR co-efficients were calculated in the multivariate logistic regression model.

P INDEX=−3.78+0.81×Age+0.46×Gender+0.78×Smoking history+0.59×Hfreq, where each phenotypic variable is assigned a binary score of 0 or 1, as designated in Table 9, and the confidence intervals for the co-efficients are presented in Table 11. The bias-corrected estimate for AUC for the P INDEX is 0.66 (95% CI: 0.55-0.67; FIG. 21).

Relationship Between Genotypic Variables and Risk of UC in Patients with Macrohematuria The G INDEX was estimated by logistic regression using the log mRNA concentrations of the five genes IGFBP5, HOXA13, MDK, CDK1 and CXCR2 in urine samples to predict UC occurrence.

G INDEX=−6.22+0.77×IGFBP5−1.11×HOXA13+ 1.56×MDK+1.24×CDK1−0.43×CXCR2

The G INDEX gives a bias-corrected AUC of 0.83 (95% CI: 0.74-0.89; FIG. 21).

Relationship Between Genotypic and Phenotypic Variables and Risk of UC in Patients with Macrohematuria The five continuous genotypic variables were then combined with the four binary phenotypic variables to estimate the G+P INDEX using mulitvariate logistic regression.

G+P INDEX=−8.46+(0.79×IGF−1.60×HOXA+2.10× MDK+0.95×CDC−0.38×IL8R)+(0.64×Age+ 1.11×Gender+0.98×Smoking history+0.56× Hfreq)

The G+P INDEX gives a bias-corrected AUC of 0.86 (95% CI: 0.80-0.91).

Comparison Between G INDEX and G+P INDEX

There is overlap between the confidence intervals for the G INDEX and G+P INDEX, so a bootstrap version of a paired test was constructed by determining the difference in AUC for the G INDEX and G+P INDEX for each bootstrap sample. Ten thousand bootstrap samples with a sample size of n=587 were generated by random sampling with replacement from the original 587 samples available for analysis. The resulting 95% CI for the difference between models was 0.01-0.08. Thus the probability that the true difference between the two AUCs is less than 0.01 is <0.025, indicating that there is a high likelihood of the AUC for the G+P INDEX being significantly greater than the AUC for the G INDEX.

NPV and Sensitivity of Models

Figure 22:
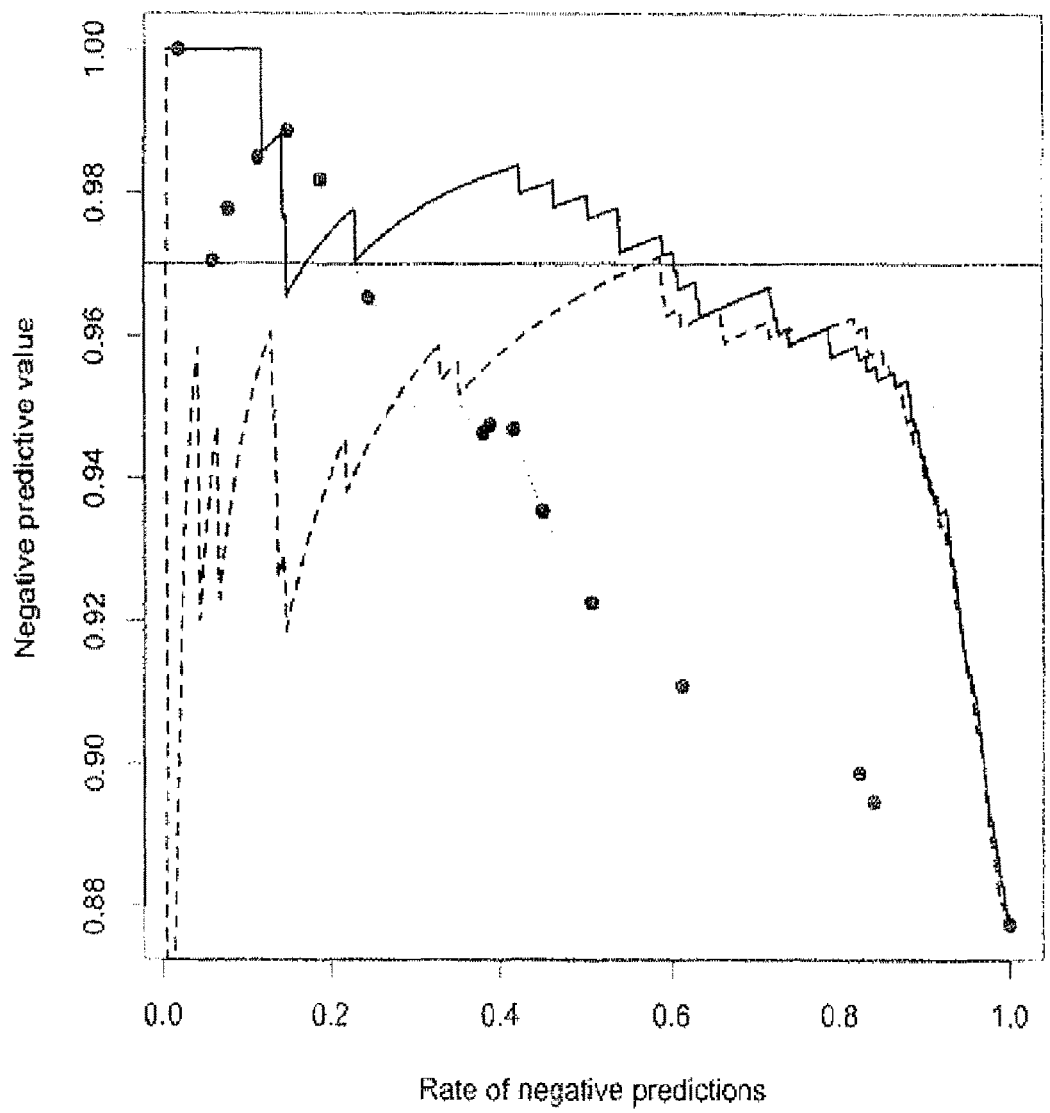
FIG. 22 depicts NPV versus proportion of patients with haematuria testing negative according each model. P INDEX (dotted line), G INDEX (dashed line), and G+P INDEX (solid line).
Figure 23:
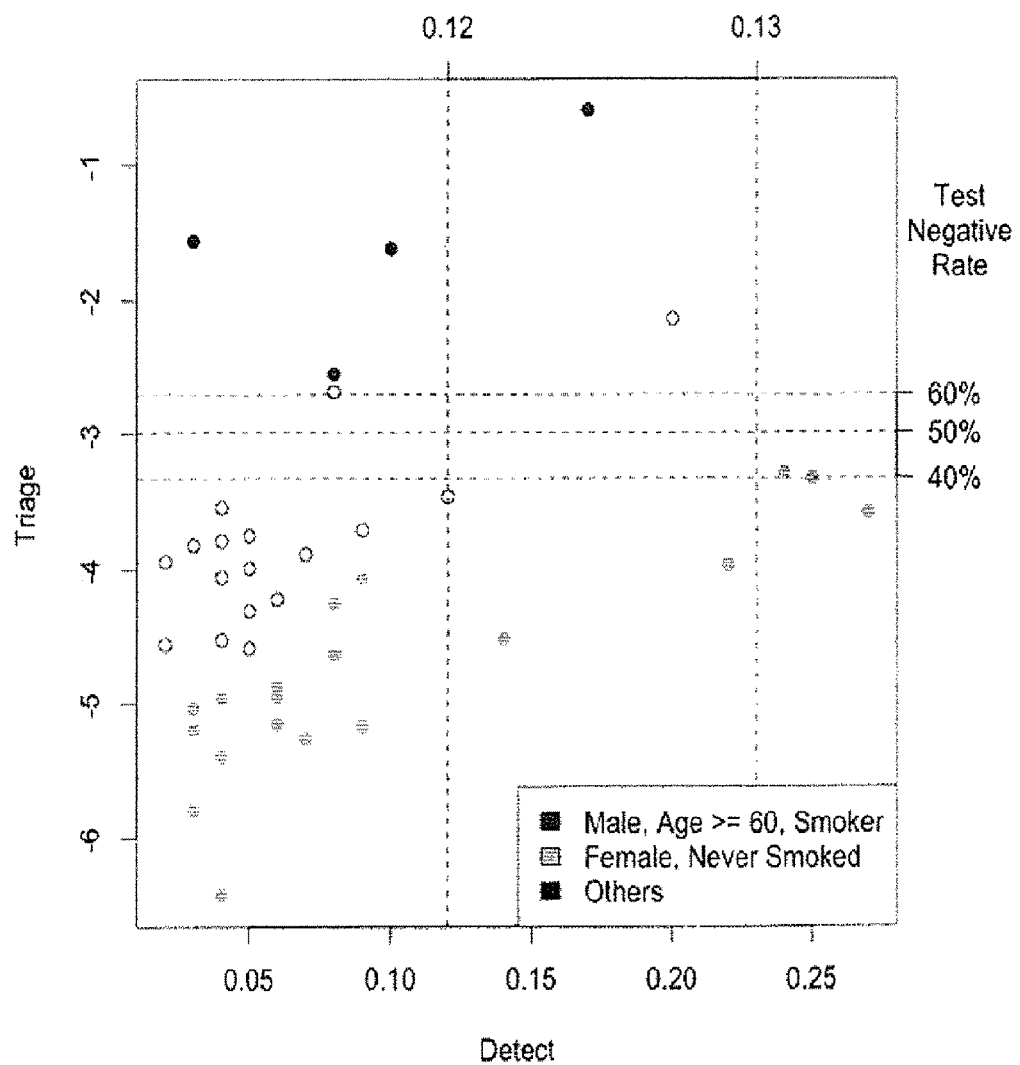
FIG. 23 depicts a graph of the relationship between detect results (horizontal axis) versus Triage result (vertical axis).

The G+P INDEX generated an NPV >0.97 over the range of test-negative rates from 0.2 to 0.7 and was almost always higher than the NPV for the G INDEX model (FIG. 22). The G+P INDEX offered performance characteristics of sensitivity of 0.95 and NPV 0.98 when the test-negative rate was 0.4 (Table 12; FIG. 22). In contrast, the G INDEX only achieved sensitivity of 0.86 and an NPV of 0.96 when the test-negative rate was 0.4 (Table 12).

TABLE 12

Performance Characteristics of Each Model When Thresholds Are Set For Varying Test Negative Rates

| Threshold (logOR) | Test-negative rate (95% CI) | NPV (95% CI) | Sensitivity (95% CI) | Specificity (95% CI) |
|---|---|---|---|---|

| P INDEX | | | | |
|---|---|---|---|---|
| −2.54 | 0.25 (0.21-0.28) | 0.97 (0.92-0.99) | 0.93 (0.85-0.98) | 0.27 (0.23-0.31) |
| −2.52 | 0.38 (0.34-0.42) | 0.95 (0.91-0.97) | 0.83 (0.74-0.91) | 0.41 (0.37-0.45) |
| −2.39 | 0.42 (0.37-0.45) | 0.95 (0.91-0.97) | 0.82 (0.72-0.90) | 0.45 (0.40-0.49) |
| −1.95 | 0.51 (0.47-0.54) | 0.92 (0.89-0.95) | 0.68 (0.56-0.78) | 0.53 (0.49-0.57) |
| −1.93 | 0.51 (0.46-0.55) | 0.92 (0.89-0.95) | 0.68 (0.56-0.78) | 0.53 (0.49-0.58) |
| −1.73 | 0.82 (0.79-0.85) | 0.90 (0.87-0.92) | 0.32 (0.22-0.43) | 0.84 (0.81-0.87) |
| G INDEX | | | | |
| −3.46 | 0.20 (0.17-0.23) | 0.94 (0.88-0.97) | 0.90 (0.80-0.95) | 0.22 (0.18-0.25) |
| −3.23 | 0.30 (0.26-0.34) | 0.95 (0.91-0.98) | 0.89 (0.80-0.95) | 0.33 (0.28-0.37) |
| −3.04 | 0.40 (0.36-0.44) | 0.96 (0.92-0.98) | 0.86 (0.77-0.93) | 0.44 (0.40-0.48) |
| −2.86 | 0.50 (0.46-0.54) | 0.97 (0.94-0.98) | 0.86 (0.77-0.93) | 0.55 (0.51-0.59) |
| −2.63 | 0.60 (0.56-0.63) | 0.96 (0.94-0.98) | 0.82 (0.71-0.90) | 0.66 (0.62-0.69) |
| −2.41 | 0.70 (0.66-0.73) | 0.96 (0.94-0.98) | 0.78 (0.65-0.86) | 0.77 (0.73-0.80) |
| G + P INDEX | | | | |
| −4.02 | 0.20 (0.17-0.23) | 0.97 (0.93-0.99) | 0.96 (0.88-0.99) | 0.22 (0.19-0.26) |
| −3.67 | 0.30 (0.26-0.33) | 0.98 (0.94-0.99) | 0.94 (0.87-0.99) | 0.33 (0.29-0.37) |
| −3.33 | 0.40 (0.36-0.44) | 0.98 (0.95-1.00) | 0.95 (0.86-0.98) | 0.45 (0.40-0.49) |
| −2.99 | 0.50 (0.46-0.54) | 0.98 (0.96-0.99) | 0.92 (0.83-0.97) | 0.56 (0.52-0.60) |
| −2.71 | 0.60 (0.56-0.64) | 0.97 (0.95-0.99) | 0.86 (0.76-0.93) | 0.67 (0.63-0.71) |
| −2.37 | 0.70 (0.66-0.73) | 0.97 (0.94-0.98) | 0.80 (0.70-0.88) | 0.77 (0.73-0.80) |

Application of the G+P INDEX in Patients with Microhematuria

While the G+P INDEX was developed using data from patients with macrohematuria, its robustness was tested in a further 40 samples from patients with microhematuria (Hfreq=0). A higher test-negative rate was expected in a microhaematuria population as the incidence of UC is lower in this population, and using a test negative rate of 0.4, 32 (80%) patients tested negative and would be correctly triaged out, therefore not requiring a full urological work-up for the determination of UC.

Discussion

This study defines a clinical tool that offers clinicians and physicians the ability to effectively triage-out patients presenting with hematuria from the need to have a full urological work-up for the detection of UC. The study presents an internally validated genotypic-phenotypic model, G+P INDEX, with bootstrap-based CI estimates, that offers a combination of high sensitivity and high NPV (i.e. a low probability of an individual patient with UC providing a false-negative result and a high proportion of all negative results being true) that is not offered by models derived exclusively from genotypic or phenotypic data alone. This provides clinicians and physicians with a unique opportunity to triage out patients with both micro- and macrohematuria, in particular by identifying patients with a low risk of having UC who do not require a full urological work up.

A high test-negative rate in the context of high sensitivity is an important consideration for an effective triage-out test that aims to direct patients with a low probability of UC away from a full clinical work-up [37]. Accordingly, at a test-negative rate of 0.4 the sensitivity of the G+P INDEX presented here maximizes both the sensitivity and NPV (0.95 and 0.98, respectively). This can be compared with the best fit selected from the genotypic model published in [33] (sensitivity=0.82; NPV=0.97) and is also comparable with the sensitivity and NPV of both cystoscopy (sensitivity=0.89-0.98; NPV=0.99) and virtual cystoscopy using computed tomography (CT) scans or magnetic resonance imaging (MRI) (sensitivity=0.94 and 0.91, respectively) [38-40].

It is acknowledged that the sample population used to derive the G INDEX, P INDEX and G+P INDEX in this instance consisted of patients with macrohematuria. However, the high sensitivity of this test at a test negative rate of 0.4 in patients with macrohematuria allows the G+P INDEX to be applied across both macro- and microhematuria populations. Presuming that patients with and without UC are similarly distributed amongst the micro- and macrohematuria patient populations, but with an expected UC prevalence of 4% in the microhematuria population, a high NPV can also be expected in the microhematuria patient population.

By applying the G+P INDEX to the sample population of patients with microhematuria who do not have UC it was shown that 80% of the patients would have been triaged out on the basis of the result. Only 20% would be referred for a full urological work-up. This compares with conventional guidelines that would currently see all of the patients (100%) with microhematuria that cannot be attributed to a benign cause undergoing a full urological work-up, incurring significant unnecessary costs and negatively impacting patient QoL.

Severity of hematuria is correlated with the probability of a patient having UC, but not the stage or grade of any tumour, and an estimated 96% and 77-88% of patients with micro- and macrohematuria, respectively, referred to a urologist will not have UC [2-6]. Therefore, avoiding potentially unnecessary urological work-ups for patients with hematuria has several benefits. Cystoscopy may be associated with adverse effects, such as pain on voiding, bleeding, UTIs, male sexual dysfunction and the anxiety that accompanies an inconclusive or unconfirmed UC diagnosis [9-11]. Most notably, this novel approach has the potential to reduce the burden on resources and the financial cost associated with a full urological work-up on UC-negative patients. For example, in the UK, avoiding cystoscopy in patients with hematuria with an initial negative cytology and/or tumor biomarker test has been estimated to save approximately US$770 per patient (£483 per patient) evaluated [13]. The G+P INDEX described here provides an effective alternative to the use of urine cytology when used in a primary evaluation setting. This is particularly relevant in settings where primary evaluation is carried out by primary care physicians.

On this basis, if we assign an arbitrary 'nominal cost' of US$4,500 for each full urological work up, the total cost for working up 1,000 patients with microhematuria would approach US$4.5 million. In contrast, if 80% of patients with microhematuria are triaged out using the G+P INDEX at an arbitrary nominal cost of US$2,500, the total direct cost of testing and full urological work-ups for the remaining 20% of patients would total US$3.4 million. This provides a notional net saving in direct costs of approximately US$1.1 million per 1,000 patients with microhematuria.

While the genotypic algorithm developed by O'Sullivan et al. [33] comprised the same genotypic constituents as the G+P INDEX presented here, the balance between sensitivity and specificity was calibrated for the optimal primary detection of UC in symptomatic patients (i.e. presenting with hematuria) who were undergoing a full urological work-up. In contrast, the G+P INDEX in this study also incorporated phenotypic variables and has been optimized for high sensitivity and high NPV, to segregate out those patients with hematuria who do not require a full urological work-up for suspected UC. No attempt is made to define or select patients with UC. Instead the aim is to confidently rule out those who do not have UC, and as such, all patients not segregated out would progress for a full urological work-up.

While several studies have previously sought to develop predictive models that consider phenotype when assessing the risk of UC in patients presenting with hematuria, the accuracy of phenotype-dependent models alone appears to be limited. For example, Loo et al. [21] prospectively investigated whether phenotypic parameters could be used to identify patients with microhematuria who may not have required a urological referral and full work-up and concluded that age, male gender and a recent diagnosis of macrohematuria were significant predictors of UC. A history of smoking and >25 RBCs/HPF in a recent urinalysis were not statistically significant predictors of UC, in isolation, but even when included in their 'Hematuria Risk Index' to improve predictive accuracy, this index resulted in an AUC of 0.809 [21]. Interestingly, the phenotypic ORs in this study and those identified by Loo et al. are comparable, with overlapping 95% CIs for smoking history and gender, and while age, gender and smoking history have similar weightings in each model, the influence of the genotypic component of the G+P INDEX presented here is likely to account for the higher AUC [21].

Likewise, Cha et al. [20] reported that age, smoking history and degree of hematuria, but not gender, were significantly correlated with the presence of UC in patients with asymptomatic hematuria and used a multivariate model to develop a nomogram comprised of phenotypic and urine cytology data for predicting UC. As with Loo et al. [21], the reported phenotypic ORs are comparable to those reported here, but even after incorporating urine cytology into the nomogram, the AUC of 0.831 reported in [20] was lower than that of the G+P INDEX.

In another study, Tan et al. [22] retrospectively stratified patients with hematuria who had been referred to a specialist urology clinic into high- and low-risk groups using a nomogram derived from patient age, gender, smoking history and the degree of hematuria. While comparisons with this study must be made with caution given the high proportion of patients who were excluded due to an absence of data (80 out of 405 patients), the AUC of 0.804, sensitivity of 0.900 and NPV of 0.953 were all lower than the G+P INDEX described here.

Several attempts have also been made to improve the accuracy of phenotypic models by supplementing them with the results of urinary biomarker tests. When the nuclear matrix protein NMP22 point of care proteomic assay is used in isolation to detect UC it has a sensitivity of 0.557 and NPV of 0.968 [17]. Lotan et al. [41] published a multivariable algorithm comprising phenotypic factors, NMP22 and urine cytology with an AUC for predicting UC of 0.826 that was then prospectively validated with an AUC of 0.802 [31]. However, it is important to note that this model attempted to discriminate between high-risk patients who did and did not have UC, as opposed to maximizing sensitivity and NPV to triage-out patients with a low probability of UC.

The improved accuracy obtained with algorithms comprising both genotypic and phenotypic data have previously been demonstrated in breast cancer, in particular [42-45].

Likewise, Mitra et al. [30] used a combination of molecular markers and smoking intensity to calculate a multivariate model that was superior to routine clinicopathological parameters in predicting survival in patients with UC. However, the present study is the first to demonstrate that phenotypic risk factors can be combined with genotypic data to increase the accuracy of a model for separating patients with haematuria into categories requiring differential levels of urological follow up and clinical care rather than survivorship prediction.

When phenotypic data are combined with genotypic data in a model, the resolution of data is likely to impact the accuracy of the model. For example, smoking is a well understood risk factor for UC and is included in most phenotypic models for detecting UC. In Cha et al. [20], Tan et al. [22], Lotan et al. [31,41] and the current study, the binary discriminants never smoked and current/ex-smoker were used, whereas Mitra et al. [30] calculated smoking intensity on the basis of years of smoking and number of cigarettes smoked each day and Loo et al. [21] categorized smokers into never smoked, passive smokers, smokers who had ceased and current smokers. While it is known that the risk of UC increases substantially with exposure to smoking [46], arbitrarily defining phenotypic variables may limit the overall accuracy and utility of phenotypic models. In contrast, an interaction between a patient's genotypic and phenotypic variables would not be unexpected. However, combining the impact of phenotypic factors and genetic variables in a single tool improved the accuracy of the model described in this study. A similar principle also applies to describing hematuria phenotype. Patients presenting with micro- or macrohematuria are essentially on a biological continuum and have different likelihoods of having UC [2-6,21]. Accordingly, despite all patients with microhematuria in this study having a Hfreq score of 0, the severity of their hematuria, in combination with other phenotypic factors, is likely to be indirectly accounted for in the genotypic component of the G+P INDEX.

References

The articles recited immediately below refer to Example 4, and are all incorporated herein fully by reference.

1. Kelly J D, Fawcett D P, Goldberg L C: Assessment and management of non-visible haematuria in primary care. *BMJ* 2009, 338:a3021.
2. Davis R, Jones J S, Barocas D A, Castle E P, Lang E K, Leveillee R J, Messing E M, Miller S D, Peterson A C, Turk T M T, Weitzel W: Diagnosis, evaluation and follow-up of asymptomatic microhematuria (AMH) in adults: AUA guideline. *J Urol* 2012, 188(6 Suppl): 2473-2481.
3. Sutton J M. Evaluation of hematuria in adults. *JAMA* 1990, 263:2475-2480.
4. Khadra M H, Pickard R S, Charlton M, Powell P H, Neal D E: A prospective analysis of 1,930 patients with hematuria to evaluate clinical practice. *J Urol* 2000, 163:524-527.
5. Davidson P: Re-design of a haematuria clinic: Assessment of 2346 haematuria patients. *J Urol* 2011, 185(4S):e495.
6. Price S J, Shephard E A, Stapley S A, Barraclough K, Hamilton W T: Non-visible versus visible haematuria and bladder cancer risk: A study of electronic records in primary care. *Br J Gen Pract* 2014, 64:e584-e589.
7. Buteau A, Seideman C A, Svatek R S, Youssef R F, Chakrabati G, Reed G, Bhat D, Lotan Y: What is evaluation of hematuria by primary care physicians? Use of electronic medical records to assess practice patterns with intermediate follow-up. *Urol Oncol* 2014, 32:128-134.

8. Jimbo M: Evaluation and management of hematuria. *Prim Care* 2010, 373:461-472.
9. Herr H W: The risk of urinary tract infection after flexible cystoscopy in bladder tumor patients who did not receive prophylactic antibiotics. *J Urol* 2014 Jul. 18. pii: S0022-5347(14)03963-9.
10. Burke D M, Shackley D C, O'Reilly P H: The community-based morbidity of flexible cystoscopy. *BJU Int* 2002, 89:347-349.
11. Stay K, Leibovici D, Goren E, Livshitz A, Siegel Y I, Lindner A, Zisman A: Adverse effects of cystoscopy and its impact on patients' quality of life and sexual performance. *Isr Med Assoc J* 2004, 6:474-478.
12. Rao P K, Jones J S: How to evaluate 'dipstick hematuria': What to do before you refer. *Cleve Clin J Med* 2008, 75:227-233.
13. Rodgers M, Nixon J, Hempel S, Aho T, Kelly J, Neal D, Duffy S, Ritchie G, Kleijnen J, Westwood M: Diagnostic tests and algorithms used in the investigation of haematuria: systematic reviews and economic evaluation. *Health Technol Assess* 2006, 10:iii-iv, xi-259.
14. Falebita O A, Lee G, Sweeney P: Urine cytology in the evaluation of urological malignancy revisited: is it still necessary? *Urol Int* 2010, 84:45-49.
15. Feifer A H, Steinberg J, Tanguay S, Aprikian A G, Brimo F, Kassouf W: Utility of urine cytology in the workup of asymptomatic microscopic hematuria in low-risk patients. *Urology* 2010, 75:1278-1282.
16. Svatek R S, Hollenbeck B K, Holmang S, Lee R, Kim S, Stenzl A, Lotan Y. The economics of bladder cancer: Costs and considerations of caring for this disease. *Eur Urol* 2014, 66:253-262.
17. Grossman H B, Messing E, Soloway M, Tomera K, Katz G, Berger Y, Shen Y: Detection of bladder cancer using a point-of-care proteomic assay. *JAMA* 2005, 293:810-816.
18. Friedlander D F, Resnick M J, You C, Bassett J, Yarlagadda V, Penson D F, Barocas D A: Variation in the intensity of hematuria evaluation: a target for primary care quality improvement. *Am J Med* 2014, 127:633-640.
19. Shinagare A B, Silverman S G, Gershanik E F, Chang S L, Khorasani R: Evaluating hematuria: impact of guideline adherence on urologic cancer diagnosis. *Am J Med* 2014, 127:625-632.
20. Cha E K, Tirsar L A, Schwentner C, Hennenlotter J, Christos P J, Stenzl A, Mian C, Martini T, Pycha A, Shariat S F, Schmitz-Drager B J: Accurate risk assessment of patients with asymptomatic hematuria for the presence of bladder cancer. *World J Urol* 2012, 30:847-852.
21. Loo R K, Lieberman S F, Slezak J M, Landa L M, Mariani A J, Nicolaisen G, Aspera A M, Jacobsen S J: Stratifying risk of urinary tract malignant tumors in patients with asymptomatic microscopic hematuria. *Mayo Clin Proc* 2013, 88:129-138.
22. Tan G H, Shah S A, Ann H S, Hemdan S N, Shen L C, Galib NAFA, Singam P, Kong C H C, Hong G E, Bahadzor B, Zainuddin Z M: Stratifying patients with haematuria into high or low risk groups for bladder cancer: a novel clinical scoring system. *Asian Pac J Cancer Prev* 2013, 14:6327-6330.
23. Sultana S, Goodman C, Bryne D, Baxby K: Microscopic haematuria: urological investigation using a standard protocol. *Br J Urol* 1996, 78:691-698.
24. Sugimura K, Ikemoto S-I, Kawashima H, Nishisaka N, Kishimoto T: Microscopic hematuria as a screening marker for urinary tract malignancies. *Int J Urol* 2001, 8:1-5.
25. Viswanath S, Zelhof B, Ho E, Sethia K, Mills R: Is routine urine cytology useful in the haematuria clinic? *Ann R Coll Surg Engl* 2008, 90:153-155.
26. Steiner H, Bergmeister M, Verdorfer I, Granig T, Mikuz G, Bartsch G, Stoehr B, Brunner A: Early results of bladder-cancer screening in a high-risk population of heavy smokers. *BJU Int* 2008, 102:291-296.
27. Yeung C, Dinh T, Lee J: The health economics of bladder cancer: An updated review of the published literature. *Pharmacoeconomics* 2014, 32:1093-1104.
28. Holyoake A, O'Sullivan P, Pollock R, Best T, Watanabe J, Kajita Y, Matsui Y, Ito M, Nishiyama H, Kerr N, da Silva Tatley F, Cambridge L, Toro T, Ogawa O, Guilford P: Development of a multiplex RNA urine test for the detection and stratification of transitional cell carcinoma of the bladder. *Clin Cancer Res* 2008, 14:742-749.
29. Sapre N, Anderson P D, Costello A J, Hovens C M, Corcoran N M: Gene-based urinary biomarkers for bladder cancer: an unfulfilled promise? *Urol Oncol* 2014, 32:48.e9-e17.
30. Mitra A P, Castelao J E, Hawes D, Tsao-Wei D D, Jiang X, Shi S R, Datar R H, Skinner E C, Stein J P, Groshen S, Yu M C, Ross R K, Skinner D G, Cortessis V K, Cote R J: Combination of molecular alterations and smoking intensity predicts bladder cancer outcome. *Cancer* 2013, 119:756-765.
31. Lotan Y, Svatek R S, Krabbe L M, Xylinas E, Klatte T, Shariat S F: Prospective external validation of model for bladder cancer detection. *J Urol* 2014, 192:1343-1348.
32. Abogunrin F, O'Kane H F, Ruddock M W, Stevenson M, Reid C N, O'Sullivan J M, Anderson N H, O'Rourke D, Duggan B, Lamont J V, Boyd R E, Hamilton P, Nambirajan T, Williamson K E: The impact of biomarkers in multi-variate algorithms for bladder cancer diagnosis in patients with hematuria. *Cancer* 2012, 118:2641-2650.
33. O'Sullivan P, Sharples K, Dalphin M, Davidson P, Gilling P, Cambridge L, Harvey J, Toro T, Giles N, Luxmanan C, Felipe Alves C, Yoon H S, Hinder V, Masters J, Kennedy-Smith A, Beaven T, Guilford P: A multigene urine test for the detection and stratification of bladder cancer in patients presenting with hematuria. *J Urol* 2012, 188:741-747.
34. Epstein J I, Amin M B, Reuter V R, Mostofi F K: The World Health Organization/International Society of Urological Pathology consensus classification of urothelial (transitional cell) neoplasms of the urinary bladder. Bladder Consensus Conference Committee. *Am J Surg Pathol* 1998, 22:1435-1448.
35. Efron B, Tibshirani R J: *An introduction to the bootstrap.* New York: Chapman Hill; 1993.
36. DiCiccio T J, Tibshirani R J: Bootstrap confidence intervals. *Statist Sci* 1996, 11:189-228.
37. Van't Hoog A H, Cobelens F, Vassall A, van Kampen S, Dorman S E, Alland D, Ellner J: Optimal triage test characteristics to improve the cost-effectiveness of the Xpert MTB/RIF assay for T B diagnosis: A decision analysis. *PLoS ONE* 2013, 8:e82786.
38. Qu X, Huang X, Wu L, Huang G, Ping X, Yan W: Comparison of virtual cystoscopy and ultrasonography for bladder cancer detection: A meta-analysis. *Eur J Radiol* 2010, 80:188-197.
39. Mowatt G, N'Dow J, Vale L, Nabi G, Boachie C, Cook J A, Fraser C, Griffiths T R; Aberdeen Technology Assessment Review (TAR) Group: Photodynamic diagnosis of bladder cancer compared with white light cystoscopy: Systematic review and meta-analysis. *Int J Technol Assess Health Care* 2011, 27:3-10.

40. Blick C G, Nazir S A, Mallett S, Turney B W, Onwu N N, Roberts I S, Crew J P, Cowan N C: Evaluation of diagnostic strategies for bladder cancer using computed tomography (CT) urography, flexible cystoscopy and voided urine cytology: results for 778 patients from a hospital haematuria clinic. *BJU Int* 2012, 110:84-94.

41. Lotan Y, Capitanio U, Shariat S F, Hutterer G C, Karakiewicz P I: Impact of clinical factors, including a point-of-care nuclear matrix protein-22 assay and cytology, on bladder cancer detection. *BJU Int* 2009, 103: 1368-1374.

42. Tyrer J, Duffy S W, Cuzick J: A breast cancer prediction model incorporating familial and personal risk factors. *Stat Med* 2004, 23:1111-1130.

43. Dubsky P, Brase J C, Jakesz R, Rudas M, Singer C F, Greil R, Dietze O, Luisser I, Klug E, Sedivy R, Bachner M, Mayr D, Schmidt M, Gehrmann M C, Petry C, Weber K E, Fisch K, Kronenwett R, Gnant M, Filipits M, on behalf the Austrian Breast and Colorectal Cancer Study Group (ABCSG): The EndoPredict score provides prognostic information on late distant metastases in ER+/HER2− breast cancer patients. *Br J Cancer* 2013, 109: 2959-2964.

44. Brentnall A R, Evans D G, Cuzick J: Distribution of breast cancer risk from SNPs and classical risk factors in women of routine screening age in the UK. *Br J Cancer* 2014, 110:827-828.

45. Filipits M, Nielsen T O, Rudas M, Greil R, Stöger H, Jakesz R, Bago-Horvath Z, Dietze O, Regitnig P, Gruber-Rossipal C, Müller-Holzner E, Singer C F, Mlineritsch B, Dubsky P, Bauernhofer T, Hubalek M, Knauer M, Trapl H, Fesl C, Schaper C, Ferree S, Liu S, Cowens J W, Gnant M, Austrian Breast and Colorectal Cancer Study Group: The PAM50 risk-of-recurrence score predicts risk for late distant recurrence after endocrine therapy in postmenopausal women with endocrine-responsive early breast cancer. *Clin Cancer Res* 2014, 20:1298-1305.

46. Krabbe L M, Svatek R S, Shariat S F, Messing E, Lotan Y: Bladder Cancer Risk: Use of the PLCO and NLST to Identify as Suitable Screening Cohort. Urol Oncol. 20149 July 16): pii: S1078-1439 (14)00215-4.

Conclusions

In conclusion, the G+P INDEX reported here shows a significant opportunity to change clinical utility. G+P INDEX is able to accurately triage out patients who present to their clinician or physician with hematuria, who have a low probability of UC with a high overall test-negative rate, high level of sensitivity and high NPV. This model is suitable for use during primary evaluation of patients with hematuria to triage out patients who do not require a full urological work-up, thereby potentially reducing the number of patients with hematuria requiring referral for specialist urological evaluation for UC, helping to maintain patient QoL and helping to reduce diagnosis-related costs.

Example 5: Triage of Patents with Hematuria Using the G+P Index III ("G2")

A further use of the G+P INDEX is to categorize patients according to Risk of UC. The risk category is then used to prioritize patients for follow up investigation.

This example provides an alternative method for triaging patients using an index, herein termed the "G2+P Index." It is similar to the G+P Index described above in Example 4.

Definition of $G_2$

This classifier calculates the following formula:

$$M1 = [IGF] - [HOXA] + [MDK] + [CDC]; \text{then,}$$

$$R = -6.9802 + 0.2007 * M1 + 1.7893 * [IL8R] +$$
$$0.1552 * M1^2 - 0.2882 * [IL8R]^2 - 0.0720 * M1 * [IL8R]$$

to obtain the score:

SCORE=$e^R/(1+e^R)$, where [IGF], [HOXA], [MDK], [CDC] and [IL8R] are the logarithms of the sample concentrations for the genes IGF, HOXA, MDK, CDC and IL8R, respectively; "*" is ordinary multiplication, and e=2.718282 . . . is the base of the natural (Napierian) logarithm.

A high SCORE indicates a higher likelihood of UC being present. As an example, we may set a threshold of 0.12 and declare a SCORE>=0.12 as having a high likelihood of having UC, and those scores below 0.12 has having a low likelihood of having UC.

Example 6: Concurrent Use of [G1=P]-Index and G2 to Triage Out Patients Who Present with Hematuria Who have a Low Probability of Urothelial Carcinoma A. Patients with Micro-Haematuria
Patient Data-Set
   45 patient samples were assayed
   5 patients lack Smoking Status and were excluded from this analysis
   All patients have completed a full urological work-up and none have urothelial carcinoma.
   Phenotypic variables: Gender, Age, SmokingStatus
   Patient demographics are shown in Table 13 below.

TABLE 13

| Gender | Age | NonSmoker | ExSmoker | Smoker |
| --- | --- | --- | --- | --- |
| Female | Age < 60 | 10 | 1 | 2 |
|  | Age >= 60 | 9 | 1 | 2 |
| Male | Age < 60 | 3 | 2 | 3 |
|  | Age >= 60 | 3 | 2 | 2 |

Observed Test Negative Rate:
   Using a Test Negative Rate of 40% as the threshold, data is shown below in Table 14.

TABLE 14

| TNR 40% | LR < 0.12 | 0.12 <= LR < 0.23 | 0.23 <= LR |
| --- | --- | --- | --- |
| Triage Negative | 28 | 3 | 1 |
| Triage Positive | 4 | 2 | 2 |

Using a Negative Test Rate of 50% as the threshold, data is shown below in Table 15.

TABLE 15

| TNR 50% | LR < 0.12 | 0.12 <= LR < 0.23 | 0.23 <= LR |
| --- | --- | --- | --- |
| Triage Negative | 28 | 3 | 3 |
| Triage Positive | 4 | 2 | 0 |

Using a Negative Test Rate of 60% as the threshold gives an identical results.

The highest risk group (Male, Current or Ex-Smoker, Age>=60) were all positive for this Triage classification.

Summary and Conclusions

1. By deed of the clinical guidelines all 41 patients would normally receive a full urological work-up.
2. All 41 did receive a full-work-up and all 41 were determined to have no urothelial carcinoma.
3. At a Test Negative Rate (TNR of 50% 85% of the micro-hematuria patients would be screened out and therefore consequentially not receive a full urological work-up.
4. If Cxbladder-triage was used at a TNR of 50% (Triage Index −3.33) 85.4% of the patients would be triaged out and consequently, correctly would not receive a full urological work-up.
4. If Cxbladder-triage was used at a TNR of 40% (Triage Index −3.0) 80.5% of the patients would be triaged out and consequently, correctly would not receive a full urological work-up.

B. Patients with Macrohematuria

Patient Data Set 587 samples from Clinical Trial data and North Shore and CURT product trials were used. This data set was a subset consisting of complete data containing Age, Gender, Smoking Status and Haematuria frequency, as well as gene concentrations for IGF, HOXA, MDK, CDC, IL8R.

Figure 24:
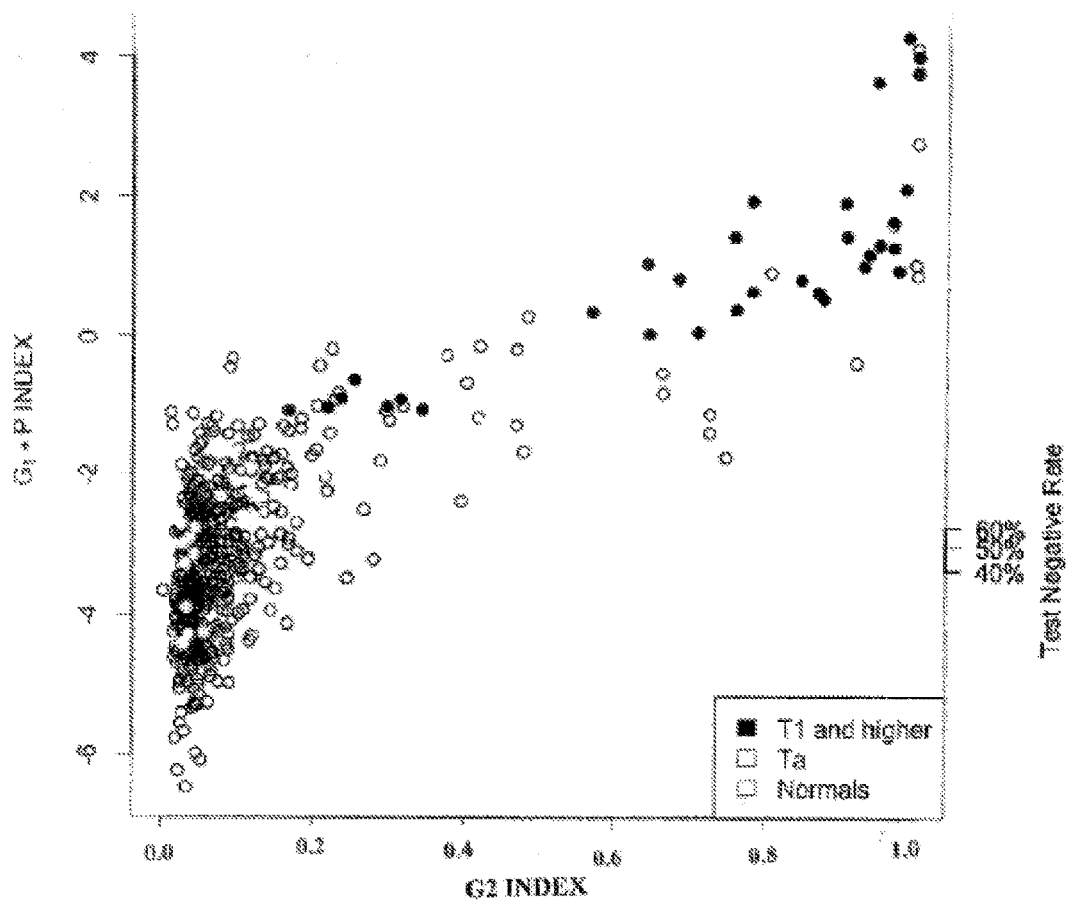
FIG. 24 depicts a graph of G2 INDEX (horizontal axis) versus G1+P INDEX (vertical axis).

We used the same data used to develop the Cxbladder-triage model below;

$G+P$ INDEX=−8.46+0.79 IGF−1.60 HOXA+2.10 MDK+0.95 CDC−0.38 IL8R+0.98 SNS+0.56 Hfreq+1.11 Gender+0.64 Age We plotted the triage score against G2 diagnostic score in FIG. 24. The Triage thresholds −3.33, −2.99 and −2.71 correspond to Test Negative rates of 40%, 50% and 60% respectively. The verticals are the Cxbladder thresholds of 0.12 and 0.23. Filled circles correspond to tumours; green are Ta, and red are all other higher stage tumours. Table 16 shows the clinical findings.

TABLE 16

| Stage | No-cancer | T1 | T2 | T2a | T3 | Ta | Tis |
|---|---|---|---|---|---|---|---|
| Count | 515 | 16 | 10 | 1 | 2 | 40 | 3 |

We considered the counts in the 4 quadrants of FIG. 24 and determined by various cutoffs for Triage Index and G2.

The threshold for the Cxbladder-triage (Triage Index) of −3 corresponds to a Test Negative rate of 50%. Table 17 shows these results.

TABLE 17

| Quadrant | Thresholds | Control | TCC |
|---|---|---|---|
| Bottom Left | Triage < −3 AND G2 < 0.12 | 272 | 6 |
| Top Left | Triage > −3 AND G2 < 0.12 | 155 | 7 |
| Bottom Left | Triage < −3 AND G2 >= 0.12 | 16 | 0 |
| Top Right | Triage > −3 AND G2 >= 0.12 | 72 | 59 |

Using a Cxbladder-triage threshold of −3.33 (Test Negative Rate of 40%) with the same G2 threshold of 0.12, we observed the data shown in Table 18.

TABLE 18

| Quadrant | Thresholds | Control | TCC |
|---|---|---|---|
| Bottom Left | Triage < −3.33 AND G2 < 0.12 | 222 | 4 |
| Top Left | Triage > −3.33 AND G2 < 0.12 | 205 | 9 |
| Bottom Right | Triage < −3.33 AND G2 >= 0.12 | 9 | 0 |
| Top Right | Triage > −3.33 AND G2 >= 0.12 | 79 | 59 |

Summary and Conclusions

1. Use of a serial combination of Cxbladder Triage (G+P) and Cxbladder Detect (G2) on the same patients in the same time interval provided a comprehensive segregation of patients into four key clinical groupings.
2. For a combined population of patients presenting with micro and macro hematuria and using a Test Negative Rate of 40% there was a total of 235 of the 587 patients (40.0%) of the patients triaged out. We conclude that these patients will not need a full work-up for UC.
3. For the same population the corresponding residual group of 352 (60%) patients will receive a full urological work-up.
4. This residual group contained all high grade and late stage tumours. These patients were not triaged out and would therefore consequently, correctly receive a full urological work-up.
5. A total of 4 low-grade Ta's (5.6% of the total number of tumours) will be triaged out and will not receive the full work-up.
6. If the triage rules allow triage out of all patients below the 40% Test Negative Rate and with G2 scores <0.12 then there were a total of 13 low grade Ta's triaged out that will not receive a full work-up and all high grade late stage tumours will be caught and receive a full urological work-up.
7. These modified triage rules also resulted in a total of 440 patients triaged out of a total of 587 (75%).

Advantages and General Conclusions

In conclusion, the G+P INDEX reported here shows a significant opportunity to change clinical utility. G+P INDEX is able to accurately triage out patients who present to their clinician or physician with haematuria, who have a low probability of UC with a high overall test-negative rate, high level of sensitivity and high NPV. This model is suitable for use by primary care physicians to triage out patients who do not require a full urological work up, thereby reducing the number of patients with haematuria requiring referral for specialist urological evaluation for UC, helping to maintain patient quality of life and reducing diagnosis-related costs. The disclosed methods provided unexpectedly accurate assessment of the lack of need for follow-up investigation for those with hematuria. These represent excellent effects that could not have been achieved without use of the disclosures contained herein.

INCORPORATION BY REFERENCE

All patents, patent applications and non-patent literature citations are herein incorporated fully by reference as if separately so incorporated.

INDUSTRIAL APPLICABILITY

Embodiments of this invention are useful in the fields of healthcare and medicine.

TECHNICAL ARTS

Embodiments of this invention provide highly accurate, sensitive, and specific computer-implemented methods for triaging patients to determine which patients do not require substantial short-term procedures or follow up. The methods improve computer operations by providing new and non-obvious computer operations based on analysis of specific genetic and phenotypic information from patients with hematuria that yield tangible, useful, and concrete results to improve the quality of health care and reduce cost.

What is claimed is:

1. A method for treating a patient for urothelial carcinomma comprising the steps:

a) providing a sample of urine from a patient;

b) quantifying a value, M1, comprising detecting and quantifying the levels of expression of the human genotypic markers, midkine (MDK), cyclin dependent kinase 1 (CDC2), homeobox A13 (HOXA13), insulin like growth factor binding protein (IGFBP5) in said sample where MI=[IGFBP5]−[HOXA13]+[MDK]+[CDC2] in said sample, where the square brackets "[ ]" are defined as the log of concentrations in the sample of urine of each of said genotypic markers;

c) detecting the log concentration of IL8Rb in said sample;

d) assessing the phenotypic variables: detecting in the urine of 3 or more red blood cells per high power field in a 6-month period (HFREQ), subject's age greater than 50 years AgeGT50), gender, smoking history (SMK), and detecting the red blood cell count (RBC) of said patient and e) quantifying a value of G+P INDEX according to either:

$$G+P \text{ INDEX}=(1*\text{HFREQ}+3*\text{Gender}+4*\text{SMK})+(5*M1+2*\text{IL8Rb}), \text{ or} \quad \text{formula (i)},$$

$$G+P \text{ INDEX}=(\omega 1*\text{HFREQ}+w2*\text{AgeGT50}+w3*\text{Gender}+w4*\text{SMK}+w5*\text{RBC})+(\omega 6*M1+w7*\text{IL8Rb}), \text{ or}$$

$$G+P \text{ INDEX}=-8.46+0.79 \text{ IGF}-1.60 \text{ HOXA}+2.10 \text{ MDK}+0.95 \text{ CDC}-0.38 \text{ IL8Rb}+0.98 \text{ SNS}+0.56 \text{ Hfreq}+1.11 \text{ Gender}+0.64 \text{ Age}; \quad \text{formula (ii)},$$

where the terms w1-w7 are respectively the weights assigned to each of the variables; where HFREQ means the frequency of finding 3 or more red blood cells per high power field in a 6-month period; if frequency is low, then HFREQ is set to 0, and if higher than 3 red blood cells per high power field, then HFREQ is set to 1;

AgeGT50 refers to subject's age, if greater than 50 years then AgeGT50 is set to 1, and if less than 50 years, then AgeGT50 is set to 0;

Gender is assigned a value of 1 for male, and 0 for female;

SMK means whether the subject is a current or ex-smoker; if non-smoker then SMK is set to 0 and if a smoker, then SMK is set to 1;

RBC means red blood cell count: if 25 or more then RBC is set to 1, and if less than 25, then RBS is set to 0;

M1 is a combination of expression of the genetic markers MDK, CDC, IGFBP5, and HOXA13; if M1>4.5 then M1 is set to 1, if M1 is less than 4.5, then M1 is set to 0;

IL-8 refers to expression level of RNA for IL-8R; if IL-8R>2.5 then IL-8R is set to 1, if IL8Rb is less than 2.5, IL8Rb is set to 0;

the symbols "*" means the multiplication operator, and weighting factors, w1-w7 are respectively the weights assigned to each of the variables listed in the G+P INDEX; and if the G+P INDEX has value of from 6-10, said patient undergoes additional clinical or laboratory tests.

2. The method of claim 1, where if the G+P INDEX has a value of from 11-15, said patient is treated immediately for urothelial carcinoma.

3. The method of claim 1 for treating a patient having an inflammatory condition of the bladder, comprising the steps:
  a) providing a sample of urine from said patient;
  b) detecting the log concentration of IL8Rb in said sample; wherein if the level of IL8Rb in said sample is greater than the levels of IL8Rb in a group of patients not having an inflammatory condition of the bladder, said patient is treated using an antiinflammatory agent.

* * * * *

UNITED STATES PATENT AND TRADEMARK OFFICE
CERTIFICATE OF CORRECTION

PATENT NO. : 10,131,955 B2
APPLICATION NO. : 15/159359
DATED : November 20, 2018
INVENTOR(S) : David Darling et al.

Page 1 of 1

It is certified that error appears in the above-identified patent and that said Letters Patent is hereby corrected as shown below:

In the Specification

Column 7, Line 47, please delete "mRNA" and replace it with --cDNA--.

In the Claims

Column 78, Line 51, please delete the term "ω1" and replace it with --w1--.

Column 78, Line 51, please add the term --formula (ii)-- right justified.

Column 79, Line 5, please delete the term "RBS" and replace it with --RBC--.

Signed and Sealed this
Fifth Day of March, 2019

Andrei Iancu
*Director of the United States Patent and Trademark Office*